(12) United States Patent
Seung et al.

(10) Patent No.: US 12,209,248 B2
(45) Date of Patent: Jan. 28, 2025

(54) METHODS FOR ALTERING STARCH GRANULE PROFILE

(71) Applicant: Plant Bioscience Limited, Norwich (GB)

(72) Inventors: David Seung, Norwich (GB); Jiawen Chen, Norwich (GB)

(73) Assignee: PLANT BIOSCIENCE LIMITED, Norfolk (GB)

( * ) Notice: Subject to any disclaimer, the term of this patent is extended or adjusted under 35 U.S.C. 154(b) by 0 days.

(21) Appl. No.: 17/279,978

(22) PCT Filed: Sep. 26, 2019

(86) PCT No.: PCT/GB2019/052727
§ 371 (c)(1),
(2) Date: Mar. 25, 2021

(87) PCT Pub. No.: WO2020/065331
PCT Pub. Date: Apr. 2, 2020

(65) Prior Publication Data
US 2022/0119834 A1 Apr. 21, 2022

(30) Foreign Application Priority Data
Sep. 26, 2018 (GB) ..................... 1815672

(51) Int. Cl.
C12N 15/82 (2006.01)
C12N 15/11 (2006.01)
C12Q 1/6895 (2018.01)

(52) U.S. Cl.
CPC .......... *C12N 15/8245* (2013.01); *C12N 15/11* (2013.01); *C12N 15/8216* (2013.01); *C12Q 1/6895* (2013.01); *C12Q 2600/13* (2013.01); *C12Q 2600/156* (2013.01)

(58) Field of Classification Search
CPC ................ C12N 15/8245; C12N 15/11; C12N 15/8216; C12Q 1/6895; C12Q 2600/13; C12Q 2600/156
See application file for complete search history.

(56) References Cited

U.S. PATENT DOCUMENTS 9,150,839 B2 * 10/2015 Slade et al. ............ C12N 9/107
2005/0160496 A1 7/2005 Singletary et al.

FOREIGN PATENT DOCUMENTS

WO WO2006059130 A2 6/2006

OTHER PUBLICATIONS

Vandromme et al. "Pll1: a protein involved in starch initiation that determines granule number and size in *Arabidopsis* chloroplast" Apr. 2018 bioRxiv doi: https://doi.org/10.1101/310003 (35 total pages). (Year: 2018).*

(Continued)

*Primary Examiner* — Brent T Page
*Assistant Examiner* — Rebecca Stephens
(74) *Attorney, Agent, or Firm* — Greer, Burns & Crain, Ltd.

(57) ABSTRACT

The invention relates to methods for altering the size distribution of starch granules in starch storage organs. Also described are genetically altered plants characterised by the above phenotype as well as methods of producing such plants.

8 Claims, 25 Drawing Sheets
Specification includes a Sequence Listing.

(56) References Cited

OTHER PUBLICATIONS

Seung et al. "Two Plastidial Coiled-Coil Proteins Are Essential for Normal Starch Granule Initiation in *Arabidopsis*" Jun. 4, 2018 Plant Cell 30:1523-1542 (Year: 2018).*
Rhazi et al. "Genetic and Environmental Variation in Starch Content, Starch Granule Distribution and Starch Polymer Molecular Characteristics of French Bread Wheat" 2021 Foods 10(205): https://doi.org/10.3390/foods10020205, 15 total pages. (Year: 2021).*
Streb & Zeeman "Starch Metabolism in *Arabidopsis*" in The *Arabidopsis* Book (2012 American Society of Plant Biologists) (33 total pages). (Year: 2012).*
Scofield et al. "Starch storage in the stems of wheat plants: localization and temporal changes" 2009 Annals of Botany 103:859-868. (Year: 2009).*
Tosi et al. "Gradients in compositions in the starchy endosperm of wheat have implications for milling and processing" 2018 Trends in Food Science & Technology 82:1-7 (document is 9 total pages). (Year: 2018).*
Sueng, D., et al., "Two Plastidial Coiled-Coil Proteins are Essential for Normal Starch Granule Initiation in *Arabidopsis*", The Plant Cell, Jul. 2018, pp. 1523-1542, vol. 30, No. 7.
Vandromme, C., et al., "Pll1: a Protein Involved in Starch Initiation that Determines Granule Number and Size in *Arabidopsis* Chloroplast", New Phytologist, 2019, pp. 356-370, vol. 221, No. 1.
Jaganathan, D. et al., "CRISPR for Crop Improvement: An Update Review", Frontiers in Plant Science, Jul. 17, 2018, pp. 1-17, vol. 9.
Lee, S., et al., "Review: Crucial role of inorganic pyrophosphate in integrating carbon metabolism from sucrose breakdown to starch synthesis in rice endosperm", Plant Science, Jun. 19, 2022, pp. 1-6, vol. 298.
Xiao, Q., et al., "Profiling of transcriptional regulators associated with starch biosynthesis in sorghum (*Sorghum bicolor* L.)", Frontiers in Plant Science, Aug. 30, 2022, pp. 1-14,.
Tong. C., et al., "Toward an understanding of potato starch structure, function, biosynthesis, and applications", Food Frontiers, Feb. 25, 2023, pp. 1-21.
Finegan, C., et al., Genetic Perturbation of the Starch Biosynthesis in Maize Endosperm Reveals Sugar-Responsive Gene Networks, Frontiers in Plant Science, Feb. 8, 2022, pp. 1-16, vol. 12, No. 800326.
Collins, H., et al., "Genes That Mediate Starch Metabolism in Developing and Germinated Barley Grain", Original Research, Mar. 1, 2021, pp. 1-15, vol. 12, No. 641325.
Kamal-Eldin, A. et al., "11—Rye bread and other rye products", Technology of Functional Cereal Products, Woodhead Publishing Series in Food Science, Technology and Nutrition, (2008), pp. 222-260.

* cited by examiner

Figure 6
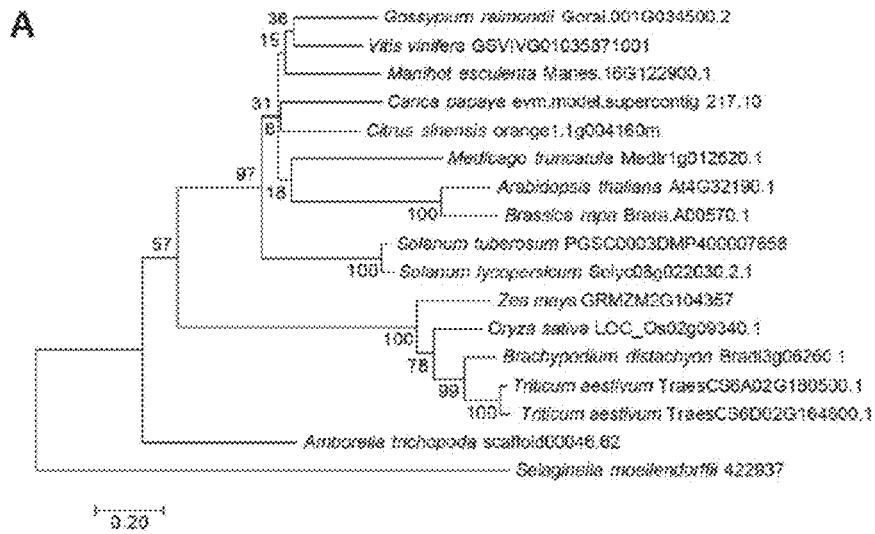
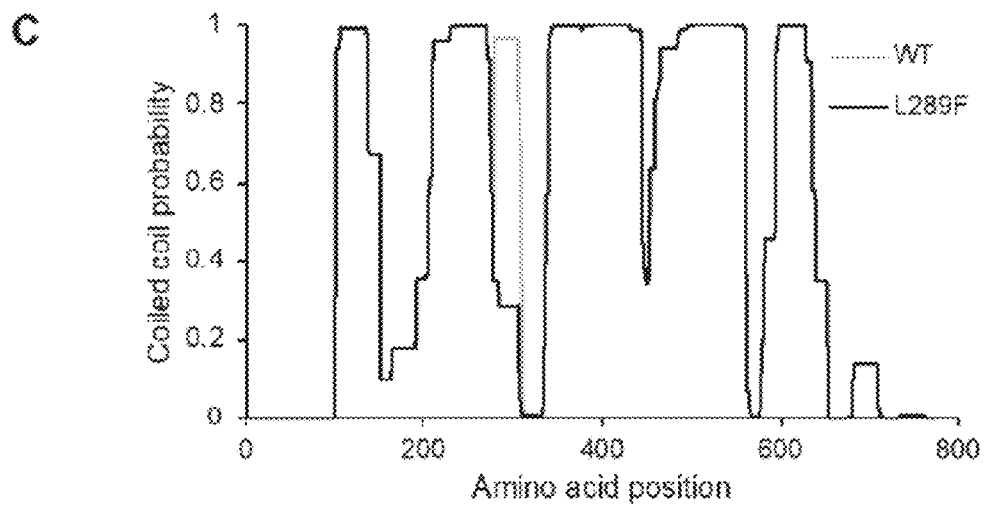

Figure 8
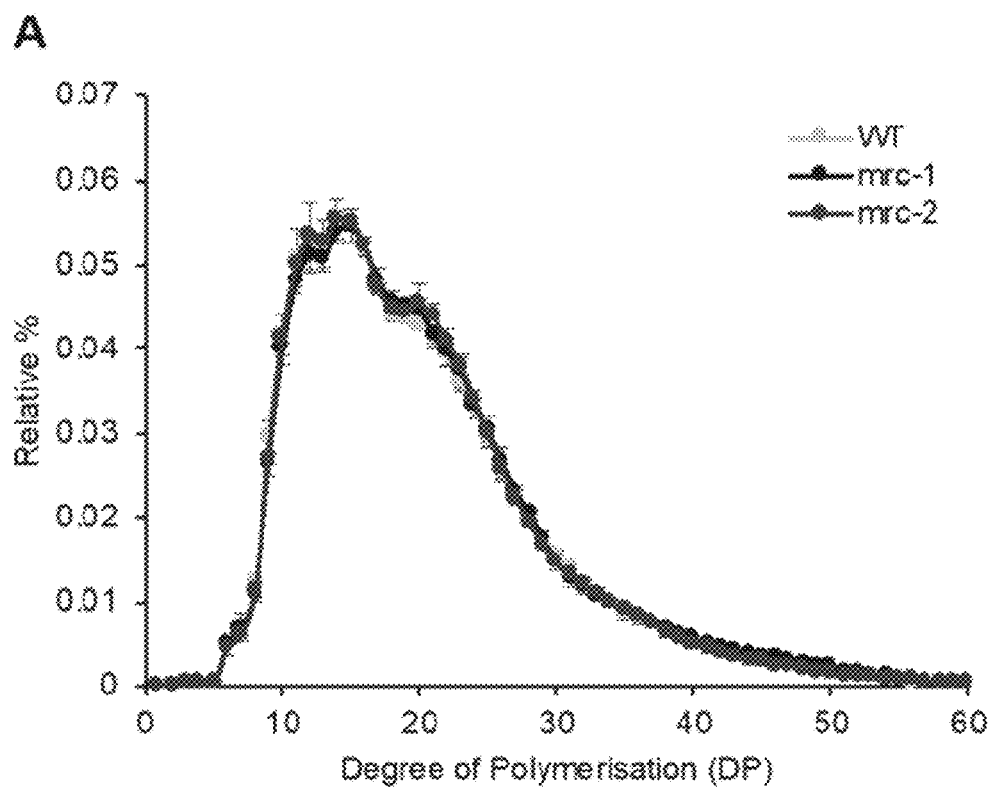
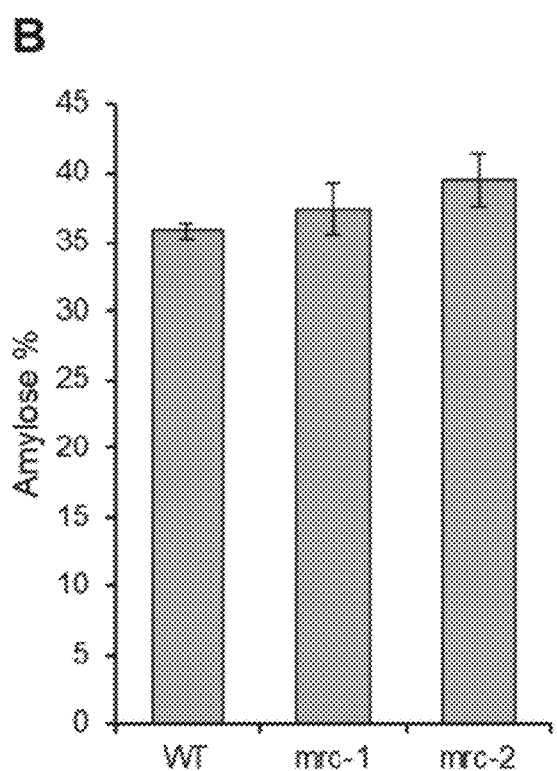

Figure 9

| Granule size and B-type granule content in *mrc* mutants ||||
| --- | --- | --- | --- |
|  | A-type granule mean size (μm) | B-type granule mean size (μm) | B-type granule content (%) |
| Kronos WT | 23.0 ± 0.2 | 6.9 ± 0.1 | 8.0 ± 0.5 |
| *mrc-1* | 17.6 ± 0.3* | 7.6 ± 0.2 | 22.8 ± 2.0* |
| *mrc-2* | 21.3 ± 0.1* | 8.1 ± 0.3* | 15.2 ± 1.6* |
| *mrc-3* | 17.8 ± 1.3* | 6.6 ± 0.3 | 19.2 ± 1.0* |
|  |  |  |  |

Figure 10

| Total starch content of mature grains from *mrc* mutants | | | |
|---|---|---|---|
| Genotype | | Starch content (% dry weight) | |
| | | Experiment 1 | Experiment 2 |
| Kronos WT | | 68.6 ± 0.3 | 77.5 ± 3.7 |
| *mrc-1* | *aa* BB | 70.9 ± 0.2 | 67.4 ± 2.5 |
| | AA *bb* | 61.3 ± 0.5 | - |
| | *aa bb* | 79.7 ± 0.3 | - |
| *mrc-2* | *aa bb* | - | 70.2 ± 5.1 |
| *mrc-3* | *aa* BB | - | 62.8 ± 7.9 |

Figure 11

| Wheat mrc mutants in cv. Kronos and Cadenza | | | | |
|---|---|---|---|---|
| | Line identifier | Effect of mutation | KASP markers (5' → 3') | SEQ ID NOs |
| Mutants in cv. Kronos | | | | |
| TaMRC 6A | Kronos3272 | Q258→STOP (CAG>TAG) | wt: agcaacagttagggagctgc<br>mut: agcaacagttagggagctgt<br>common: cctcgattcatttgatctggcg | SEQ ID NO: 73<br>SEQ ID NO: 74<br>SEQ ID NO: 75 |
| | Kronos4681 | Q550→STOP (CAA>TAA) | wt: catacggctcagatgctcgc<br>mut: catacggctcagatgctcgt<br>common: gcaagatcgccagtgagc | SEQ ID NO: 76<br>SEQ ID NO: 77<br>SEQ ID NO: 78 |
| | Kronos775 | L394F | wt: attcaaggaagacacaggagC<br>mutant: attcaaggaagacacaggagT<br>common: tcatgacaacgagactgtgcA | SEQ ID NO: 79<br>SEQ ID NO: 80<br>SEQ ID NO: 81 |
| | Kronos2485 | A625T | wt: cttgatctttggcatcaagtgC<br>mutant: cttgatctttggcatcaagtgT<br>common: acagccctcgagtccaatttA | SEQ ID NO: 82<br>SEQ ID NO: 83<br>SEQ ID NO: 84 |
| | Kronos2096 | P681S | wt: tgtaggagagatggagctGC<br>mutant: tgtaggagagatggagctGT<br>common: gcttcgacctccGcagcA | SEQ ID NO: 85<br>SEQ ID NO: 86<br>SEQ ID NO: 87 |
| TaMRC 6B (pseudogene) | Kronos3078 | Q226→STOP (CAG>TAG) | wt: ctcgttgtcatgaacttgaatcac<br>mut: ctcgttgtcatgaacttgaatcat<br>common: tcgacctctcccttcctg | SEQ ID NO: 88<br>SEQ ID NO: 89<br>SEQ ID NO: 90 |
| | Kronos4305 | W26→STOP (TGG>TGA) | wt: ttgagaagcagagttaggatgg<br>mut: ttgagaagcagagttaggatga<br>common: acgtttgaagtcagtgataatacca | SEQ ID NO: 91<br>SEQ ID NO: 92<br>SEQ ID NO: 93 |
| Mutants in cv. Cadenza | | | | |
| TaMRC 6A | Cadenza0199 | Q727→STOP (CAA>TAA) | wt: acttggttgcatcagagagtc<br>mut: acttggttgcatcagagagtt<br>common: acttccattttaggatcgcattaa | SEQ ID NO: 94<br>SEQ ID NO: 95<br>SEQ ID NO: 96 |
| | Cadenza0377 | Q360→STOP (CAG>TAG) | wt: cgagttcctgtacttgttcctg<br>mut: cgagttcctgtacttgttccta<br>common: gatgctgtacgctctgaattg | SEQ ID NO: 97<br>SEQ ID NO: 98<br>SEQ ID NO: 99 |
| TaMRC 6B (pseudogene) | Cadenza1715 | E221→K (GAG>AAG) | wt: tggctgttcaagaaaaggattcag<br>mut: tggctgttcaagaaaaggattcaa<br>common: tgaagctcagcaatttcactgc | SEQ ID NO: 100<br>SEQ ID NO: 101<br>SEQ ID NO: 102 |
| TaMRC 6D | Cadenza1012 | Q258→STOP (CAG>TAG) | wt: agcaacagttagggagctgc<br>mut: agcaacagttagggagctgt<br>common: attcatttgatctggcgatatcg | SEQ ID NO: 103<br>SEQ ID NO: 104<br>SEQ ID NO: 105 |
| | Cadenza1092 | Q482→STOP (CAA>TAA) | wt: ccttttcttgaacagccaattg<br>mut: ccttttcttgaacagccaatta<br>common: cttcagaaggagcttgttcg | SEQ ID NO: 106<br>SEQ ID NO: 107<br>SEQ ID NO: 108 |

SEQ ID NO:

```
38  AtMRC                    REISVQKELLEDLREELQREKPLLELAMHDISVIQDELYKKANAFQVSQNLLQEKESSLV  465
10  HvMRC                    SYLLQEMEKVESLEAELTREKQSLEHRTEEVDPLQKELVQKENECTKSQELVKVKEFELL  465
3   TaMRC_6D_(cv._Cadenza)   SQLLQEMEKVESLETELTREKQSLDHRTEEVGPLQKELVRKENECTKSQELVKVKEFELL  465
1   TaMRC_6A_(cv._Kronos)    SQLLKEMEKVESLEAELTKEKQSLEHRTEEVGPLQKELVQKENECTKSQELVKVKEFELL  465
2   TaMRC_6A_(cv._Cadenza)   SQLLKEMEKVESLEAELTKEKQSLEHRTEEVGPLQKELVQKENECTKSQELVKVKEFELL  465
                              : * :*.*. ** **:  *:  ..:..:*.** :* *    **:*:: ** .*:

38  AtMRC                    EAKLEIQHLKSEQASLELLLQEKDEELAEARRKLGEVNQEVTELKALMISREDQLMEATE  525
10  HvMRC                    EARYEVQDMKLKVESIQLAVQEKDSELSATQSRLTEVSSEVVKLQQLLRSKEDQLVQART  525
3   TaMRC_6D_(cv._Cadenza)   EARQEVQDMKLKVESIQLAVQEKDSELSDTQSRLTEVSSEIVELQQLLRSKKDQLVQART  525
1   TaMRC_6A_(cv._Kronos)    EARQEVQDMKLKVESIQLAVQEKDSELSDTQSRLTEVSSEIVELQQLLRSKKDQLVQART  525
2   TaMRC_6A_(cv._Cadenza)   EARQEVQDMKLKVESIQLAVQEKDSELSDTQSRLTEVSSEIVELQQLLRSKKDQLVQART  525
                            **: *:*.:*   : *:* :****.**:  ::.:* **.,*:.:*:  *:  *::****:*

38  AtMRC                    MLKEKDVHLHRIEGELGSSKLKVTEAEMVVERIAELTNPLLMSTTNGQNQNAMRINNEIS  585
10  HvMRC                    ELHDKEQRIETLESELDNIRLRCSQAESVVQRMAELTGDLASSVKTGETDIYTLLDDEIA  585
3   TaMRC_6D_(cv._Cadenza)   ELHDKEQRIETLESELDSIRFRCSQAESMVQRMAELTGDLASSVKAGEMDIYTLLDDEIS  585
1   TaMRC_6A_(cv._Kronos)    ELHDKEQRIETLESELDSIRLRCSQAESMVQRMAELTGDLASSVKAGEMDIYTLLDDEIS  585
2   TaMRC_6A_(cv._Cadenza)   ELHDKEQRIETLESELDSIRLRCSQAESMVQRMAELTGDLASSVKAGEMDIYTLLDDEIS  585
                             *:::*:  *:..:*.*  .::  **  * :* *****. .  *: *:      :::*:

38  AtMRC                    TDSMQQPLEKPHDDYGMENKRLVMELSPTRENLRMKEMEVLAVQRALTFKDEEINVVMGR  645
10  HvMRC                    SAGTT--LES----NLRKHDQLEADIEMLRECLRHKDMDLRAAHEALDAKTQELKAVLKK  639
3   TaMRC_6D_(cv._Cadenza)   STGTA--LES----NLRKHNQLEADIEMLRECLRHKDMDLRAAHEALDAKDQELKAVLKK  639
1   TaMRC_6A_(cv._Kronos)    STSTA--LES----NLRKHNQLEADIEMLRECLRHKDMELRAAHEALDAKDQELKAVLKK  639
2   TaMRC_6A_(cv._Cadenza)   STSTA--LES----NLRKHNQLEADIEMLRECLRHKDMELRAAHEALDAKDQELKAVLKK  639
                            .      **.          :::*  ::.:  ** ** *:*:  *.:.** **:::.*: :

38  AtMRC                    LEAKEQELKKLKEETINDSEDLKVLYALAQERVGEKTMGDLAIEMLQLEAANLEVEAATS  705
10  HvMRC                    WDVKERELRELEELL---DPSATNELACFSNETTEGGVVGEMELQELQIGAAEVEALAATT  697
3   TaMRC_6D_(cv._Cadenza)   WDVKERELRELEELP---DPSATNELAVFSSETTEDGIVGEMELPELQIEAASGVEALAATT  697
1   TaMRC_6A_(cv._Kronos)    WDVKERELRELEELP---DPSATNELAGFSSETTEGGIVGEMELPELQIDAAEVEALAATT  697
2   TaMRC_6A_(cv._Cadenza)   WDVKERELRELEELP---DPSATNELAGFSSETTEGGIVGEMELPELQIDAAEVEALAATT  697
                             :.**:**:**:*:*     *  *  ::.*      .  *:: :  ** ** .*: ***:

38  AtMRC                    ALQKLAKMSTELLTQADMSIEADTT------HTVMP---ERSYSESSNECLGEVKTEVVRLWS  759
10  HvMRC                    ALRKLADMTKDLFKHDKGDSGIDLAASGSQKLRNCDGKMEVHKKTDVILEAEKETIRLFS  757
3   TaMRC_6D_(cv._Cadenza)   ALRKLADMTKDFFKRGKADSGIDLVASESQKISKCDPKMEVHKKTDVILEAEKEIVRLFS  757
1   TaMRC_6A_(cv._Kronos)    ALRKLADMTKDFFKHVKADSGINLVASESQKIIKCDPKMEVHKKTDVILEAEKEIVRLFS  757
2   TaMRC_6A_(cv._Cadenza)   ALRKLADMTKDFFKHVKADSGINLVASESQKIIKCDPKMEVHKKTDVILEAEKEIVRLFS  757
                            **:***.*::::: .:   .      :       :    : .  .::*:.*::*:**:*

38  AtMRC                    LTEKLLENAGIVAGTSTCMEGVILA              763
10  HvMRC                    LTKQIVTDDIINDVDER*--------             774
3   TaMRC_6D_(cv._Cadenza)   LTKQIVTDDTINNLEE*--------              773
1   TaMRC_6A_(cv._Kronos)    LTKQIVTDDIINDVEE*--------              773
2   TaMRC_6A_(cv._Cadenza)   LTKQIVTDDIINDVEE--------               773
                            **::::  *    .
```

Figure 13

| Gelatinisation temperature of mrc-1 aabb starch | | | | |
|---|---|---|---|---|
| | Onset (°C) | Peak (°C) | Peak-Onset (°C) | Enthalpy (J/g) |
| WT | 50.2 ± 0.5 | 56.3 ± 0.3 | 6.2 ± 0.3 | 6.5±0.3 |
| mrc-1 aa bb | 52.2 ± 0.3* | 57.8 ± 0.3* | 5.7 ± 0.1 | 7.0±0.1 |

| | A granule size (µm) | B granule size (µm) | B granule content (% volume) |
|---|---|---|---|
| Kronos WT | 20.8 ± 0.1 | 7.0 ± 0.1 | 11.3 ± 0.3 |
| mrc-1 | 17.1 ± 0.2* | 7.4 ± 0.2 | 26.0 ± 1.2* |
| mrc-3 | 17.8 ± 1.3* | 6.6 ± 0.3 | 19.2 ± 1.0* |
| K2485 | 22.0 ± 0.3* | 8.8 ± 0.3 | 8.8 ± 0.6* |

Figure 19
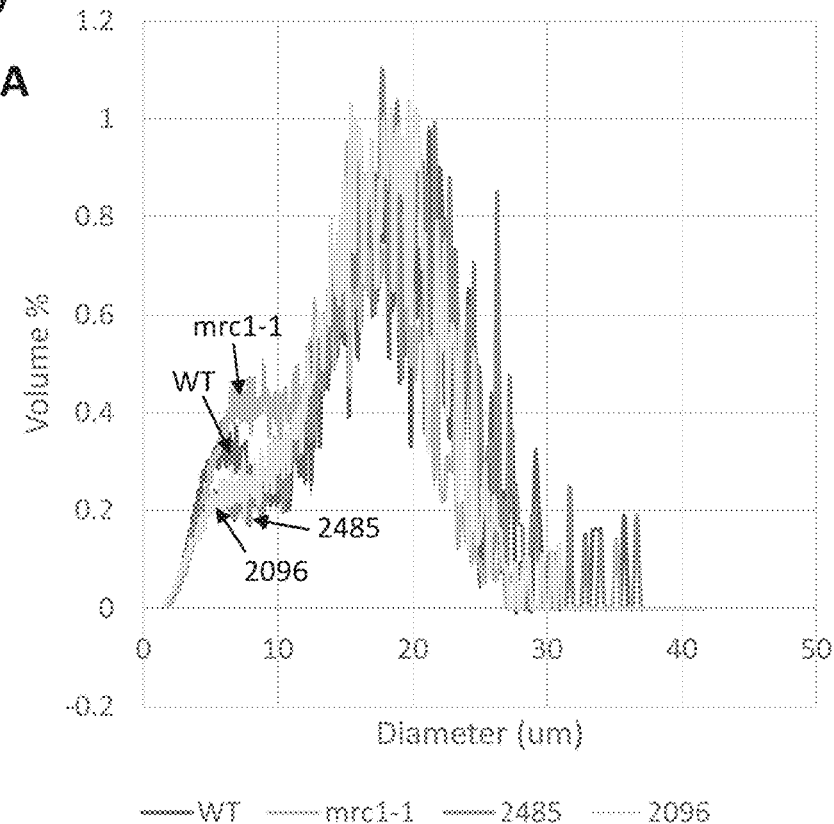
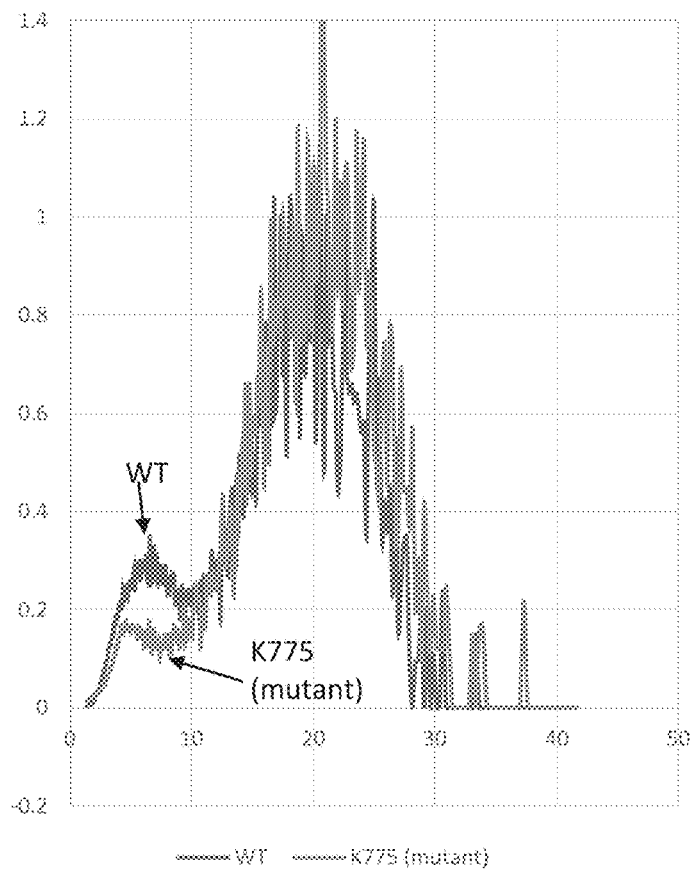

Figure 21

| Gelatinisation temperature of mrc-1 aabb starch | | | | |
|---|---|---|---|---|
| | Onset (°C) | Peak (°C) | Peak-Onset (°C) | Enthalpy (J/g) |
| WT | 50.2 ± 0.5 | 56.3 ± 0.3 | 6.2 ± 0.3 | 6.5±0.3 |
| mrc-1 aa bb | 52.2 ± 0.3* | 57.8 ± 0.3* | 5.7 ± 0.1 | 7.0±0.1 |

Figure 22
A
*At*MRC
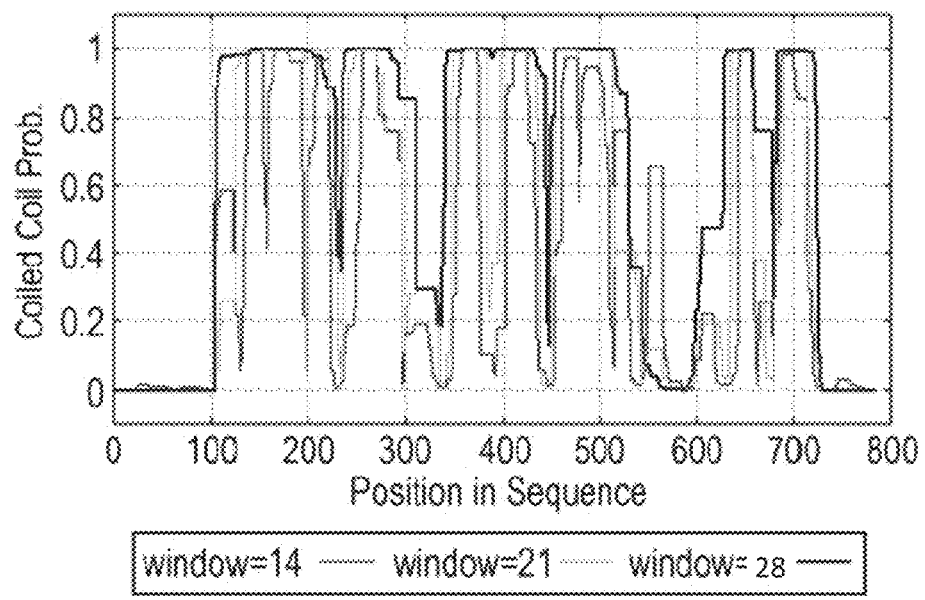
B
*Ta*MRC 6A (Kronos)
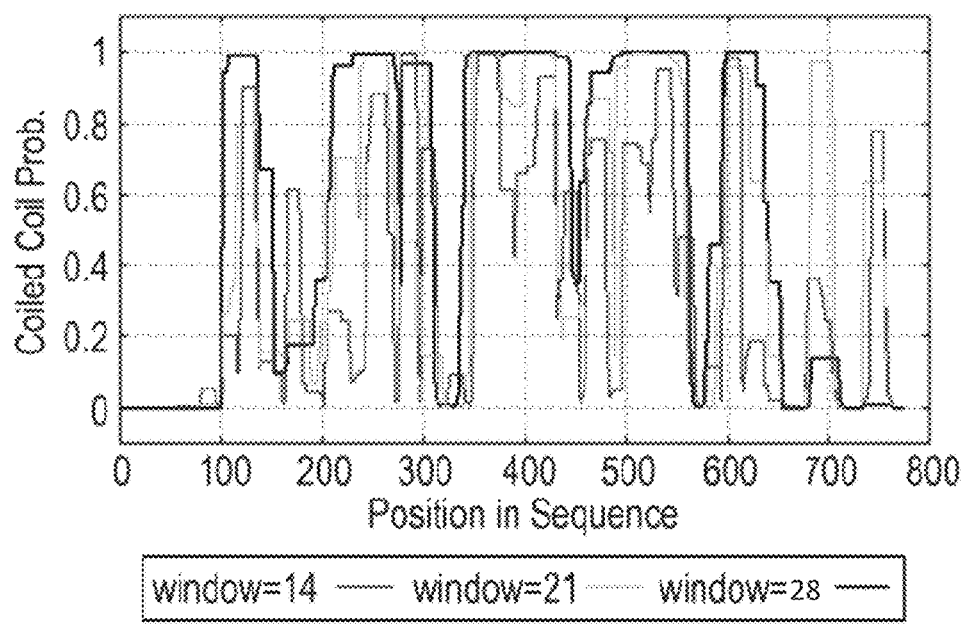

Figure 23

| TaMRC expression during grain development | | | | | | |
|---|---|---|---|---|---|---|
| | Expression level in starchy endosperm (tpm) | | | | | |
| dpa: | 6 | 9 | 12 | 14 | 20 | 30 |
| 6A | 2.27 | 2.71 | 0.85 | 0.15 | 0.16 | 0.22 |
| 6D | 2.09 | 2.04 | 0.92 | 0.27 | 0.32 | 0.38 |

METHODS FOR ALTERING STARCH GRANULE PROFILE

CROSS-REFERENCE TO RELATED APPLICATIONS

This application is the U.S. National phase application corresponding to PCT/GB2019/052727 which was assigned an international filing date of Sep. 26, 2019 and associated with publication WO 2020/065331 A1 and which claims priority to GB 1815672.9, filed on Sep. 26, 2018, the disclosures of which are expressly incorporated herein by reference.

REFERENCE TO A SEQUENCE LISTING

This application includes an electronically submitted sequence listing in .txt format. The .txt file contains a sequence listing entitled "5609.145467_ST25.txt" created on Oct. 9, 2024 and is 222,998 bytes in size. The sequence listing contained in this .txt file is part of the specification and is hereby incorporated herein by reference in its entirety.

FIELD OF THE INVENTION

The invention relates to methods for altering the size distribution of starch granules in starch storage organs. Also described are genetically altered plants characterised by the above phenotype as well as methods of producing such plants.

BACKGROUND OF THE INVENTION

Starch is a vital source of calories in human diets and an important industrial raw material for the manufacture of many food and non-food products (such as biofuels, paper, pharmaceuticals and textiles) (Jobling, 2004; Smith, 2008; Santelia and Zeeman, 2010). Most plants store a portion of carbon fixed through photosynthesis during the day as starch in leaf chloroplasts. This starch is then degraded to provide energy for growth and metabolism at night. Some plants also accumulate high levels of starch in amyloplasts (i.e. non-photosynthetic chloroplasts for starch storage) of seeds and storage organs. Starch is the major carbohydrate component of many of our staple crops, including cereal grains (wheat, barley, maize, rice, rye, oat), tubers and storage roots (potato, cassava, yam, sweet potato), and banana fruits.

Native starch exists as insoluble, semi-crystalline granules that are composed of two distinct glucose polymers, amylopectin and amylose (Zeeman et al., 2010; Pfister and Zeeman, 2016; Goren et al., 2018). Amylopectin is the major component of the starch granule and is a highly branched polymer consisting of α-1,4-linked glucan chains with α-1,6-linked branch points. The structure of amylopectin facilitates the formation of double helices between adjacent branches, which form the crystalline regions of the starch granule. Amylose consists of long linear α-1,4-linked chains with very few branches, and is thought to reside in the more amorphous regions of the starch granule. The ratio of amylopectin to amylose, as well as the size and shape of starch granules vary greatly depending on botanical source and organ. In *Arabidopsis* leaves, starch granules are approximately 1 μm in diameter, and contain about 8-10% amylose (Zeeman et al., 2002; Seung et al., 2015). Cereal starches typically contain approximately 15-30% amylose, but the morphology of the granules vary greatly between species (Jane, 1994; Jane et al., 1999). In rice and maize, starch granules have a size distribution between 3-8 μm and 5-20 μm respectively (Jane, 1994; Lindeboom et al., 2004). Cereal crops of the Triticeae (wheat, rye and barley) have a bimodal distribution of granule size, with larger A-type granules and smaller B-type granules. In wheat, A-type granules are 20-30 μm in diameter, while B-type granules (which initiate about 10 days after the initiation of A-type granules) are 2-7 μm in diameter (Bechtel et al., 1990; Howard et al., 2011). A-type granules account for more than 70% of wheat endosperm starch by weight, but less than 10% of the granules by number (Lindeboom et al., 2004).

Previously, little was known about the mechanisms that initiate starch granules in plastids, or factors determining the number of granules per plastid, granule shape and size. In *Arabidopsis* leaves, each chloroplast contains 5-7 starch granules, and there is relatively little variation in this number (Crumpton-Taylor et al., 2012). The STARCH SYNTHASE 4 (SS4) enzyme was the only protein known to be required for proper granule initiation. Most chloroplasts in *Arabidopsis* mutants lacking SS4 produce one large starch granule rather than as multiple granules (Roldán et al., 2007; Crumpton-Taylor et al., 2013). Recently, we discovered the PROTEIN TARGETING TO STARCH (PTST) family of proteins in *Arabidopsis* (Seung et al., 2015, 2017), and two members of this family (PTST2 and PTST3) are required for normal starch granule initiation in *Arabidopsis* chloroplasts (Seung et al., 2017). Most chloroplasts in *Arabidopsis* mutants deficient in PTST2 have one large granule per chloroplast, while mutants deficient in PTST3 have only a slight reduction in granule number per chloroplast relative to the wild type. However, granule number is more severely reduced in the ptst2 ptst3 double mutant than either single mutant, suggesting some redundancy between PTST2 and PTST3.

There is significant industrial interest in manipulating the distribution of granule sizes within a plant starch storage organ (Lindeboom et al., 2004). Granule size influences the physico-chemical behaviour of starch, particularly during the gelatinisation process (the swelling and disintegration of the starch granule when heated in the presence of water—a process that occurs during cooking and industrial processing of starch).

In particular, on the one hand, larger starch granules tend to have high swelling power and viscosity, while smaller granules tend to provide smoother paste textures (Santelia and Zeeman, 2010). This means that an increased number of small granules (or a narrower granule size distribution) is desirable for the papermaking and plastic industries, and also for use as a binder or carrier material in the pharmaceutical and cosmetics industries (Lindeboom et al., 2004; Santelia and Zeeman, 2010). Small granule starch is also more effectively digested than larger granules, due to their larger surface area to volume ratio (Dhital et al., 2010). Thus, increasing the number of small starch granules may be desirable for applications where complete and efficient starch digestion is required (e.g. animal feed or bioethanol production). Small granule starches have distinct textural properties that can impart a smooth, cream-like mouth feel to foods, and is particularly suited to carbohydrate-based fat replacers (Lindeboom et al., 2004). While smaller starch granules in general have lower swelling power than larger granules, wheat B-type granules have a higher rate of water absorption than A-type granules (Chiotelli and LeMeste, 2002), possibly due to differences in polymer arrangement or granule morphology. Having more of the small B-type granules in wheat starch positively affects pasta quality, due to the higher rate of water absorption (Soh et al., 2006).

On the other hand, decreasing the number of small/smaller granules (or increasing the size and/or number of the large/larger granules) can be beneficial in certain applications and may improve grain quality. Aside from the higher swelling power of large granules mentioned above, small granules are easily lost during some wet-processing procedures, which results in starch loss and difficult waste management (Stoddard & Starker, 2000). Increasing the overall granule size may reduce the available surface area for digestion, which could reduce the glycemic index of food. In species that have bimodal starch granules, reducing the content of small B-granules would result in a more unimodal size distribution of granules. The bimodal distribution of starch granule size in wheat and barley also causes processing problems, particularly in the brewing industry (Langeveld et al., 2000; Howard et al., 2011). Fewer small granules has also been proposed to be beneficial for beer making (Howard et al., 2011).

Thus, the distribution of granule sizes in a plant starch storage organ is an important parameter for end-use quality. However, the specific changes required to improve this quality will depend on the particular application. Approaches to manipulate the distribution of granule sizes in plants have been limited by our lack of basic knowledge of the starch biosynthesis process. In particular, we did not understand how starch granules initiate, and how the number of granules per plastid is controlled. Granule number per plastid is directly linked to granule size—the same amount of starch can be made as fewer larger granules, or more smaller granules.

There is therefore a need to understand the mechanism controlling the initiation of starch granules in plants, and furthermore to be able to manipulate granule size distribution as required. The present invention addresses this need.

SUMMARY OF THE INVENTION

We have identified that modulating the expression or activity of at least one MRC (MYOSIN-RESEMBLING CHLOROPLAST PROTEIN) nucleic acid or polypeptide affects starch granule initiation and leads to a change in granule starch distribution. Specifically, we have found that mutating the MRC gene in the endosperm can be used to shift the distribution of granule sizes present in a starch storage organ towards the smaller or the larger granule size, resulting in either smaller granules or larger granules.

The effect of modulating the activity of MRC on the distribution of granule sizes in the endosperm was unexpected from the published research in *Arabidopsis* leaves (Seung et al. 2018; Vandromme et al., 2018). Multiple granules form in chloroplasts of wild-type *Arabidopsis*, whereas a single starch granule forms in most chloroplasts of the *Arabidopsis* mrc mutant. The reduced number of starch granules observed in the loss-of-function mrc mutant suggests that MRC promotes granule initiation in *Arabidopsis* chloroplasts. By contrast, we have identified wheat mrc mutants that have the same amount of total starch in grains, but produce vast numbers of B-type granules, and an overall increase in the number of granules per grain. Here we report on an unexpected role of MRC in the temporal control of granule initiation in the endosperm. Wheat mrc mutants initiated B-type granules very early during endosperm development (already observed at 10 dpa), leading to a highly altered starch granule size distribution relative to the wild type. Our results reveal a key difference in the granule initiation mechanism between leaves and endosperm, and reveal MRC as a major biotechnological target for the genetic modification of the distribution of starch granule size.

In one aspect of the invention there is provided a method for altering starch granule size distribution in a starch storage organ, the method comprising altering the expression of at least one MRC (MYOSIN-RESEMBLING CHLOROPLAST PROTEIN) nucleic acid and/or altering the activity of a MRC polypeptide, wherein the plant is not *Arabidopsis*.

In one embodiment, the method comprises altering the distribution of granule size in a plant storage organ, such as a grain or tuber. In a further embodiment, the method comprises altering the granule size distribution in a plastid of a plant storage organ.

In one embodiment, altering the granule size distribution comprises shifting the granule size distribution towards smaller granules or larger granules. In an additional or alternative embodiment, altering the granule size distribution comprises increasing or decreasing the mean granule size in a population of starch granules.

Preferably, the method comprises altering the expression of at least one MRC nucleic acid and/or altering the activity of a MRC polypeptide in at least one plastid, preferably an amyloplast. In a preferred embodiment, the method comprises reducing or abolishing the expression of at least one MRC nucleic acid and/or reducing or abolishing the activity of a MRC polypeptide in at least one plastid. In an alternative embodiment, the method comprises increasing the expression of at least one MRC nucleic acid and/or increasing the activity of a MRC polypeptide in at least one plastid, preferably an amyloplast.

In another aspect of the invention, there is provided a method of altering a physiochemical property of starch, the method comprising altering the expression of at least one MRC nucleic acid and/or altering the activity of a MRC polypeptide. Preferably, the physiochemical property is selected from gelatinisation temperature, swelling power and viscosity.

In one embodiment, the method comprises introducing at least one mutation into at least one nucleic acid sequence encoding a MRC polypeptide. In one embodiment the mutation is a gain of function mutation. In an alternative embodiment, the mutation is a loss of function mutation.

In one embodiment, the nucleic acid sequence encodes a MRC polypeptide as defined in one of SEQ ID NO: 1 to 3 or 29 to 30 or a functional variant or homolog thereof. More preferably, the nucleic acid sequence comprises a sequence selected from SEQ ID NO: 4 to 9 or 31 to 34 or a functional variant or homolog thereof.

In one embodiment, the mutation is introduced using targeted genome modification, preferably ZFNs, TALENs or CRISPR/Cas9 (or Cpf1). Alternatively, the mutation is introduced using mutagenesis, preferably TILLING or T-DNA insertion.

In a further alternative embodiment, the method comprises using RNA interference to reduce or abolish the expression of at least one MRC nucleic acid.

Preferably, the level of MRC expression and/or activity is reduced compared to a control or wild-type plant. More preferably, the starch granule size distribution in a plant is altered compared to a control or wild-type plant.

In one embodiment, the plant may be selected from wheat, barley, rye, maize, potato, sorghum and rice. Most preferably the plant is wheat.

In another aspect of the invention there is provided a genetically altered plant, part thereof or plant cell, wherein said plant is characterised by altered expression of at least one MRC nucleic acid and/or altered activity of a MRC polypeptide, wherein the plant is not *Arabidopsis*. In one embodiment, the genetically altered plant, part thereof or plant cell is characterised by reduced or abolished expression of at least one MRC nucleic acid and/or reduced or abolished activity of a MRC polypeptide, wherein the plant is not *Arabidopsis* and wherein the reduced or abolished expression or activity is compared to a control or wild-type plant. In an alternative embodiment, the genetically altered plant, part thereof or plant cell is characterised by increased expression of at least one MRC nucleic acid and/or increased activity of a MRC polypeptide, wherein the plant is not *Arabidopsis* and wherein the increased expression or activity is compared to a control or wild-type plant.

In one embodiment, the plant comprises at least one mutation in at least one nucleic acid encoding a MRC polypeptide. In one embodiment, said mutation is a complete or partial loss of function mutation. In an alternative embodiment, said mutation is a gain of function mutation.

Preferably the plant is also characterised by an alteration in starch granule size distribution. In one embodiment, the plant is characterised by a shift in the granule size distribution towards smaller or larger granules. In an alternative embodiment, the plant is characterised by an increase or decrease in the mean granule size in a population of starch granules.

In a further embodiment, the mutation is introduced using targeted genome modification, preferably ZFNs, TALENs or CRISPR/Cas9. Alternatively, the mutation is introduced using mutagenesis, preferably TILLING or T-DNA insertion.

In one embodiment, the nucleic acid sequence encodes a MRC polypeptide as defined in one of SEQ ID NO: 1 to 3 or 29 or 30 or a functional variant or homolog thereof. More preferably, the nucleic acid sequence comprises a sequence selected from SEQ ID NO: 4 to 9 or 31 to 34 or a functional variant or homolog thereof.

In a further alternative embodiment, the plant comprises an RNA interference construct that reduces or abolishes the expression of at least one MRC nucleic acid.

In one embodiment, the plant may be selected from wheat, barley, rye, maize, potato, sorghum and rice. Most preferably the plant is wheat. In a preferred embodiment, the plant part is grain or a seed.

In another aspect of the invention, there is provided a method of producing a plant with an alteration in starch granule size distribution, the method comprising altering the expression of at least one MRC nucleic acid and/or altering the activity of a MRC polypeptide, wherein the plant is not *Arabidopsis*.

In one embodiment, the method comprises reducing or abolishing the expression of at least one MRC nucleic acid and/or reducing or abolishing the activity of a MRC polypeptide in at least one plastid, preferably an amyloplast. In an alternative embodiment, the method comprises increasing the expression of at least one MRC nucleic acid and/or increasing the activity of a MRC polypeptide in at least one plastid, preferably an amyloplast.

In another embodiment, the method comprises introducing at least one mutation into at least one nucleic acid sequence encoding a MRC polypeptide. Preferably the mutation is introduced using targeted genome modification, preferably ZFNs, TALENs or CRISPR/Cas9. Alternatively, the mutation is introduced using mutagenesis, preferably TILLING or T-DNA insertion.

In one embodiment, the nucleic acid sequence encodes a MRC polypeptide as defined in one of SEQ ID NO: 1 to 3 or 29 or 30 or a functional variant or homolog thereof. More preferably, the nucleic acid sequence comprises a sequence selected from SEQ ID NO: 4 to 9 or 31 to 34 or a functional variant or homolog thereof.

In another embodiment, the method comprises using RNA interference to reduce or abolish the expression of at least one MRC nucleic acid.

Preferably, the level of MRC expression and/or activity is reduced or abolished compared to a control or wild-type plant. More preferably, the starch granule size distribution in a plant is altered compared to a control or wild-type plant.

In a further embodiment, the method further comprises measuring an alteration in starch granule size distribution. More preferably, the method further comprises regenerating a plant and screening for an alteration in starch granule size distribution.

In another aspect of the invention there is provided a plant, plant part or plant cell obtained or obtainable by any of the methods described herein.

There is also provided grain derived from the genetically altered plant as described herein. Preferably, the grain is characterised by an altered starch granule size distribution compared to a control or wild-type plant. More preferably, the grain comprises at least one mutation in at least one nucleic acid encoding a MRC gene and/or at least one mutation in a MRC promoter.

In another aspect of the invention, there is provided starch obtained or obtainable from at least one plant cell of the genetically altered plant as described herein or the grain described herein. There is also provided a food or feed composition prepared from the grain as described herein or the starch described herein.

In another aspect of the invention, there is provided the use of the grain as described herein or the starch as described herein as a food or feedstuff. Alternatively, there is provided the use of the grain as described herein or the starch as described herein in any pharmaceutical or industrial application.

In another aspect of the invention there is provided a nucleic acid construct comprising a nucleic acid sequence encoding at least one DNA-binding domain or protospacer element that can bind to at least one target sequence in a MRC gene and/or promoter, wherein preferably the target sequence is selected from SEQ ID NO: 39 to 42 or a variant thereof.

In a preferred embodiment, the sequence of the protospacer element is selected from SEQ ID Nos 43 to 46 or a variant thereof.

In a further preferred embodiment, the construct further comprises a nucleic acid sequence encoding a CRISPR RNA (crRNA) sequence, wherein said crRNA sequence comprises at least one protospacer element sequence and additional nucleotides. More preferably, the construct further comprises a nucleic acid sequence encoding a transactivating RNA (tracrRNA), wherein preferably the tracrRNA is defined in SEQ ID NO.47 or a functional variant thereof.

In another aspect of the invention there is provided a nucleic acid construct, wherein the construct encodes at least one single-guide RNA (sgRNA), wherein said sgRNA comprises the tracrRNA sequence and the crRNA or protospacer sequence, wherein the sgRNA comprises or consists of a sequence selected from SEQ ID Nos 48 to 51 or a functional variant thereof.

In any of the above described constructs, the construct comprises a promoter, wherein preferably the promoter is operably linked to the protospacer element or sgRNA nucleic acid sequence. Preferably, the promoter is a constitutive promoter.

In a further embodiment, the nucleic acid construct further comprises a nucleic acid sequence encoding a CRISPR enzyme. Preferably, the CRISPR enzyme is a Cas or Cpf1 protein. More preferably, the Cas protein is Cas9 or a functional variant thereof.

In an alternative embodiment, the nucleic acid construct encodes a TAL effector. Preferably, the nucleic acid construct further comprises a sequence encoding an endonuclease or DNA-cleavage domain thereof. More preferably, the endonuclease is FokI.

In another aspect of the invention, there is provided a single guide (sg) RNA molecule wherein said sgRNA comprises a crRNA sequence and a tracrRNA sequence, wherein the crRNA sequence can bind to at least one sequence selected from SEQ ID Nos 39 to 42 or a variant thereof. Preferably the sgRNA has a RNA sequence comprising or consisting of a sequence selected from SEQ ID NO: 52 to 55 or a functional variant thereof.

In a further aspect there is provided an isolated plant cell transfected with at least one nucleic acid construct as described herein or the sgRNA molecule as described herein.

In one embodiment, the isolated plant cell is transfected with at least one nucleic acid construct comprising a sgRNA nucleic acid sequence and a second nucleic acid construct, wherein said second nucleic acid construct comprises a nucleic acid sequence encoding a Cas protein, preferably a Cas9 or Cpf1 protein or a functional variant thereof. In a preferred embodiment, the second nucleic acid construct is transfected before, after or concurrently with the nucleic acid construct comprising a sgRNA nucleic acid sequence.

In another aspect of the invention, there is provided a genetically modified plant, wherein said plant comprises the transfected cell as defined herein. Preferably, the nucleic acid encoding the sgRNA and/or the nucleic acid encoding a Cas or Cpf1 protein is integrated in a stable form.

In another aspect of the invention, there is provided a method of altering starch granule size distribution in a plant, the method comprising introducing and expressing in a plant the nucleic acid construct as described herein or the sgRNA molecule as described herein, wherein preferably said increase is relative to a control or wild-type plant.

In a further aspect, there is provided a plant obtained or obtainable by any method described herein.

In another aspect, there is provided the use of a nucleic acid construct as described herein or the sgRNA molecule as described herein to alter starch granule size distribution in a plant. Preferably, the nucleic acid construct or sgRNA molecule reduces the expression and/or activity of MRC in a plant.

In a further aspect of the invention, there is provided a method for obtaining the genetically modified plant as described herein, the method comprising:
 a. selecting a part of the plant;
 b. transfecting at least one cell of the part of the plant of paragraph (a) with the nucleic acid construct as described herein or the sgRNA molecule as described herein; and
 c. regenerating at least one plant derived from the transfected cell or cells; selecting one or more plants obtained according to paragraph (c) that show reduced expression and/or activity of at least one MRC nucleic acid in said plant.

In a final aspect of the invention, there is provided a method for identifying and/or selecting a plant that has, or will have, altered starch granule size distribution, preferably compared to a wild-type or control plant, the method comprising detecting in the plant or plant germplasm at least one polymorphism or mutation in the MRC gene and/or MRC promoter and selecting said plant or progeny thereof. Preferably, the polymorphism is an insertion, deletion and/or substitution. More preferably, the method further comprises introgressing the chromosomal region comprising at least one polymorphism in the MRC gene and/or MRC promoter into a second plant or plant germplasm to produce an introgressed plant or plant germplasm

DESCRIPTION OF THE FIGURES

The invention is further described in the following non-limiting figures.

The endosperm was dissected from developing grains of the wild type (WT) and the mrc-1 mutant harvested at 8, 14, 20 and 30 dpa. A) Purified endosperm starch granules were observed using scanning electron microscopy (SEM).

Bars=20 µm. B) Starch granule size distribution of endosperm starch characterised with a coulter counter. Distributions are the average of measurements carried out on grains (3 per measurement) harvested from three different plants. The solid line shows the mean curve, while the shading represents the standard error of the mean.

Figure 5:
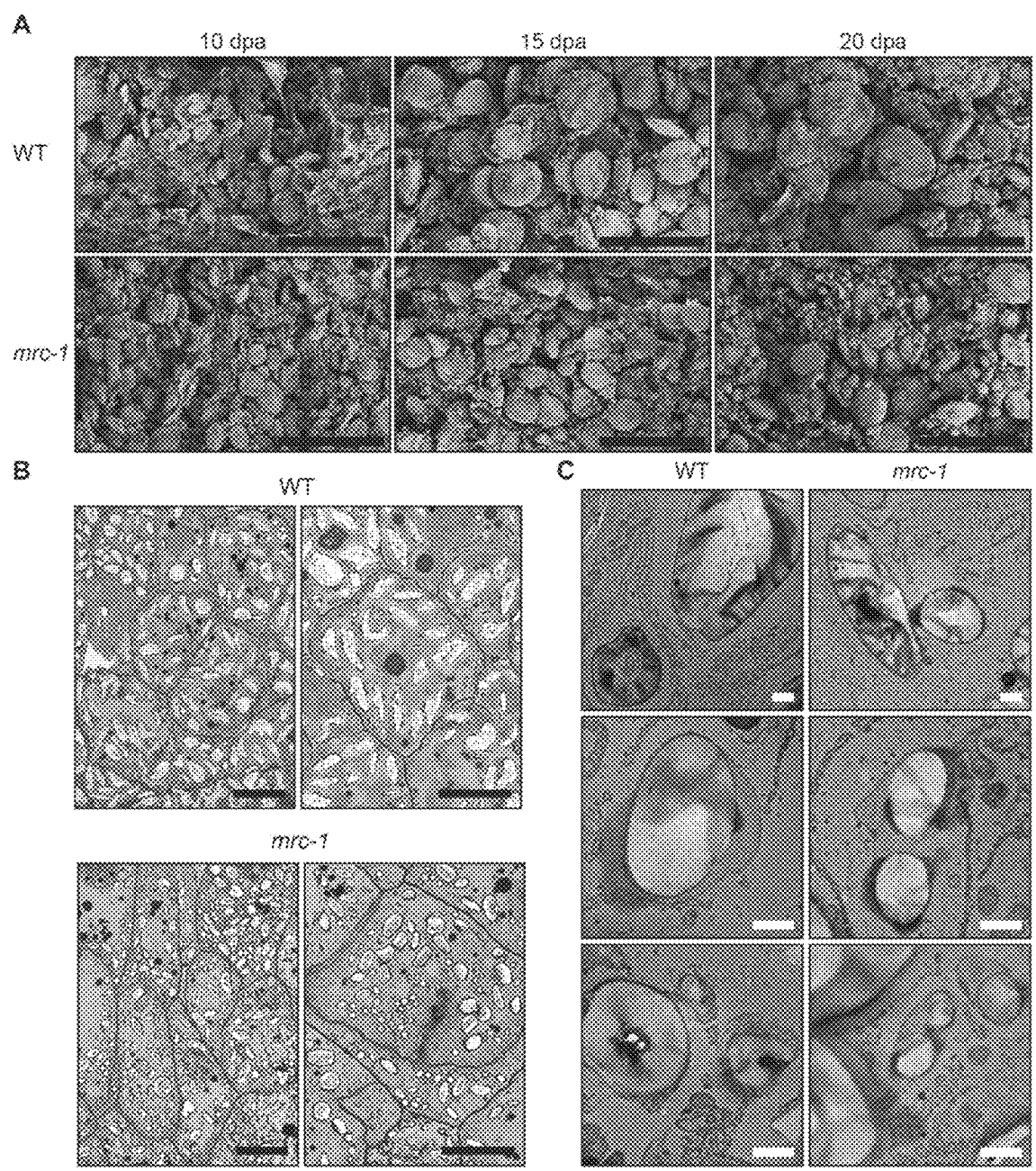

FIG. 5 shows the observation of starch granules within developing endosperm tissue. A) Scanning electron micrographs of developing endosperm tissue subjected to critical point drying. Grains were harvested from the wild type (WT) and mrc-1 mutant at 10, 15 and 20 days post anthesis (dpa). Bars=50 µm. B) Light micrographs of endosperm sections. Semi-thin sections of embedded developing grains (15 dpa) were stained with toluidine blue as a negative stain for starch granules. Examples of A-type granules and B-type granules are marked with arrows respectively. Bars=50 µm. C) Endosperm sections observed using TEM.

FIG. 6 shows a phylogenetic analysis of wheat MRC sequences. A) Phylogenetic tree of MRC orthologs. The amino acid sequences of the orthologs identified in Seung et al. 2018 were aligned with the wheat sequences. A maximum likelihood tree was assembled with 1000 bootstraps. Bootstrap values are shown next to each node. Branch lengths indicate the number of substitutions per site. B) Multiple sequence alignment of MRC orthologs generated with Clustal O. The region surrounding Leu289 (highlighted in yellow) is shown. Symbols under the alignment indicate conserved residues with: complete identity (*), highly similar properties (:) or weakly similar properties (.) C) Coiled coil prediction of TaMRC 6A wild type (WT) sequence and the Leu289Phe (L289F) mutant using COILS/PCOILS. The probability was calculated using the 28 amino acid window.

Figure 7:
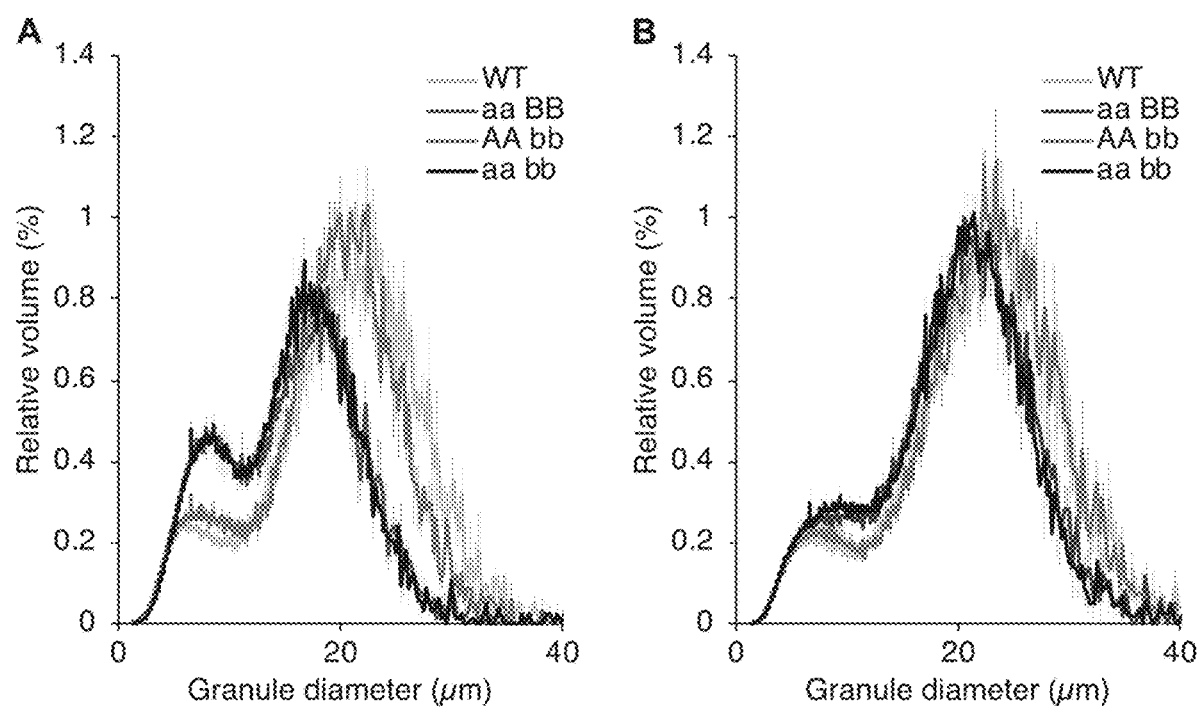

FIG. 7 shows the 6B pseudogene does not contribute to granule size distribution. Size distributions were determined by measuring at least 100,000 granules per replicate with a Coulter counter. The solid line shows the mean curve (shading represents the SEM) from three replicate determinations. Each replicate used starch purified from three individual grains, and the three replicates represent grains from three different plants. A) Starch from genotypes isolated from the mrc-1 cross: the single A homolog mutant (aa BB), the single B pseudogene mutant (AA bb), and the double mutant (aa bb). B) Same as A), but with genotypes from the mrc-2 cross.

FIG. 8 shows the chain length distribution and amylose content of the mrc mutants. A) Chain length distribution of mrc-1 and mrc-2 starch. Purified starch was debranched and analysed with High Performance Anion Exchange Chromatography with Pulsed Amperometric Detection (HPAEC-PAD). Relative peak areas show the mean±SEM from three replicate measurements. B) Amylose content of mrc-1 and mrc-2 starch quantified using iodine colourimetry. Values represent mean±SEM from three replicate measurements.

FIG. 9 shows a table of granule size and B-type granule content in mrc mutants. Granule size distributions were calculated using a Coulter counter (n=3 per genotype). The mean size of A-type and B-type granules and the content of B-type granules (by percentage volume) were calculated by fitting a bimodal mixed gaussian curve to the size distributions. Values marked with an asterisk (*) are significantly different to the wild-type value under a two-tailed t-test ($p<0.05$).

FIG. 10 shows a table of starch content of mature grains from mrc mutants. Note that there are no significant differences in starch content between mutants and the wild type.

FIG. 11 shows a table of wheat mrc mutants from a TILLING database.

FIG. 12 shows a multiple sequence alignment of AtMRC (SEQ ID NO: 38), HvMRC (SEQ ID NO:10) and TaMRC; homeologs from Cadenza and Kronos: TaMCR_6D_(cv.Cadenza), SEQ ID NO:3; TaMCR_6A_(cv.Kronos), SEQ ID NO: 1; TaMCR_6A_(cv.Cadenza), SEQ ID NO:2. Symbols under the alignment indicate conserved residues with: complete identity (*), highly similar properties (:) or weakly similar properties (.).

FIG. 13 shows a table of the gelatinisation temperature of mrc-1 aabb starch. Values marked with an asterisk (*) are significantly different from the WT value under a two-tailed t-test at $p<0.05$.

Figure 14:
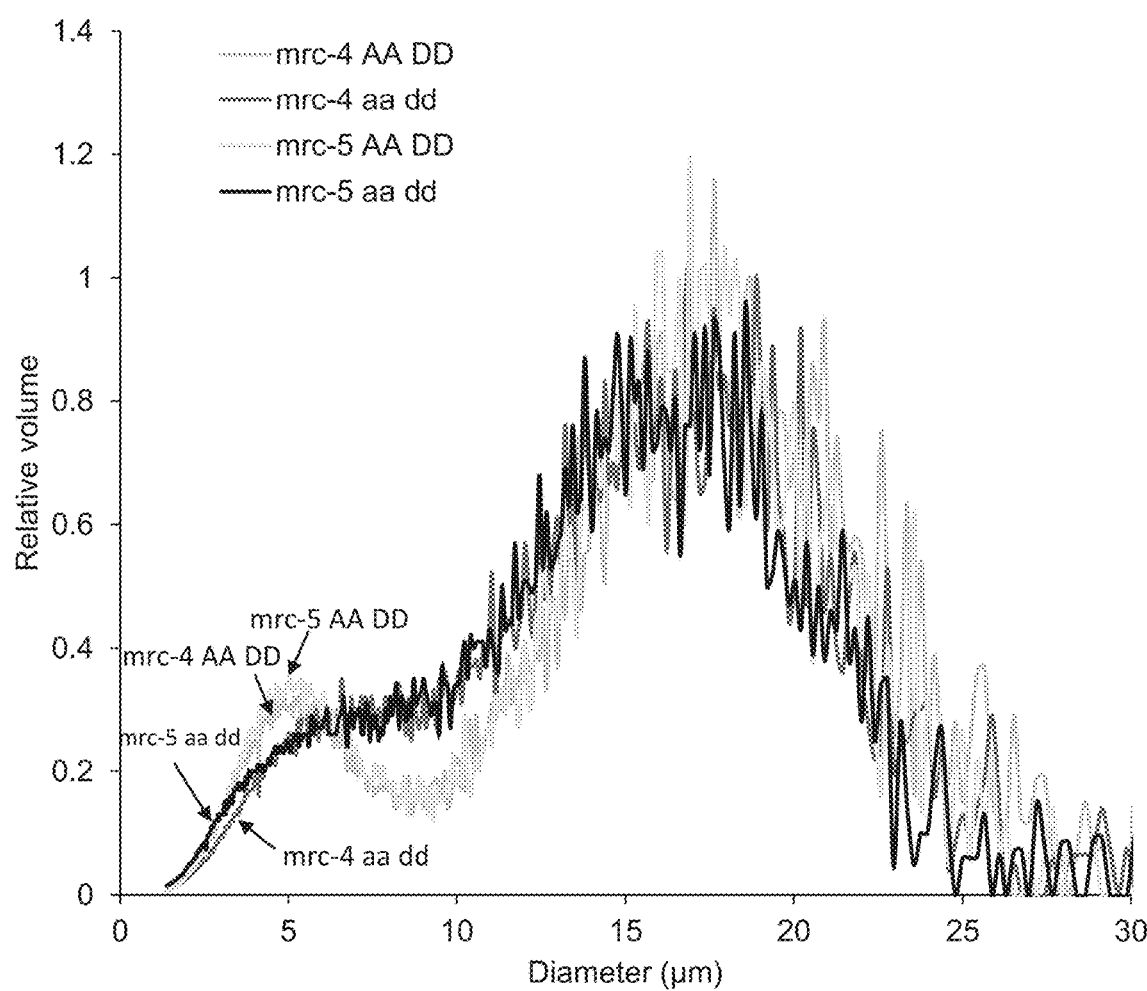

FIG. 14 shows the size distribution of endosperm starch from mrc mutants in the hexaploid bread wheat cultivar, Cadenza. Starch was purified from mature grains and the size distribution was quantified on a Coulter counter.

Figure 15:
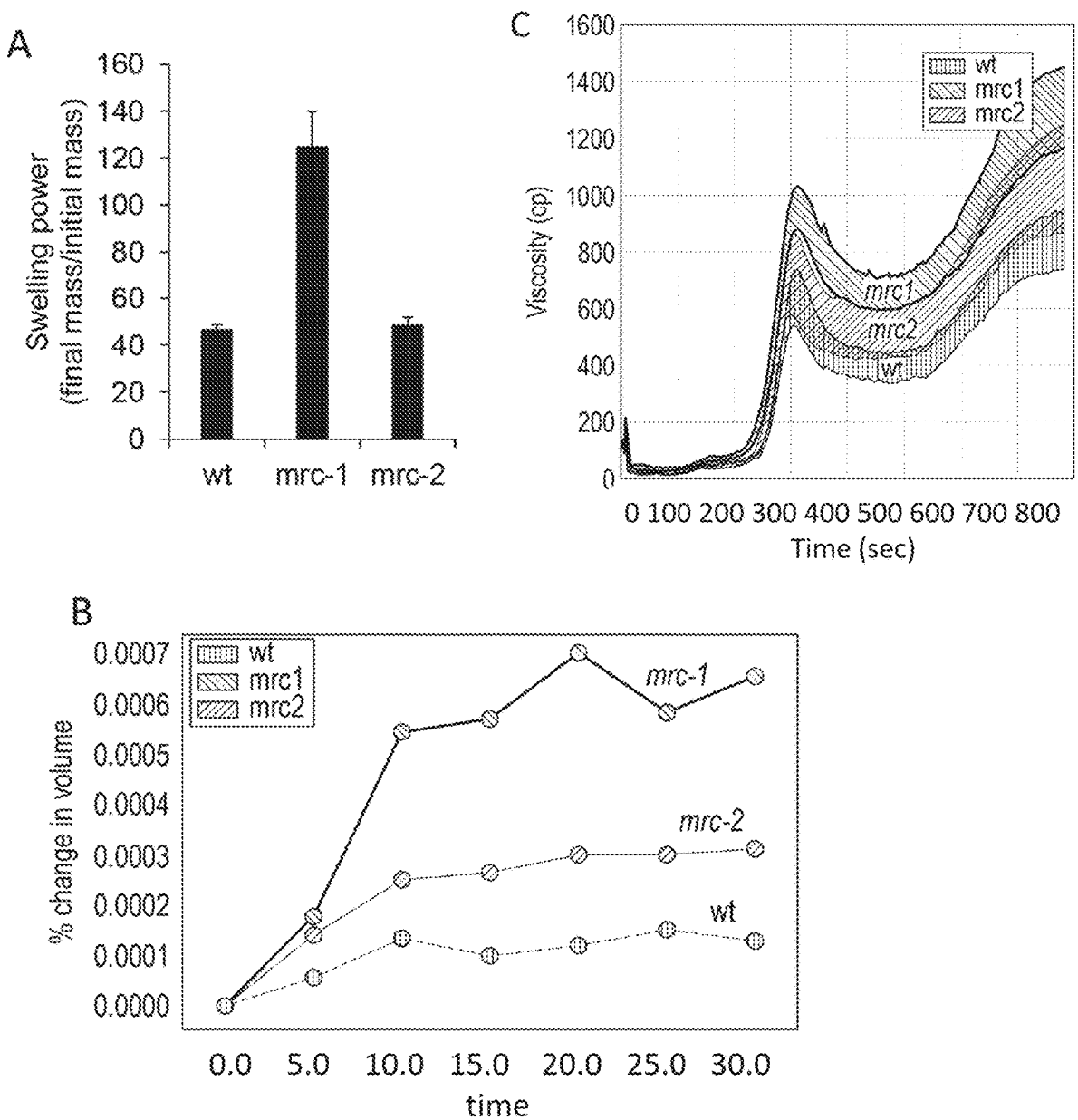

FIG. 15 shows swelling power of starches from the mrc mutants. Purified starches were heated in water at 100° C. for 30 mins and allowed to settle for 1 hour at room temperature. (A) Swelling power was calculated as mass after swelling relative to the initial mass. (B) The increase in the average volume of granules (relative to initial volume) throughout a 30 mins incubation in water at 60° C. Volumes were quantified using a Coulter counter. (C) shows starch viscosity of mrc wheat starch compared to wild-type during gelatinisation, measured with a Rapid Visco Analyser (RVA). Two runs were carried out per sample and the shading indicates the area between the two replicate curves.

Figure 16:
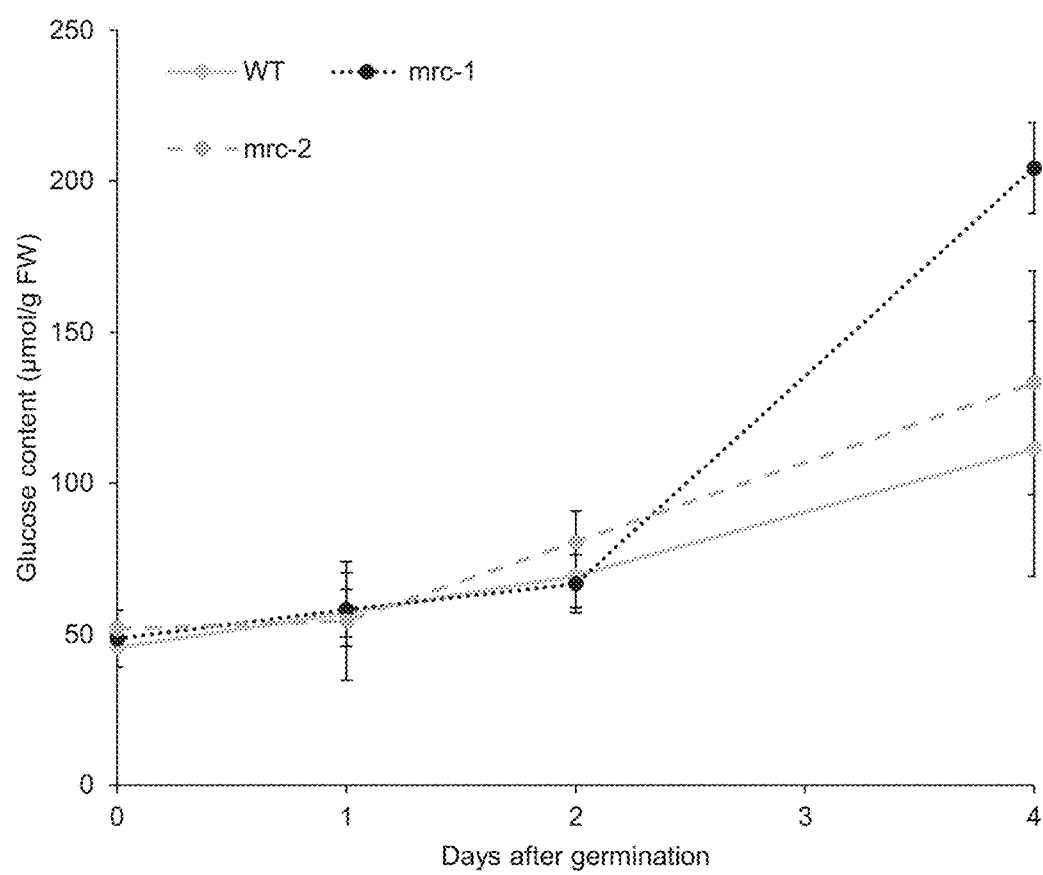

FIG. 16 shows the glucose content of the endosperm during the initial phase of grain germination. Glucose was measured using the hexokinase/glucose-6-phosphate dehydrogenase method. Values are the mean±SE of measurements from n=6-9 grains. The mrc-1 mutant has significantly higher glucose in the endosperm at day four of germination than the WT and mrc-2 grains under a two-tailed t-test with $p<0.05$.

Figure 17:
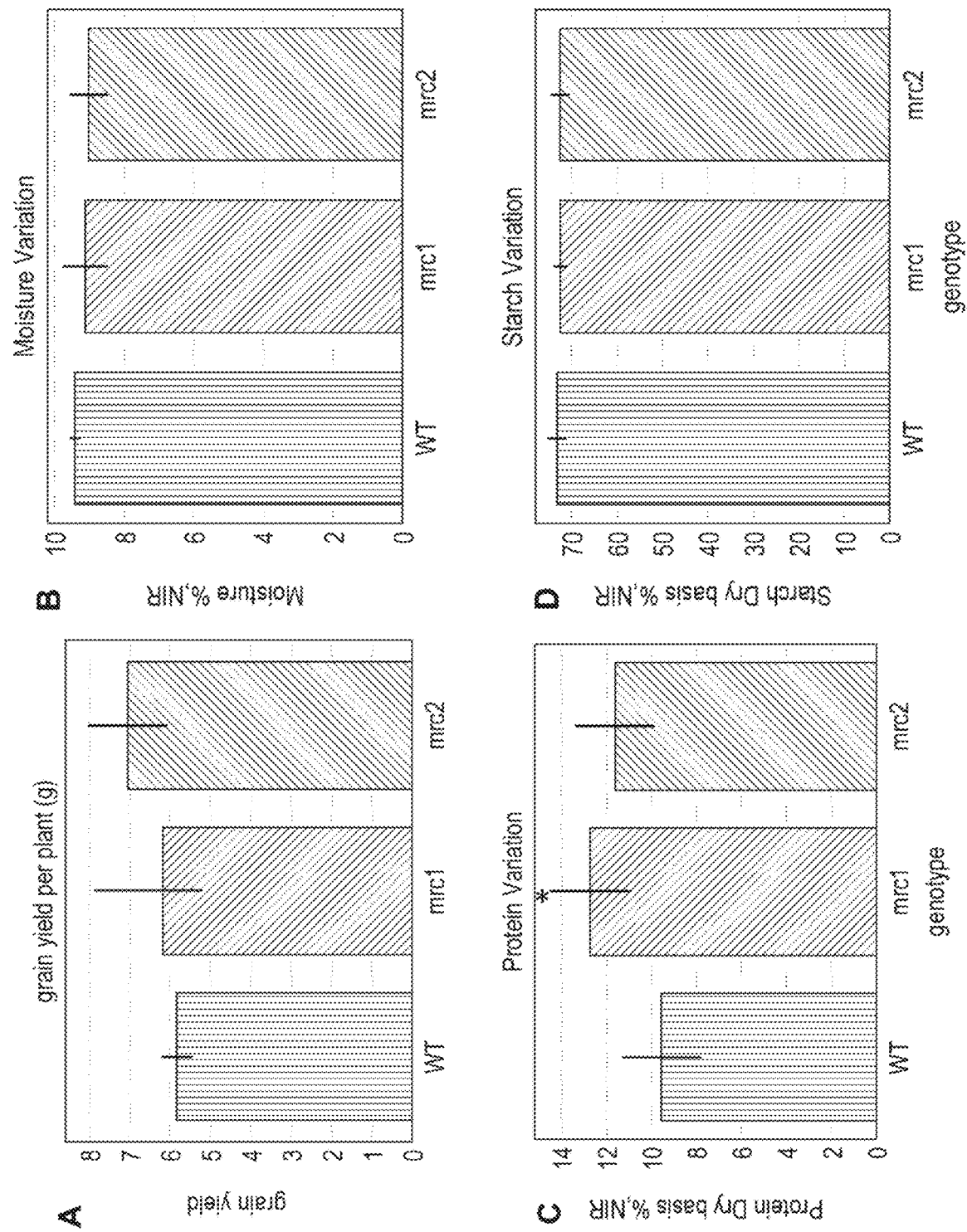

FIG. 17 shows the yield and composition of mrc grains. The absence of large significant differences in these parameters suggest that the impact of mrc mutations is specific to starch granule size, and not other important aspects of grain yield and quality. A. Grain yield per plant (in grams) was calculated for WT, mrc-1 and mrc-2. Values are mean±SE. There are no significant differences B-D) Near infrared (NIR) grain analysis was used to determine the percentage of the total grain mass that is moisture (B), protein (C) and starch (D). Bars marked with an asterisk (*) are significantly different to the wild-type under a two-tailed t-test ($p<0.05$).

Figure 18:
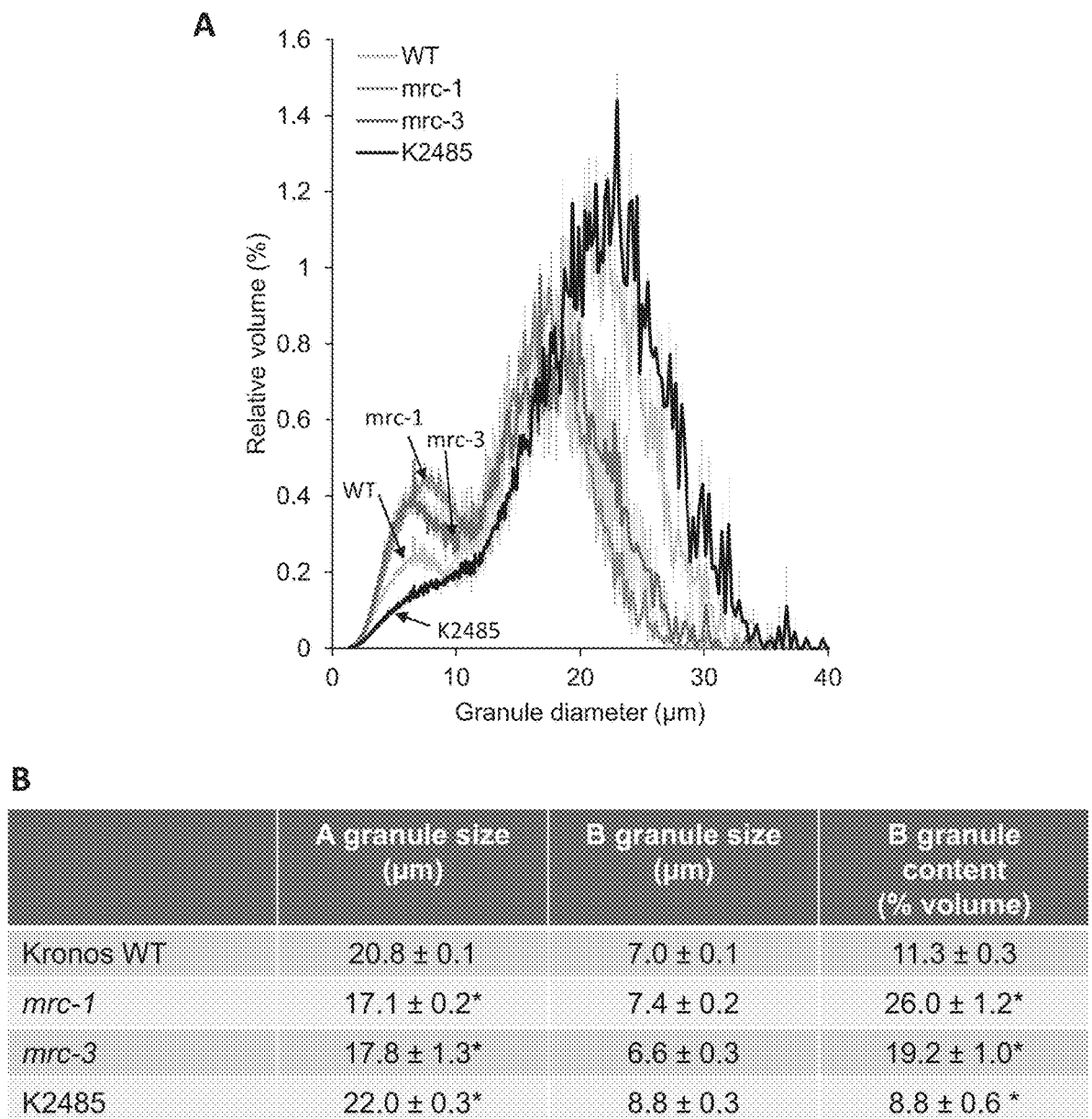

FIG. 18 shows the size distribution of endosperm starch from the Kronos2485 mutant compared to the mrc-1 and mrc-3 mutants in Kronos. A) Size distributions were determined using the Coulter counter. The solid line shows the mean curve (shading represents the SEM) from three replicate determinations. Each replicate used starch purified from three individual grains, and the three replicates represent grains from three different plants. B) Table showing the mean sizes of A- and B-type granules, and B-type granule content. Data are derived from the distribution plots in A). Values marked with an asterisk (*) are significantly different to the wild-type under a two-tailed t-test ($p<0.05$).

FIG. 19 shows the size distribution of endosperm starch from the Kronos2485, Kronos2096 (A) and Kronos775 mutants (B). Starch was purified from mature grains and the size distribution was quantified on a Coulter counter. All three of these mutants have fewer B-type granules than the wild type.

Figure 20:
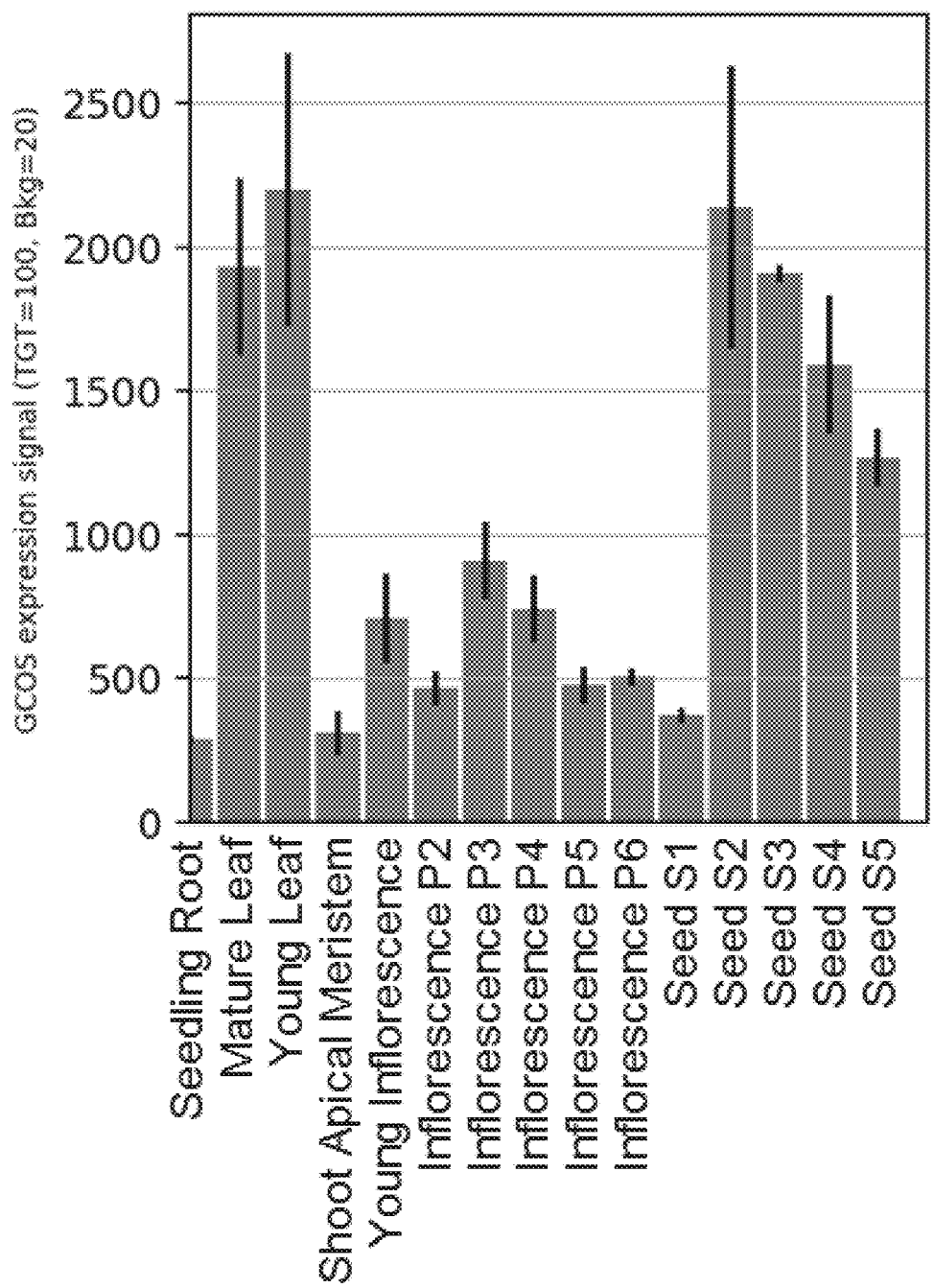

FIG. 20 shows the tissue-specific expression of OsMRC in rice. Publicly available tissue-specific expression data were retrieved for OsMRC (LOC Os02g09340.1) using the rice eFP browser (bar.utoronto.ca). Strong expression of the gene is observed in leaves, as well as in the developing seed—at several different developmental stages: S1: 0-2 dpa, S2: 3-4 dpa, S3: 5-10 dap, S4: 11-20 dpa, and S5: 21-29 dpa.

FIG. 21 is a table showing the gelatinisation temperature of mrc-1 aabb starch. Values marked with an asterisk (*) are significantly different from the WT value under a two-tailed t-test at $p<0.05$.

FIG. 22 shows the prediction of coiled coils in AtMRC (A) and TaMRC (B) using the COILS program. The position of each amino acid in the protein sequence is plotted on the x-axis, while the probability of forming a coiled coil is plotted on the y-axis. The green line represents probabilities calculated using a 14-amino-acid prediction window, the blue line using a 21-amino-acid prediction window, and the purple line using a 28-amino-acid prediction window.

FIG. 23 is a table showing the expression levels of TaMRC in starchy endosperm during grain development. Publicly available expression data were retrieved from the wheat expression browser. Values are in transcript per kilobase million (tpm). Values corresponding to low expression (tpm<2) are shown in grey.

Figure 24:
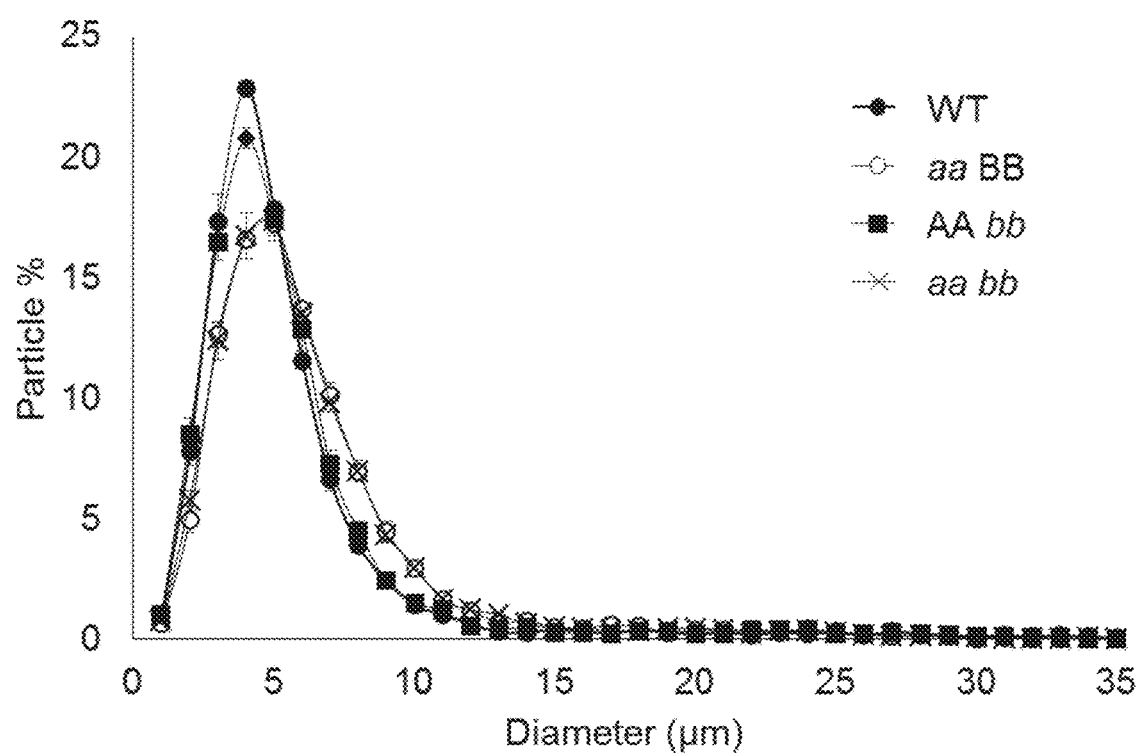

FIG. 24 shows that granule size distribution in mrc-1 mutants by microscopy. The AA BB, aa BB, AA bb and aa bb mutants from the mrc-1 set were analysed.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

The aspects of the invention involve recombinant DNA technology and exclude embodiments that are solely based on generating plants by traditional breeding methods.

In a first aspect of the invention, there is provided a method for altering a starch characteristic. Preferably said starch characteristic is starch granule size distribution in a plant, the method comprising altering the expression of at least one MYOSIN-RESMEBLING CHLOROPLAST PROTEIN (referred to herein as "MRC") nucleic acid and/or altering the activity of a MRC polypeptide. MRC may also be referred to as PROTEIN INVOLVED IN STARCH INITIATION "PII1" and such terms may be used interchangeably. In one embodiment, the plant is not *Arabidopsis*.

In one embodiment, the method has no (obvious detectable) effect on total starch content and/or plant growth.

The terms "seed" and "grain" as used herein can be used interchangeably. The terms "increase", "improve" or "enhance" as used herein are also interchangeable. Similarly, the terms starch "grain" or "granule" are also interchangeable.

The present invention has identified methods to modify the properties of starch granules. It is understood that starch granules will have a range of sizes within a starch storage organ. Such a distribution can be considered as a standard or characteristic distribution curve for the plant. The characteristic distribution curve for starch granules will vary plant by plant. The present invention has identified methods to vary the distribution curve of starch granules from the otherwise standard or characteristic distribution. In an embodiment, varying may involve shifting the distribution towards smaller granules. In a different embodiment, varying may involve shifting the distribution towards larger granules. In a yet further embodiment, varying may modify the distribution curve towards a narrower curve, e.g. the standard deviation from the mean granule size is reduced compared against a standard distribution curve. Such a change will result in more uniform granules. This may occur at the same time as shifting the granule size. The present invention therefore alters starch granule size distribution.

In an embodiment, there is provided a method of altering granule size distribution that results in increasing or decreasing the mean granule size in a population of starch granules. In an embodiment, the granule size may be increased or decreased by 3% or more, 5% or more, 10% or more, 15% or more, 20% or more, 25% or more, 30% or more, 35% or more, 40% or more or 45% or more compared to the mean granule size in a control or wild-type plant.

In a yet further embodiment, there is provided a method of altering the standard deviation of starch granule size, particularly reducing the standard deviation thereby leading to more uniform starch granule size. In an embodiment, the standard deviation of starch granule size is reduced by 3% or more, 5% or more, 10% or more, 15% or more, 20% or more, 25% or more, 30% or more, 35% or more, 40% or more or 45% or more compared to the starch granule size standard deviation in a control or wild-type plant.

Granule size may be measured by a number of techniques that would be known to the skilled person. In one embodiment, granule size can be measured using a particle size analyser, which uses laser scattering to measure the total volume of particles of a given size, expressed as a percentage of the total volume of all particles. In one example, purified starch can be suspended in water and measured on a particle size analyser, such as a Beckman-Coulter Multisizer 4e Coulter counter, or the Coulter LS-230 laser-scattering instrument (Beckman Coulter). In another embodiment, granule size can be measured using light microscopy. As described below, starch granule area in the images was measured using the Particle Analysis plugin of ImageJ software (v.2.0.0) The area was used to calculate diameter, assuming the granules were perfect circles. Unlike the first method with the particle size analyser, this method calculates of the percentage of granules with a given size relative to the total number of granules (rather than as volumes as measured on a Coulter counter), and is a direct measure of size (rather than inferred from laser scattering).

As used herein, the terms "reducing" means a decrease in the levels of MRC expression and/or activity by up to or more than 10%, 20%, 30%, 40%, 50%, 60%, 70%, 80% or 90% when compared to the level in a wild-type or control plant. In one embodiment, reducing means a decrease in at least 50% compared to the level in a wild-type or control plant. Reducing may or may not encompass changes in the absolute MRC transcript level, preferably it does not. Reducing also may or may not encompass abolishing expression. The term "abolish" expression means that no expression of MRC is detectable (no transcript) or that no functional MRC polypeptide is produced. Methods for determining the level of MRC expression and/or activity would be well known to the skilled person. These reductions can be measured by any standard technique known to the skilled person. For example, a reduction in the expression and/or content levels of at least MRC expression may be a measure of protein and/or nucleic acid levels and can be measured by any technique known to the skilled person, such as, but not limited to, any form of quantitative PCR, gel electrophoresis and immunoblotting or chromatography (e.g. HPLC). In one embodiment, the mutation is a complete or partial loss-of-function mutation. In one embodiment, the mutation reduces or abolishes the protein-interacting activity of MRC. MRC interacts with SS4 directly, as well as associates with PTST2 and MFP1 (either directly or indirectly). It may also interact with other proteins in the wheat endosperm. Accordingly, the method may comprise measuring these protein-protein interactions, using techniques standard in the art, such as, but not limited to, interaction assays using recombinant proteins, yeast-2-hybrid, immunoprecipitation or bimolecular fluorescence.

As used herein, the terms "increasing" means an increase in the level of MRC expression and/or activity by up to or more than 10%, 20%, 30%, 40%, 50%, 60%, 70%, 80% or 90% when compared to the level in a wild-type or control plant. In one embodiment, increasing means an increase in at least 50% compared to the level in a wild-type or control plant. Increasing may or may not encompass changes in the absolute MRC transcript level, preferably it does not. As described above, methods for determining the level of MRC expression and/or activity would be well known to the skilled person. In one embodiment, increasing the activity of the MRC polypeptide may be achieved by introducing a gain of function mutation. In one example, the gain of function mutation increases the protein-interacting activity of MRC, as described above. Again, an increase in the activity of the MRC polypeptide may be determined by measuring these protein-protein interactions, using techniques standard in the art, such as, but not limited to, interaction assays using recombinant proteins, yeast-2-hybrid, immunoprecipitation or bimolecular fluorescence.

In a particular embodiment, the method comprises reducing or abolishing the expression of at least one MRC nucleic acid and/or reducing or abolishing the activity of a MRC polypeptide in a starch storage organ, such as a tuber or grain. In a further embodiment, the method comprises reducing or abolishing the expression of at least one MRC nucleic acid and/or reducing or abolishing the activity of a MRC polypeptide in an amyloplast preferably in the endosperm of the plant. As a result, the size distribution of starch granules is altered in at least one plastid in a plant. More specifically, reducing or abolishing expression or activity of MRC biases the distribution of granules in favour of the small or smaller sizes (i.e. shifts the distribution curve towards the left). This means that there is in an increase in the number of small granules and a decrease in the number and/or size of the large granules. This can also be considered as a decrease in the mean granule size. As discussed above, the advantages of such a starch granule profile are numerous. For example, such a granule profile may be useful where complete and efficient digestion of starch is required, for example, in animal feed or bioethanol production—or for its distinct textural or swelling properties that can improve quality of the final food product.

In an alternative embodiment, the method comprises increasing the expression of at least one MRC nucleic acid and/or increasing the activity of at least one MRC polypeptide in a plastid, preferably a grain or tuber. In a further embodiment, the method comprises increasing the expression of at least one MRC nucleic acid and/or increasing the activity of a MRC polypeptide in an amyloplast preferably in the endosperm of the plant. As a result, granule size distribution is altered in at least one plastid in a plant, preferably in the endosperm of the plant. More specifically, increasing expression or activity of MRC biases the distribution of granules in favour of the larger granule sizes (i.e. shifts the distribution curve to the right). This means that there is in an increase in the size and/or number of larger granule size. This can also be considered as an increase in the mean granule size. Again, as discussed above, altering the size distribution of granules has numerous benefits, reduced digestibility, increased viscosity of starch gels, and improved milling/processing efficiency.

By "at least one mutation" is meant that where the MRC gene is present as more than one copy or homoeologue (with the same or slightly different sequence) there is at least one mutation in at least one gene. In one embodiment, all genes are mutated. In another embodiment, where the plant is a tetraploid, for example tetraploid wheat, the MRC gene is mutated on the A genome only or the A and B genome. In another embodiment, where the plant is a hexaploid, for example hexaploid wheat, the MRC gene is mutated on the A and/or B and/or D genome or more preferably, the A and D genome only.

In one embodiment, the method comprises introducing at least one mutation into the, preferably endogenous, gene encoding MRC and/or the MRC promoter. Preferably said mutation is in the coding region of the MRC gene. Alternatively, said mutation is in an intronic sequence or the 5'UTR or 3'UTR. In a further embodiment, at least one mutation or structural alteration may be introduced into the MRC promoter such that the MRC gene is either not expressed (i.e. expression is abolished) or expression is reduced, as defined herein. In an alternative embodiment, at least one mutation may be introduced into the MRC gene such that the altered gene does not express a full-length (i.e. expresses a truncated) MRC protein or does not express a fully functional MRC protein. In this manner, the activity of the MRC polypeptide can be considered to be reduced or abolished as described herein. In any case, the mutation may result in the expression of MRC with no, significantly reduced or altered biological activity in vivo. Alternatively, MRC may not be expressed at all.

In an alternative embodiment, at least one mutation may be introduced into the, preferably endogenous, gene encoding MRC and/or the promoter such that the expression of the MRC nucleic acid or the activity of the MRC polypeptide is increased. Such a mutation is called a gain-of function or activating mutation.

In one embodiment, the sequence of the MRC gene comprises or consists of a nucleic acid sequence selected from SEQ ID NO: 4 to 6 (genomic) or 7 to 9 (CDS) or a functional variant or homologue thereof and encodes a polypeptide as defined in one of SEQ ID NO: 1 to 3 respectively or a functional variant or homologue thereof. The genomic DNA sequences of the 6A homeolog (for Kronos and Cadenza) is shown in SEQ ID NO: 4 and 5 respectively, and the 6D (homeolog for Cadenza) is shown in SEQ ID NO: 6. The cDNA sequences are shown in SEQ ID NOs 7 (6A—Kronos), 8 (6A—Cadenza) and 8 (6D—Cadenza). The genomic DNA sequence and the CDS sequence of the 6B homeolog in Kronos is shown in SEQ ID NO: 31 and 33 respectively and in Cadenza in SEQ ID NO: 32 and 34 respectively.

As used throughout, by "MRC promoter" is meant a region extending at least or approx. 1.5 kbp upstream of the ATG codon of the MRC ORF. In one embodiment, the sequence of the MRC promoter comprises or consists of a nucleic acid sequence as defined in any one of SEQ ID NO: 22 to 24 and 35 to 36 or a functional variant or homologue thereof. Examples of promoter homologues are shown in SEQ ID NOs 25 to 28. In one embodiment, the MRC promoter may also include 5' UTR sequences.

In the above embodiments an 'endogenous' nucleic acid may refer to the native or natural sequence in the plant genome. Also included in the scope of this invention are functional variants (as defined herein) and homologs of the above identified sequences.

Examples of homologs are shown in SEQ ID NOs: 10 to 21 and 60 to 62. Accordingly, in one embodiment, the homolog encodes a polypeptide selected from SEQ ID NOs: 10, 13, 18 19 and 60; or the homolog comprises or consists of a nucleic acid sequence selected from SEQ ID NOs: 11, 12, 14, 15, 16, 17, 18, 20, 21, 61 and 62.

The term "functional variant" (or "variant") as used herein with reference to any of the sequences described herein refers to a variant sequence or part of the sequence which retains the biological function of the full non-variant sequence. A functional variant also comprises a variant of the gene of interest which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence which result in the production of a different amino acid at a given site that do not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

In one embodiment, a functional variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence.

The term homolog, as used herein, also designates a MRC promoter or MRC gene orthologue from other plant species. A homolog may have, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the amino acid represented by any of SEQ ID NO: 1 to 3, 29 and 30 or to the nucleic acid sequences as shown by SEQ ID NOs: 4 or 9, 31 to 34. A MRC promoter orthologue may have, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the nucleic acid sequences as shown in SEQ ID NOs 22 to 24, 35 and 36. In one embodiment, overall sequence identity is at least 37%. In one embodiment, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%.

Functional variants of MRC homologs as defined above are also within the scope of the invention.

MRC does not have any recognisable conserved domains. However, the majority of the MRC protein forms coiled coils, which are alpha-helices that can mediate protein-protein interaction. Coiled coils typically form from a (a-b-c-d-e-f-g), heptad repeat, where a and d are non-polar resides, and e and g are polar residues (Mason and Arndt, 2004). Coiled coils are therefore variable in sequence as long as the heptad repeat is conserved, and thus, no strictly conserved amino acid motifs were found in the polypeptide sequence of the coiled coils from MRC orthologs. Also, the length and position of coiled coils appears to be variable among AtMRC and TaMRC. The mutation in MRC may reside in the coiled coils, and result in amino acid substitutions that break the coiled coil heptad.

Accordingly, in one embodiment the MRC protein comprises at least one coiled coil and at least one mutation is introduced into at least one coiled coil to affect protein function.

Additionally, all higher plant MRC proteins have an L(L/F)(D/E)(K/R) LF motif towards the N-terminal end of the protein, after the chloroplast transit peptide but before the start of the coiled coils. The strict conservation of this motif among MRC orthologs implies that it plays an important role in MRC function. The mutation may encode an amino acid substitution that disrupts the function of this motif. Also, the mutation may reside in the chloroplast transit peptide (the first 17 amino acids of TaMRC). The length of the transit peptide may be predicted for MRC orthologs using ChloroP program (Emanuelsson et al., 2007). The mutation may alter the transit peptide sequence in a way that the MRC polypeptide can no longer be delivered to chloroplasts/amyloplasts.

Accordingly, in a further embodiment, the MRC nucleic acid (coding) sequence encodes a MRC protein with at least one conserved domain with the following sequence:

SEQ ID NO: 37:
L $X_1$ $X_2$ $X_3$LF where $X_1$ is L or F, $X_2$ is D or E and $X_3$ is K or R or a variant thereof, wherein the variant has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to SEQ ID NO: 37.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognised that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Non-limiting examples of algorithms that are suitable for determining percent sequence identity and sequence similarity are the BLAST and BLAST 2.0 algorithms.

Suitable homologues can be identified by sequence comparisons and identifications of conserved domains. There are predictors in the art that can be used to identify such sequences. The function of the homologue can be identified as described herein and a skilled person would thus be able to confirm the function, for example when knocked-out in a plant.

Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologs. Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labelled with a detectable group, or any other detectable marker. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than 24 hours, usually about 4 to 12. Stringent conditions may also be achieved with the addition of destabilizing agents such as formamide.

In a further embodiment, a variant as used herein can comprise a nucleic acid sequence encoding a MRC polypeptide as defined herein that is capable of hybridising under stringent conditions as defined herein to a nucleic acid sequence as defined in any of SEQ ID NOs: 4 to 9, 11, 12, 14, 15, 16, 17, 20, 21, 22 to 28, 31 to 37 and 61 to 62.

In one embodiment, the method comprises altering the expression of at least one nucleic acid encoding a MRC polypeptide or altering the activity of an MRC polypeptide, as described herein, wherein the method comprises introducing at least one mutation into at least one MRC gene and/or promoter, wherein the MRC gene comprises or consists of
  a. a nucleic acid sequence encoding a polypeptide as defined in one of SEQ ID NOs: 1 to 3, 10, 13, 18, 19, 29 to 30 and 60; or
  b. a nucleic acid sequence as defined in one of SEQ ID NOs: 4 to 9, 11, 12, 14, 15, 16, 17, 20, 21, 31 to 34, 61 and 62; or
  c. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to either (a) or (b); or
  d. a nucleic acid sequence encoding a MRC polypeptide as defined herein that is capable of hybridising under stringent conditions as defined herein to the nucleic acid sequence of any of (a) to (c);
and wherein the MRC promoter comprises or consists of
  e. a nucleic acid sequence as defined in one of SEQ ID NOs: 22 to 28, 35 and 36
  f. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to (e); or
  g. a nucleic acid sequence capable of hybridising under stringent conditions as defined herein to the nucleic acid sequence of any of (e) to (f).

In one embodiment, a mutation is introduced into two MRC genes, wherein the first MRC gene encodes a protein as defined in SEQ ID NO: 2 (preferably the MRC gene comprises or consists of a nucleic acid sequence as defined in SEQ ID NO: 5 or 8) and wherein the second MRC gene encodes a protein as defined in SEQ ID NO: 3 (preferably the MRC gene comprises or consists of a nucleic acid sequence as defined in SEQ ID NO: 6 or 9). In an alternative embodiment, a mutation is introduced into two MRC genes, wherein the first MRC gene encodes a protein as defined in SEQ ID NO: 1 (preferably the MRC gene comprises or consists of a nucleic acid sequence as defined in SEQ ID NO: 4 or 7) and wherein the second MRC gene encodes a protein as defined in SEQ ID NO: 29 (preferably the MRC gene comprises or consists of a nucleic acid sequence as defined in SEQ ID NO: 31 or 33). In a further embodiment, a mutation is introduced into three MRC genes, wherein the first MRC gene encodes a protein as defined in SEQ ID NO: 2 (preferably the MRC gene comprises or consists of a nucleic acid sequence as defined in SEQ ID NO: 5 or 8) and wherein the second MRC gene encodes a protein as defined in SEQ ID NO: 3 (preferably the MRC gene comprises or consists of a nucleic acid sequence as defined in SEQ ID NO: 6 or 9) and wherein the third MRC gene encodes a protein as defined in SEQ ID NO: 30 (preferably the MRC gene comprises or consists of a nucleic acid sequence as defined in SEQ ID NO: 32 or 34).

In one embodiment, the mutation is a loss-of function mutation. Preferably the loss of function mutation is at the start of the of protein coding sequence (e.g. in the N-terminus of the protein). In one embodiment, the loss of function is in the first 258 amino acids of the MRC polypeptide.

In a preferred embodiment, the mutation that is introduced into the endogenous MRC gene or promoter thereof to alter the biological activity and/or expression levels of the MRC gene or protein can be selected from the following mutation types
  1. a "missense mutation", which is a change in the nucleic acid sequence that results in the substitution of one amino acid for another amino acid;
  2. a "nonsense mutation" or "STOP codon mutation", which is a change in the nucleic acid sequence that results in the introduction of a premature STOP codon and, thus, the termination of translation (resulting in a truncated protein); in plants, the translation stop codons may be selected from "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
  3. an "insertion mutation" of one or more nucleotides or one or more amino acids, due to one or more codons having been added in the coding sequence of the nucleic acid;
  4. a "deletion mutation" of one or more nucleotides or of one or more amino acids, due to one or more codons having been deleted in the coding sequence of the nucleic acid;
  5. a "frameshift mutation", resulting in the nucleic acid sequence being translated in a different frame downstream of the mutation. A frameshift mutation can have various causes, such as the insertion, deletion or duplication of one or more nucleotides.
  6. a "splice site" mutation, which is a mutation that results in the insertion, deletion or substitution of a nucleotide at the site of splicing.

In one embodiment, the mutation is a STOP codon mutation. For example, in one embodiment, the mutation is selected from at least one of the following:
  A Q to STOP (TAG) at position 258 of SEQ ID NO: 1 or a homologous (corresponding) position in a homologous sequence;
  A Q to STOP (TAA) at position 550 of SEQ ID NO: 1 or a homologous (corresponding) position in a homologous sequence;
  A Q to STOP (TAA) at position 727 of SEQ ID NO: 2 or a homologous (or corresponding-such terms may be used interchangeably) position in a homologous sequence;
  A Q to STOP (TAG) at position 360 of SEQ ID NO: 2 or a homologous (corresponding) position in a homologous sequence;
  A Q to STOP (TAG) at position 258 of SEQ ID NO: 3 or a homologous (corresponding) position in a homologous sequence;
  A Q to STOP (TAA) at position 482 of SEQ ID NO: 3 or a homologous (corresponding) position in a homologous sequence;

In a further embodiment, the method comprises introducing one or more mutations in the MRC nucleic acid sequence, which results in an amino acid mutation at one or more of the following positions, and biases the distribution of granule size in a population towards the small or smaller sizes (as described above):
  Position 258 of SEQ ID NO: 1 or a homologous position in a homologous sequence. Preferably said mutation results in the termination of the protein at position 258 of SEQ ID NO: 1 or a homologous position in a homologous sequence. Preferably said mutation in the amino acid sequence arises from a mutation of one or more nucleotides in the nucleic acid sequence, wherein the mutation is at positions 1263 to 1265 of SEQ ID NO: 4 or a homologous position in a homologous sequence. Even more preferably, the mutation is a CAG to TAG mutation at positions 1263 to 1265 of SEQ ID NO: 4 or a homologous position in a homologous sequence. As used herein, this mutation may be referred to herein as K3272; and/or Position 289 of SEQ ID NO: 1 or a homologous position in a homologous sequence. Preferably said mutation results in a substitution at position 289 of SEQ ID NO: 1 or a homologous position in a homologous sequence. In one embodiment, the homologous position is 288 in SEQ ID NO: 18 (maize), 287 in SEQ ID NO: 19 (rice) and position 285 in SEQ ID NO: 60 (potato). Even more preferably, the mutation is a L to F substitution. Preferably, said mutation in the amino acid sequence arises from a mutation of one or more nucleotides in the nucleic acid sequence, wherein the mutation is at positions 1356 to 1358 of SEQ ID NO: 4 or a homologous position in a homologous sequence. Even more preferably, the mutation is a CTT to TTT mutation at positions 1356 to 1358 of SEQ ID NO: 4 or a homologous position in a homologous sequence. As used herein, this mutation may be referred to herein as K598; and/or Position 550 of SEQ ID NO: 1 or a homologous position in a homologous sequence. Preferably said mutation results in the termination of the protein at position 550 of SEQ ID NO: 1 or a homologous position in a homologous sequence. Preferably said mutation in the amino acid sequence arises from a mutation of one or more nucleotides in the nucleic acid sequence, wherein the mutation is at positions 2139 to 2141 of SEQ ID NO: 4 or a homologous position in a homologous sequence. Even more preferably, the mutation is a CAA to TAA mutation at positions 2139 to 2141 of SEQ ID NO: 4 or a homologous position in a homologous sequence. As used herein, this mutation may be referred to herein as K4681; and/or Position 226 of SEQ ID NO: 29 or a homologous position in a homologous sequence. Preferably said mutation results in the termination of the protein at position 226 of SEQ ID NO: 29 or a homologous position in a homologous sequence. Preferably said mutation in the amino acid sequence arises from a mutation of one or more nucleotides in the nucleic acid sequence, wherein the mutation is at positions 682 to 684 of SEQ ID NO: 31 or a homologous position in a homologous sequence. Even more preferably, the mutation is a CAG to TAG mutation at positions 682 to 684 of SEQ ID NO: 31 or a homologous position in a homologous sequence. As used herein, this mutation may be referred to herein as K3078; and/or Position 26 of SEQ ID NO: 29 or a homologous position in a homologous sequence. Preferably said mutation results in the termination of the protein at position 26 of SEQ ID NO: 29 or a homologous position in a homologous sequence. Preferably said mutation in the amino acid sequence arises from a mutation of one or more nucleotides in the nucleic acid sequence, wherein the mutation is at positions 82 to 84 of SEQ ID NO: 31 or a homologous position in a homologous sequence. Even more preferably, the mutation is a TGG to TGA mutation at positions 82 to 84 of SEQ ID NO: 31 or a homologous position in a homologous sequence. As used herein, this mutation may be referred to herein as K4305.

In one embodiment, the method may comprise introducing one or more of the K372, K598 and/or K4681 mutations (or homologous mutations) as described herein into a MRC nucleic acid. In a further embodiment, the method may comprise introducing the following mutations.

a K3272 and a K3078 mutation (or homologous mutations) into a MRC nucleic acid. A plant comprising both mutations is described herein as mrc-1; or a K4681 and a K4305 mutation (or homologous mutations) into a MRC nucleic acid. A plant comprising both mutations is described herein as mrc-2; or a K598 (or homologous mutations) into a MRC nucleic acid. A plant comprising both mutations is described herein as mrc-3.

In an alternative embodiment, the one or more mutations in the MRC nucleic acid sequence results in an amino acid mutation at one or more of the following positions, and biases the distribution of granule size in a population towards the small or smaller sizes (as described above):

Position 727 of SEQ ID NO: 2 or a homologous position in a homologous sequence. Preferably said mutation results in the termination of the protein at position 727 of SEQ ID NO: 2 or a homologous position in a homologous sequence. Preferably said mutation in the amino acid sequence arises from a mutation of one or more nucleotides in the nucleic acid sequence, wherein the mutation is at positions 2670 to 2672 of SEQ ID NO: 5 or a homologous position in a homologous sequence. Even more preferably, the mutation is a CAA to TAA mutation at positions 2670 to 2672 of SEQ ID NO: 5 or a homologous position in a homologous sequence. As used herein, this mutation may be referred to herein as Cadenza0199; and/or Position 360 of SEQ ID NO: 2 or a homologous position in a homologous sequence. Preferably said mutation results in the termination of the protein at position 360 of SEQ ID NO: 2 or a homologous position in a homologous sequence. Preferably said mutation in the amino acid sequence arises from a mutation of one or more nucleotides in the nucleic acid sequence, wherein the mutation is at positions 1569 to 1571 of SEQ ID NO: 5 or a homologous position in a homologous sequence. Even more preferably, the mutation is a CAG to TAG mutation at positions 1569 to 1571 of SEQ ID NO: 5 or a homologous position in a homologous sequence. As used herein, this mutation may be referred to herein as Cadenza0377; and/or Position 221 of SEQ ID NO: 30 or a homologous position in a homologous sequence. Preferably said mutation results in an amino acid substitution, preferably a E to K substitution at position 221 of SEQ ID NO: 30 or a homologous position in a homologous sequence. Preferably said mutation in the amino acid sequence arises from a mutation of one or more nucleotides in the nucleic acid sequence, wherein the mutation is at positions 667 to 669 of SEQ ID NO: 32 or a homologous position in a homologous sequence. Even more preferably, the mutation is a GAG to AAG mutation at positions 667 to 669 of SEQ ID NO: 32 or a homologous position in a homologous sequence. As used herein, this mutation may be referred to herein as Cadenza1715; and/or Position 258 of SEQ ID NO: 3 or a homologous position in a homologous sequence. Preferably said mutation results in the termination of the protein at position 258 of SEQ ID NO: 3 or a homologous position in a homologous sequence. Preferably said mutation in the amino acid sequence arises from a mutation of one or more nucleotides in the nucleic acid sequence, wherein the mutation is at positions 1353 to 1355 of SEQ ID NO: 6 or a homologous position in a homologous sequence. Even more preferably, the mutation is a CAG to TAG mutation at positions 1353 to 1355 of SEQ ID NO: 6 or a homologous position in a homologous sequence. As used herein, this mutation may be referred to herein as Cadenza1012; and/or Position 482 of SEQ ID NO: 3 or a homologous position in a homologous sequence. Preferably said mutation results in the termination of the protein at position 482 of SEQ ID NO: 3 or a homologous position in a homologous sequence. Preferably said mutation in the amino acid sequence arises from a mutation of one or more nucleotides in the nucleic acid sequence, wherein the mutation is at positions 2025 to 2027 of SEQ ID NO: 6 or a homologous position in a homologous sequence. Even more preferably, the mutation is a CAA to TAA mutation at positions 2025 to 2027 of SEQ ID NO: 6 or a homologous position in a homologous sequence. As used herein, this mutation may be referred to herein as Cadenza1092.

In one embodiment, the method may comprise introducing one or more of the Cadenza 0199, 0377, 1715, 1012 and/or 1092 mutations (or homologous mutations) as described herein into a MRC nucleic acid. In a further embodiment, the method may comprise introducing the following mutations:
 a Cadenza 0199, 1715 and 1012 mutation (or homologous mutations) into a MRC nucleic acid. A plant comprising both mutations is described herein as mrc-4; or
 a Cadenza 0199, 1715 and 1092 mutation (or homologous mutations) into a MRC nucleic acid. A plant comprising both mutations is described herein as mrc-5; or
 a Cadenza 0377, 1715 and 1012 mutation (or homologous mutations) into a MRC nucleic acid. A plant comprising both mutations is described herein as mrc-6; or
 a Cadenza 0377, 1715 and 1092 mutation (or homologous mutations) into a MRC nucleic acid. A plant comprising both mutations is described herein as mrc-7.

In an alternative embodiment, the one or more mutations in the MRC nucleic acid sequence results in an amino acid mutation at one or more of the following positions, and biases the distribution of granule size in a population towards the larger sizes (as described above):
 Position 394 of SEQ ID NO: 1 or a homologous position in a homologous sequence. Preferably said mutation results in an amino acid substitution, preferably an L to F substitution at position 394 of SEQ ID NO: 1 or a homologous position in a homologous sequence. Preferably said mutation in the amino acid sequence arises from a mutation of one or more nucleotides in the nucleic acid sequence, wherein the mutation is at positions 1671 to 1673 of SEQ ID NO: 4 or a homologous position in a homologous sequence. Even more preferably, the mutation is a CTC to TTC mutation at positions 1671 to 1673 of SEQ ID NO: 4 or a homologous position in a homologous sequence. As used herein, this mutation may be referred to herein as Kronos775;
 Position 681 of SEQ ID NO: 1 or a homologous position in a homologous sequence. Preferably said mutation results in an amino acid substitution, preferably a P to S substitution at position 681 of SEQ ID NO: 1 or a homologous position in a homologous sequence. Preferably said mutation in the amino acid sequence arises from a mutation of one or more nucleotides in the nucleic acid sequence, wherein the mutation is at positions 2532 to 2534 of SEQ ID NO: 4 or a homologous position in a homologous sequence. Even more preferably, the mutation is a CCA to TCA mutation at positions 2532 to 2534 of SEQ ID NO: 4 or a homologous position in a homologous sequence. As used herein, this mutation may be referred to herein as Kronos2096; and/or Position 625 of SEQ ID NO: 1 or a homologous position in a homologous sequence. Preferably said mutation results in an amino acid substitution, preferably an A to T substitution at position 625 of SEQ ID NO: 1 or a homologous position in a homologous sequence. Preferably said mutation in the amino acid sequence arises from a mutation of one or more nucleotides in the nucleic acid sequence, wherein the mutation is at positions 2364 to 2366 of SEQ ID NO: 4 or a homologous position in a homologous sequence. Even more preferably, the mutation is a GCA to ACA mutation at positions 2364 to 2366 of SEQ ID NO: 4 or a homologous position in a homologous sequence. As used herein, this mutation may be referred to herein as Kronos2485.

In general, the skilled person will understand that at least one mutation as defined above and which leads to the insertion, deletion or substitution of at least one nucleic acid or amino acid compared to the wild-type MRC promoter or MRC nucleic acid or protein sequence can affect the biological activity of the MRC protein.

In another embodiment, the method comprises introducing at least one mutation into the plant genome, where the mutation is the insertion of at least one additional copy of a nucleic acid sequence encoding at least one MRC polypeptide such that the nucleic acid is operably linked to a regulatory sequence, and wherein the wherein the mutation is introduced using targeted genome editing. Alternatively, the method comprises introducing one or more mutations into the promoter of a MRC nucleic acid. Preferably, the mutation is introduced using ZFNs, TALENs or CRISPR/Cas9. In one embodiment, the MRC polypeptide sequence is selected from one of SEQ ID Nos 1 2 and/or 3. In a further embodiment, the nucleic acid sequence is selected from SEQ ID Nos 4, 5, 6, 7, 8, 9, 31, 32, 33, 34 and/or 35 or a functional variant or homolog thereof. A functional variant or homolog is defined herein.

In one embodiment a mutation may be introduced into the MRC promoter and at least one mutation is introduced into the MRC gene.

The skilled person would understand that suitable homologues and the homologous positions in these sequences can be identified by sequence comparisons (e.g. BLAST, alignments) and identifications of conserved domains. Phylogenetic tree analysis using nucleotide or amino acid sequences can be used to establish orthology to MRC. There are predictors in the art that can be used to identify such sequences. The function of the homologue can be identified as described herein and a skilled person would thus be able to confirm the function. Homologous positions can thus be determined by performing sequence alignments once the homologous sequence has been identified. For example, homologues can be identified using a BLAST search of the plant genome of interest using the wheat (Kronos or Cadenza) MRC as a query (i.e. one of the sequences defined in SEQ ID NOs: 1 to 9).

In one embodiment, the mutation is introduced using mutagenesis or targeted genome editing. That is, in one embodiment, the invention relates to a method and plant that has been generated by genetic engineering methods as described above, and does not encompass naturally occurring varieties.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Cermak T et al. describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct. Accordingly, using techniques known in the art it is possible to design a TAL effector that targets a MRC gene or promoter sequence as described herein.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted (Wiles et al., 2015).

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Accordingly, using techniques known in the art it is possible to design sgRNA molecules that targets a MRC gene or promoter sequence as described herein. In one embodiment, the method comprises using any of the nucleic acid constructs or sgRNA molecules described herein.

Cas9 expression plasmids for use in the methods of the invention can be constructed as described in the art.

In one embodiment, the method uses a sgRNA to introduce a targeted SNP or mutation, in particular one of the substitutions described herein, into a MRC gene. As explained herein, the introduction of a template DNA strand, following a sgRNA-mediated snip in the double-stranded DNA, can be used to produce a specific targeted mutation (i.e. a SNP) in the gene using homology directed repair. In an alternative embodiment, at least one mutation may be introduced into the MRC gene and/or promoter, particularly at the positions described above, using any CRISPR technique known to the skilled person. In another example, sgRNA (for example, as described herein) can be used with a modified Cas9 protein, such as nickase Cas9 or nCas9 or a "dead" Cas9 (dCas9) fused to a "Base Editor"—such as an enzyme, for example a deaminase such as cytidine deaminase, or TadA (tRNA adenosine deaminase) or ADAR or APOBEC. These enzymes are able to substitute one base for another. As a result no DNA is deleted, but a single substitution is made.

Alternatively, more conventional mutagenesis methods can be used to introduce at least one mutation into a MRC gene or MRC promoter sequence. These methods include both physical and chemical mutagenesis. A skilled person will know further approaches can be used to generate such mutants, and methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein.

In one embodiment, insertional mutagenesis is used, for example using T-DNA mutagenesis (which inserts pieces of the T-DNA from the *Agrobacterium tumefaciens* Ti-Plasmid into DNA causing either loss of gene function or gain of gene function mutations), site-directed nucleases (SDNs) or transposons as a mutagen. Insertional mutagenesis is an alternative means of disrupting gene function and is based on the insertion of foreign DNA into the gene of interest (see Krysan et al, The Plant Cell, Vol. 11, 2283-2290 December 1999). Accordingly, in one embodiment, T-DNA is used as an insertional mutagen to disrupt MRC gene or MRC promoter expression. T-DNA not only disrupts the expression of the gene into which it is inserted, but also acts as a marker for subsequent identification of the mutation. Since the sequence of the inserted element is known, the gene in which the insertion has occurred can be recovered, using various cloning or PCR-based strategies. The insertion of a piece of T-DNA in the order of 5 to 25 kb in length generally produces a disruption of gene function. If a large enough population of T-DNA transformed lines is generated, there are reasonably good chances of finding a transgenic plant carrying a T-DNA insert within any gene of interest. Transformation of spores with T-DNA is achieved by an *Agrobacterium*-mediated method which involves exposing plant cells and tissues to a suspension of *Agrobacterium* cells.

The details of this method are well known to a skilled person. In short, plant transformation by *Agrobacterium* results in the integration into the nuclear genome of a sequence called T-DNA, which is carried on a bacterial plasmid. The use of T-DNA transformation leads to stable single insertions. Further mutant analysis of the resultant transformed lines is straightforward and each individual insertion line can be rapidly characterized by direct sequencing and analysis of DNA flanking the insertion. Gene expression in the mutant is compared to expression of the MRC nucleic acid sequence in a wild type plant and phenotypic analysis is also carried out.

In another embodiment, mutagenesis is physical mutagenesis, such as application of ultraviolet radiation, X-rays, gamma rays, fast or thermal neutrons or protons. The targeted population can then be screened to identify an MRC mutant with reduced expression or activity.

In another embodiment of the various aspects of the invention, the method comprises mutagenizing a plant population with a mutagen. The mutagen may be a fast neutron irradiation or a chemical mutagen, for example selected from the following non-limiting list: ethyl methanesulfonate (EMS), methylmethane sulfonate (MMS), N-ethyl-N-nitrosurea (ENU), triethylmelamine (1'EM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloroethyl)aminopropylamino] acridine dihydrochloride (ICR-170) or formaldehyde. Again, the targeted population can then be screened to identify a MRC gene or promoter mutant.

In another embodiment, the method used to create and analyse mutations is targeting induced local lesions in genomes (TILLING), reviewed in Henikoff et al, 2004. In this method, seeds are mutagenised with a chemical mutagen, for example EMS. The resulting M1 plants are self-fertilised and the M2 generation of individuals is used to prepare DNA samples for mutational screening. DNA samples are pooled and arrayed on microtiter plates and subjected to gene specific PCR. The PCR amplification products may be screened for mutations in the MRC target gene using any method that identifies heteroduplexes between wild type and mutant genes. For example, but not limited to, denaturing high pressure liquid chromatography (dHPLC), constant denaturant capillary electrophoresis (CDCE), temperature gradient capillary electrophoresis (TGCE), or by fragmentation using chemical cleavage. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program. Any primer specific to the MRC nucleic acid sequence may be utilized to amplify the MRC nucleic acid sequence within the pooled DNA sample. Preferably, the primer is designed to amplify the regions of the MRC gene where useful mutations are most likely to arise, specifically in the areas of the MRC gene that are highly conserved and/or confer activity as explained elsewhere. To facilitate detection of PCR products on a gel, the PCR primer may be labelled using any conventional labelling method. In an alternative embodiment, the method used to create and analyse mutations is EcoTILLING. EcoTILLING is molecular technique that is similar to TILLING, except that its objective is to uncover natural variation in a given population as opposed to induced mutations. The first publication of the EcoTILLING method was described in Comai et al. 2004.

Rapid high-throughput screening procedures thus allow the analysis of amplification products for identifying a mutation conferring the reduction or inactivation of the expression of the MRC gene as compared to a corresponding non-mutagenised wild type plant. Once a mutation is identified in a gene of interest, the seeds of the M2 plant carrying that mutation are grown into adult M3 plants and screened for the phenotypic characteristics associated with the target gene MRC. Loss of and reduced function mutants with an altered starch granule size, number and/or distribution compared to a control can thus be identified.

Plants obtained or obtainable by such method which carry a functional mutation in the endogenous MRC gene or promoter locus are also within the scope of the invention.

In an alternative embodiment, the expression of the MRC gene may be reduced at either the level of transcription or translation. For example, expression of a MRC nucleic acid or MRC promoter sequence, as defined herein, can be reduced or silenced using a number of gene silencing methods known to the skilled person, such as, but not limited to, the use of small interfering nucleic acids (siNA) against MRC. "Gene silencing" is a term generally used to refer to suppression of expression of a gene via sequence-specific interactions that are mediated by RNA molecules. The degree of reduction may be so as to totally abolish production of the encoded gene product, but more usually the abolition of expression is partial, with some degree of expression remaining. The term should not therefore be taken to require complete "silencing" of expression.

In one embodiment, the siNA may include, short interfering RNA (siRNA), double-stranded RNA (dsRNA), micro-RNA (miRNA), antagomirs and short hairpin RNA (shRNA) capable of mediating RNA interference.

The inhibition of expression and/or activity can be measured by determining the presence and/or amount of MRC transcript using techniques well known to the skilled person (such as Northern Blotting, RT-PCR and so on).

Transgenes may be used to suppress endogenous plant genes. This was discovered originally when chalcone synthase transgenes in *petunia* caused suppression of the endogenous chalcone synthase genes and indicated by easily visible pigmentation changes. Subsequently it has been described how many, if not all plant genes can be "silenced" by transgenes. Gene silencing requires sequence similarity between the transgene and the gene that becomes silenced. This sequence homology may involve promoter regions or coding regions of the silenced target gene. When coding regions are involved, the transgene able to cause gene silencing may have been constructed with a promoter that would transcribe either the sense or the antisense orientation of the coding sequence RNA. It is likely that the various examples of gene silencing involve different mechanisms that are not well understood. In different examples there may be transcriptional or post-transcriptional gene silencing and both may be used according to the methods of the invention.

The mechanisms of gene silencing and their application in genetic engineering, which were first discovered in plants in the early 1990s and then shown in *Caenorhabditis elegans* are extensively described in the literature.

RNA-mediated gene suppression or RNA silencing according to the methods of the invention includes co-suppression wherein over-expression of the target sense RNA or mRNA, that is the MRC sense RNA or mRNA, leads to a reduction in the level of expression of the genes concerned. RNAs of the transgene and homologous endogenous gene are co-ordinately suppressed. Other techniques used in the methods of the invention include antisense RNA to reduce transcript levels of the endogenous target gene in a plant. In this method, RNA silencing does not affect the transcription of a gene locus, but only causes sequence-specific degradation of target mRNAs. An "antisense" nucleic acid sequence comprises a nucleotide sequence that is complementary to a "sense" nucleic acid sequence encoding a MRC protein, or a part of the protein, i.e. complementary to the coding strand of a double-stranded cDNA molecule or complementary to an mRNA transcript sequence. The antisense nucleic acid sequence is preferably complementary to the endogenous MRC gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire MRC nucleic acid sequence as defined herein, but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine-substituted nucleotides may be used. Examples of modified nucleotides that may be used to generate the antisense nucleic acid sequences are well known in the art. The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention hybridize with or bind to mRNA transcripts and/or insert into genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using vectors.

RNA interference (RNAi) is another post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

Artificial and/or natural microRNAs (miRNAs) may be used to knock out gene expression and/or mRNA translation. MicroRNAs (miRNAs) miRNAs are typically single stranded small RNAs typically 19-24 nucleotides long. Most plant miRNAs have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. miRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes. Artificial microRNA (amiRNA) technology has been applied in *Arabidopsis thaliana* and other plants to efficiently silence target genes of interest. The design principles for amiRNAs have been generalized and integrated into a web-based tool.

Thus, according to the various aspects of the invention a plant may be transformed to introduce a RNAi, shRNA, snRNA, dsRNA, siRNA, miRNA, ta-siRNA, amiRNA or cosuppression molecule that has been designed to target the expression of an MRC nucleic acid sequence and selectively decreases or inhibits the expression of the gene or stability of its transcript. Preferably, the RNAi, snRNA, dsRNA, shRNA siRNA, miRNA, amiRNA, ta-siRNA or cosuppression molecule used according to the various aspects of the invention comprises a fragment of at least 17 nt, preferably 22 to 26 nt and can be designed on the basis of the information shown in any of SEQ ID NOs: 4 to 9, 11, 12, 14, 15, 17, 18, 20, 21, 22 to 28 and 31 to 37. Guidelines for designing effective siRNAs are known to the skilled person. Briefly, a short fragment of the target gene sequence (e.g., 19-40 nucleotides in length) is chosen as the target sequence of the siRNA of the invention. The short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, 5) a sequence from the target gene mRNA that is unique to the target gene, 6) avoids regions within 75 bases of a start codon. The sequence fragment from the target gene mRNA may meet one or more of the criteria identified above. The selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides that are typically made by chemical synthesis. In addition to siRNA which is complementary to the mRNA target region, degenerate siRNA sequences may be used to target homologous regions. siRNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligonucleotide synthesis suppliers.

siRNA molecules according to the aspects of the invention may be double stranded. In one embodiment, double stranded siRNA molecules comprise blunt ends. In another embodiment, double stranded siRNA molecules comprise overhanging nucleotides (e.g., 1-5 nucleotide overhangs, preferably 2 nucleotide overhangs). In some embodiments, the siRNA is a short hairpin RNA (shRNA); and the two strands of the siRNA molecule may be connected by a linker region (e.g., a nucleotide linker or a non-nucleotide linker). The siRNAs of the invention may contain one or more modified nucleotides and/or non-phosphodiester linkages. Chemical modifications well known in the art are capable of increasing stability, availability, and/or cell uptake of the siRNA. The skilled person will be aware of other types of chemical modification which may be incorporated into RNA molecules.

In one embodiment, recombinant DNA constructs as described in U.S. Pat. No. 6,635,805, incorporated herein by reference, may be used.

The silencing RNA molecule is introduced into the plant using conventional methods, for example a vector and *Agrobacterium*-mediated transformation. Stably transformed plants are generated and expression of the MRC gene compared to a wild type control plant is analysed.

Silencing or reducing expression levels of MRC nucleic acid may also be achieved using virus-induced gene silencing.

Thus, in one embodiment of the invention, the plant expresses a nucleic acid construct comprising a RNAi, shRNA snRNA, dsRNA, siRNA, miRNA, ta-siRNA, amiRNA or co-suppression molecule that targets the MRC nucleic acid sequence as described herein and reduces expression of the endogenous MRC nucleic acid sequence. A gene is targeted when, for example, the RNAi, snRNA, dsRNA, siRNA, shRNA miRNA, ta-siRNA, amiRNA or cosuppression molecule selectively decreases or inhibits the expression of the gene compared to a control plant. Alternatively, a RNAi, snRNA, dsRNA, siRNA, miRNA, ta-siRNA, amiRNA or cosuppression molecule targets a MRC nucleic acid sequence when the RNAi, shRNA snRNA, dsRNA, siRNA, miRNA, ta-siRNA, amiRNA or co-suppression molecule hybridises under stringent conditions to the gene transcript.

A further approach to gene silencing is by targeting nucleic acid sequences complementary to the regulatory region of the gene (e.g., the promoter and/or enhancers) of MRC to form triple helical structures that prevent transcription of the gene in target cells. Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

In one embodiment, the suppressor nucleic acids may be anti-sense suppressors of expression of the MRC polypeptides. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene.

An anti-sense suppressor nucleic acid may comprise an anti-sense sequence of at least 10 nucleotides from the target nucleotide sequence. It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Suppressor nucleic acids may be operably linked to tissue-specific or inducible promoters. For example, seed and endosperm-specific promoters can be used to specifically down-regulate an MRC nucleic acid in developing seeds to alter granule size in that organ specifically.

Nucleic acid which suppresses expression of an MRC polypeptide as described herein may be operably linked to a heterologous regulatory-sequence, such as a promoter, for example a constitutive, inducible, tissue-specific or developmental specific promoter. The construct or vector may be transformed into plant cells and expressed as described herein. Plant cells comprising such vectors are also within the scope of the invention.

In another aspect, the invention relates to a silencing construct obtainable or obtained by a method as described herein and to a plant cell comprising such construct.

Thus, aspects of the invention involve targeted mutagenesis methods, specifically genome editing, and in a preferred embodiment exclude embodiments that are solely based on generating plants by traditional breeding methods.

In another embodiment, the method of increasing the expression of a MRC nucleic acid comprises introducing and expressing a nucleic acid construct comprising a nucleic acid encoding a MRC polypeptide operably linked to a regulatory sequence wherein the at least one MRC polypeptide is selected from SEQ ID Nos 1, 2, 3, 29 or 30 or a functional variant or homolog as defined herein. In one embodiment, the nucleic acid sequence encodes at least one MRC polypeptide selected from SEQ ID Nos 1 or 2 or 2 or 2 and 3. In a further embodiment, the nucleic acid sequence is selected from SEQ ID Nos 4, 5, 6, 7, 8, 9, 31, 32, 33, 34 and 35 or a functional variant or homolog thereof. A functional variant or homolog is defined herein. In one embodiment, the regulatory sequence is a promoter. In one embodiment, the promoter is a constitutive promoter such as 35S or the Ubiquitin promoter. In another embodiment, the promoter is a tissue-specific promoter such as the HMW glutenin promoter.

In another aspect, the invention extends to a plant obtained or obtainable by a method as described herein.

In a further aspect of the invention, there is provided a method of altering a physiochemical property of starch, the method comprising altering the expression of at least one MRC (MYOSIN-RESEMBLING CHLOROPLAST PROTEIN) nucleic acid and/or altering the activity of a MRC polypeptide as described above. As shown in FIG. 15, in one embodiment, the physiochemical property is selected from gelatinisation temperature, swelling power and viscosity. In a preferred embodiment, the method increases or decreases at least one of starch digestion rate, gelatinisation temperature, swelling power and viscosity. More preferably, the method comprises increasing the onset and gelatinisation temperature. An increase as used herein may be at least 1%, 2%, 3%, 4%, 5%, 6%, 7%, 8%, 9%, 10% 11%, 12%, 13%, 14%, 15%, 16%, 17%, 18%, 19%, 20%, 30%, 40% or 50% in comparison to a control plant.

In another aspect of the invention, there is provided a method of altering a plant with a bimodal size distribution of starch granules towards a unimodal distribution of starch granules, the method comprising reducing or abolishing the expression of at least one MRC nucleic acid and/or reducing or abolishing the activity of a MRC polypeptide as described above.

In a further aspect of the invention, there is provided a method of altering the initiation of granule formation in a starch storage organ of a plant, the method comprising alerting the expression of at least one MRC nucleic acid and/or altering the activity of at least one MRC polypeptide as described above.

In another aspect of the invention there is provided a method of altering at least one of starch granule size, number and distribution in a plant, the method comprising reducing or abolishing the expression of at least one MRC nucleic acid and/or reducing or abolishing the activity of a MRC polypeptide (using any of the methods described herein), wherein the plant is not *Arabidopsis*. In one embodiment, the plant has a bimodal size distribution of starch granules, such as wheat, rye and barley, wherein preferably said bimodal distribution comprises a first population of starch granules of a first size or size range and a second population of starch granules of a second size or size range. More preferably, the method comprises decreasing the size of starch granules and/or increasing the number of starch granules in the first and/or second population of starch granules. In one embodiment, the method comprises decreasing the size of granules in the first population and/or increasing the number of granules in the second population. Alternatively, the method comprises increasing the size of granules in the first population and/or decreasing the number of starch granules in the second population. An increase or decrease is described elsewhere.

In one embodiment, the first population of starch granules comprises granules with an average spherical diameter over 15 µm, and wherein the second population of starch granules comprises granules with an average spherical diameter between 1 and 15 µm. Also described herein, is a genetically altered plant, part thereof or plant cell characterised by reduced or abolished expression (as described herein) or at least one MRC nucleic acid and/or reduced or abolished activity of a MRC polypeptide, wherein the plant is not *Arabidopsis*. In one example, the plant has a bimodal distribution of starch granules.

Genetically Altered or Modified Plants and Methods of Producing Such Plants

In another aspect of the invention there is provided a genetically altered plant, part thereof or plant cell characterised in that the expression of MRC is altered, the plant does not express a functional MRC protein or expresses a MRC protein with reduced or increased function and/or activity. In one embodiment, the plant is a reduction (knock down) or loss of function (knock out) mutant wherein the function of the MRC nucleic acid sequence is reduced or lost compared to a wild type or control plant. Preferably, the plant is a knock down and not a knock out, meaning that the plant has reduced levels of MRC expression or expresses a MRC protein with reduced function and/or activity. To this end, a mutation is introduced into either the MRC gene sequence or the corresponding promoter sequence which disrupts the transcription of the gene. Therefore, preferably said plant comprises at least one mutation in the promoter and/or at least one gene for MRC. In one embodiment the plant may comprise a mutation in both the promoter and the at least one gene for MRC.

In an alternative embodiment, the plant is a gain-of-function mutation where the function or activity of the MRC polypeptide is increased compared to the wild-type or control plant. Again, to this end, a mutation is introduced into either the MRC gene sequence or the corresponding promoter sequence to either increase the transcription of the gene or increase the activity of the polypeptide. Therefore, preferably said plant comprises at least one mutation in the promoter and/or at least one gene for MRC. In one embodiment the plant may comprise a mutation in both the promoter and the at least one gene for MRC.

In a further aspect of the invention, there is provided a plant, part thereof or plant cell characterised by an alteration in the size distribution of starch granules in a starch storage organ. A definition of an alteration in a granule size distribution is described above.

The plant may be produced by introducing a mutation, preferably a deletion, insertion or substitution into the MRC gene and/or promoter sequence by any of the above described methods. Preferably said mutation is introduced into a least one plant cell and a plant regenerated from the at least one mutated plant cell.

In one embodiment, the plant is characterised by a shift in the distribution of granule size towards the smaller granule size. In other words, the plant may be characterised by an increase in the number of smaller granules, compared to a wild-type or control plant. In a further embodiment, the plant is characterised by a decrease in the average granule size. In a further embodiment, the plant comprises at least one loss of function mutation in a MRC gene and/or promoter as described herein.

In an alternative embodiment, the plant is characterised by a shift in the distribution of granule size towards the larger granule size. In other words, the plant may be characterised by an increase in the size and/or number of larger granule sizes, compared to a wild-type or control plant. In a further embodiment, the plant is characterised by an increase in the average granule size. In a further embodiment, the plant comprises at least one gain of function mutation in a MRC gene and/or promoter as described herein.

Alternatively, the plant or plant cell may comprise a nucleic acid construct expressing an RNAi molecule targeting the MRC gene as described herein. In one embodiment, said construct is stably incorporated into the plant genome. These techniques also include gene targeting using vectors that target the gene of interest and which allows for integration of a transgene at a specific site. The targeting construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene will be translated into a nonfunctional protein, if it is translated at all.

In another aspect of the invention, there is provided a nucleic acid construct comprising a nucleic acid sequence encoding at least one MRC polypeptide operably linked to a regulatory sequence, wherein the at least one MRC polypeptide is selected from SEQ ID Nos 1, 2, 3, 29 or 30 or a functional variant or homolog as defined herein. In one embodiment, the nucleic acid sequence encodes at least one MRC polypeptide selected from SEQ ID Nos 1 or 2 or 2 or 2 and 3. In a further embodiment, the nucleic acid sequence is selected from SEQ ID Nos 4, 5, 6, 7, 8, 9, 31, 32, 33, 34 and 35 or a functional variant or homolog thereof. A functional variant or homolog is defined herein.

In one embodiment, the regulatory sequence is a promoter. In one embodiment, the promoter is a constitutive promoter such as 35S or the Ubiquitin promoter. In another embodiment, the promoter is a tissue-specific promoter such as the HMW glutenin promoter.

In another aspect of the invention, there is also provided a transgenic plant expressing the above-described nucleic acid construct.

In a further aspect of the invention, there is provided a method of making a transgenic plant, the method comprising introducing and expressing in a plant or plant cell the above-described nucleic acid construct. Method for introducing (or transforming) a plant or plant cell are described above. The method may further comprise regenerating a transgenic plant from the plant or plant cell and obtaining progeny plant, wherein the progeny plant comprises in its genome a nucleic acid sequence encoding MRC as described herein, linked to a regulatory sequence, wherein the progeny plant also display an alteration in starch granule size distribution compared to a wild-type or control plant. Methods of regenerating a plant are described elsewhere herein.

In another aspect of the invention there is provided a method for producing a genetically altered plant as described herein. In one embodiment, the method comprises introducing at least one mutation into the MRC gene and/or MRC promoter of preferably at least one plant cell using any mutagenesis technique described herein. Preferably said method further comprising regenerating a plant from the mutated plant cell.

The method may further comprise selecting one or more mutated plants, preferably for further propagation. Preferably said selected plants comprise at least one mutation in the MRC gene and/or promoter sequence. Preferably said plants are characterised by an altered of MRC expression and/or a reduced or abolished level of MRC polypeptide activity. Expression and/or activity levels of MRC can be measured by any standard technique known to the skilled person. A reduction is as described herein.

The selected plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In a further aspect of the invention there is provided a plant obtained or obtainable by the above described methods.

For the purposes of the invention, a "genetically altered plant" or "mutant plant" is a plant that has been genetically altered compared to the naturally occurring wild type (WT) plant. In one embodiment, a mutant plant is a plant that has been altered compared to the naturally occurring wild type (WT) plant using a mutagenesis method, such as any of the mutagenesis methods described herein. In one embodiment, the mutagenesis method is targeted genome modification or genome editing. In one embodiment, the plant genome has been altered compared to wild type sequences using a mutagenesis method. Such plants have an altered phenotype as described herein, such as an altered starch granule size distribution. Therefore, in this example, altered starch granule size distribution is conferred by the presence of an altered plant genome, for example, a mutated endogenous MRC gene or MRC promoter sequence. In one embodiment, the endogenous promoter or gene sequence is specifically targeted using targeted genome modification and the presence of a mutated gene or promoter sequence is not conferred by the presence of transgenes expressed in the plant. In other words, the genetically altered plant can be described as transgene-free.

A plant according to the various aspects of the invention, including the transgenic plants, methods and uses described herein may be a monocot or a dicot plant. Preferably, the plant is a crop plant or a biofuel plant. By crop plant is meant any plant which is grown on a commercial scale for human or animal consumption or use. In a preferred embodiment, the plant is a cereal.

In a most preferred embodiment, the plant is selected from wheat, barley, rye, maize, potato, sorghum and rice. In a further embodiment, the plant is wheat.

The term "plant" as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein. The term "plant" also encompasses plant cells, suspension cultures, callus tissue, embryos, meristematic regions, gametophytes, sporophytes, pollen and microspores, again wherein each of the aforementioned comprises the nucleic acid construct as described herein.

The invention also extends to harvestable parts of a plant of the invention as described herein, but not limited to seeds, leaves, fruits, flowers, stems, roots, rhizomes, tubers and bulbs. The aspects of the invention also extend to products derived, preferably directly derived, from a harvestable part of such a plant, such as dry pellets or powders, oil, fat and fatty acids, starch or proteins. Another product that may derived from the harvestable parts of the plant of the invention is biodiesel. The invention also relates to food products and food supplements comprising the plant of the invention or parts thereof. In one embodiment, the food products may be animal feed. In another aspect of the invention, there is provided a product derived from a plant as described herein or from a part thereof.

In a most preferred embodiment, the plant part or harvestable product is a seed or grain. Therefore, in a further aspect of the invention, there is provided a seed or grain produced from a genetically altered plant as described herein.

In another embodiment of the invention, the plant part is a starch storage organ comprising starch granules which have a mean granule size which is increased or decreased by 3% or more, 5% or more, 10% or more, 15% or more, 20% or more, 25% or more, 30% or more, 35% or more, 40% or more or 45% or more compared to the mean granule size in a control or wild-type plant. Preferably, the size is decreased. Alternatively the size is increased.

In a yet further embodiment, there is provided a starch storage organ comprising starch granules which have a granule size standard deviation which is increased or decreased by 3% or more, 5% or more, 10% or more, 15% or more, 20% or more, 25% or more, 30% or more, 35% or more, 40% or more or 45% or more compared to the starch granule size standard deviation in a control or wild-type plant. Preferably the standard deviation is reduced, e.g. narrowed.

In an alternative embodiment, the plant part is pollen, a propagule or progeny of the genetically altered plant described herein. Accordingly, in a further aspect of the invention there is provided pollen, a propagule or progeny of the genetically altered plant as described herein.

In another aspect of the invention, there is provided starch or a starch component obtained or obtainable from at least one plant cell of the genetically altered plant described herein or the grain of a genetically altered plant described herein.

There is also provided a food or feed composition prepared from the grain or starch or starch composition described herein.

Finally, there is also provided the use of the grain or starch described herein as a food or feedstuff, in biofuel (bioethanol) production or in any pharmaceutical, cosmetic or industrial application. Examples of industrial applications include the brewing, papermaking and plastic industries. Examples of food include bread, biscuits, baked goods based on wheat flour and pasta.

A control plant as used herein according to all of the aspects of the invention is a plant which has not been modified according to the methods of the invention. Accordingly, in one embodiment, the control plant does not have altered expression of a MRC nucleic acid and/or altered activity of a MRC polypeptide, as described herein. In an alternative embodiment, the plant been genetically modified, as described above. In one embodiment, the control plant is a wild type plant. The control plant is typically of the same plant species, preferably having the same genetic background as the modified plant.

Genome Editing Constructs for Use with the Methods for Targeted Genome Modification Described Herein By "crRNA" or CRISPR RNA is meant the sequence of RNA that contains the protospacer element and additional nucleotides that are complementary to the tracrRNA.

By "tracrRNA" (transactivating RNA) is meant the sequence of RNA that hybridises to the crRNA and binds a CRISPR enzyme, such as Cas9 thereby activating the nuclease complex to introduce double-stranded breaks at specific sites within the genomic sequence of at least one MRC nucleic acid or promoter sequence.

By "protospacer element" is meant the portion of crRNA (or sgRNA) that is complementary to the genomic DNA target sequence, usually around 20 nucleotides in length. This may also be known as a spacer or targeting sequence.

By "sgRNA" (single-guide RNA) is meant the combination of tracrRNA and crRNA in a single RNA molecule, preferably also including a linker loop (that links the tracrRNA and crRNA into a single molecule). "sgRNA" may also be referred to as "gRNA" and in the present context, the terms are interchangeable. The sgRNA or gRNA provide both targeting specificity and scaffolding/binding ability for a Cas nuclease. A gRNA may refer to a dual RNA molecule comprising a crRNA molecule and a tracrRNA molecule.

By "TAL effector" (transcription activator-like (TAL) effector) or TALE is meant a protein sequence that can bind the genomic DNA target sequence (a sequence within the MRC gene or promoter sequence) and that can be fused to the cleavage domain of an endonuclease such as FokI to create TAL effector nucleases or TALENS or meganucleases to create megaTALs. A TALE protein is composed of a central domain that is responsible for DNA binding, a nuclear-localisation signal and a domain that activates target gene transcription. The DNA-binding domain consists of monomers and each monomer can bind one nucleotide in the target nucleotide sequence. Monomers are tandem repeats of 33-35 amino acids, of which the two amino acids located at positions 12 and 13 are highly variable (repeat variable diresidue, RVD). It is the RVDs that are responsible for the recognition of a single specific nucleotide. HD targets cytosine; NI targets adenine, NG targets thymine and NN targets guanine (although NN can also bind to adenine with lower specificity).

In another aspect of the invention there is provided a nucleic acid construct wherein the nucleic acid construct comprises a nucleic acid sequence that encodes at least one DNA-binding domain. In one embodiment, the DNA-binding domain can bind to a sequence in the MRC gene and/or promoter. Preferably said sequence is selected from one of SEQ ID NO: 39 to 42 and are target sequences in a MRC gene. In one embodiment, the nucleic acid construct comprises one or more DNA-binding domains, such that the construct can bind to one or more, preferably at least two or three sequences in the MRC gene. In one embodiment, the target sequences are selected from one of SEQ ID NO: 39 to 42.

In a further embodiment, said construct further comprises a nucleic acid encoding at least one sequence specific nuclease (SSN) such as FokI or a Cas protein.

In one embodiment, the nucleic acid construct encodes at least one protospacer element wherein the sequence of the protospacer element is selected from SEQ ID NO: 43 to 46 or a variant thereof. In one example, the nucleic acid construct may comprise one, two or three protospacer sequences, wherein the sequence of the protospacer sequences is selected from SEQ ID NO: 43 to 46.

In a further embodiment, the nucleic acid construct comprises a crRNA-encoding sequence. As defined above, a crRNA sequence may comprise the protospacer elements as defined above and preferably additional nucleotides that are complementary to the tracrRNA. An appropriate sequence for the additional nucleotides will be known to the skilled person as these are defined by the choice of Cas protein.

In another embodiment, the nucleic acid construct further comprises a tracrRNA sequence. Again, an appropriate tracrRNA sequence would be known to the skilled person as this sequence is defined by the choice of Cas protein. Nonetheless, in one embodiment said sequence comprises or consists of a sequence as defined in SEQ ID NO: 47 (used successfully in wheat in Shan et al. 2014) or a variant thereof.

In a further embodiment, the nucleic acid construct comprises at least one nucleic acid sequence that encodes a sgRNA (or gRNA). Again, as already discussed, sgRNA typically comprises a crRNA sequence or protospacer sequence and a tracrRNA sequence and preferably a sequence for a linker loop. In a preferred embodiment, the nucleic acid construct comprises at least one nucleic acid sequence that encodes a sgRNA sequence as defined in any of SEQ ID NO: 52 to 55 or variant thereof. More preferably the nucleic acid sequence that encodes a sgRNA comprises or consists of a sequence selected from SEQ ID NO: 48 to 51 or a variant thereof.

In a further embodiment, the nucleic acid construct may further comprise at least one nucleic acid sequence encoding an endoribonuclease cleavage site. Preferably the endoribonuclease is Csy4 (also known as Cas6f). Where the nucleic acid construct comprises multiple sgRNA nucleic acid sequences the construct may comprise the same number of endoribonuclease cleavage sites. In another embodiment, the cleavage site is 5' of the sgRNA nucleic acid sequence. Accordingly, each sgRNA nucleic acid sequence is flanked by a endoribonuclease cleavage site.

The term 'variant' refers to a nucleotide sequence where the nucleotides are substantially identical to one of the above sequences. The variant may be achieved by modifications such as insertion, substitution or deletion of one or more nucleotides. In a preferred embodiment, the variant has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to any one of the above described sequences. In one embodiment, sequence identity is at least 90%. In another embodiment, sequence identity is 100%. Sequence identity can be determined by any one known sequence alignment program in the art.

The invention also relates to a nucleic acid construct comprising a nucleic acid sequence operably linked to a suitable plant promoter. A suitable plant promoter may be a constitutive or strong promoter or may be a tissues-specific promoter. In one embodiment, suitable plant promoters are selected from, but not limited to, cestrum yellow leaf curling virus (CmYLCV) promoter or switchgrass ubiquitin 1 promoter (PvUbi1) wheat U6 RNA polymerase III (TaU6) CaMV35S, wheat U6 or maize ubiquitin (e.g. Ubi1) promoters. Alternatively, expression can be specifically directed to particular tissues of wheat seeds through gene expression-regulating sequences. In one embodiment, the promoter is selected from the U6 promoter (for example as defined in SEQ ID NO: 58) and the ubiquitin 1 promoter (for example as defined in SEQ ID NO: 59). In a preferred embodiment the sequences are codon-optimised for the plant in question.

The nucleic acid construct of the present invention may also further comprise a nucleic acid sequence that encodes a CRISPR enzyme. By "CRISPR enzyme" is meant an RNA-guided DNA endonuclease that can associate with the CRISPR system. Specifically, such an enzyme binds to the tracrRNA sequence. In one embodiment, the CRIPSR enzyme is a Cas protein ("CRISPR associated protein), preferably Cas 9 or Cpf1, more preferably Cas9. In a specific embodiment Cas9 is codon-optimised Cas9 (optimised for the plant in which it is expressed). In one example, Cas9 has the sequence described in SEQ ID NO: 56 or a functional variant or homolog thereof. In another embodiment, the CRISPR enzyme is a protein from the family of Class 2 candidate x proteins, such as C2c1, C2C2 and/or C2c3. In one embodiment, the Cas protein is from *Streptococcus pyogenes*. In an alternative embodiment, the Cas protein may be from any one of *Staphylococcus aureus, Neisseria meningitides, Streptococcus* thermophiles of *Treponema denticola*.

The term "functional variant" as used herein with reference to Cas9 refers to a variant Cas9 gene sequence or part of the gene sequence which retains the biological function of the full non-variant sequence, for example, acts as a DNA endonuclease, or recognition and/or binding to DNA. A functional variant also comprises a variant of the gene of interest which has sequence alterations that do not affect function, for example non-conserved residues. Also encompassed is a variant that is substantially identical, i.e. has only some sequence variations, for example in non-conserved residues, compared to the wild type sequences as shown herein and is biologically active. In one embodiment, a functional variant of SEQ ID NO. 56 has at least 90%, 91%, 92%, 93%, 94%, 95%, 96%, 97%, 98%, or 99% overall sequence identity to the nucleic acid represented by SEQ ID NO: 56. In a further embodiment, the Cas9 protein has been modified to improve activity.

Suitable homologs or orthologs can be identified by sequence comparisons and identifications of conserved domains. The function of the homolog or ortholog can be identified as described herein and a skilled person would thus be able to confirm the function when expressed in a plant.

In a further embodiment, the Cas9 protein has been modified to improve activity. For example, in one embodiment, the Cas9 protein may comprise the D10A amino acid substitution, this nickase cleaves only the DNA strand that is complementary to and recognized by the gRNA. In an alternative embodiment, the Cas9 protein may alternatively or additionally comprise the H840A amino acid substitution, this nickase cleaves only the DNA strand that does not interact with the sRNA. In this embodiment, Cas9 may be used with a pair (i.e. two) sgRNA molecules (or a construct expressing such a pair) and as a result can cleave the target region on the opposite DNA strand, with the possibility of improving specificity by 100-1500 fold. In a further embodiment, the Cas9 protein may comprise a D1135E substitution. The Cas 9 protein may also be the VQR variant. Alternatively, the Cas protein may be comprise a mutation in both nuclease domains, HNH and RuvC-like and therefore is catalytically inactive. Rather than cleaving the target strand, this catalytically inactive Cas protein can be used to prevent the transcription elongation process, leading to a loss of function of incompletely translated proteins when co-expressed with a sgRNA molecule. An example of a catalytically inactive protein is dead Cas9 (dCas9) caused by a point mutation in RuvC and/or the HNH nuclease domains (Komor et al., 2016 and Nishida et al., 2016).

In a further embodiment, a Cas protein, such as Cas9 may be further fused with a repression effector, such as a histone-modifying/DNA methylation enzyme or a Cytidine deaminase (Komor et al. 2016) to effect site-directed mutagenesis. In the latter, the cytidine deaminase enzyme does not induce dsDNA breaks, but mediates the conversion of cytidine to uridine, thereby effecting a C to T (or G to A) substitution.

In a further embodiment, the nucleic acid construct comprises an endoribonuclease. Preferably the endoribonuclease is Csy4 (also known as Cas6f) and more preferably a codon optimised csy4, for example as defined in SEQ ID NO: 57. In one embodiment, where the nucleic acid construct comprises a cas protein, the nucleic acid construct may comprise sequences for the expression of an endoribonuclease, such as Csy4 expressed as a 5' terminal P2A fusion (used as a self-cleaving peptide) to a cas protein, such as Cas9.

In one embodiment, the cas protein, the endoribonuclease and/or the endoribonuclease-cas fusion sequence may be operably linked to a suitable plant promoter. Suitable plant promoters are already described above, but in one embodiment, may be the *Zea Mays* Ubiquitin 1 promoter or U6 promoter.

Suitable methods for producing the CRISPR nucleic acids and vectors system are known, and for example are published in Molecular Plant (Ma et al., 2015, Molecular Plant, DOI: 10.1016/j.molp.2015.04.007), which is incorporated herein by reference.

In an alternative aspect of the invention, the nucleic acid construct comprises at least one nucleic acid sequence that encodes a TAL effector, wherein said effector targets a MRC gene and/or promoter sequence, preferably selected from SEQ ID NO 40 to 43. Methods for designing a TAL effector would be well known to the skilled person, given the target sequence. Examples of suitable methods are given in Sanjana et al., and Cermak T et al, both incorporated herein by reference. Preferably, said nucleic acid construct comprises two nucleic acid sequences encoding a TAL effector, to produce a TALEN pair. In a further embodiment, the nucleic acid construct further comprises a sequence-specific nuclease (SSN). Preferably such SSN is a endonuclease such as FokI. In a further embodiment, the TALENs are assembled by the Golden Gate cloning method in a single plasmid or nucleic acid construct.

In another aspect of the invention, there is provided a sgRNA molecule, wherein the sgRNA molecule comprises a crRNA sequence and a tracrRNA sequence and wherein the crRNA sequence can bind to at least one sequence selected from SEQ ID NOs 39 to 42 or a variant thereof. In one embodiment, the nucleic sequence of the sgRNA molecule is defined in any of SEQ ID NO: 48 to 51 or variant thereof. In other words, the RNA sequence of the sgRNA is encoded by a nucleic acid sequence selected from SEQ ID NO: 48 to 51. In one example only, the RNA sequence of one sgRNA of the invention is defined in SEQ ID NO: 52 to 55 or a variant thereof. A "variant" is as defined herein. In one embodiment, the sgRNA molecule may comprise at least one chemical modification, for example that enhances its stability and/or binding affinity to the target sequence or the crRNA sequence to the tracrRNA sequence. Such modifications would be well known to the skilled person, and include for example, but not limited to, the modifications described in Rahdar et al., 2015, incorporated herein by reference. In this example the crRNA may comprise a phosphorothioate backbone modification, such as 2'-fluoro (2'-F), 2'-O-methyl (2'-O-Me) and S-constrained ethyl (CET) substitutions.

In another aspect of the invention, there is provided an isolated nucleic acid sequence that encodes for a protospacer element (as defined in any of SEQ ID NOs 43 to 46), or a sgRNA (as described in any of SEQ ID NO: 48 to 51). There is also provided an isolated sgRNA molecule as defined in any of SEQ ID NO: 52 to 55.

In another aspect of the invention, there is provided a plant or part thereof or at least one isolated plant cell transfected with at least one nucleic acid construct as described herein. Cas9 and sgRNA may be combined or in separate expression vectors (or nucleic acid constructs, such terms are used interchangeably). In other words, in one embodiment, an isolated plant cell is transfected with a single nucleic acid construct comprising both sgRNA and Cas9 as described in detail above. In an alternative embodiment, an isolated plant cell is transfected with two nucleic acid constructs, a first nucleic acid construct comprising at least one sgRNA as defined above and a second nucleic acid construct comprising Cas9 or a functional variant or homolog thereof. The second nucleic acid construct may be transfected below, after or concurrently with the first nucleic acid construct. The advantage of a separate, second construct comprising a cas protein is that the nucleic acid construct encoding at least one sgRNA can be paired with any type of cas protein, as described herein, and therefore are not limited to a single cas function (as would be the case when both cas and sgRNA are encoded on the same nucleic acid construct).

In one embodiment, the nucleic acid construct comprising a cas protein is transfected first and is stably incorporated into the genome, before the second transfection with a nucleic acid construct comprising at least one sgRNA nucleic acid. In an alternative embodiment, a plant or part thereof or at least one isolated plant cell is transfected with mRNA encoding a cas protein and co-transfected with at least one nucleic acid construct as defined herein. Alternatively, as described in Example 2, the nucleic acid constructs can be transiently expressed in the target plant cell.

Cas9 expression vectors for use in the present invention can be constructed as described in the art. In one example, the expression vector comprises a nucleic acid sequence as defined in SEQ ID NO: 56 or a functional variant or homolog thereof, wherein said nucleic acid sequence is operably linked to a suitable promoter. Examples of suitable promoters include the Actin, CaMV35S, wheat U6 or maize ubiquitin (e.g. Ubi1) promoter, as described above.

In an alternative aspect of the present invention, there is provided an isolated plant cell (transiently or stably) transfected with at least one nucleic acid construct or sgRNA molecule as described herein.

In a further aspect of the invention, there is provided a genetically modified or edited plant comprising the transfected cell described herein. In one embodiment, the nucleic acid construct or constructs may be integrated in a stable form. In an alternative embodiment, the nucleic acid construct or constructs are not integrated (i.e. are transiently expressed). Accordingly, in a preferred embodiment, the genetically modified plant is free of any sgRNA and/or Cas protein nucleic acid. In other words, the plant is transgene free.

The term "introduction", "transfection" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art.

The transfer of foreign genes into the genome of a plant is called transformation. Transformation of plants is now a routine technique in many species. Any of several transformation methods known to the skilled person may be used to introduce the nucleic acid construct or sgRNA molecule of interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant (microinjection), gene guns (or biolistic particle delivery systems (biolistics)) as described in the examples, lipofection, transformation using viruses or pollen and microprojection. Methods may be selected from the calcium/polyethylene glycol method for protoplasts, ultrasound-mediated gene transfection, optical or laser transfection, transfection using silicon carbide fibers, electroporation of protoplasts, microinjection into plant material, DNA or RNA-coated particle bombardment, infection with (non-integrative) viruses and the like. Transgenic plants, can also be produced via *Agrobacterium tumefaciens* mediated transformation, including but not limited to using the floral dip/*Agrobacterium* vacuum infiltration method as described in Clough & Bent (1998) and incorporated herein by reference.

Accordingly, in one embodiment, at least one nucleic acid construct or sgRNA molecule as described herein can be introduced to at least one plant cell using any of the above described methods. In an alternative embodiment, any of the nucleic acid constructs described herein may be first transcribed to form a preassembled Cas9-sgRNA ribonucleoprotein and then delivered to at least one plant cell using any of the above described methods, such as lipofection, electroporation or microinjection.

Optionally, to select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. As described in the examples, a suitable marker can be bar-phosphinothricin or PPT. Alternatively, the transformed plants are screened for the presence of a selectable marker, such as, but not limited to, GFP, GUS (β-glucuronidase). Other examples would be readily known to the skilled person. Alternatively, no selection is performed, and the seeds obtained in the above-described manner are planted and grown and MRC expression or protein levels measured at an appropriate time using standard techniques in the art. This alternative, which avoids the introduction of transgenes, is preferable to produce transgene-free plants.

Following DNA transfer and regeneration, putatively transformed plants may also be evaluated, for instance using PCR to detect the presence of the gene of interest, copy number and/or genomic organisation. Alternatively or additionally, integration and expression levels of the newly introduced DNA may be monitored using Southern, Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

In a further related aspect of the invention, there is also provided, a method of obtaining a genetically modified plant as described herein, the method comprising
  a. selecting a part of the plant;
  b. transfecting at least one cell of the part of the plant of paragraph (a) with at least one nucleic acid construct as described herein or at least one sgRNA molecule as described herein, using the transfection or transformation techniques described above;
  c. regenerating at least one plant derived from the transfected cell or cells;
  d. selecting one or more plants obtained according to paragraph (c) that show altered expression or activity of MRC.

In a further embodiment, the method also comprises the step of screening the genetically modified plant for SSN (preferably CRISPR)-induced mutations in the MRC gene or promoter sequence. In one embodiment, the method comprises obtaining a DNA sample from a transformed plant and carrying out DNA amplification to detect a mutation in at least one MRC gene or promoter sequence.

In a further embodiment, the methods comprise generating stable T2 plants preferably homozygous for the mutation (that is a mutation in in at least one MRC gene or promoter sequence).

Plants that have a mutation in at least one MRC gene or promoter sequence can also be crossed with another plant also containing at least one mutation in at least one MRC gene or promoter sequence to obtain plants with additional mutations in the MRC gene or promoter sequence. The combinations will be apparent to the skilled person. Accordingly, this method can be used to generate a T2 plants with mutations on all or an increased number of homologs, when compared to the number of homolog mutations in a single T1 plant transformed as described above.

A plant obtained or obtainable by the methods described above is also within the scope of the invention.

A genetically altered plant of the present invention may also be obtained by transference of any of the sequences of the invention by crossing, e.g., using pollen of the genetically altered plant described herein to pollinate a wild-type or control plant, or pollinating the gynoecia of plants described herein with other pollen that does not contain a mutation in at least one of the MRC gene or promoter sequence. The methods for obtaining the plant of the invention are not exclusively limited to those described in this paragraph; for example, genetic transformation of germ cells from the ear of wheat could be carried out as mentioned, but without having to regenerate a plant afterward.

In a further final aspect of the invention, there is provided a method of screening a population of plants and identifying and/or selecting a plant that will have altered expression and/or activity of MRC and therefore an alteration in granule size distribution in a plant, as described herein, compared to a control or wild-type plant, the method comprising detecting at least one polymorphism or mutation in the MRC gene and/or promoter, wherein said mutation or polymorphism leads to an alteration in the level of expression and/or activity of the MRC protein compared to the level in a plant not carrying said mutation or polymorphism (e.g. a control or wild-type plant). Said mutation or polymorphism may comprise at least one insertion and/or at least one deletion and/or substitution.

Suitable tests for assessing the presence of a polymorphism would be well known to the skilled person, and include but are not limited to, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). In one embodiment, Kompetitive Allele Specific PCR (KASP) genotyping is used.

The method may also comprise the step of assessing whether the polymorphism has an effect on starch granule size distribution as described herein. Methods to screen for an effect on granule size distribution would be well known to the skilled person, but could be carried out using a coulter counter, a microscope, a flow cytometer or any other particle sizing instrument.

In one embodiment, the method comprises
  a) obtaining a nucleic acid sample from a plant and
  b) carrying out nucleic acid amplification of one or more MRC gene and/or promoter alleles using one or more primer pairs.

In a further embodiment, the method may further comprise introgressing the chromosomal region comprising at least one of said low-MRC-expressing/activity polymorphisms into a second plant or plant germplasm to produce an introgressed plant or plant germplasm. Preferably the expression or activity of MRC in said second plant will be altered (compared to a control or wild-type plant), and more preferably said second plant will display an alteration in at least one of starch granule size, number and distribution, as described above.

In a further aspect of the invention there is provided a method of altering starch granule size distribution, as described above in a plant, the method comprising
  a. screening a population of plants for at least one plant with at least one of the above described polymorphisms or mutations; and
  b. further altering (i.e. reducing/abolishing or increasing) the expression of at least one MRC nucleic acid and/or altering (i.e. reducing/abolishing or increasing) the activity of a MRC polypeptide in said plant by introducing at least one mutation into the nucleic acid sequence encoding MRC or at least one mutation into the promoter of MRC as described herein or using RNA interference as described herein.

By "further altering" is meant reducing or increasing the level of MRC expression to a level lower or higher than that in the plant with the at least one of the above-described MRC polymorphisms. The terms "reducing" or "increasing"

means a decrease or increase in the levels of MRC expression and/or activity by up to 10%, 20%, 30%, 40%, 50%, 60%, 70%, 80% or 90% when compared to the level in a control plant.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"And/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is now described in the following non-limiting examples.

Example I

MRC Orthologs are Encoded on Chromosomes 6A and 6D

As a first step to determining the role of the starch granule initiation protein, MRC, in wheat endosperm, we scanned the wheat genome for genes encoding MRC orthologs. We ran a BLASTp search using the amino acid sequence of *Arabidopsis* MRC (AtMRC, At4g32190) against the protein database from the RefSeq v1.0 wheat genome on Ensembl plants. The two top protein hits, TraesCS6D02G164600.1 (encoded on chromosome 6D) and TraesCS6A02G180500.1 (encoded on chromosome 6A) both had 33% identity to AtMRC and had low E values (7.6E-39 and 1.0E-38, respectively). The two wheat proteins shared 95% identity, suggesting that they could be homeologs. However, there was no protein hit corresponding to a homeolog on chromosome 6B. To determine whether the 6A- and 6D-encoded proteins were true orthologs of AtMRC, we repeated the phylogenetic analyses of MRC homologs from our previous study (Seung et al., 2018) and included the wheat protein sequences. The 6A and 6D proteins grouped closely together on the tree, distinctly within the grass clade containing the rice and maize sequences (FIG. 6). This confirms that the two proteins are the wheat orthologs of MRC, and will hereafter be referred as TaMRC-6A (TraesCS6A02G180500) and TaMRC-6D (TraesCS6D02G164600).

Figure 1:
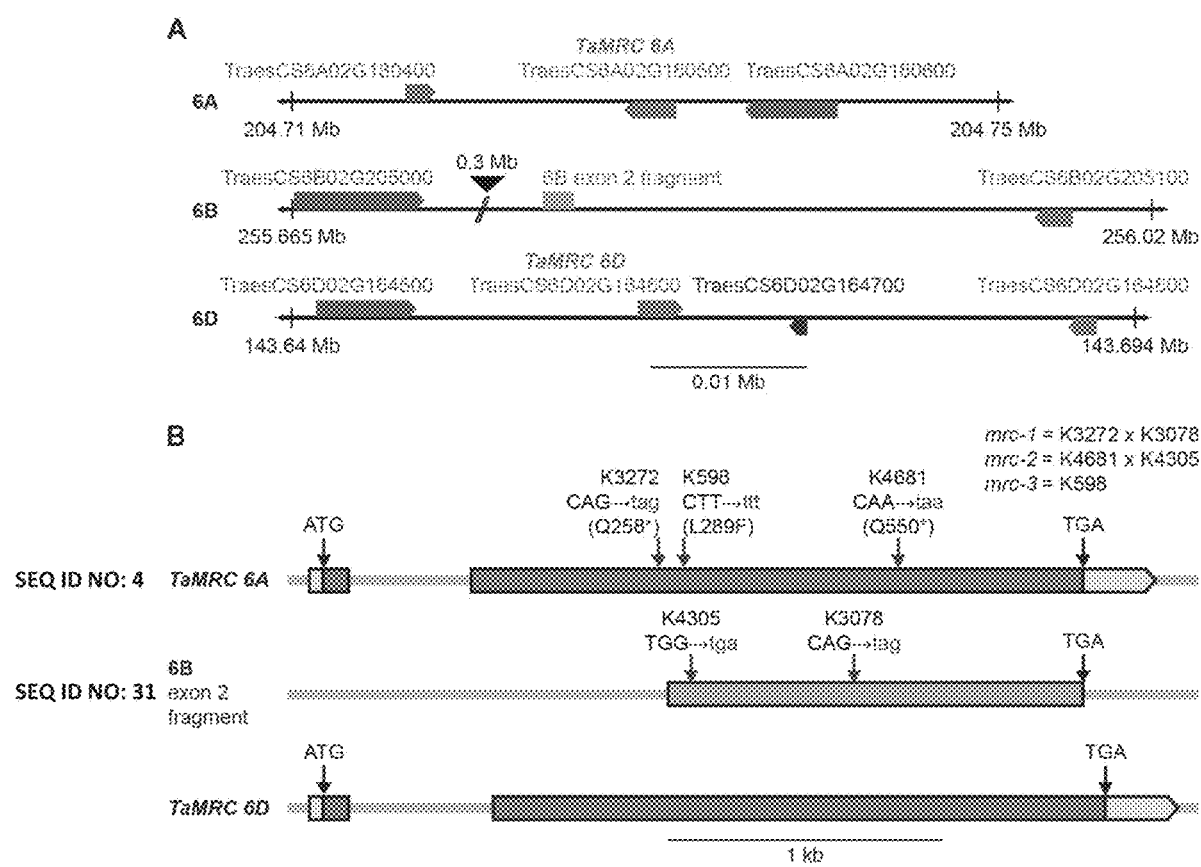
FIG. 1 shows schematic illustrations of MRC homeologs in wheat. A) Location of TaMRC homeologs on chromosome 6A and 6D. The pink boxes represent TaMRC homeologs, while homeologs of the adjacent genes are shown in green (cytochrome P450 family protein), purple (respiratory burst oxidase homolog) and blue (uncharacterised protein). Arrowheads on the boxes indicate direction of transcription. The syntenic region on chromosome 6B has a large insertion, depicted with a black arrowhead. The diagram is drawn to scale, and chromosome coordinates of the region are indicated. B) Gene models of the TaMRC 6A and 6D homeologs and 6B pseudogene. Exons are represented with pink boxes, while light pink boxes represent the 5' and 3' UTRs. The locations of the mutations in the mrc mutants are depicted with red arrows, and the mutated codons/amino acids are shown in red letters.

To examine the wheat gene models and investigate why no homeolog was detected on chromosome 6B, we looked at the genomic regions around the TaMRC-6A and TaMRC-6D loci. The loci were in syntenous positions on the A and D genomes, confirming that they are homeologs (FIG. 1A). Close examination of the gene model showed that the loci had a two-exon structure (FIG. 1B), like the *Arabidopsis* gene (At4g32190.1; Seung et al., 2018). In the syntenous region on chromosome 6B, there was a stretch of sequence that had homology to exon 2, but we failed to find regions with homology to exon 1 upstream of this sequence. Thus, we could not find a full TaMRC gene model in the syntenic position on chromosome 6B, or anywhere else on the B genome. Interestingly, the distance between the exon 2 fragment on chromosome 6B and its upstream neighbouring gene (a respiratory burst oxidase homolog) was much larger than the distance between TaMRC and the homeologs of the same neighbouring gene on 6A and 6D (FIG. 1A). This led us to hypothesise that the 6B copy had been interrupted by a large insertion and had become a pseudogene during the course of wheat evolution.

We then looked at expression data of TaMRC orthologs using the wheat expression browser (Borrill et al., 2016). Transcripts of the 6A and 6D homeologs were detected in both leaves and grains, suggesting that MRC plays a role in these tissues. Transcripts for both homeologs were also detected in the developing endosperm tissue, but only during the early stages of grain development before 12 dpa.

To study the function of MRC in starch synthesis in the wheat endosperm, we obtained mutants in tetraploid wheat (*Triticum turgidum*) defective in MRC. We used the wheat in silico TILLING mutant resource, which contains an EMS-mutagenised population of the durum wheat cultivar, Kronos, and exome-capture sequencing data for identification of lines with mutations of interest (Krasileva et al., 2017). We ordered three mutants that were likely to cause a loss of function in TaMRC-6A (FIG. 1B). The K3272 and K4681 lines contained premature stop codons after the $257^{th}$ and $550^{th}$ amino acids respectively. In addition, we ordered a third line that contained a missense Leu289Phe mutation, which was predicted to be deleterious to protein function by SIFT scoring (Ng and Henikoff, 2006). The $Leu^{289}$ residue is highly conserved in all MRC orthologs, and its mutation to a Phe residue is predicted to disrupt coiled coil formation in the region of the residue (FIG. 6).

Since tetraploid wheat lacks a D genome, and the 6B homeolog of MRC has likely become a pseudogene, we predicted that TaMRC-6A would be the only functional MRC homolog in *T. turgidum*. However, to rule out the possibility that the fragment of exon 2 on chromosome 6B has an effect on MRC function, we also obtained the K4305 and K3078 lines, which contain two different premature stop codon mutations in the putative reading frame of the exon. We generated the mrc-1 lines by crossing K3272 and K3078, and isolated lines homozygous for either the 6A or 6B mutation, or both. The mrc-2 lines were generated in the same way, but the K4681 and K4305 lines were crossed. The mrc-3 line contained the K598 missense mutation, and no crossing was conducted.

MRC is Required for Normal Starch Granule Size Distributions in the Endosperm

Since MRC is involved in granule initiation in *Arabidopsis*, we hypothesised that our wheat mutants would have fewer, but larger starch granules in the endosperm. We therefore first examined starch granule size in iodine-stained thin sections of mature grains of the wheat mrc mutants using light microscopy. The endosperms of the wild type and the mutant grains contained both large A-type granules and smaller B-type granules. However, the mrc-1 and mrc-3 mutants had a noticeable change in granule size, both appearing to contain smaller A-type granules and more B-type granules than the wild type (FIG. 2A). To gain a more detailed view of starch granule size and morphology, we purified granules from mature grains of the wild type and mutants, and examined them with scanning electron microscopy (SEM). Similar to the observations made in the sections of FIG. 2A, the mrc-1 and mrc-3 mutants had smaller A-type granules and more numerous B-type granules than the wild type. Aside from the altered granule size, none of the mutants showed any defect in granule shape: the A-type granules in the wild type and mutants had their characteristic flattened morphology, while the B-type granules had near-spherical morphology that sometimes contained flattened edges (FIG. 2B).

We used a coulter counter to quantify starch granule size in the mutants. Granule size distributions were plotted by measuring the size of at least 100,000 purified starch granules from the wild type and mutants. We observed clear bimodal distributions for all genotypes, with a peak corresponding to A-type granules (>10 μm), and a peak corresponding to B-type granules (<10 μm). However, the area of the B-type granule peak was larger in all mrc mutants than in the wild-type, indicating that starch from the mutants contain a higher proportion of B-type granules (by volume) than wild-type starch (FIG. 2C). Also, the A-type granule peak in the mutants was shifted towards the smaller size range. These alterations in granule size distribution were more severe in mrc-1 and mrc-3 than in mrc-2. We fitted a bimodal mixed gaussian distribution to the data to estimate the total volume of B-type granules, as well as the mean size of the A-type and B-type granules. In mrc-1 and mrc-3, the B-type fraction constituted 19-23% of total starch volume, which was higher than in the mrc-2 mutant (15%) and the wild type (8%) (FIG. 9). However, the mean size of the B-type granules was not significantly altered in the mutants, with the exception of mrc-2, where they were slightly larger. This suggests that the increased proportion of B-type granules in the mrc mutants is primary due to a change in A to B-type granule ratio rather than larger individual B-type granules. However, the increase in the proportion of B-type granules in the mutants was accompanied by a significant decrease in A-type granule size.

To confirm that the TaMRC-6A is the only functional homeolog of MRC in tetraploid wheat, we quantified starch granule size distribution in the full set of homozygous genotypes resulting from the crosses that yielded the mrc-1 and mrc-2 mutants [indicated as aa BB (6A mutant), AA bb (6B mutant) and aa bb (6A and 6B double mutant)]. The size distribution of starch granules was identical between wild type and AA bb, and were similarly altered in aa BB and aa bb genotypes. This provides experimental evidence that the fragment of exon 2 on chromosome 6B does not contribute to granule size distribution and is likely to be a pseudogene (FIG. 7).

These data suggest that TaMRC is required for the normal size distribution of starch granules in wheat endosperm. The difference in the severity of the phenotype between the different mrc mutants could be explained by the position of the premature stop codons in the MRC coding sequence. In mrc-1, the premature stop codon occurs earlier in the coding sequence than in mrc-2. It is possible that the truncated protein in mrc-2 is partially functional. The size distribution of mrc-3 was very similar to that of mrc-1, suggesting that the Leu289Phe mutation severely inhibits protein function.

To test whether these changes in granule size distribution were accompanied by altered total starch content, we measured total starch in the mature grains of the mrc mutants, but we did not observe any significant differences (FIG. 10). We also tested whether starch polymer structure or composition was altered in the mutant. However, even the mutant with the strongest alteration in granule size distribution had normal amylopectin structure and amylose content (FIG. 8). The mrc-1 mutant produced the same grain yield per plant as the wild type and did not have any noticeable growth defects.

Loss of MRC Results in the Early Initiation of B-Type Granules

In wheat endosperm, loss of MRC alters the ratio of A-type and B-type granules, in favour of B-type granules. We reasoned that this could result from two possible scenarios: 1) loss of MRC reduces the number of A-type granules, resulting in a relative increase in B-type granules, or 2) loss of MRC results in more B-type granules and does not affect the number of A-type granules. To distinguish between these two possibilities, we investigated granule initiation in the developing endosperm of the mrc-1 mutant in more detail. We dissected the endosperm of developing grains harvested 8, 14, 20 and 30 days post anthesis (dpa), and measured both the total starch content and numbers of starch granules. The total starch content of the endosperm increased between each time point, and there was no significant difference between the mutant and the wild type at any time point (FIG. 3A). We then quantified the total number of starch granules in the endosperm using the coulter counter. At the 8 dpa timepoint, the mutant and the wild type contained a similar number of starch granules. Interestingly, for the two subsequent time points (14 dpa and 20 dpa), the mutant endosperms contained almost double the number of starch granules of the wild type, despite similar starch contents (FIG. 3B). The largest increase in granule number during grain filling was observed between the 20 and 30 dpa timepoints in the wild type, but was between the 14 and 20 dpa timepoints in the mutant. At the 30 dpa timepoint, the difference in granule number between the mutant and the wild type became less apparent, with no significant differences observed. However, quantification of starch granule number in mature grains showed that the mrc-1 mutant $[(201\pm12)\times10^6$ granules per grain] had significantly more granules than wild type grains $[(157\pm7)\times10^6$ granules per grain] ($p<0.05$ under a two-tailed t-test). We also noted that in both the wild type and mutant, the number of starch granules decreased between 8 and 15 dpa timepoints. The reason for this is unknown, but it has also been observed in previous studies (Howard et al., 2011).

Figure 3:
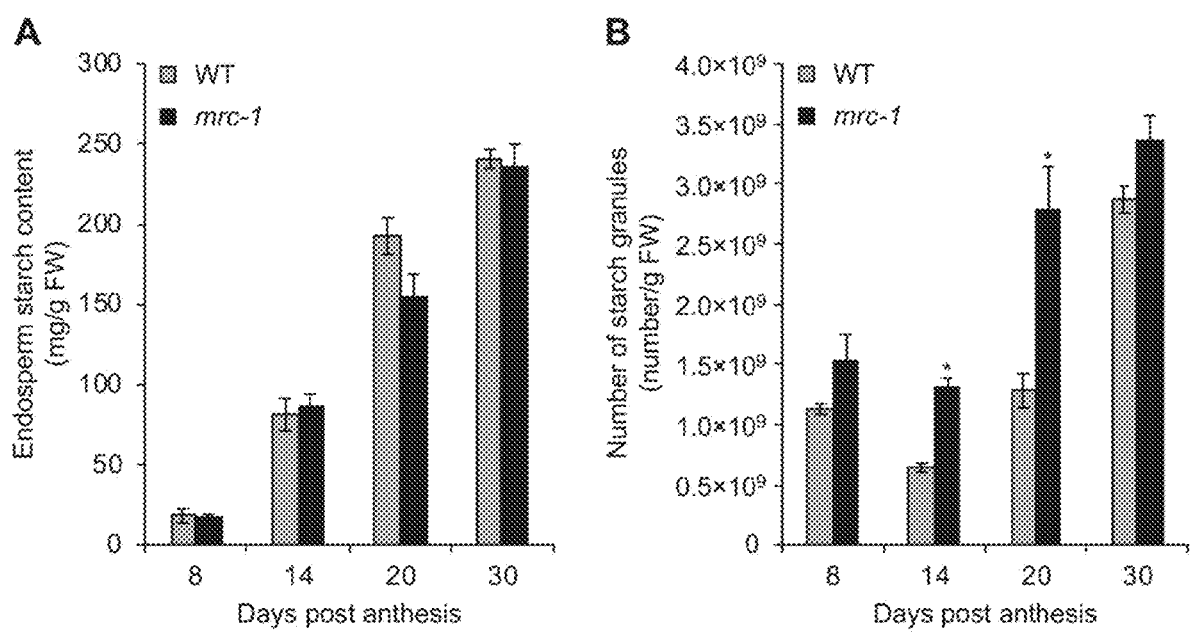
FIG. 3 shows the starch content and granule count in developing endosperm tissue. The endosperm was dissected from developing grains of the wild type (WT) and mrc-1 mutant, harvested at 8, 14, 20 and 30 dpa. A) Starch content of the endosperm. Values are expressed relative to the fresh weight of the dissected endosperm, and are mean±SE of measurements from 3-4 endosperms from developing grains harvested from separate plants. B) Starch granule number in the endosperm. Starch was purified from dissected endosperm and the number of granules was determined using a coulter counter. Values are expressed relative to the fresh weight of the dissected endosperm, and are mean±SE of measurements from 3-4 endosperms from developing grains harvested from separate plants.
Figure 4:
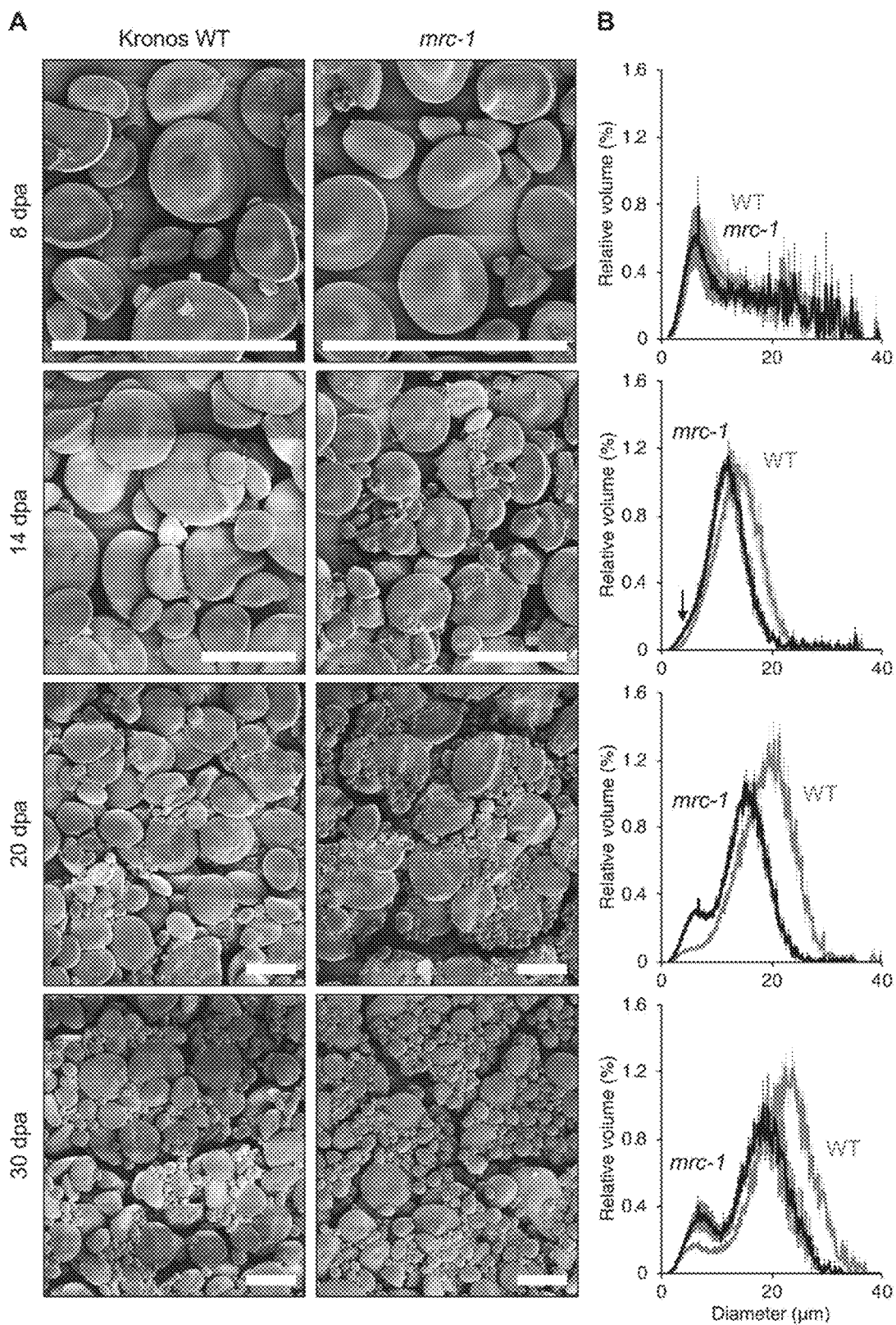
FIG. 4 shows the starch granule size distributions in developing endosperm tissue.

To observe changes in A to B-type granule ratio throughout grain development, we used both scanning electron microscopy and the coulter counter to examine the morphology and size of endosperm starch granules. In the wild type, only A-type granules with their characteristic flattened morphology were observed at the 8 and 14 dpa timepoints, but they grew substantially in size between the two timepoints (FIG. 4). This was consistent with the size distributions from the coulter counter, which showed unimodal distributions for wild-type at both time points. Small, round B-type granules only became prominent at the 20 dpa timepoint in the wild type, but were already present at the 14 dpa timepoint in the mrc-1 mutant. This could be seen as a distinct shoulder that appeared in the granule size distribution of mrc-1 starch at the 14 dpa timepoint, and bimodal distributions at subsequent time points. The A-type granules in the mutant were the same size as those of the wild type at the 8 dpa time point, but gradually became smaller as grain development progressed, particularly as B-type granules were initiated. Taken together, these data suggest that the elevated number of granules between 14-20 dpa in mrc-1 endosperm (observed in FIG. 3B) is due to the premature initiation of B-type granules in the mutant. Presumably, this also restricts the growth of the A-type granules as they compete with the B-type granules for the substrates of starch synthesis.

Normally within amyloplasts, several B-type granules initiate in close proximity-appearing as 'clusters' in between the A-type granules- and at least some B-type granules form in amyloplast stromules (Parker, 1985; Langeveld et al., 2000). Given the unusual timing of B-type granule initiation in mrc-1, we explored whether the loss of MRC also affected the location of B-type granule initiation. First, we harvested grains during their development, subjected them to critical point drying, and imaged sections through the endosperm tissue using SEM. Consistent with the findings from the purified starch granules, B-type granules were prominent already at 15 dpa in the mutant, whereas they only became prominent after 20 dpa in the wild type (FIG. 5A). The B-type granules occurred in clusters in the mutant that resembled those of the wild type. Interestingly, even at the 10 dpa timepoint, clusters of tiny B-type granules were visible in the mutant. In a second approach, we produced sections from developing grain tissue (15 dpa) embedded in resin blocks for imaging by light and electron microscopy. For light microscopy, sections were stained with toluidine blue (a negative stain for starch). At 15 dpa, the most starch granules in the wild type endosperm were flattened A-type granules, and there were very few B-type granules visible (FIG. 5B). However, in the endosperm of the mrc-1 mutant, many clustered B-type granules were present at this time point. Thus, we used transmission electron microscopy (TEM) to investigate whether the multiple B-type granules in mrc-1 occurred within single amyloplasts, particularly in stromules. Indeed, multiple B-type granules were enclosed within a single set of amyloplast membranes, and the elongated morphology of these amyloplast regions strongly suggested that they are stromules (FIG. 5C). Stromules are difficult to observe in two-dimensional electron microscopy sections, and it is difficult to determine the exact percentage of B-type granules in stromules relative to those that are not. Overall, aside from their earlier occurrence in the mutant, we did not notice anything unusual about the location of B-type granules in the mrc-1 mutant.

To conclude, B-type granule initiation during grain development is under both spatial and temporal control. MRC appears to be required for this temporal control, as its absence stimulates the early formation of B-type granules. However, no defects in the spatial control of B-type granule formation were observed in mrc-1 mutants. We therefore propose that MRC acts as a repressor of B-type granule formation in the developing wheat endosperm.

A Novel Role for MRC in Endosperm Starch Synthesis

Figure 2:
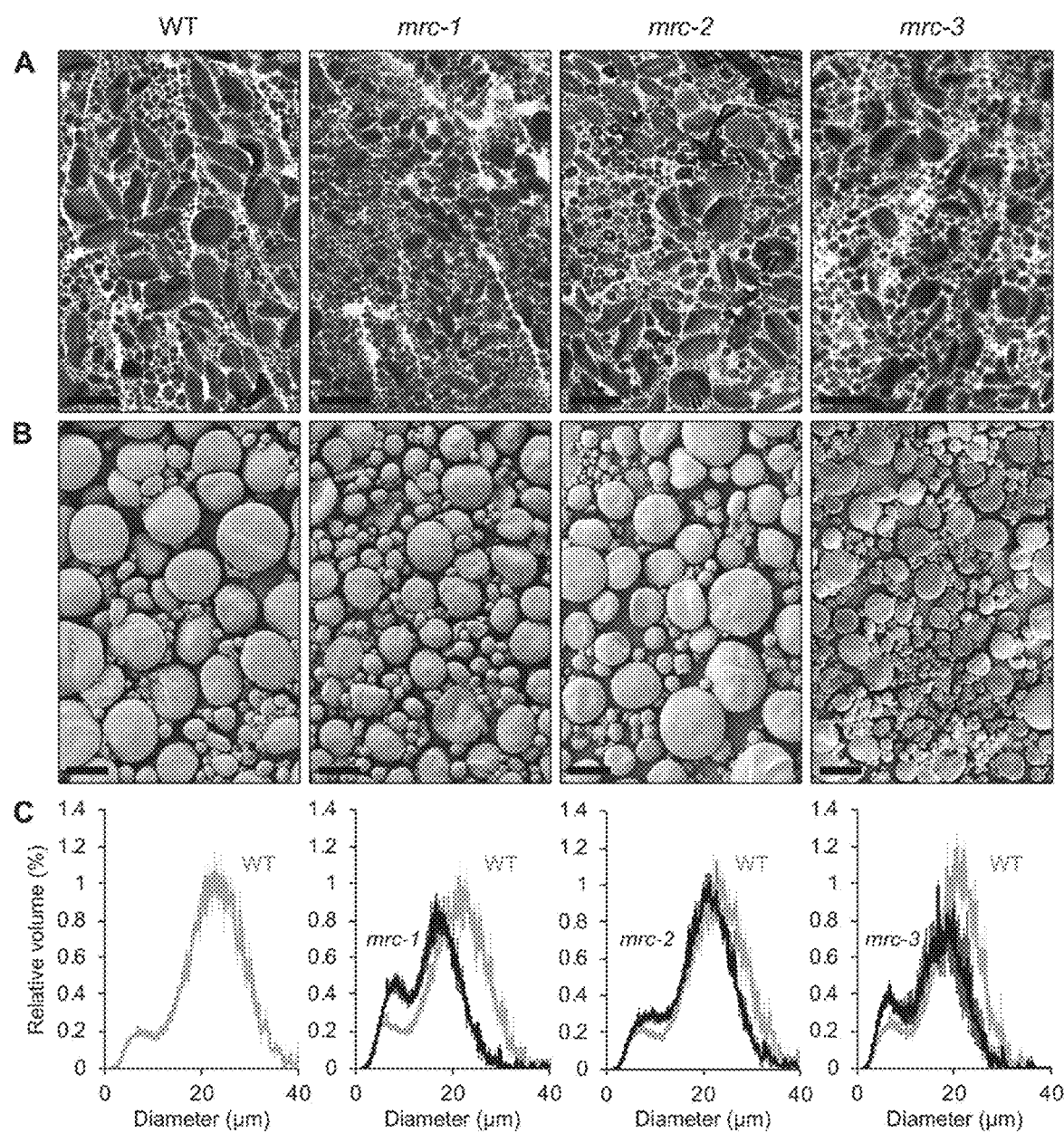
FIG. 2 shows altered starch granule size distribution of endosperm starch in wheat mrc mutants. A) Thin sections of mature endosperm tissue were stained with Lugol's solution and imaged using light microscopy. Bar=40 µm. B) Purified endosperm starch granules were observed using scanning electron microscopy (SEM). Bar=20 µm. C) Starch granule size distribution of endosperm starch. Size distributions were determined by measuring at least 100,000 granules per replicate with a coulter counter. The solid line shows the mean curve (shading represents the SEM) from three replicate determinations. Each replicate used starch purified from three individual grains, and the three replicates represent grains from three different plants.

Factors that regulate the unique spatio-temporal pattern of starch granule initiation in Triticeae endosperm are poorly understood. Here, we discovered a novel role for MRC in the temporal control of granule initiation in the wheat endosperm. Starch from multiple independent TILLING mutants of tetraploid wheat defective in TaMRC-6A had a higher percentage volume of B-type granules than the wild type (FIG. 2). These B-type granules initiated in the mutant up to 10 days earlier than in the wild type (FIGS. 3-5). Despite the unusual timing of initiation, the B-type granules in the mutant had normal round morphology, and as in the wild type, at least some were in amyloplast stromules. Further, the mutants had normal total starch content, amylopectin structure and amylose content. Thus in wheat endosperm, as in *Arabidopsis* leaves, MRC appears to be specifically involved in controlling the initiation step of starch biosynthesis. The premature initiation of B-type granules also appears to have no effect on total starch synthesis rates in the endosperm (FIG. 3; FIG. 10).

Interestingly, MRC is required for the temporal control of B-type granule initiation, but A-type granule initiation appears to proceed normally in its absence. We demonstrated that the increased proportion of B-type granule volume in starch of the mrc mutant does not arise from a suppression of A-type granule initiation. If this were to be the case, we would have expected fewer, larger A-type granules in the mutant. However, at the early stages of grain development (8 dpa), the size, shape and number of A-type granules were identical between the mutant and the wild type (FIGS. 3-4). It was only at the later stages of grain development following B-type granule initiation that the A-type granules became distinctively smaller in the mutant compared to the wild-type. It is likely that the A-type granules in the mutant compete with the early-initiated B-type granules for substrates of granule growth (i.e.: ADP-Glucose). The final number of starch granules per grain was about 25-30% greater in the mutant than the wild type, and granule numbers in the endosperm of both mutant and wild type increased steadily throughout grain development—indicating that granules are continuously initiated after the main wave of B-type granule initiated, albeit at a lower rate. Thus the early initiation of B-type granules in the mutant results in an increased final number of B-type granules. Interestingly, we did not pick up on consistent differences in B-type granule size between mutant and wild type. Taken together, the mrc mutant contains more B-type granules by percentage volume than the wild type because it has a higher number of B-type granules and the same number of smaller A-type granules that occupy less volume.

Overall, our findings that MRC specifically affects the timing of B-type granule initiation supports the hypothesis that the initiation of A- and B-type granules occur through distinct biochemical mechanisms. This hypothesis is also supported by mutants in various Triticeae with reduced B-type granule abundance (e.g.: PTST2 knockdown mutants, discussed below) (Howard et al., 2011; Chia et al., 2017, 2019), and natural variation in B-type granule content (Stoddard, 1999; Stoddard and Sarker, 2000).

MRC can Suppress or Promote Granule Initiation Depending on Tissue

Our work reveals that MRC can both suppress or promote granule initiation depending on tissue. MRC appears to limit B-type granule initiation in the endosperm during early grain development, but promotes granule initiation in leaf chloroplasts. Consistent with this model, MRC is expressed primarily during early grain development, but not at later stages (FIG. 10). By contrast, MRC appears to have an overall promotive effect on granule initiation in *Arabidopsis*, since chloroplasts of mrc mutants have much fewer starch granules than wild-type chloroplasts (Seung et al., 2018;

Vandromme et al., 2018). The role of MRC in promoting granule initiation in leaf chloroplasts is conserved in wheat, since chloroplasts of wheat mrc mutants had a reduced number of starch granules compared to the wild type (FIG. 6). Thus, in wheat, MRC appears to promote granule initiation in leaves, and repress B-type granule initiation in the endosperm.

We do not know how MRC can exert opposite effects in different tissues. Wheat mutants with reduced gene dosage of PTST2 (also called FLO6) have fewer B-type granules with no apparent impact on A-type granules (Chia et al., 2017, 2019). This is the opposite phenotype of mrc mutants, and could suggest that PTST2 and MRC have opposing roles in B-type granule initiation in wheat endosperm. However, full knockout mutants in PTST2 have distorted granule morphology (including A-type granules), resulting from the initiation of compound granule-like structures (Chia et al., 2019). This suggests that PTST2 acts to promote B-type granule initiation, and suppress A-type granule initiation; whereas MRC exclusively suppresses B-type granule formation during early grain development.

The mechanism by which MRC acts in granule initiation in general is not known. Since MRC is a long coiled-coil protein with no known enzymatic domains, it is possible that it can exert opposite functions by interacting with different interaction partners. The Arabidopsis MRC interacts with other granule initiation proteins: it co-purified with PTST2 in leaf extracts (Seung et al., 2018), and interacted directly with SS4 in yeast-two-hybrid experiments (Vandromme et al., 2018). Consistent with these interactions, leaves of Arabidopsis mutants defective in MRC, PTST2 or SS4 all had reduced numbers of starch granules relative to wild type (Roldán et al., 2007; Seung et al., 2017, 2018). We are currently working to determine whether MRC acts with the same interaction partners in the endosperm. However, the lack of similarity between MRC and PTST2 mutants of wheat suggests that MRC may either interact with different partner proteins in the endosperm, or that the dynamics of the interactions between the known partner proteins is different. Interestingly, the Arabidopsis MRC interacts directly with SS4 in yeast-two-hybrid experiments (Vandromme et al., 2018). However, the effect of a full SS4 knockout on granule numbers beyond Arabidopsis leaves in wheat is not yet known.

Alternatively, MRC may play a different role in the endosperm due to a difference in MRC localisation in the endosperm. In Arabidopsis chloroplasts, MRC localises to discrete puncta (Seung et al., 2018). We do not with know where MRC localises in wheat endosperm amyloplasts, particularly in relation to the stromules that contain B-type granules. Also, the fact that B-type granules initiated early in the mrc mutant suggests that there is no substrate-limitation that restricts the formation B-type granule formation earlier in grain development, for example maltooligosaccharides that may act as primers for granule initiation. The formation of stromules does not appear to be limiting, as at least some granules formed in stromules. This could suggest that stromules form earlier than B-type granules in wild type, or that they form as a result of B-type granule initiation. This is currently difficult to investigate using transmission electron microscopy It is also possible that MRC controls the initiation of stromule formation, thus determining the timing of B-type granule initiation.

MRC as a Gene Target for Biotechnological Modification of Starch Granule Size

There is significant industrial interest to manipulate starch granule size in crop species, as granule size affects the physico-chemical properties of starch as well as digestibility (Lindeboom et al., 2004; Jobling, 2004). Our results establish MRC as a promising gene target for modifying starch granule size distribution in wheat, specifically to achieve smaller starch granules and a narrower granule size distribution range than conventional cultivars. Small granules are more efficiently digested than large granules, due to their larger surface area to volume ratio (Dhital et al., 2010). B-type granules in particular have a higher rate of water absorption than A-type granules (Chiotelli and Le Meste, 2002). Wheat mrc starch within the food industry include pasta making, where more B-type granules positively affect pasta quality due to their higher rate of water absorption (Soh et al., 2006). They are also desirable for use in papermaking and biodegradable plastics, and as a binder or carrier material in the pharmaceutical and cosmetics industries (Lindeboom et al., 2004; Santelia and Zeeman, 2010). We demonstrated that there is only one functional homeolog of MRC in tetraploid wheat, and likely only two in hexaploid wheat. This is due to the TaMRC 6B becoming a pseudogene, before the more recent second polyploidisation event that created the hexaploidy. The absence of a homeolog makes it more easier to manipulate gene levels in wheat, since less homeologs need to be mutated. Functional tests can be directly performed on our material to provide a proof of concept that the altered granule size distribution in the mutant improves grain/starch quality in these applications.

The repression of B-type granule initiation is likely to be a role specific to those Triticeae species that have a bimodal size distribution of starch granule size in the endosperm. Thus, it remains to be determined what the role of MRC is in cereal species that do not have a bimodal distribution of starch granules, but those that have compound granules (e.g.: in rice). Also, in oats have a bimodal distribution of starch granules, with large compound granules and smaller simple granules. However, in oat, the smaller granules initiate at the same time as the larger compound granules. Thus, it would be interesting to determine whether MRC also has a role in timing the initiation of the small granules during oat endosperm development.

Materials and Methods

Plant Materials and Growth

EMS mutants of tetraploid wheat (Triticum turgidum cv. Kronos) carrying mutations in TaMRC 6A and the chromosome 6B pseudogene were identified from the wheat in silico TILLING database (Krasileva et al., 2017) and obtained from the John Innes Centre Germplasm Resource Unit. The selected mutants for TaMRC 6A were Kronos3272 (K3272), Kronos598 (K598) and Kronos4681 (K4681); while Kronos4305 (K4305) and Kronos3078 (K3078) were selected for the 6B pseudogene. From these mutants, we generated three different sets of lines. The mrc-1 lines descend from a cross between K3272 and K3078, while the mrc-2 lines descend from a cross between K4681 and K4305. For both crosses, aa BB, AA bb and aa bb genotypes were obtained in the F2 generation. The mrc-3 lines are uncrossed K598 mutants. The KASP markers used to genotype the mutations are provided in FIG. 9.

For all experiments on grains, plants were grown in soil in a controlled environment room fitted with fluorescent lamps and supplemented with LED panels. The chambers were set to provide a 16-h light/8-h dark cycle, with light intensity of 300 µmol photons $m^{-2}$ $s^{-1}$ and relative humidity of 60%. Temperature was set to 20° C. during the light period, and 16° C. during the dark period. Grains were harvested when the entire spike had senesced and dried (approximately 4 months after sowing). The grains from the first three tillers were used for analysis. For experiments on leaves, plants were grown in a controlled environment chamber set to provide 12-h light/12-h dark cycles and constant temperature (20° C.) and relative humidity (60%).

Starch Purification from Mature Grains or Developing Endosperm

Starch was purified from grains using a method modified from (Peng et al., 1999), using 3-6 grains per extraction. Dry grains were soaked overnight at 4° C. in 5 mL of sterile water. The softened grains were homogenised in 10 mL sterile water using a mortar and pestle, and the homogenate was filtered through a 100 µm mesh. The starch was pelleted by centrifugation at 3,000 g for 5 minutes, and resuspended in 2 ml of water. The resuspended starch was loaded on top of a 5 mL 90% Percoll (Sigma) cushion buffered with 50 mM Tris-HCl, pH 8, and was spun at 2,500 g for 15 minutes. We verified that no intact granules were left in the Percoll interface after the spin. The starch pellet was washed twice times with wash buffer (50 mM Tris-HCl, pH 6.8; 10 mM EDTA; 4% SDS; and 10 mM DTT), then three times with water, followed by a final wash in absolute ethanol. The starch was then air dried overnight.

For starch extraction from developing endosperm, the developing grains were harvested at the indicated timepoints and were frozen until analysis. Each grain was thawed just prior to extraction and the endosperm was carefully dissected and placed into a chilled tube and weighed. The tissue was then homogenised in sterile water with a pestle, then filtered through a 60 µm mesh. The pellet was washed three times in 90% Percoll (Sigma) buffered with 50 mM Tris-HCl, pH 8, then three times with wash buffer (as above), followed by three times with water.

Coulter Counter Analysis of Starch Granule Size and Number

For profiles of granule size distribution, purified starch was suspended in Isoton II diluent (Beckman Coulter) and analysed with a Multisizer 4e coulter counter fitted with a 70 µm aperture (Beckman Coulter). At least 100,000 granules were counted and sized for the calculation of size distributions. To calculate the mean A- and B-type granule size, as well as relative B-type granule volume, we fitted a mixed bimodal gaussian curve to the distribution using R.

For calculating numbers of granules per grain or in developing endosperm tissue, starch was purified as described above from a known amount of grains or tissue, and was resuspended in a known volume of Isoton II. The coulter counter was used in volumetric mode to determine granule concentrations within a 1.5 mL or 2 mL aliquot of the starch suspension in Isoton II, which was then used to calculate the number of granules in the original grain/endosperm sample.

Light and Electron Microscopy

For light microscopy of endosperm sections from mature grains, thin sections (1 µm thick) of mature grains were made using a microtome fitted with a glass knife. Sections were mounted onto a glass slide and stained with 3% Lugol's iodine solution (Sigma) prior to imaging.

For light/electron microscopy of developing endosperm tissue, developing grains (15 dpa) were harvested into 4% paraformaldehyde, 2.5% glutaraldehyde in 0.05 M sodium cacodylate, pH 7.4. The osmium post-fixation, dehydration and embedding into LR white resin was done as described above for leaves. For light microscopy, semi-thin sections were stained with toluidine blue, as described for leaves above. For transmission electron microscopy, ultra-thin sections were produced from the embedded grains, and were stained in Uranyl acetate. . . . Imaging was done in a Talos F200C TEM (FEI).

For scanning electron microscopy: For imaging starch granules, a drop of purified starch suspended in water (5 mg/mL) was air-dried onto a glass coverslip attached onto an SEM stub. For imaging sections through developing endosperm, harvested grains were fixed in 2.5% glutaraldehyde in 0.05 M sodium cacodylate, pH 7.4. The fixative was removed by washing with 0.05 M sodium cacodylate, pH 7.4, after which the grains were dehydrated in an ascending ethanol series, and then subjected to critical point drying in a CPD300 instrument (Leica) according to the manufacturer's instructions. Thick transverse sections were produced from the dried grains and were glued onto SEM stubs. All stubs were sputter coated with gold and observed using either a Supra 55 VPFEG (Zeiss) or Nova NanoSEM 450 (FEI) SEM instrument.

Quantification of Starch Content in Leaves and Endosperm

Starch was quantified in leaf tissue according to Smith and Zeeman (2006). Briefly, frozen leaf tissue was ground into a powder with a ball mill and then extracted with perchloric acid. Starch in the insoluble fraction of the extraction was gelatinised at 95° C., and digested to glucose with a-amylase (Megazyme) and amyloglucosidase (Roche). The glucose released was measured using the hexokinase/glucose-6-phosphate dehydrogenase method (Roche). Starch content (in glucose equivalents) was calculated relative to the original dry weight of the analysed grains.

A similar method to leaves was used for starch quantification in grains. Mature grains (5-6 grains) were soaked overnight at 4° C. in 5 mL of sterile water and were homogenised using a mortar and pestle. Developing endosperm tissue was extracted in 1 mL of sterile water with the pestle. Insoluble material in an aliquot of the homogenate was collected by centrifugation at 5,000 g for 5 mins, then washed once in 0.7 M perchloric acid, once in sterile water, then three times in 80% ethanol. The pellet was then resuspended in water. Starch in the pellet was gelatinised by heating at 95° C. for 15 min, then digested using a-amylase (Megazyme) and amyloglucosidase (Roche).

Analysis of Amylopectin Structure and Amylose Content

Amylopectin structure and amylose content was analysed using purified starch. Amylopectin structure in terms of chain length distribution was quantified using High Performance Anion Exchange Chromatography with Pulsed Amperometric Detection (HPAEC-PAD). For amylose content, granules were dispersed in DMSO and quantified using an iodine-binding method.

Example II

Using the TILLING mutant population in hexaploid wheat (cv. Cadenza) (Krasileva et al., 2017), we have isolated mutants defective in each of the genes encoding the MRC proteins in wheat. The wheat mrc mutants have significantly altered starch granule size distribution in the endosperm (FIG. 14). Unlike *Arabidopsis* mrc mutants, which produce larger granules, the endosperm starch of the wheat mrc mutants unexpectedly contains more and smaller granules compared to wild type plants. This is due to the production of smaller A-type granules, and more B-type granules. These alterations in granule size distribution also affect gelatinisation temperature—a key parameter in the physico-chemical behaviour of starch. As such starch from the wheat mrc mutant is expected to have applications in the food industry (such as pasta making where more B-type granules positively improve quality; see above reference), applications where the effective digestion of starch is required (biofuels and feed), and in industries where small starch granules are preferred (e.g., papermaking and pharmaceuticals).

Wheat genome sequences (of cultivars Kronos and Cadenza) were obtained from the Grassroots database (Clavijo et al., 2017). This identified that MRC in wheat is encoded on the short arm of chromosome 6A and 6D. Like in *Arabidopsis* (Seung et al., 2018), the gene has two exons. The genomic DNA sequences of the 6A homeolog (for Kronos and Cadenza) is shown in SEQ ID NO: 4 and 5 respectively, and the 6D (homeolog for Cadenza) is shown in SEQ ID NO: 6. The coding sequences are shown in SEQ ID NOS 7 (6A—Kronos), 8 (6A—Cadenza) and 8 (6D—Cadenza).

Again, no complete homeolog of TaMRC was detected on chromosome 6B. A region with homology to most of exon 2 was detected (sequence provided below), but no region with homology to exon 1 was found. The sequencing data in the region that should contain the first exon was incomplete for both Kronos and Cadenza. However, a complete sequence of the region was available for hexaploid wheat cv. Robigus in the same Grassroots database (*Triticum_aestivum*_Robigus_Elv1.1_scaffold_041678). Using this scaffold, we determined that there is no exon 1 within a 16 kb region upstream of the start of exon 2. It is thus very unlikely that the part of exon 2 detected on 6B is part of a functioning gene, and the 6B homeolog may have been pseudogenised. This is consistent with the results provided in the following sections, where we show that mutation in the 6B pseudogene has no effect on phenotype.

Using the wheat in silico TILLING database (Krasileva et al., 2017), we identified EMS-mutagenised Cadenza lines carrying mutations likely to disrupt the function of the TaMRC 6A and 6D homeologs, and the 6B pseudogene. The TILLING database contains exome-capture sequence data from all individuals in the mutant population (Krasileva et al., 2017). Scaffolds corresponding to the TaMRC genes were found by running the BLAST search function of the database using our gene models as the input. We selected lines with mutations that introduce a premature stop codon in the protein coding sequence, as this is most likely to disrupt gene function (FIG. 11). However, for the 6B pseudogene in Cadenza, we selected one missense mutations as premature stop mutations were not available. The effect of each mutation on protein translation is indicated in FIG. 11 (amino acid numbering is based on the translated sequences provided below). KASP markers that were used to identify and genotype these mutations are also provided in FIG. 11.

To combine mutations in multiple homeologs in the same plant, we conducted a series of crosses. In Cadenza, we have crossed the A homeolog mutants with the B homeolog mutants, and individuals from the F1 generation heterozygous for these mutations were crossed with D homeolog mutants. The F1 generation from the latter cross therefore contains individuals that are heterozygous for mutations in all three homeologs. Using this approach, we isolated the following sets:

mrc-4—Cadenza0199×Cadenza1715×Cadenza1012
mrc-5—Cadenza0199×Cadenza1715×Cadenza1092
mrc-6—Cadenza0377×Cadenza1715×Cadenza1012
mrc-7—Cadenza0377×Cadenza1715×Cadenza1092.

FIG. 12 shows a multiple sequence alignment of AtMRC, HvMRC and TaMRC homeologs from Cadenza and Kronos. The AtMRC and the TaMRC_6A (Cadenza) protein share 33% identity and 58% similarity. Asterisks (*) indicate conserved amino acids, colons (:) indicate highly similar amino acids (according to side chain properties), while point (.) indicate weakly similar amino acids.

Granule size distribution was determined for Cadenza mrc-4 and mrc-5 mutants defective in the A and D homeologs of MRC using a Coulter counter. Two different genotypes were analysed for both mutants—mutants defective in both the 6A and 6D copies of MRC (aa dd), and the negative segregant from the cross (AA DD). The additional mutation of the 6B copy (Cadenza1715) from the cross was segregated out, given that we demonstrated in our Kronos lines that the 6B copy is a pseudogene. As shown in FIG. 14, both aa dd mutants had an altered granule size profile compared to the lines with wild type MRC (AA DD), containing larger B-type granules and smaller A-type granules. The size distribution in these lines most resembled the mrc-2 mutant of Kronos. This is because both mrc-4 and mrc-5 contain a common mutant allele of MRC-6A (Cadenza0199), where the premature stop codon is towards the end of the coding sequence, as in the mrc-2 line of Kronos.

Example III

Specific mutations can be introduced in the MRC gene using established protocols for CRISPR/Cas9-mediated genome editing in wheat (Shan et al., 2014). The method may involve stable wheat transformation (through tissue culture) to introduce a transgene encoding the single guide RNAs (sgRNAs) targeting the MRC sequence, and encoding the Cas9 enzyme. Regenerated plants containing edits in the MRC gene may be detected in the transformants (the T0 generation), and the transgene may be segregated out in the T1 generation. However, a transgene-free approach may also be taken to transiently express the gene-editing components in wheat cells, using the PEG-mediated transformation of wheat protoplasts (Shan et al., 2014) or biolistic bombardment (Zhang et al., 2016; as in the example described below); or biolistic delivery of CRISPR/Cas9 ribonucleoprotein complexes (Liang et al., 2017).

In this example, biolistic transformation of immature wheat embryos allow transient expression of Cas9 with sgRNAs targeting the MRC gene. This is followed by callus induction, and regeneration of edited plants. All steps in this procedure is described in Zhang et al. (2016). First, the appropriate sgRNA (see below) is cloned into the pGE-sgRNA vector (Zhang et al. 2016), which encodes a plant codon-optimised Cas9 driven by the maize Ubiquitin 1 promoter (Wang et al., 2014), and a cloning site for synthetic sgRNA to be synthesised as oligonucleotides and cloned into the vector using the AarI restriction site (Shan et al., 2014). The expression of the sgRNA is driven by the TaU6 promoter. The single pGE-sgRNA vector is then bombarded into isolated wheat embryos. After bombardment, embryos are transferred to callus induction medium. Calli can then be transferred to regeneration medium for plantlet formation. Plantlets are subsequently transferred to rooting medium for shoot formation. Genomic DNA can be extracted from the regenerated plantlets and regions of the MRC gene spanning the sgRNA target site can be amplified using PCR with specific primers. Sequencing the PCR products can reveal plantlets with edited MRC (preferably 1-2 nt deletions or insertions that alter the reading frame for protein translation).

Given the very close similarity in sequence between the 6A and 6D MRC copies, it is possible to produce sgRNAs that target both copies. An ideal sgRNA would be: GCGGC- CATGCGCCTCTCCATCGG (SEQ ID NO: 38) where the start codon of the gene is underlined and the Protospacer Adjacent Motif (PAM) is indicated in italics. A BLAST search against the wheat genome shows no off-targets with the same protospacer sequence next to a PAM. This ideal sgRNA would allow edits to occur at or shortly after the start codon, and if it results in a 1-2 nt deletion or addition, would impact the translation of the rest of the protein. Other ideal sgRNAs that target Exon 1, or the first 100 bp of exon 2 include:

CAGGCAGAAGCTGAGTTTCA*TGG* (SEQ ID NO: 39)

ATTAGATCAAATATAACTGA*TGG* (SEQ ID NO: 40)

AATATAACTGATGGTGATAA*TGG* (SEQ ID NO: 41)

All of these sgRNA target both 6A and 6D copies in Cadenza with no mismatches, and have no detectable off-targets. Similarly these sgRNAs would be able to target MRC 6A in Kronos.

Example IV

We investigated whether the altered granule size distributions in mrc-1 aa bb starch had an impact on the physicochemical properties of starch.
1. Gelatinisation
The gelatinisation temperature of starch was examined using Differential Scanning calorimetry (DSC). Starch (50 mg) was suspended in 1 mL ddH$_2$O in a DSC pan, and a reference pan contained 1 mL ddH$_2$O only. Gelatinisation in the sample was monitored in a MC-DSC instrument (TA instruments), heating from 10° C. to 150° C. at a rate of 1° C./min. The mrc-1 aa bb starch had significantly higher onset and peak gelatinisation temperatures compared to the wild type (FIG. 13). The higher peak temperature was expected from the higher proportion of B-type granules in mrc-1 aa bb starch, since it is known that B-type granules have a higher peak gelatinisation temperature than A-type granules (Singh et al., 2003). There was no significant difference between the mutant and wild type was detected for gelatinisation enthalpy, or in the temperature difference between the measured peak and onset temperatures. Thus, mrc-1 aa bb starch has alterations in the physicochemical properties of starch. However, it should be noted that gelatinisation temperature is only one parameter of starch physicochemical behaviour.
2. Swelling Power
Swelling power is calculated as the change in starch granule volume after incubation in water at a set temperature. We measured swelling power at both 60° C. and 100° C. Panel A of FIG. 15 shows that the mrc-1 mutant has a swelling power at 100° C. that is almost three-fold higher than the wild-type. Panel B of FIG. 15 shows the change in the average volume of granules over time at 60° C., quantified with a Coulter counter. Starch from mrc-1 swells more and faster than starch from the wild type.
Method for Calculating Swelling Power
Starch (around 100 mg-precise mass recorded) was added to 10 mL ddH$_2$O and heated to 60° C. or 100° C. in a water bath for 30 minutes and mixed regularly. Aliquots (250 µL) were collected every 5 minutes and granule size was measured immediately using the Coulter counter. The samples which were used to measure swelling power (as sediment volume change) were removed from the water bath after 30 minutes and left to settle at room temperature for an hour, after which the water was pipetted off to leave only the sediment. The mass of the sediment was then measured, and the swelling power in was calculated using:

$$\text{Swelling power} = \frac{mass_{sediment}}{mass_{initial}}$$

3. Viscosity
Purified endosperm starch (2 g) from wild type (wt), mrc-1 or mrc-2 grains was heated in 25 ml of water, and the resulting viscosity was measured on a Rapid Visco Analyser (RVA; Perten Instruments). The mrc-1 starch had an altered viscosity/pasting profile compared to the wild type starch (FIG. 15C). The mrc-2 starch had a similar alteration, that was an intermediate between the wt and mrc-1. This suggests that altered starch granule size distributions in the mrc mutants can modify the viscosity during gelatinisation and pasting.

Example V

Conversion of Starch to Glucose During Germination
We tested whether grains of the mrc mutants can convert starch to simple sugars more efficiently during germination than the wild type. α-Amylase is synthesised de novo in the aleurone layer within the first two days of germination and is secreted into the endosperm. α-Amylase initiates the digestion of starch, which is eventually degraded to glucose. The overall decrease in granule size in the mutant could allow for a higher starch digestion rate, due to an increase in surface area available for germination. Thus, we measured glucose accumulation in the endosperm at the onset of starch degradation. As shown in FIG. 16, four days into germination, grains of the mrc-1 mutant accumulated significantly more glucose than the wild type and the mrc-2 mutant grains, under a two-tailed t-test (p<0.05).
This process mimics malting, which involves the controlled germination of grains for 4-6 days, and suggests that malt from the mrc mutant grains will have more starting sugars available for fermentation. The more efficient breakdown of starch in vivo may also translate to the later stages of brewing, where the remaining starch in the malted grain is digested during mashing.
Methods:
Grains were germinated on damp filter paper in petri dishes in the dark at 20° C. At each timepoint, three replicate grain samples each containing three grains, were flash frozen in liquid nitrogen. The embryo/sprout was removed from the grain prior to collection. Sugars were then extracted from the grains by homogenising in 0.7 M perchloric acid using a ball mill. Insoluble material was removed, and the supernatant was neutralised using 2 M KOH, 400 mM MES. Glucose was assayed using the hexokinase/glucose-6-phosphate dehydrogenase method (Roche)

Example VI

Kronos2485 (K2485) has the opposite phenotype of mrc-1, mrc-2 and mrc-3, in that it has larger A-type granules and fewer B-type granules than the wild type. Kronos2485 was discovered in an experiment that aimed to use the wheat TILLING mutant resource (described above) to discover mutants carrying amino acid substitutions in MRC that alter granule size distribution. Lines with substitutions in otherwise conserved amino acid positions were obtained from the resource. Starch was extracted from grains from these lines and analysed on a Coulter counter (as described for example 1). Kronos2485 contained significantly fewer B-type granules (FIG. 18). This was accompanied by an increase in A-type granule size. This changes in granule size distribution are opposite to that of mrc-1, suggesting that the amino acid substitution (A625T) is an activating or gain-of-function mutation. MRC protein containing this substitution is likely to over-suppress B-type granule formation, leading to fewer B-type granules. This would provide more substrates (i.e.: ADP-Glucose) for A-type granule growth during grain development, leading to the larger A-type granules.

During this experiment, two more lines with a similar granule size distribution to Kronos2485 were discovered. Kronos2096 (containing a P681S substitution) and Kronos775 (containing a L394F substitution) both had fewer B-type granules than the wild type.

These results demonstrate that depending on the type of MRC mutation, granule size distributions can be altered in opposite directions (smaller or larger). In species with bimodal granule size distributions like wheat, the reduction in B-type granule content induced by these activating mutations achieve an overall reduction in bimodality. Thus, starch from these lines may have some of benefits of starch with a unimodal granule distribution, described above.

Example VII

To briefly investigate the potential of using MRC to introduce similar changes in starch granule size distribution in other cereal crops, we checked a public gene expression database to determine if MRC was also expressed in developing rice grains. The gene was robustly expressed in all stages of seed development, particularly at 3-4 dpa (FIG. 20), when starch granules initiate in rice (Matsushima et al., 2015). This hints that the role of MRC in endosperm starch synthesis may be conserved among cereals.

Example VIII

Given that the AtMRC protein forms extensive coiled coils along almost the entire length of the protein (Seung et al., 2018), we used the COILS program (Lupas, 1995; Zimmermann et al., 2017) to predict whether the wheat orthologs also contain coiled coils. Very similar patterns of strong coiled coil predictions were obtained for the AtMRC and TaMRC (6A) proteins (FIG. 22). Thus, TaMRC is also a long coiled coil protein. The exact role of these coiled coils is not known, but since coiled coils can mediate protein-protein interaction with other coiled coil-containing proteins, and AtMRC interacts with AtSS4 (which also contains coiled coils), it is likely that at least some of these coiled coils in MRC mediate an interaction with SS4.

To investigate whether TaMRC could play a role in endosperm starch formation, we used the wheat expression browser to check whether the gene is expressed in the starchy endosperm during grain development (Borrill et al., 2016) (FIG. 23). The 6A and 6D homeologs showed similar levels and patterns of expression, with expression higher in the early stages of grain development (6-9 dpa) than the later stages (12-30 dpa). Interestingly, this peak in expression during early grain development corresponds to when the synthesis of the A-type granules initiate.

To investigate whether the size distribution of endosperm starch was affected by the absence of TaMRC, we isolated starch from the endosperm of the mrc-1 and mrc-2 mutants. The mutants and wild type plants were grown in soil (1 L capacity pots) in a controlled environment room (Conviron) fitted with fluorescent lamps and supplemented with LED panels. The chambers were set to provide a 16-h light/8-h dark cycle, with light intensity of 300 µmol photons $m^{-2}$ $s^{-1}$ and humidity of 60%. Temperature was set to 20° C. during the light period, and 16° C. during the dark period. Grains were harvested when the entire spike had senesced and dried. The grains from the middle of the first three spikes were used for analysis.

Starch was isolated from 6 grains per biological replicate (each replicate being an individual plant). The dry grains were soaked overnight at 4° C. in 5 mL of sterile $ddH_2O$. The softened grains were homogenised in 10 mL sterile $ddH_2O$ using a mortar and pestle, and the homogenate was filtered through a 100 um mesh. The starch was pelleted by centrifugation at 4,000 g for 5 minutes, and then resuspended in 2 mL of water. The resuspended starch was loaded on top of a 90% Percoll cushion (5 mL; Sigma), and was spun at 2,500 g for 10 minutes. The starch pellet was washed three times with wash buffer (50 mM Tris-HCl, pH 6.8; 10 mM EDTA; 4% SDS; and 10 mM DTT), then three times with water, followed by a final wash in absolute ethanol. The starch was then air dried overnight.

The starch granule morphology was then observed by Scanning Electron Microscopy (SEM). The purified starch was resuspended in water (5 mg/mL) and 2 µL was applied to a SEM stub. The starch was air dried overnight on the stub before sputter coating with gold, and was observed using a Supra 55 VP FEG SEM (Zeiss).

The starch granules from the mrc-1 aa bb mutant was noticeably different in size from the wild-type WT Kronos (AA BB) starch (FIG. 2B). The starch in the mutant appeared to contain more B-type granules than the starch from the wild type, and the A-type granules were noticeably smaller in the mutant. The mrc-2 aa bb mutant also had smaller granules than the wild type, but to a lesser extent than mrc-1 aa bb. Aside from the difference in size, no other morphological alterations were observed. In both WT and mutant starch, the A-type granules had their typical lenticular shape, while the B-type granules were round.

Since qualitative alterations in granule size distribution were observed in the mrc mutant starch with SEM, we then quantitatively measured granule size using two different methods. Firstly, we used a particle size analyser, which uses laser scattering to measure the total volume of particles of a given size, expressed as a percentage of the total volume of all particles. Purified starch was suspended in water and measured on the Coulter LS-230 instrument (Beckman Coulter). In WT starch, a clear bimodal distribution was observed, with an A-type granule peak around 28 µm, and a B-type granule peak around 5 µm (FIG. 2C). However, the starch from mrc-1 aa bb mutants had a highly altered size profile compared to the wild type—the A-type granule peak was shifted to 21 µm, and the B-type granule peak was higher and shifted towards the larger sizes, appearing as a peak at 8 µm which was not completely resolved from the A-type granule peak. Since the A-type granules are smaller in the mutant, and B-type granules are larger, the profile more closely resembled unimodal distribution of granule size. Similar changes were observed in mrc-2 aa bb mutants, although the phenotype was not as strong as in mrc-1 aa bb.

We also analysed starch granule size using light microscopy. Purified starch was resuspended at 5 mg/mL in water, and 2 uL of the suspension was added to 100 uL 10% Lugol's iodine solution (Sigma) in a well of a microtitre plate. The starch in the well was imaged using an AxioObserver microscope (Zeiss). Starch granule area in the images was measured using the Particle Analysis plugin of ImageJ software (v.2.0.0;). The area was used to calculate diameter, assuming the granules were perfect circles. Unlike the first method with the particle size analyser, this method calculates of the percentage of granules with a given size relative to the total number of granules (rather than as volumes), and is a direct measure of size (rather than inferred from laser scattering). This analysis is not able to measure A-type granule size distribution accurately, as they constitute less than 10% of the total number of granules. However, B-type granule size can be measured accurately. The mrc-1 aa bb mutant had a clear increase in B-type granule size relative to the wild type, with fewer granules in the 1-5 µm size range, and more granules in the 6-13 µm size range (FIG. 24). Interestingly, exactly the same B-type granule size profile was obtained between mrc-1 aa bb and mrc-1 aa BB, suggesting that the mutation in the A homeolog of Kronos alone is sufficient to observe the phenotype. This is consistent with the hypothesis that the B genome copy is a pseudogene.

We investigated whether the altered granule size distributions in mrc-1 aa bb starch had an impact on the gelatinisation temperature of starch using Differential Scanning calorimetry (DSC). Starch (50 mg) was suspended in 1 mL ddH$_2$O in a DSC pan, and a reference pan contained 1 mL ddH$_2$O only. Gelatinisation in the sample was monitored in a MC-DSC instrument (TA instruments), heating from 10° C. to 150° C. at a rate of 1° C./min. The mrc-1 aa bb starch had significantly higher onset and peak gelatinisation temperatures compared to the wild type (FIG. 21). The higher peak temperature was expected from the higher proportion of B-type granules in mrc-1 aa bb starch, since it is known that B-type granules have a higher peak gelatinisation temperature than A-type granules (Singh et al., 2003). No significant difference between the mutant and wild type was detected for gelatinisation enthalpy, or in the temperature difference between the measured peak and onset temperatures. Thus, mrc-1 aa bb starch has alterations in the physicochemical properties of starch. However, it should be noted that gelatinisation temperature is only one parameter of starch physicochemical behaviour.

To briefly investigate the potential of using MRC to introduce similar changes in starch granule size distribution in other cereal crops, we checked a public gene expression database to determine if MRC was also expressed in developing rice grains. The gene was robustly expressed in all stages of seed development, particularly at 3-4 dpa (FIG. 20), when starch granules initiate in rice (Matsushima et al., 2015). This hints that the role of MRC in endosperm starch synthesis may be conserved among cereals.

The mrc-1 and mrc-2 aa bb mutants were indistinguishable from wild type Kronos plants in terms of plant size and morphology, as well as tiller number and flowering time. The mature grains from the mutants were similar in size and morphology to wild-type grains.

To verify that the mrc mutations did not affect the amount of starch in the mature grains, we measured grain total starch content. The mature grains (5-6 grains) were soaked overnight at 4° C. in 5 mL of sterile ddH$_2$O, and were homogenised using a mortar and pestle. Insoluble material in the homogenate was collected by centrifugation at 5,000 g for 5 mins, then washed once in 0.7 M perchloric acid, once in ddH$_2$O, then three times in 80% EtOH. The pellet was then resuspended in ddH$_2$O. Starch in the pellet was gelatinised by heating at 95° C. for 15 min, then digested using a-amylase (Megazyme) and amyloglucosidase (Roche). The glucose released was measured using the hexokinase/glucose-6-phosphate dehydrogenase method (Roche). Starch content (in glucose equivalents) was calculated relative to the original dry weight of the analysed grains.

No changes in total starch content was observed in any of the mrc-1 mutants (FIG. 10). This suggests that the mutation can alter the size distribution of granules in the endosperm with no negative impact on the total amount of starch synthesised.

REFERENCES

Bechtel D B, Zayas I, Kaleikau L, Pomeranz Y. 1990. Size-distribution of wheat starch granules during endosperm development. Cereal Chemistry 67, 59-63.

Borrill P, Ramirez-Gonzalez R, Uauy C. 2016. expVIP: a customisable RNA-seq data analysis and visualisation platform. Plant Physiology 170, pp. 01667.2015.

Cermak, T et al. Efficient design and assembly of custom TALEN and other TAL effector-based constructs for DNA targeting. Nucleic acid Res. 39 (2011).

Chia, T.; Adamski, N. M.; Saccomanno, B.; Greenland, A.; Nash, A.; Uauy, C.; Trafford, K.; Lunn, J. 2017 Transfer of a starch phenotype from wild wheat to bread wheat by deletion of a locus controlling B-type starch granule content. J. Exp. Bot.

Chia T, Chirico M, King R, Ramirez-Gonzalez R, Saccomanno B, Seung D, Simmonds J, Trick M, Uauy C, Verhoeven T, Trafford K. 2019. A carbohydrate-binding protein, FLOURY ENDOSPERM 6 influences the initiation of A- and B-type starch granules in wheat (Preprint)

Chiotelli, E. and Le Meste, M. (2002). Effect of Small and Large Wheat Starch Granules on Thermomechanical Behavior of Starch. Cereal Chem. 79:286-293.

Clavijo B J, Venturini L, Schudoma C, et al. 2017. An improved assembly and annotation of the allohexaploid wheat genome identifies complete families of agronomic genes and provides genomic evidence for chromosomal translocations. Genome Research 27, 885-896.

Clough S J, Bent A F. 1998. Floral dip: a simplified method for *Agrobacterium*-mediated transformation of *Arabidopsis thaliana*. Plant J. 16 (6): 735-43.

Comai L, Young K, Till B J, Reynolds S H, Greene E A, Codoma C A, Enns L C, Johnson J E, Burtner C, Odden A R, Heinkoff. 2004. Efficient discovery of DNA polymorphisms in natural populations by Ecotilling. Plant J. 37 (5): 778-86.

Crumpton-Taylor M, Grandison S, Png K M Y, Bushby A J, Smith A M. 2012. Control of starch granule numbers in *Arabidopsis* chloroplasts. Plant Physiology 158, 905-916.

Crumpton-Taylor M, Pike M, Lu K J, Hylton C M, Feil R, Eicke S, Lunn J E, Zeeman S C, Smith A M. 2013. Starch synthase 4 is essential for coordination of starch granule formation with chloroplast division during *Arabidopsis* leaf expansion. New Phytologist 200, 1064-1075.

Dhital S, Shrestha A K, Gidley M J. 2010. Relationship between granule size and in vitro digestibility of maize and potato starches. Carbohydrate Polymers 82, 480-488.

Emanuelsson O, Brunak S, von Heijne G, Nielsen H. 2007. Locating proteins in the cell using TargetP, SignalP and related tools. Nature protocols 2, 953-971.

Goren A, Ashlock D, Tetlow I J. 2018. Starch formation inside plastids of higher plants. Protoplasma, 1-22.

Henikoff S, Till B J, Comai L. 2004. TILLING. Traditional mutagenesis meets functional genomics. Plant Physiol. 135 (2): 630-6.

Howard T, Rejab N A, Griffiths S, Leigh F, Leverington-Waite M, Simmonds J, Uauy C, Trafford K. 2011. Identification of a major QTL controlling the content of B-type starch granules in *Aegilops*. Journal of Experimental Botany 62, 2217-2228.

Jane J F. 1994. Anthology of Starch Granule Morphology by Scanning Electron Microscopy. Stach/Stärke 46, 121-129.

Jane J, Chen Y Y, Lee L F, Mcpherson A E, Wong K S, Radosavljevic M, Kasemsuwan T. 1999. Effects of amylopectin branch chain length and amylose content on the gelatinization and pasting properties of starch. Cereal Chemistry 76, 629-637.

Jobling S. 2004. Improving starch for food and industrial applications. Current Opinion in Plant Biology 7, 210-218.

Komor, A. C.; Kim, Y. B.; Packer, M. S.; Zuris, J. A.; Liu, D. R. 2016. Programmable editing of a target base in genomic DNA without double-stranded DNA cleavage. *Nature* 533, 420-424

Krasileva K V., Vasquez-Gross H A, Howell T, et al. 2017. Uncovering hidden variation in polyploid wheat. Proceedings of the National Academy of Sciences 114, E913-E921.

Krysan P J, Young J C, Sussman M R. 1999. T-DNA as an insertional mutagen in *Arabidopsis*. Plant Cell. 11 (12): 2283-90.

Kunkel T A. 1985. Rapid and efficient dite-specifc mutagenesis without phenotypic selection. PNAS. 82 (2): 488-92.

Kunkel T A, Roberts J D, Zakour R A. 1987. Rapid and efficient dite-specifc mutagenesis without phenotypic selection. Methods Enzmol. 154. 367-82.

Langeveld S M J, Van wijk R, Stuurman N, Kijne J W, de Pater S. 2000. B-type granule containing protrusions and interconnections between amyloplasts in developing wheat endosperm revealed by transmission electron microscopy and GFP expression. Journal of Experimental Botany 51, 1357-1361.

Liang Z, Chen K, Li T, et al. 2017. Efficient DNA-free genome editing of bread wheat using CRISPR/Cas9 ribonucleoprotein complexes. Nature Communications 8, 1-5.

Lindeboom N, Chang P R, Tyler R T. 2004. Analytical, biochemical and physicochemical aspects of starch granule size, with emphasis on small granule starches: a review. Starch Stärke 56, 89-99.

Lupas A. 1995. Prediction and analysis of coiled-coil structures. Methods in Enzymology 266, 513-525.

Ma X, Zhang Q, Zhu Q, Liu W, Chen Y, Qiu R, Wang B, Yang Z, Li H, Lin Y, Xie Y, Shen R, Chen S, Wang Z, Chen Y, Guo J, Chen L, Zhao X, Dong Z, Liu Y. 2015. A Robust CRISPR/Cas9 System for Convenient, High-Efficiency Multiplex Genome Editing in Monocot and Dicot Plants. 8 (8): 1274-84.

Mason J M, Arndt K M. 2004. Coiled coil domains: stability, specificity, and biological implications. Chembiochem: a European journal of chemical biology 5, 170-176.

Matsushima R, Maekawa M, Sakamoto W. 2015. Geometrical Formation of Compound Starch Grains in Rice Implements Voronoi Diagram. Plant and Cell Physiology 56, 2150-2157.

Ng P C, Henikoff S. Predicting the effects of amino acid substitutions on protein function. Annu Rev Genomics Hum Genet. 2006; 7:61-80. doi: 10.1146/annurev.genom.7.080505.115630

Parker M L. 1985. The relationship between A-type and B-type starch granules in the developing endosperm of wheat. Journal of Cereal Science 3, 271-278.

Peng, M., Gao, M., Abdel-Aal, E-S. M., Hucl, P., Chibbar, R. N., 1999. Separation and characterization of A- and B-type starch granules in wheat endosperm. Cereal Chem. 76, 375-379.

Pfister B, Zeeman S C. 2016. Formation of starch in plant cells. Cellular and Molecular Life Sciences.

Roldán I, Wattebled F, Mercedes Lucas M, Delvallé D, Planchot V, Jiménez S, Pérez R, Ball S, D'Hulst C, Mérida A. 2007. The phenotype of soluble starch synthase I V defective mutants of *Arabidopsis thaliana* suggests a novel function of elongation enzymes in the control of starch granule formation. Plant Journal 49, 492-504.

Radhar M, McMahon M A, Prakash T P, Swayze E E, Bennett F, Cleveland D W. 2015. Synthetic CRISPR RNA-Cas9-guided genome editing in human cells. PNAS. 112 (51) E7110-E7117.

Neville E Sanjana, Le Cong, Yang Zhou, Margaret M Cunniff, Guoping Feng & Feng Zhang. 2012. A transcription activator-like effector toolbox for genome engineering. Nature Protocols 7, 171-192

Sambrook, et al., (1989) Molecular Cloning: A Library Manual (2d ed., Cold Spring Harbor Laboratory Press, Plainview, New York).

Santelia D, Zeeman S C. 2010. Progress in *Arabidopsis* starch research and potential biotechnological applications. Current Opinion in Biotechnology 22, 271-280.

Seung D, Boudet J, Monroe J D, Schreier T B, David L C, Abt M, Lu K-J, Zanella M, Zeeman S C. 2017. Homologs of PROTEIN TARGETING TO STARCH control starch granule initiation in *Arabidopsis* leaves. The Plant Cell 29, 1657-1677.

Seung D, Schreier T, Bürgy L, Eicke S, Zeeman S. 2018. Two plastidial coiled-coil proteins are essential for normal starch granule initiation in *Arabidopsis*. Plant Cell, In press.

Seung D, Soyk S, Coiro M, Maier B A, Eicke S, Zeeman S C. 2015. PROTEIN TARGETING TO STARCH is required for localising GRANULE-BOUND STARCH SYNTHASE to starch granules and for normal amylose synthesis in *Arabidopsis*. PLOS Biology 13, e1002080.

Shan Q, Wang Y, Li J, Gao C. 2014. Genome editing in rice and wheat using the CRISPR/Cas system. Nature Protocols 9, 2395-2410.

Singh N, Singh J, Kaur L, Sodhi N S, Gill B S. 2003. Morphological, thermal and rheological properties of starches from different botanical sources. Food Chemistry 81, 219-231.

Smith A M. 2008. Prospects for increasing starch and sucrose yields for bioethanol production. Plant Journal 54, 546-558.

Soh H N, Sissons M J, Turner M A. 2006. Effect of Starch Granule Size Distribution and Elevated Amylose Content on Durum Dough Rheology and Spaghetti Cooking Quality. Cereal Chemistry 83, 513-519.

Stoddard F L. Survey of starch particle-size distribution in wheat and related species, Cereal Chemistry, 1999, vol. 76 (pg. 145-149)

Stoddard F L, Sarker R. Characterization of starch in *Aegilops* species, Cereal Chemistry, 2000, vol. 77 (pg. 445-447)

Vandromme C, Spriet C, Dauvill D, Courseaux A, Putaux J, Wychowski A, Facon M, D'Hulst C, Wattebled F. 2018. PII1: a protein involved in starch initiation that determines granule number and size in *Arabidopsis* chloroplast. New Phytologist Wang Y, Cheng X, Shan Q, Zhang Y, Liu J, Gao C, Qiu J L. 2014. Simultaneous editing of three homoeoalleles in hexaploid bread wheat confers heritable resistance to powdery mildew. Nature Biotechnology 32, 947-951.

Wiles M V, Qin W, Cheng A W, Wang H (2015) CRISPR-Cas9-mediated genome editing and guide RNA design. Mamm Genome 26:501-510

Zeeman S C, Kossmann J, Smith A M. 2010. Starch: its metabolism, evolution, and biotechnological modification in plants. Annual Review of Plant Biology 61, 209-234.

Zeeman S C, Tiessen A, Pilling E, Kato K L, Donald A M, Smith A M. 2002. Starch synthesis in *Arabidopsis*. Granule synthesis, composition, and structure. Plant Physiology 129, 516-529.

Zhang Y, Liang Z, Zong Y, Wang Y, Liu J, Chen K, Qiu J L, Gao C. 2016. Efficient and transgene-free genome editing in wheat through transient expression of CRISPR/Cas9 DNA or RNA. Nature Communications 7, 1-8.

Zimmermann L, Stephens A, Nam S Z, Rau D, Kübler J, Lozajic M, Gabler F, Söding J, Lupas A N, Alva V. 2017. A Completely Reimplemented MPI Bioinformatics Toolkit with a New HHpred Server at its Core. Journal of Molecular Biology 430, 2237-2243.

SEQUENCE LISTING

TaMRC 6A amino acid sequence (cv. Kronos (4n))

SEQ ID NO: 1

```
MRLSIGSPSPSPPPAVAAALRSTPPSRRTASHVMFRQKLSFMEAFQTQHLKYAPRLIKSVVKGI
RSNITDGDNGTTEPARELLERLFARTQSLDTGASHDSELSVSIEVLKSEFEGALSILRNKERDLR
SAEKRVSDDRIRLSKTKQDLDQREEAIRKAYVRQQGIEKALKKASRDLALRVKQISDLKLLVEGQ
DRTIARSQALLSQKVTEVENLKRDMFKKNEEADLMRSEIRSKEKLLLTANQAIAQQEATVRELQ
SEIKRKTMDIARSNESRKTNEEKLKVAEQELEKQSLGWLAAQQELKELAQLAFKDTDDIKGIITD
FKRVRSLLDAVRSELISSKDAFASSRRQIEDQAVQLQEQVQELEDQRVLLMSYTHDLEAAQLEI
QGKTQELNYAQSRCHELESQLLKEMEKVESLEAELTKEKQSLEHRTEEVGFLQKELVQKENEC
TKSQELVKVKEFELLEARQEVQDMKLKVESIQLAVQEKDSELSDTQSRLTEVSSEIVELQQLLN
SKKDQLVQARTELHDKEQHIETLESELDSIRLRCSQAESMVQRMAELTGDLASSVKAGEMDIYT
LLDDEISSTSTALESNLHKHNQLEADIEMLRECLRHKDMELRAAHEALDAKDQELKAVLKKWDV
KERELRELEELPDPSATNELAGFSSETTEGGIVGEMELPELQIDAAEVEALAATTALRKLADMTK
DFFKHVKADSGINLVASESQKIIKCDPKMEVHKKTDVILEAEKEIVRLFSLTKQIVTDDIINDVEE*
```

TaMRC 6A amino acid sequence (cv. Cadenza (6n))

SEQ ID NO: 2

```
MRLSIGSPSPSPPPAVAAALRSTPPSRRTASHVMFRQKLSFMEAFQTQHLKYAPRLIKSVVKGI
RSNITDGDNGTTEPARELLERLFARTQSLDTGASHDSELSVSIEVLKSEFEGALSILRNKERDLR
SAEKRVSDDRIRLSKTKQDLDQREEAIRKAYVRQQGIEKALKKASRDLALRVKQISDLKLLVEGQ
DRTIARSQALLSQKVTEVENLKRDMFKKNEEADLMRSEIRSKEKLLLTANQAIAQQEATVRELQ
SEIKRKTMDIARSNESRKTNEEKLKVAEQELEKQSLGWLAAQQELKELAQLAFKDTDDIKGIITD
FKRVRSLLDAVRSELISSKDAFASSRRQIEDQAVQLQEQVQELEDQRVLLMSYTHDLEAAQLEI
QGKTQELNYAQSRCHELESQLLKEMEKVESLEAELTKEKQSLEHRTEEVGFLQKELVQKENEC
TKSQELVKVKEFELLEARQEVQDMKLKVESIQLAVQEKDSELSDTQSRLTEVSSEIVELQQLLN
SKKDQLVQARTELHDKEQHIETLESELDSIRLRCSQAESMVQRMAELTGDLASSVKAGEMDIYT
LLDDEISSTSTALESNLHKHNQLEADIEMLRECLRHKDMELRAAHEALDAKDQELKAVLKKWDV
KERELRELEELPDPSATNELAGFSSETTEGGIVGEMELPELQIDAAEVEALAATTALRKLADMTK
DFFKHVKADSGINLVASESQKIIKCDPKMEVHKKTDVILEAEKEIVRLFSLTKQIVTDDIINDVEE
```

TaMRC 6D amino acid sequence (cv. Cadenza (6n))

SEQ ID NO: 3

```
MRLSIGSPSPSPPPAVAAALRSTSPSCRTASHVMFRQKLSFMVASQTQHLKYAPRLIKSVIKGIR
SNITDGDNGTTEPARELLERLFAKTQSLDTGASHDSELSVSIEVLKSEFEGALSILRNKERDLRS
AEKRVSDDRIRLSKTKQDLDQREEAIRKAYVRQQGIEKALKKASRDLALRVKQISNLKLQVEGQ
DRTIASSQALLSQKVIEVENLKRDMFKKNEEADLVRSEIRSKEQQLLTANKAIAQQEATVRELQS
EIKRKTIDIARSNESRKTNEEKLKVAEQELEKQSLGWLAAQQELKELAQLAFKDTDDIKGIITDFK
RVRSLLDAVRCELISSKDAFASSRRQIEDQAVQLQKQALELEDQQVLLMSYTHDLEAAQLEIQG
KTQELKYAQSRCHELESQLLQEMEKVESLETELTKERQSLDHRTEEVGFLQKELVRKENECTK
SQELVKVKEFELLEARQEVQDMKLKVESIQLAVQEKDSELSDTQSRLTEVSSEIVELQQLLNSK
KDQLVQARTELHDKEQHIETLESELDSIRFRCSQAESMVQRMAELTGDLASSVKAGEMDIYTLL
DDEISSTGTALESNLHKHNQLEADIEMLRECLRHKDMDLRAAHEALDAKDQELKAVLKKWDVK
ERELRELEELPDPSATNELAVFSSETTEDGIVGEMELPELQIEAAGVEALAATTALRKLADMTKD
FFKHGKADSGIDLVASESQKISKCDPKMEVHKKTDVILEAEKEIVRLFSLTKQIVTDDTINNLEE*
```

TaMRC 6A (cv. Kronos (4n)) genomic nucleic acid sequence (5' UTR and 3'UTR are italicised)

SEQ ID NO: 4

*CGATCGCGCCCGGGCCGCGGTGGTTCCCTCTCCCATGTTCCGCGGCC*ATGCG
CCTCTCCATCGGCTCCCCATCCCCGTCGCCGCCGCCGGCGGTGGCCGCCGCTC
TCCGCAGCACACCCCCGTCGCGCCGTACCGCCAGTCATGTGAGCGCCCGCTGAT
CTTTTCTTCCTTTTCTCATATCGCTGTTTCGTGGTACCACGCTGCTCACTGTTACAT
GGACTGCTTGCGTTCGTGTTTTCCCGATTCCGTGCCCGTCCACATGTGTTTGAAG
TAGAAGGATACCAGATTCGGTGTCCTAATTCATGTTCTGCTAGTACTAGTACTTTTT
TTAAAAACTTTTCTGGAATTGGTTCAATTGTGATAAATTCAGTAAACTGCGATCAAA
TTTCATCAGTTATGATACTTCACCTTATGTAGCAGTGAGTTTCTGAAGTTCAGTGTA
CTGTCCTTCAGTTCTTCCATTTACAAAACAAATTTTTACGTGCTTAGTTTGAGGAAA
GGATATTCCTCAGATTGCTTCACTAGGTTGTGACCATTTCCTTATCCTAATATCCTA
CTTATGCATTGTTTCCTGCAACTCTCTCAGGTTATGTTCAGGCAGAAGCTGAGTTT
CATGGAGGCATTTCAGACTCAGCATCTGAAATATGCTCCTCGTTTGATCAAATCAG
TCGTAAAAGGTATTAGATCAAATATAACTGATGGTGATAATGGAACGACTGAGCCA
GCTAGAGAGTTGCTGGAGCGGCTATTTGCGAGGACACAAAGTTTAGACACTGGTG
CTTCTCATGATAGTGAACTGAGCGTGAGCATTGAGGTCCTGAAGTCTGAATTCGA
GGGTGCCTTGTCTATCCTCAGAAACAAAGAGAGGGATCTTCGCAGCGCAGAGAA

```
GAGGGTTTCCGATGATCGGATAAGGTTGAGCAAGACAAAGCAGGACCTTGATCAG
AGAGAGGAAGCGATCCGCAAAGCTTATGTAAGGCAACAAGGAATAGAGAAAGCAC
TGAAAAAGGCAAGTAGAGATCTGGCGTTGCGAGTGAAGCAGATCAGTGATCTGAA
GCTTCTGGTTGAGGGGCAAGACAGGACTATTGCCAGGTCACAAGCTTTGCTTTCT
CAGAAGGTAACTGAAGTGGAAAATCTCAAACGAGATATGTTCAAGAAGAACGAGG
AAGCAGACCTGATGCGTTCAGAGATCAGGTCCAAAGAAAAGCTGCTTCTTACAGC
TAATCAAGCTATTGCGCAGCAAGAAGCAACAGTTAGGGAGCTGCAGAGTGAAATT
AAAAGAAAGACAATGGATATCGCCAGATCAAATGAATCGAGGAAAACTAATGAAGA
GAAACTGAAAGTTGCTGAACAGGAACTTGAGAAGCAGAGTTTAGGATGGTTAGCA
GCACAACAAGAGTTAAAGGAACTTGCACAACTGGCATTCAAAGATACAGATGATAT
CAAGGGTATTATCACTGACTTCAAACGTGTGAGGTCTCTGCTAGATGCTGTACGCT
CTGAATTGATCTCTTCAAAAGATGCTTTCGCTTCCTCTCGCAGACAAATAGAAGAT
CAAGCGGTTCAGTTGCAGGAACAAGTACAGGAACTCGAGGACCAAAGGGTATTAC
TGATGTCTTACACCCATGATTTGGAGGCTGCTCAACTGGAGATTCAAGGGAAGAC
ACAGGAGCTCAATTATGCACAGTCTCGTTGTCATGAACTTGAATCACAGTTACTTA
AGGAAATGGAGAAGGTCGAGTCTCTAGAAGCCGAATTAACGAAAGAAAAACAGAG
CTTAGAACATAGAACTGAAGAAGTAGGCTTTCTTCAGAAGGAGCTTGTTCAGAAAG
AAAATGAGTGCACCAAATCACAAGAACTTGTTAAAGTAAAAGAGTTTGAGCTGTTA
GAAGCCAGACAGGAAGTCCAAGATATGAAGTTAAAGGTAGAGTCTATTCAATTGG
CTGTTCAAGAAAAGGATTCAGAGCTTTCTGATACACAGAGCAGACTAACTGAAGTC
AGCAGTGAAATTGTTGAGCTTCAGCAGTTGCTAAATAGCAAGAAGGATCAACTGG
TTCAGGCTAGAACTGAATTACATGATAAAGAACAACATATAGAAACACTGGAGAGT
GAGTTGGATAGCATACGGCTCAGATGCTCGCAAGCTGAATCCATGGTTCAAAGGA
TGGCTGAGCTCACTGGCGATCTTGCTAGTTCCGTAAAAGCCGGAGAAATGGACAT
CTATACATTACTGGATGATGAAATTTCAAGCACAAGTACAGCCCTCGAGTCCAATT
TACATAAGCATAATCAACTGGAGGCTGACATAGAGATGTTAAGAGAATGCTTGCG
GCATAAGGACATGGAGTTGAGAGCTGCTCATGAAGCACTTGATGCCAAAGATCAA
GAGCTGAAGGCAGTACTTAAAAAAATGGGATGTGAAGGAGAGGGAACTACGTGAGT
TGGAAGAGTTACCGGATCCCAGTGCCACAAATGAACTTGCTGGTTTTTCCAGTGA
GACAACAGAGGGCGGTATTGTAGGAGAGATGGAGCTGCCAGAGCTTCAAATTGAT
GCTGCGGAGGTCGAAGCACTTGCTGCTACGACTGCATTGAGGAAGCTTGCGGAT
ATGACTAAGGATTTCTTCAAACACGTCAAAGCTGATTCTGGTATTACTTGGTTGC
ATCAGAGAGTCAAAAAATCATTAAATGCGATCCTAAAATGGAAGTACACAAGAAGA
CGGATGTGATTCTTGAAGCTGAAAAAGAAATAGTTAGGCTCTTCTCATTGACAAAA
CAGATTGTCACTGATGACATAATAAACGATGTTGAGGAATGATAGCTTCAAACTAA
AGCATGTAGTCTTCCAATTCTATCAAGGTAGATCTTCCAAGATAGCTTCAGAGTAG
AGATATACCAGATAGATCGTTCGAACATTTATGGACAGCGATGTCGCCCAGAAGG
ATGAGATCTTCTCTGGTTGATTTCACAAACTGCCATTTTGAAAAAGGGTAACATGTT
GAGCAGAAGCTGGTCATCTGATCCTTTGTGCTCTTTTTGTAATGTGCCTCAAACTA
TTCCTCAGATCTTTGTTCAATG
```

TaMRC 6A (cv. Cadenza (6n)) genomic nucleic acid sequence (5' UTR and 3'UTR are italicised)

SEQ ID NO: 5

```
CGATCGCGCCCGGGCCGCGGTGGTTCCCTCTCCCCATGTTCCGCGGCCATGCG
CCTCTCCATCGGCTCCCCATCCCCGTCGCCGCCGCCGGCGGTGGCCGCCGCTC
TCCGCAGCACACCCCCGTCGCGCCGTACCGCCAGTCATGTGAGCGCCCGCTGAT
CTTTTCTTCCTTTTCTCATATCGCTGTTTCGTGGTACCACGCTGCTCACTGTTACAT
GGACTGCTTGCGTTCGTGTTTTCCCGATTCCGTGCCCGTCCACATGTGTTTGAAG
TAGAAGGATACCAGATTCGGTGTCCTAATTCATGTTCTGCTAGTACTAGTACTTTTT
TTAAAAACTTTTCTGGAATTGGTTCAATTGTGATAAATTCAGTAAACTGCGATCAAA
TTTCATCAGTTATGATACTTCACCTTATGTAGCAGTGAGTTTCTGAAGTTCAGTGTA
CTGTCCTTCAGTTCTTCCATTTACAAAACAAATTTTTACGTGCTTAGTTTGAGGAAA
GGATATTCCTCAGATTGCTTCACTAGGTTGTGACCATTTCCTTATCCTAATATCCTA
CTTATGCATTGTTTCCTGCAACTCTCTCAGGTTATGTTCAGGCAGAAGCTGAGTTT
CATGGAGGCATTTCAGACTCAGCATCTGAAATATGCTCCTCGTTTGATCAAATCAG
TCGTAAAAGGTATTAGATCAAATATAACTGATGGTGATAATGGAACGACTGAGCCA
GCTAGAGAGTTGCTGGAGCGGCTATTTGCGAGGACACAAAGTTTAGACACTGGTG
CTTCTCATGATAGTGAACTGAGCGTGAGCATTGAGGTCCTGAAGTCTGAATTCGA
GGGTGCCTTGTCTATCCTCAGAAACAAAGAGAGGGATCTTCGCAGCGCAGAGAA
GAGGGTTTCCGATGATCGGATAAGGTTGAGCAAGACAAAGCAGGACCTTGATCAG
AGAGAGGAAGCGATCCGCAAAGCTTATGTAAGGCAACAAGGAATAGAGAAAGCAC
TGAAAAAGGCAAGTAGAGATCTGGCGTTGCGAGTGAAGCAGATCAGTGATCTGAA
GCTTCTGGTTGAGGGGCAAGACAGGACTATTGCCAGGTCACAAGCTTTGCTTTCT
CAGAAGGTAACTGAAGTGGAAAATCTCAAACGAGATATGTTCAAGAAGAACGAGG
AAGCAGACCTGATGCGTTCAGAGATCAGGTCCAAAGAAAAGCTGCTTCTTACAGC
TAATCAAGCTATTGCGCAGCAAGAAGCAACAGTTAGGGAGCTGCAGAGTGAAATT
AAAAGAAAGACAATGGATATCGCCAGATCAAATGAATCGAGGAAAACTAATGAAGA
GAAACTGAAAGTTGCTGAACAGGAACTTGAGAAGCAGAGTTTAGGATGGTTAGCA
GCACAACAAGAGTTAAAGGAACTTGCACAACTGGCATTCAAAGATACAGATGATAT
CAAGGGTATTATCACTGACTTCAAACGTGTGAGGTCTCTGCTAGATGCTGTACGCT
CTGAATTGATCTCTTCAAAAGATGCTTTCGCTTCCTCTCGCAGACAAATAGAAGAT
CAAGCGGTTCAGTTGCAGGAACAAGTACAGGAACTCGAGGACCAAAGGGTATTAC
TGATGTCTTACACCCATGATTTGGAGGCTGCTCAACTGGAGATTCAAGGGAAGAC
ACAGGAGCTCAATTATGCACAGTCTCGTTGTCATGAACTTGAATCACAGTTACTTA
AGGAAATGGAGAAGGTCGAGTCTCTAGAAGCCGAATTAACGAAAGAAAAACAGAG
CTTAGAACATAGAACTGAAGAAGTAGGCTTTCTTCAGAAGGAGCTTGTTCAGAAAG
```

SEQUENCE LISTING

```
AAAATGAGTGCACCAAATCACAAGAACTTGTTAAAGTAAAAGAGTTTGAGCTGTTA
GAAGCCAGACAGGAAGTCCAAGATATGAAGTTAAAGGTAGAGTCTATTCAATTGG
CTGTTCAAGAAAAGGACTCAGAGCTTTCTGATACACAGAGCAGACTAACTGAAGT
CAGCAGTGAAATTGTTGAGCTTCAGCAGTTGCTAAATAGCAAGAAGGATCAACTG
GTTCAGGCTAGAACTGAATTACATGATAAAGAACAACATATAGAAACACTGGAGAG
TGAGTTGGATAGCATACGGCTCAGATGCTCGCAAGCTGAATCCATGGTTCAAAGG
ATGGCTGAGCTCACTGGCGATCTTGCTAGTTCCGTAAAAGCCGGAGAAATGGACA
TCTATACATTACTGGATGATGAAATTTCAAGCACAAGTACAGCCCTCGAGTCCAAT
TTACATAAGCATAATCAACTGGAGGCTGACATAGAGATGTTAAGAGAATGCTTGCG
GCATAAGGACATGGAGTTGAGAGCTGCTCATGAAGCACTTGATGCCAAAGATCAA
GAGCTGAAGGCAGTACTTAAAAAATGGGATGTGAAGGAGAGGGAACTACGTGAGT
TGGAAGAGTTACCGGATCCCAGTGCCACAAATGAACTTGCTGGTTTTTCCAGTGA
GACAACAGAGGGCGGTATTGTAGGAGAGATGGAGCTGCCAGAGCTTCAAATTGAT
GCTGCGGAGGTCGAAGCACTTGCTGCTACGACTGCATTGAGGAAGCTTGCGGAT
ATGACTAAGGATTTCTTCAAACACGTCAAAGCTGATTCTGGTATTAACTTGGTTGC
ATCAGAGAGTCAAAAAATCATTAAATGCGATCCTAAAATGGAAGTACACAAGAAGA
CGGATGTGATTCTTGAAGCTGAAAAGAAATAGTTAGGCTCTTCTCATTGACAAAA
CAGATTGTCACTGATGACATAATAAACGATGTTGAGGAATGATAGCTTCAAACTAA
AGCATGTAGTCTTCCAATTCTATCAAGGTAGATCTTCCAAGATAGCTTCAGAGTAG
AGATATACCAGATAGATCGTTCGAACATTTATGGACAGCGATGTCGCCCAGAAGG
ATGAGATCTTCTCTGGTTGATTTCACAAACTGCCATTTTGAAAAAGGGTAACATGTT
GAGCAGAAGCTGGTCATCTGATCCTTTGTGCTCTTTTTGTAATGTGCCTCAAACTA
TTCCTCAGATCTTTGTTCAATG
```

TaMRC 6D (cv. Cadenza (6n)) genomic nucleic acid sequence (5' UTR
and 3'UTR are italicised)

SEQ ID NO: 6

```
CGATCGCGCCCGGGCGGCGGTGGTTCCCTCTCCCCATGTTCCGCGGCCATGCG
CCTCTCCATCGGCTCCCCATCCCCGTCGCCGCCGCCGGCGGTGGCCGCCGCTC
TCCGCAGCACATCCCCGTCGTGCCGTACCGCCAGTCATGTGAGCGCCCGCTGAT
CTTTTCTTCCTTTTCTCATATCGCTGTTTCGTGGTACCACGCTGCTCACTGTTACAT
GGGCTGCTTGCGTTCGTGTTTTCCCGATTCCGTGCCCGTCCACATGTGTTTGAAG
TAGAAGGATGCCAGATTTGGTGTCCTAATTCATGTTCTGCTAGTACTAGTACCTTT
TTTAAAACTTTTCTGGAATTGGTTCGATTGTGATAAATTCAGTAAACTGCACCTGGC
TGAACAAATCTTGATTGGAGAACGGCCTATGAACTCAAAAAAAATTACTGAACAGA
TGAAATGTTTATGCAGAGGTAGGCTTGAGATCAAATTTCATCGGTTATGATACTTC
ACCTTATATAGCAGTGAATTTCTGAAGTTCAGTGTACTGTCTTTCAGTTCTTCGATT
TACAAAACAAATTTTTACGTGCTTAGTTTGAGGAAAGGATATTCCTCAGATTGCTTC
ACTAGGTTGTGACCATTTCCTTATCCTACTATCCTACTTATGCATTGTTTCCTGCAA
CTCTCTCAGGTTATGTTCAGGCAGAAGCTGAGTTTCATGGTGGCATCTCAGACTC
AGCATCTGAAATATGCTCCTCGTTTGATCAAATCAGTCATAAAAGGTATTAGATCAA
ATATAACTGATGGTGATAATGAACGACTGAGCCAGCTAGAGAGTTGCTGGAGCG
GCTATTTGCAAAGACACAAAGTTTAGACACTGGTGCTTCTCATGATAGTGAACTGA
GCGTGAGCATTGAGGTCCTGAAGTCTGAATTCGAGGGTGCCTTGTCTATCCTCAG
AAACAAAGAGAGGGATCTTCGCAGCGCAGAGAAGAGGGTTTCCGATGATCGGAT
AAGGTTGAGCAAGACAAAGCAGGACCTTGATCAGAGAGAGGAAGCGATCCGCAA
AGCTTATGTAAGGCAACAAGGAATAGAGAAAGCACTGAAAAAGGCAAGTAGAGAT
CTGGCGTTGCGAGTGAAGCAGATCAGTAATCTGAAGCTTCAGGTTGAGGGGCAA
GACAGGACTATTGCCAGTTCACAAGCTTTGCTTTCTCAGAAGGTAATTGAGGTGG
AAAATCTCAAACGAGATATGTTCAAGAAGAACGAGGAAGCCGACCTGGTGCGTTC
AGAGATCAGGTCCAAAGAGCAGCAGCTTCTTACAGCTAATAAAGCTATTGCGCAG
CAAGAAGCAACAGTTAGGGAGCTGCAGAGTGAAATTAAAAGAAAGACAATCGATA
TCGCCAGATCAAATGAATCGAGGAAAACTAATGAAGAGAAACTGAAAGTTGCTGA
ACAGGAACTTGAGAAGCAGAGTTTAGGATGGTTAGCAGCACAACAAGAGTTAAAG
GAACTTGCACAACTGGCATTCAAAGATACAGATGATATCAAGGGTATTATCACTGA
CTTCAAACGTGTGAGGTCTCTCCTAGATGCTGTACGCTGTGAATTAATCTCTTCGA
AAGATGCTTTCGCTTCCTCTCGCAGACAAATAGAAGATCAAGCGGTGCAGTTGCA
GAAACAAGCACTGGAACTCGAGGACCAACAGGTATTACTGATGTCTTACACCCAT
GATTTGGAAGCTGCTCAACTGGAGATTCAAGGGAAGACACAGGAGCTCAAGTACG
CACAGTCTCGTTGTCATGAACTTGAATCACAGTTACTTCAGGAAATGGAGAAGGTC
GAGTCTCTTGAAACCGAATTAACCAAAGAAAGACAGAGCTTAGATCATAGAACTGA
AGAAGTAGGCTTTCTTCAGAAGGAGCTTGTTCGGAAAGAAAATGAGTGCACCAAA
TCACAAGAACTTGTTAAAGTAAAAGAGTTTGAGCTGTTAGAAGCCAGACAGGAAGT
CCAAGATATGAAGTTAAAGGTAGAGTCTATTCAATTGGCTGTTCAAGAAAAGGATT
CAGAGCTTTCTGATACACAGAGCAGACTAACTGAAGTCAGCAGTGAAATTGTTGA
GCTTCAGCAGTTGCTAAATAGCAAGAAGGATCAACTGGTTCAGGCTAGAACTGAA
TTACATGATAAAGAACAACATATAGAAACACTGGAGAGTGAGTTGGATAGCATACG
GTTCAGATGCTCGCAAGCTGAATCCATGGTTCAAAGGATGGCTGAGCTCACTGGC
GATCTTGCTAGTTCCGTAAAAGCTGGAGAAATGGACATCTATACATTACTGGATGA
TGAAATTTCAAGCACAGGTACAGCCCTCGAGTCCAATTTGCATAAGCATAATCAAC
TGGAGGCTGACATAGAGATGTTAAGAGAATGCTTGCGGCATAAGGACATGGACTT
GAGAGCTGCTCATGAAGCACTTGATGCCAAAGATCAAGAGCTGAAGGCAGTACTT
AAAAAGTGGGATGTGAAGGAGAGGGAACTACGTGAGTTGGAAGAGTTACCGGAT
CCCAGTGCCACAAATGAACTTGCTGTTTTTTCCAGTGAGACAACAGAGGACGGCA
TTGTAGGAGAGATGGAGCTCCCTGAGCTTCAAATTGAAGCTGCGGGGGTCGAAG
CACTTGCTGCTACGACTGCATTGAGGAAGCTTGCGGATATGACTAAGGATTTCTTC
AAACACGGCAAAGCTGATTCTGGTATTGACTTGGTTGCATCAGAGAGTCAAAAAAT
```

| SEQUENCE LISTING | |
|---|---|
| CAGTAAATGTGATCCTAAAATGGAAGTACACAAGAAGACGGATGTGATTCTTGAAG<br>CTGAAAAAGAAATAGTTAGGCTCTTCTCATTGACAAAACAGATTGTCACTGATGAC<br>ACAATAAACAATCTTGAGGAATGATAGCTTCAAACTAAAGCATGTAGTCTTCCAATT<br>*CTATCAAGGTAGATCTTCCAAGATAGCTTCAGAGTAGAGATATACCAGATAGATCT*<br>*TTCAAACATTGATGGACAGCGACGTCGCCCAGAAGGATGAGATCTTCTCTGGTTG*<br>*ATATCACAACTGCCATTTTGAAAAAGGGTAACATGTTGAGCAGAAGCTGGTCATCT*<br>*GATCTTTTGTGCTCCTTTTGTATTGTACCTCAAGCTATTCCTCAGATCTTTGTTCAA*<br>*TG* | |
| TaMRC 6A (cv. Kronos (4n)) CDS nucleic acid sequence | SEQ ID NO: 7 |
| ATGCGCCTCTCCATCGGCTCCCCATCCCCGTCGCCGCCGCCGGCGGTGGCCGCCGCTCT<br>CCGCAGCACACCCCCGTCGCGCCGTACCGCCAGTCATGTTATGTTCAGGCAGAAGCTGAG<br>TTTCATGGAGGCATTTCAGACTCAGCATCTGAAATATGCTCCTCGTTTGATCAAATCAGTCG<br>TAAAAGGTATTAGATCAAATATAACTGATGGTGATAATGGAACGACTGAGCCAGCTAGAGA<br>GTTGCTGGAGCGGCTATTTGCGAGGACACAAAGTTTAGACACTGGTGCTTCTCATGATAGT<br>GAACTGAGCGTGAGCATTGAGGTCCTGAAGTCTGAATTCGAGGGTGCCTTGTCTATCCTCA<br>GAAACAAAGAGAGGGATCTTCGCAGCGCAGAGAAGAGGGTTTCCGATGATCGGATAAGGT<br>TGAGCAAGACAAAGCAGGACCTTGATCAGAGAGAGGAAGCGATCCGCAAAGCTTATGTAA<br>GGCAACAAGGAATAGAGAAAGCACTGAAAAAGGCAAGTAGAGATCTGGCGTTGCGAGTGA<br>AGCAGATCAGTGATCTGAAGCTTCTGGTTGAGGGGCAAGACAGGACTATTGCCAGGTCAC<br>AAGCTTTGCTTTCTCAGAAGGTAACTGAAGTGGAAAATCTCAAACGAGATATGTTCAAGAAG<br>AACGAGGAAGCAGACCTGATGCGTTCAGAGATCAGGTCCAAAGAAAAGCTGCTTCTTACA<br>GCTAATCAAGCTATTGCGCAGCAAGAAGCAACAGTTAGGGAGCTGCAGAGTGAAATTAAAA<br>GAAAGACAATGGATATCGCCAGATCAAATGAATCGAGGAAAACTAATGAAGAGAAACTGAA<br>AGTTGCTGAACAGGAACTTGAGAAGCAGAGTTTAGGATGGTTAGCAGCACAACAAGAGTTA<br>AAGGAACTTGCACAACTGGCATTCAAAGATACAGATGATATCAAGGGTATTATCACTGACTT<br>CAAACGTGTGAGGTCTCTGCTAGATGCTGTACGCTCTGAATTGATCTCTTCAAAAGATGCTT<br>TCGCTTCCTCTCGCAGACAAATAGAAGATCAAGCGGTTCAGTTGCAGGAACAAGTACAGGA<br>ACTCGAGGACCAAAGGGTATTACTGATGTCTTACACCCATGATTTGGAGGCTGCTCAACTG<br>GAGATTCAAGGGAAGACACAGGAGCTCAATTATGCACAGTCTCGTTGTCATGAACTTGAAT<br>CACAGTTACTTAAGGAAATGGAGAAGGTCGAGTCTCTAGAAGCCGAATTAACGAAAGAAAA<br>ACAGAGCTTAGAACATAGAACTGAAGAAGTAGGCTTTCTTCAGAAGGAGCTTGTTCAGAAA<br>GAAAATGAGTGCACCAAATCACAAGAACTTGTTAAAGTAAAAGAGTTTGAGCTGTTAGAAG<br>CCAGACAGGAAGTCCAAGATATGAAGTTAAAGGTAGAGTCTATTCAATTGGCTGTTCAAGA<br>AAAGGATTCAGAGCTTTCTGATACACAGAGCAGACTAACTGAAGTCAGCAGTGAAATTGTT<br>GAGCTTCAGCAGTTGCTAAATAGCAAGAAGGATCAACTGGTTCAGGCTAGAACTGAATTAC<br>ATGATAAAGAACAACATATAGAAACACTGGAGAGTGAGTTGGATAGCATACGGCTCAGATG<br>CTCGCAAGCTGAATCCATGGTTCAAAGGATGGCTGAGCTCACTGGCGATCTTGCTAGTTCC<br>GTAAAAGCCGGAGAAATGGACATCTATACATTACTGGATGATGAAATTTCAAGCACAAGTA<br>CAGCCCTCGAGTCCAATTTACATAAGCATAATCAACTGGAGGCTGACATAGAGATGTTAAG<br>AGAATGCTTGCGGCATAAGGACATGGAGTTGAGAGCTGCTCATGAAGCACTTGATGCCAA<br>AGATCAAGAGCTGAAGGCAGTACTTAAAAAATGGGATGTGAAGGAGAGGGAACTACGTGA<br>GTTGGAAGAGTTACCGGATCCCAGTGCCACAAATGAACTTGCTGGTTTTTCCAGTGAGACA<br>ACAGAGGGCGGTATTGTAGGAGAGATGGAGCTGCCAGAGCTTCAAATTGATGCTGCGGAG<br>GTCGAAGCACTTGCTGCTACGACTGCATTGAGGAAGCTTGCGGATATGACTAAGGATTTCT<br>TCAAACACGTCAAAGCTGATTCTGGTATTAACTTGGTTGCATCAGAGAGTCAAAAAATCATT<br>AAATGCGATCCTAAAATGGAAGTACACAAGAAGACGGATGTGATTCTTGAAGCTGAAAAAG<br>AAATAGTTAGGCTCTTCTCATTGACAAAACAGATTGTCACTGATGACATAATAAACGATGTT<br>GAGGAATGA | |
| TaMRC 6A (cv. Cadenza (6n)) CDS nucleic acid sequence | SEQ ID NO: 8 |
| ATGCGCCTCTCCATCGGCTCCCCATCCCCGTCGCCGCCGCCGGCGGTGGCCGC<br>CGCTCTCCGCAGCACACCCCCGTCGCGCCGTACCGCCAGTCATGTTATGTTCAG<br>GCAGAAGCTGAGTTTCATGGAGGCATTTCAGACTCAGCATCTGAAATATGCTCCT<br>CGTTTGATCAAATCAGTCGTAAAAGGTATTAGATCAAATATAACTGATGGTGATAAT<br>GGAACGACTGAGCCAGCTAGAGAGTTGCTGGAGCGGCTATTTGCGAGGACACAA<br>AGTTTAGACACTGGTGCTTCTCATGATAGTGAACTGAGCGTGAGCATTGAGGTCC<br>TGAAGTCTGAATTCGAGGGTGCCTTGTCTATCCTCAGAAACAAAGAGAGGGATCT<br>TCGCAGCGCAGAGAAGAGGGTTTCCGATGATCGGATAAGGTTGAGCAAGACAAA<br>GCAGGACCTTGATCAGAGAGAGGAAGCGATCCGCAAAGCTTATGTAAGGCAACAA<br>GGAATAGAGAAAGCACTGAAAAAGGCAAGTAGAGATCTGGCGTTGCGAGTGAAG<br>CAGATCAGTGATCTGAAGCTTCTGGTTGAGGGGCAAGACAGGACTATTGCCAGGT<br>CACAAGCTTTGCTTTCTCAGAAGGTAACTGAAGTGGAAAATCTCAAACGAGATATG<br>TTCAAGAAGAACGAGGAAGCAGACCTGATGCGTTCAGAGATCAGGTCCAAAGAAA<br>AGCTGCTTCTTACAGCTAATCAAGCTATTGCGCAGCAAGAAGCAACAGTTAGGGA<br>GCTGCAGAGTGAAATTAAAAGAAAGACAATGGATATCGCCAGATCAAATGAATCG<br>AGGAAAACTAATGAAGAGAAACTGAAAGTTGCTGAACAGGAACTTGAGAAGCAGA<br>GTTTAGGATGGTTAGCAGCACAACAAGAGTTAAAGGAACTTGCACAACTGGCATT<br>CAAAGATACAGATGATATCAAGGGTATTATCACTGACTTCAAACGTGTGAGGTCTC<br>TGCTAGATGCTGTACGCTCTGAATTGATCTCTTCAAAAGATGCTTTCGCTTCCTCT<br>CGCAGACAAATAGAAGATCAAGCGGTTCAGTTGCAGGAACAAGTACAGGAACTCG<br>AGGACCAAAGGGTATTACTGATGTCTTACACCCATGATTTGGAGGCTGCTCAACT<br>GGAGATTCAAGGGAAGACACAGGAGCTCAATTATGCACAGTCTCGTTGTCATGAA<br>CTTGAATCACAGTTACTTAAGGAAATGGAGAAGGTCGAGTCTCTAGAAGCCGAATT<br>AACGAAAGAAAAACAGAGCTTAGAACATAGAACTGAAGAAGTAGGCTTTCTTCAGA | |

SEQUENCE LISTING

```
AGGAGCTTGTTCAGAAAGAAAATGAGTGCACCAAATCACAAGAACTTGTTAAAGTA
AAAGAGTTTGAGCTGTTAGAAGCCAGACAGGAAGTCCAAGATATGAAGTTAAAGG
TAGAGTCTATTCAATTGGCTGTTCAAGAAAAGGACTCAGAGCTTTCTGATACACAG
AGCAGACTAACTGAAGTCAGCAGTGAAATTGTTGAGCTTCAGCAGTTGCTAAATAG
CAAGAAGGATCAACTGGTTCAGGCTAGAACTGAATTACATGATAAAGAACAACATA
TAGAAACACTGGAGAGTGAGTTGGATAGCATACGGCTCAGATGCTCGCAAGCTGA
ATCCATGGTTCAAAGGATGGCTGAGCTCACTGGCGATCTTGCTAGTTCCGTAAAA
GCCGGAGAAATGGACATCTATACATTACTGGATGATGAAATTTCAAGCACAAGTAC
AGCCCTCGAGTCCAATTTACATAAGCATAATCAACTGGAGGCTGACATAGAGATGT
TAAGAGAATGCTTGCGGCATAAGGACATGGAGTTGAGAGCTGCTCATGAAGCACT
TGATGCCAAAGATCAAGCTGAAGGCAGTACTTAAAAAATGGGATGTGAAGGAG
AGGGAACTACGTGAGTTGGAAGAGTTACCGGATCCCAGTGCCACAAATGAACTTG
CTGGTTTTTCCAGTGAGACAACAGAGGGCGGTATTGTAGGAGAGATGGAGCTGC
CAGAGCTTCAAATTGATGCTGCGGAGGTCGAAGCACTTGCTGCTACGACTGCATT
GAGGAAGCTTGCGGATATGACTAAGGATTTCTTCAAACACGTCAAAGCTGATTCTG
GTATTAACTTGGTTGCATCAGAGAGTCAAAAAATCATTAAATGCGATCCTAAAATG
GAAGTACACAAGAAGACGGATGTGATTCTTGAAGCTGAAAAAGAAATAGTTAGGC
TCTTCTCATTGACAAAACAGATTGTCACTGATGACATAATAAACGATGTTGAGGAA
TGA
```

TaMRC 6D (cv. Cadenza (6n)) CDS nucleic acid sequence                    SEQ ID NO: 9

```
ATGCGCCTCTCCATCGGCTCCCCATCCCCGTCGCCGCCGCCGGCGGTGGCCGC
CGCTCTCCGCAGCACATCCCCGTCGTGCCGTACCGCCAGTCATGTTATGTTCAGG
CAGAAGCTGAGTTTCATGGTGGCATCTCAGACTCAGCATCTGAAATATGCTCCTC
GTTTGATCAAATCAGTCATAAAAGGTATTAGATCAAATATAACTGATGGTGATAATG
GAACGACTGAGCCAGCTAGAGAGTTGCTGGAGCGGCTATTTGCAAAGACACAAA
GTTTAGACACTGGTGCTTCTCATGATAGTGAACTGAGCGTGAGCATTGAGGTCCT
GAAGTCTGAATTCGAGGGTGCCTTGTCTATCCTCAGAAACAAAGAGAGGGATCTT
CGCAGCGCAGAAGAGGGTTTCCGATGATCGGATAAGGTTGAGCAAGACAAAG
CAGGACCTTGATCAGAGAGAGGAAGCGATCCGCAAAGCTTATGTAAGGCAACAAG
GAATAGAGAAAGCACTGAAAAAGGCAAGTAGAGATCTGGCGTTGCGAGTGAAGCA
GATCAGTAATCTGAAGCTTCAGGTTGAGGGGCAAGACAGGACTATTGCCAGTTCA
CAAGCTTTGCTTTCTCAGAAGGTAATTGAGGTGGAAAATCTCAAACGAGATATGTT
CAAGAAGAACGAGGAAGCCGACCTGGTGCGTTCAGAGATCAGGTCCAAAGAGCA
GCAGCTTCTTACAGCTAATAAAGCTATTGCGCAGCAAGAAGCAACAGTTAGGGAG
CTGCAGAGTGAAATTAAAAGAAAGACAATCGATATCGCCAGATCAAATGAATCGAG
GAAAACTAATGAAGAGAAACTGAAAGTTGCTGAACAGGAACTTGAGAAGCAGAGT
TTAGGATGGTTAGCAGCACAACAAGAGTTAAAGGAACTTGCACAACTGGCATTCA
AAGATACAGATGATATCAAGGGTATTATCACTGACTTCAAACGTGTGAGGTCTCTC
CTAGATGCTGTACGCTGTGAATTAATCTCTTCGAAAGATGCTTTCGCTTCCTCTCG
CAGACAAATAGAAGATCAAGCGGTGCAGTTGCAGAAACAAGCACTGGAACTCGAG
GACCAACAGGTATTACTGATGTCTTACACCCATGATTTGGAAGCTGCTCAACTGGA
GATTCAAGGGAAGACACAGGAGCTCAAGTACGCACAGTCTCGTTGTCATGAACTT
GAATCACAGTTACTTCAGGAAATGGAAGGTCGAGTCTCTTGAAACCGAATTAAC
CAAAGAAAGACAGAGCTTAGATCATAGAACTGAAGAAGTAGGCTTTCTTCAGAAG
GAGCTTGTTCGGAAAGAAAATGAGTGCACCAAATCACAAGAACTTGTTAAAGTAA
AGAGTTTGAGCTGTTAGAAGCCAGACAGGAAGTCCAAGATATGAAGTTAAAGGTA
GAGTCTATTCAATTGGCTGTTCAAGAAAAGGATTCAGAGCTTTCTGATACACAGAG
CAGACTAACTGAAGTCAGCAGTGAAATTGTTGAGCTTCAGCAGTTGCTAAATAGCA
AGAAGGATCAACTGGTTCAGGCTAGAACTGAATTACATGATAAAGAACAACATATA
GAAACACTGGAGAGTGAGTTGGATAGCATACGGTTCAGATGCTCGCAAGCTGAAT
CCATGGTTCAAAGGATGGCTGAGCTCACTGGCGATCTTGCTAGTTCCGTAAAAGC
TGGAGAAATGGACATCTATACATTACTGGATGATGAAATTTCAAGCACAGGTACAG
CCCTCGAGTCCAATTTGCATAAGCATAATCAACTGGAGGCTGACATAGAGATGTTA
AGAGAATGCTTGCGGCATAAGGACATGGACTTGAGAGCTGCTCATGAAGCACTTG
ATGCCAAAGATCAAGCTGAAGGCAGTACTTAAAAAGTGGGATGTGAAGGAGAG
GGAACTACGTGAGTTGGAAGAGTTACCGGATCCCAGTGCCACAAATGAACTTGCT
GTTTTTTCCAGTGAGACAACAGAGGACGGCATTGTAGGAGAGATGGAGCTCCCTG
AGCTTCAAATTGAAGCTGCGGGGGTCGAAGCACTTGCTGCTACGACTGCATTGAG
GAAGCTTGCGGATATGACTAAGGATTTCTTCAAACACGCAAAGCTGATTCTGGTA
TTGACTTGGTTGCATCAGAGAGTCAAAAAATCAGTAAATGTGATCCTAAATGGAA
GTACACAAGAAGACGGATGTGATTCTTGAAGCTGAAAAGAAATAGTTAGGCTCTT
CTCATTGACAAAACAGATTGTCACTGATGACACAATAAACAATCTTGAGGAATGA
```

SEQ ID NO: 10 HvMRC amino acid sequence (HORVU6Hr1G036020.1)
MRLSTGCPSPSPAAALAAAHRSTSPSCRTATHVMFRHKLSFMVAFQTQHLKYAPCLI
KSVVKSIRSNITDGDNGTTEPARELLERLFAKTQSLDTGASNDSELGVSIEVLKSEFEG
ALSILRKKERDLRNAEKRVSDDRTRLSKTKQDLDQREETIRKVYVRQQDIEKALKRAS
RDLALRVKQISNLKLLVEGQDRTIASSQALLSQKVIEVENLKQDMFTKNEEADLMRSEI
KSKEQLLLTANQAVVQQEATVRELQSEIKRKIIDIARSDELRKTNEDKLKVAEQELEKQ
NLGWLAAQQELKELAQLASDDTDDIKGIITDFKRVSLLDVVRSELISSKDAFASSRRQI
EDQAVQLREQVQELEDQRVLLMSHTHDLEAARLEIQGKTQELNYAQSRCHELESHLL
QEMEKVESLEAELTKERQSLEHRTEEVDFLQKELVQKENECTKSQELVKVKEFELLEA
RYEVQDMKLKVESIQLAVQEKDSELSATQSRLTEVSSEVVKLQQLLNSKEDQLVQAR
TELHDKEQHIETLESELDSIRLRCSQAESVVRMAELTGDLASSVKTGETDIYTLLDDEI
ASAGTTLESNLHKHNQLEADIEMLRECLRHKDMDLRAAHEALDAKDQELKAVLKKWD
```

VKERELHELEEELLDPSATNELACFSNETTEGGVVGEMELQELQIGAAEVEALAATTAL
RKLADMTKDLFKHDKGDSGIDLAASGSQKLRNCDSKMEVHKKTDVILEAEKEITRLFS
LTKQIVTDDIINDVDER*

HvMRC genomic nucleic acid sequence (HORVU6Hr1G036020 cv.
Morex) (5' UTR and 3'UTR are italicised)

SEQ ID NO: 11

*CGATCGCGCCCGGGCGGCGGTGGTTCCCTCTCCCCATGTTCCGCGGCC*ATGCG
CCTCTCCACCGGCTGCCCATCCCCTCGCCGGCGGCGGCGCTGGCCGCCGCTC
ACCGCAGCACATCCCCGTCGTGCCGTACCGCCACTCATGTGAGCACCCGCTGAT
CTTTTCTTCCTTCTCCCATATCACTGTTTCCTGGTACCACGCTGCTCACTGTTACAT
GGGCTGCTTGTGTTCACATGTGTTTGAAGTAGAGATTTGGCGTCGCTAATTCATGT
TCTGCCAGTATCGGTACTTTTTTTACTTTTCTGGAATTGGTTCTATTGTGATAAATT
CTGTAAACTGTACCTGGCTGAACAAATCTTGATTGGAGAACTGCCTATAAACTCAA
AAATTGTACCGAGCAGATGAAATATGTATGCAGGGGCAGGTTTGAGGTCAAATTT
CATCAGTTATGATACCTCACCTTATATTAATAGCAGTGAATTTGTCTGAAGAGTTGT
ACCTGATTTTTTCTTTCTGGAGTTCAGTGCCCTGCCCTTTCAGTTCTTCGATTTACA
AAACAATTTTTACGTCCTTAGTTTGAGGAAAGAATATTCCTCGGATAATAGCTTCAC
TATTGTTCTCGAAAAAGATAATAGCTTCACTAGCTTGTGCCCTGCTTCACTTATCC
TAATATGCTACTTATGCATTGTTTCCTGCAACTCTCTCAGGTTATGTTCAGACATAA
GCTGAGTTTCATGGTGGCATTTCAGACTCAGCATCTGAAATATGCTCCTTGCTTGA
TCAAATCAGTCGTAAAAGTATTAGATCAAATATAACTGATGGTGATAATGGAACG
ACTGAGCCAGCTAGAGAATTGCTGGAGCGGCTATTTGCGAAGACACAAAGTTTAG
ACACTGGTGCTTCAAATGACAGTGAACTGGGCGTGAGCATTGAGGTCCTGAAATC
TGAATTCGAGGGTGCCTTGTCTATCCTCAGAAAGAAAGAGAGGGATCTTCGCAAC
GCAGAGAAGAGGGTTTCCGATGATCGGACAAGGTTGAGCAAGACGAAGCAGGAC
CTTGATCAGAGAGAGGAGACGATCCGCAAAGTTTATGTAAGGCAACAAGATATAG
AGAAAGCACTGAAAAGGGCAAGTAGAGATCTGGCGTTGCGAGTGAAGCAGATCA
GTAATCTGAAGCTTCTGGTTGAGGGGCAAGATAGGACTATTGCCAGTTCACAAGC
TTTGCTTTCTCAGAAGGTAATTGAAGTGGAAAATCTCAAACAAGACATGTTCACAA
AGAACGAGGAAGCTGACCTGATGCGTTCAGAGATCAAGTCCAAAGAACAGCTGCT
TCTTACAGCTAATCAAGCTGTTGTGCAGCAAGAAGCAACAGTTAGGGAGCTGCAG
AGTGAAATTAAAAGAAAGATAATCGATATCGCCAGATCAGATGAATTGAGGAAAAC
TAATGAAGATAAACTGAAAGTTGCTGAACAGGAACTTGAGAAGCAGAATTTAGGAT
GGGTTAGCAGCACAGCAAGAGTTAAAGGAACTTGCCCAACTGGCATCCGATGATAC
AGATGATATCAAGGGTATTATCACTGACTTCAAACGTGTGAGGTCTCTGCTAGATG
TTGTACGCTCTGAATTGATCTCTTCAAAAGATGCTTTCGCTTCCTCTCGCAGACAA
ATAGAAGATCAAGCGGTGCAGCTGCGGGAACAAGTACAGGAACTTGAGGACCAA
AGGGTATTGCTGATGTCTCACACCCATGATTTGGAGGCTGCTCGACTGGAGATTC
AAGGGAAGACACAGGAGCTCAATTACGCACAGTCTCGTTGTCATGAACTTGAGTC
ACATTTACTTCAGGAAATGGAGAAGGTCGAGTCTCTAGAAGCCGAATTAACCAAA
GAAAGACAGAGCTTAGAACATAGAACTGAAGAAGTAGACTTTCTTCAGAAGGAGC
TTGTACAGAAAGAAATGAGTGCACCAAATCACAAGAACTTGTTAAAGTAAAAGAG
TTTGAGCTGTTAGAAGCCAGATATGAAGTCCAAGATATGAAGTTAAAGGTAGAGTC
TATTCAATTGGCTGTTCAAGAAAAGGATTCAGAGCTTTCTGCTACACAGAGCAGAC
TAACTGAAGTCAGCAGTGAAGTTGTTAAACTTCAGCAGTTGCTAAATAGCAAGGAG
GATCAACTGGTTCAGGCTAGAACTGAATTGCATGATAAAGAACAACATATAGAAAC
ACTGGAGAGTGAATTGGATAGCATACGACTCAGATGCTCGCAAGCTGAATCCGTG
GTTCAAAGGATGGCTGAGCTCACTGGCGATCTTGCTAGTTCCGTAAAAACTGGAG
AAACGGACATCTATACATTACTGGATGATGAAATTGCAAGCGCAGGTACAACCCTC
GAGTCCAATTTGCATAAGCATAATCAACTGGAGGCTGACATAGAGATGTTAAGAGA
ATGCTTGCGGCATAAGGACATGGACTTGAGAGCTGCTCATGAAGCACTTGATGCC
AAAGATCAAGAGCTGAAGGCAGTACTTAAAAAGTGGGATGTGAAGGAGAGGGAAC
TACATGAGTTGGAAGAGTTACTGGATCCCAGTGCCACAAATGAACTTGCTTGTTTC
TCCAATGAGACAACCGAGGGCGGAGTTGTAGGAGAGATGGAGCTCCAAGAGCTT
CAAATTGGAGCTGCGGAGGTGGAAGCACTTGCTGCTACGACTGCATTGAGGAAG
CTTGCAGACATGACTAAGGATCTCTTCAAACACGACAAAGGTGATTCTGGTATTGA
TTTGGCTGCATCAGGGAGTCAAAAACTCAGAAATTGTGATTCTAAAATGGAAGTAC
ACAAGAAGACGGATGTGATTCTTGAAGCTGAAAAAGAAATAACTAGGCTCTTCTCA
TTGACAAAACAGATTGTTACTGATGACATAATAAACGATGTTGATGAACGATAGCT
*TCAAACTAAAGCATGTAGTCTTCCAATTCTATCGAAGGTAGATCTTCCAAGATAGC
TTCAGAGTAGTAATATACCAGATAGATCTTTCCAACATTATGGACAGTGACGTTGC
CCAGAAAGATAAGATCTTCTCTAGTTGATTTGACAACTGCCATTTTGAAAAAGGGT
AACTTATTTAGCAGAAGCTGGTCATTTGATCCTTTGTCCCCTTTTTGTAATGTACCC
AAACTATTCCTTGTATCTTTGTTCAATTATGTTCCCTCTAAATATACGTGGG*

HvMRC CDS nucleic acid sequence (HORVU6Hr1G036020.1 cv. Morex)

SEQ ID NO: 12

ATGCGCCTCTCCACCGGCTGCCCATCCCCTCGCCGGCGGCGGCGCTGGCCGC
CGCTCACCGCAGCACATCCCCGTCGTGCCGTACCGCCACTCATGTTATGTTCAGA
CATAAGCTGAGTTTCATGGTGGCATTTCAGACTCAGCATCTGAAATATGCTCCTTG
CTTGATCAAATCAGTCGTAAAAGTATTAGATCAAATATAACTGATGGTGATAATGG
AACGACTGAGCCAGCTAGAGAATTGCTGGAGCGGCTATTTGCGAAGACACAAAGT
TTAGACACTGGTGCTTCAAATGACAGTGAACTGGGCGTGAGCATTGAGGTCCTGA
AATCTGAATTCGAGGGTGCCTTGTCTATCCTCAGAAAGAAAGAGAGGGATCTTCG
CAACGCAGAGAAGAGGGTTTCCGATGATCGGACAAGGTTGAGCAAGACGAAGCA
GGACCTTGATCAGAGAGAGGAGACGATCCGCAAAGTTTATGTAAGGCAACAAGAT

| SEQUENCE LISTING |
|---|
| ATAGAGAAAGCACTGAAAAGGGCAAGTAGAGATCTGGCGTTGCGAGTGAAGCAG
ATCAGTAATCTGAAGCTTCTGGTTGAGGGGCAAGATAGGACTATTGCCAGTTCAC
AAGCTTTGCTTTCTCAGAAGGTAATTGAAGTGGAAAATCTCAAACAAGACATGTT
ACAAAGAACGAGGAAGCTGACCTGATGCGTTCAGAGATCAAGTCCAAAGAACAGC
TGCTTCTTACAGCTAATCAAGCTGTTGTGCAGCAAGAAGCAACAGTTAGGGAGCT
GCAGAGTGAAATTAAAAGAAAGATAATCGATATCGCCAGATCAGATGAATTGAGGA
AAACTAATGAAGATAAACTGAAAGTTGCTGAACAGGAACTTGAGAAGCAGAATTTA
GGATGGTTAGCAGCACAGCAAGAGTTAAAGGAACTTGCCCAACTGGCATCCGATG
ATACAGATGATATCAAGGGTATTATCACTGACTTCAAACGTGTGAGGTCTCTGCTA
GATGTTGTACGCTCTGAATTGATCTCTTCAAAAGATGCTTTCGCTTCCTCTCGCAG
ACAAATAGAAGATCAAGCGGTGCAGCTGCGGGAACAAGTACAGGAACTTGAGGA
CCAAAGGGTATTGCTGATGTCTCACACCCATGATTTGGAGGCTGCTCGACTGGAG
ATTCAAGGGAAGACACAGGAGCTCAATTACGCACAGTCTCGTTGTCATGAACTTG
AGTCACATTTACTTCAGGAAATGGAGAAGGTCGAGTCTCTAGAAGCCGAATTAAC
CAAAGAAAGACAGAGCTTAGAACATAGAACTGAAGAAGTAGACTTTCTTCAGAAG
GAGCTTGTACAGAAAGAAAATGAGTGCACCAAATCACAAGAACTTGTTAAAGTAAA
AGAGTTTGAGCTGTTAGAAGCCAGATATGAAGTCCAAGATATGAAGTTAAAGGTAG
AGTCTATTCAATTGGCTGTTCAAGAAAAGGATTCAGAGCTTTCTGCTACACAGAGC
AGACTAACTGAAGTCAGCAGTGAAGTTGTTAAACTTCAGCAGTTGCTAAATAGCAA
GGAGGATCAACTGGTTCAGGCTAGAACTGAATTGCATGATAAAGAACAACATATA
GAAACACTGGAGAGTGAATTGGATAGCATACGACTCAGATGCTCGCAAGCTGAAT
CCGTGGTTCAAAGGATGGCTGAGCTCACTGGCGATCTTGCTAGTTCCGTAAAAAC
TGGAGAAACGGACATCTATACATTACTGGATGATGAAATTGCAAGCGCAGGTACA
ACCCTCGAGTCCAATTTGCATAAGCATAATCAACTGGAGGCTGACATAGAGATGTT
AAGAGAATGCTTGCGGCATAAGGACATGGACTTGAGAGCTGCTCATGAAGCACTT
GATGCCAAAGATCAAGAGCTGAAGGCAGTACTTAAAAAGTGGGATGTGAAGGAGA
GGGAACTACATGAGTTGGAAGAGTTACTGGATCCCAGTGCCACAAATGAACTTGC
TTGTTTCTCCAATGAGACAACCGAGGGCGAGTTGTAGGAGAGATGGAGCTCCAA
GAGCTTCAAATTGGAGCTGCGGAGGTGGAAGCACTTGCTGCTACGACTGCATTGA
GGAAGCTTGCAGACATGACTAAGGATCTCTTCAAACACGACAAAGGTGATTCTGG
TATTGATTTGGCTGCATCAGGGAGTCAAAAACTCAGAAATTGTGATTCTAAAATGG
AAGTACACAAGAAGACGGATGTGATTCTTGAAGCTGAAAAAGAAATAACTAGGCTC
TTCTCATTGACAAAACAGATTGTTACTGATGACATAATAAACGATGTTGATGAACGA
TAG

*Brachypodium* amino acid sequence (Bradi3g06260)                                    SEQ ID NO: 13

MFRGHAPLHRLPSPPPPPAAAAGALPSASPSCRTSTHVPFRPKLSFMVAFQAQHVKY
APNLIKSVVKSLRSNITDGDNGMTEPARELLERLFAKTQSLDTSASHDSELSMSIEVLK
SEFERALSILRKKERYLRNAEKRVSDDQLRLNQTKQDLDQREQEISKAHAKQQQMEK
ALKKASRDLSLRVKQINNLKLLVERQDRKIASSEALLSQKVIEVENLKQDMFKNKEAD
LIRSEIKLKEQLLLEANQDVVQQEATVRELRSETEKKAIDIAISNELRKANEEKLKIAEQE
LEKQNLGWLAAQQELKELAQLASKDTDDIKGTVTDFKRVRSLLDAVRSELISSKDNFA
SSRRQIEEQTVQLQKQVQELKDQRVLLMSYTQDLEAAQLEIQGKTKDLNAAQSRCHE
LELQLLKEMEKVESLEAELTKERENLEQKTEQVDFLQKELVQKENECGNSQKLVKIKE
AELLEARHEVQDMKSKVDSIQLAVQEKDSELSDTQSRLTEVSGEVVELQQLLNSKDD
QLVQVRTELHDKEQYIESMQSELESIRFRCSQAESVLRRMAELTGDLASSVKAGEMDI
YALLDDEISSTSTVLESNLHKHNQLEADIEMLRESLRHKDMDLRAAHEALDAKDQELK
AVVGKWDFKEKELDEVEELQKDPIDMKELPVLSNETTGGSITGEMELKKLQIEAAEVE
ALAATTALKKLADMSKKYLRCRKADSGIGLVASESANIGKANSRMELNNKMDVIFEAK
QEIVRLFSLTKELITDDAINDAEER*

*Brachypodium genomic* nucleic acid sequence (Bradi3g06260) (5' UTR
and 3'UTR are italicised)

SEQ ID NO: 14

*CTCGTGCCGTCTCGGCGTCTTCCTCCACAGTCCACAAACCCGCACGCGCATCGC
CAGCCGTCCGATCGCGCTCGGGCGGCCCTGGTCCGCTTCCTCAAATGTTCCGCG*
GCCATGCCCTCTCCACCGGCTCCCCTCGCCGCCGCCGCCACCGGCGGCGGCC
GCCGGCGCACTCCCAGCGCGTCCCGTCGTGCCGCACCTCCACTCATGTGAGC
AATTGCTGTTTTTTCTGTATCTTCCTCATATGTCTGTTTCTGATTTGGCTCTACCAC
GCTGCCTGCGCTATTGGAATCCTTCTTCGTTCCCCCGATTCCGAGCCCCGCCTGC
GTGCGTTTGAAGTGGAAGGGGACCGGATTTTGCGTTTGCTAATTCATGGTCTGTT
AGTAGTTCCTTAGTTTTCTGGAGTTAGTTCGATTTTGATAAATCCAATATAATAGCT
TCTGGTAGAACAAATCCTGATTACAGAAAGGCCTAATGGGCTATCAACTAAAAATG
GTATAGATAACAAAAGTTGAGCTTCCCTAGCCTGTGCTTATTTCCTTATCCCAATA
GTCTAAGCATTGTTTTCTGCAACCCTATCAGGTTCCCTTCAGGCCGAAGTTGAGCT
TCATGGTGGCATTTCAGGCTCAACATGTGAAATATGCTCCTAACCTGATCAAATCA
GTAGTAAAAAGTCTTAGATCAAACATCACTGATGGTGACAATGGAATGACCGAGC
CAGCTAGGGAATTGTTGGAACGGCTGTTTGCGAAGACACAGAGTCTAGACACAAG
TGCTTCTCATGATAGTGAACTGAGCATGAGCATCGAGGTCCTCAAGTCTGAATTC
GAGCGCGCCTTGTCGATTCTCAGAAAGAAAGAGAGGTACCTTCGGAATGCAGAGA
AGAGGGTTTCTGATGATCAGTTAAGGTTGAACCAGACGAAGCAGGACCTGGATCA
GAGAGAGCAAGAGATCAGCAAAGCACATGCAAAGCAGCAACAAATGGAGAAAGC
ACTGAAAAAGGCAAGTAGAGATCTGTCGTTGCGAGTGAAGCAGATCAATAATCTG
AAGCTTCTGGTTGAGAGGCAAGACAGGAAAATTGCCAGTTCAGAAGCTTTGCTTT
CTCAAAAGGTAATTGAAGTGGAAAATCTCAAACAAGATATGTTCAACAAGAATAAG
GAAGCAGACTTGATAAGATCAGAGATTAAGTTGAAAGAACAACTGCTTCTTGAAGC

| SEQUENCE LISTING |
| --- |
| TAATCAGGACGTCGTGCAGCAAGAGGCAACAGTTAGGGAGCTGCGGAGTGAAAC |
| TGAAAAAAAGGCTATTGATATTGCCATATCCAATGAATTGAGGAAGGCTAATGAAG |
| AGAAACTGAAAATTGCTGAACAGGAACTTGAGAAGCAGAATTTAGGATGGTTAGC |
| AGCACAGCAAGAATTAAAGGAACTGGCGCAACTTGCATCCAAGGACACAGATGAT |
| ATCAAGGGTACTGTCACTGACTTTAAACGTGTGAGGTCCCTGCTGGATGCTGTAC |
| GGTCTGAACTAATCTCTTCAAAAGATAATTTCGCCTCCTCTCGCAGACAAATAGAA |
| GAACAAACGGTGCAGTTGCAGAAGCAAGTGCAAGAACTCAAGGACCAAAGGGTAT |
| TGCTGATGTCTTACACCCAGGATTTGGAAGCTGCTCAACTGGAGATTCAAGGGAA |
| GACAAAAGATCTCAATGCTGCACAGTCTCGTTGCCATGAACTTGAATTGCAGTTAC |
| TTAAGGAAATGGAGAAGGTTGAGTCTCTAGAAGCCGAGTTAACCAAAGAAAGAGA |
| GAACTTGGAACAGAAAACTGAACAAGTAGACTTTCTTCAGAAGGAGCTTGTTCAGA |
| AGGAAAATGAGTGTGGTAATTCACAAAAGCTTGTTAAAATAAAAGAGGCAGAGCTA |
| TTAGAAGCCAGACATGAAGTCCAAGATATGAAATCAAAGGTAGATTCTATCCAATT |
| GGCTGTTCAAGAGAAGGATTCAGAGCTTTCGGACACACAGAGCAGACTAACTGAA |
| GTGAGCGGTGAAGTTGTTGAGCTTCAGCAGTTGCTAAATAGCAAGGATGATCAAC |
| TTGTTCAGGTTAGAACTGAGTTACATGATAAAGAACAATATATAGAATCAATGCAG |
| AGTGAATTAGAGAGCATAAGATTCAGATGCTCGCAAGCTGAATCTGTGTTGCGAA |
| GGATGGCTGAGCTCACTGGCGATCTTGCTAGTTCCGTGAAAGCTGGAGAAATGGA |
| CATTTATGCATTACTGGATGATGAAATTTCAAGCACCAGTACAGTCCTTGAGTCCA |
| ATTTGCACAAGCATAATCAACTGGAGGCTGACATAGAGATGTTAAGAGAATCCTTA |
| CGGCATAAGGACATGGACTTAAGAGCTGCTCATGAAGCACTTGATGCCAAAGATC |
| AAGAACTGAAGGCAGTAGTTGGAAAGTGGGATTTCAAGGAGAAGGAACTGGATGA |
| GGTGGAAGAGTTACAGAAAGATCCCATTGACATGAAGGAACTCCCTGTTCTTTCTA |
| ACGAGACAACAGGGGGCAGCATTACAGGAGAGATGGAGCTCAAGAACTTCAAA |
| TTGAAGCTGCCGAGGTGGAGGCACTTGCTGCTACTACTGCACTAAAGAAGCTTGC |
| GGATATGAGTAAGAAATACTTGAGATGCCGCAAAGCTGATTCTGGGATTGGTTTG |
| GTTGCATCAGAAAGTGCAAACATTGGTAAAGCGAATTCTAGGATGGAATTAAACAA |
| CAAGATGGATGTGATTTTTGAAGCTAAACAAGAAATTGTTAGACTATTTTCATTGAC |
| AAAAGAGCTCATCACTGATGACGCAATAAATGATGCTGAGGAACGATAACTTTAGA |
| *GCTAAAATATTCAGCCAGCCAATTCTACCAAGATAGCTTCAGAATAGAGGTATGGC* |
| *AGATAGATCTCAGACATTTATGAGCAGCTGGGTCGCATAGCAAGACCAAAATCTG* |
| *TCGCTGGTTGATTCGGCAAATGGCGTTCTAACAAAGGATAAAAGAAACTGTCCAT* |
| *GTGTGTATTTTCGGAGACGAACCTCAAACTCTTCCTAATAATGTTTTCCGATGTGTT* |
| *GCTGTAAATATATGTGGGGAGTTACTGGTATGGCATTTGGTGCTGGTTGTCCCCA* |
| *CACACTGTACATTGGACGATGCTCCAGGTTTTGTTGTTGGTTAACTGAAATGATGT* |
| *TCAGTGTTTGCTATTGTTGTTGCACCACAAAGTGGATGATGTTCCAAATTAGAGCA* |
| *ACAAGGAAAGAAAGGGAGATGACTGTCAAGAAAAAGGGAAAGAAAGGAGATAGCT* |
| *ATAGTTCATCTAAAAAGGGGAGATGGAAATTTTGAGCTGGAAGTCACCAATCTTCA* |
| *AGGCGCAACCTTTTAAATTTTGCACAGAAAGTATTCAGTATTTCAGGGTTTAACTGT* |
| *TAGGATTCTGTTATTTGTAGAGTCTTTAAGATTCTATTCCAAGTGCAATGCCCCTCA* |
| *ATGTCACTTCGAGGCAGAGACAAACTCTATCTCTATGCTTTCTCAGTTTCTCTTAAC* |
| *TCCAGGTCACCAAAATTCTTATGTGGCAATACCCTTACAGGTAGTTGATGTAAGCC* |
| *TATGCATACATTGCATAGTCAGTTCTTTCTCTGATTGAGAGGCACTAACTTTCTTCA* |
| *TCAGATAAA* |

*Brachypodium* CDS nucleic acid sequence (Bradi3g06260)   SEQ ID NO: 15

| |
| --- |
| ATGTTCCGCGGCCATGCCCCTCTCCACCGGCTCCCCTCGCCGCCGCCGCCACCG |
| GCGGCGGCCGCCGGCGCACTCCCCAGCGCGTCCCCGTCGTGCCGCACCTCCAC |
| TCATGTTCCCTTCAGGCCGAAGTTGAGCTTCATGGTGGCATTTCAGGCTCAACAT |
| GTGAAATATGCTCCTAACCTGATCAAATCAGTAGTAAAAAGTCTTAGATCAAACAT |
| CACTGATGGTGACAATGGAATGACCGAGCCAGCTAGGGAATTGTTGGAACGGCT |
| GTTTGCGAAGACACAGAGTCTAGACACAAGTGCTTCTCATGATAGTGAACTGAGC |
| ATGAGCATCGAGGTCCTCAAGTCTGAATTCGAGCGCGCCTTGTCGATTCTCAGAA |
| AGAAAGAGAGGTACCTTCGGAATGCAGAGAAGAGGGTTTCTGATGATCAGTTAAG |
| GTTGAACCAGACGAAGCAGGACCTGGATCAGAGAGCAAGAGATCAGCAAAGC |
| ACATGCAAAGCAGCAACAAATGGAGAAAGCACTGAAAAAGGCAAGTAGAGATCTG |
| TCGTTGCGAGTGAAGCAGATCAATAATCTGAAGCTTCTGGTTGAGAGGCAAGACA |
| GGAAAATTGCCAGTTCAGAAGCTTTGCTTTCTCAAAAGGTAATTGAAGTGGAAAAT |
| CTCAAACAAGATATGTTCAACAAGAATAAGGAAGCAGACTTGATAAGATCAGAGAT |
| TAAGTTGAAAGAACAACTGCTTCTTGAAGCTAATCAGGACGTCGTGCAGCAAGAG |
| GCAACAGTTAGGGAGCTGCGGAGTGAAACTGAAAAAAAGGCTATTGATATTGCCA |
| TATCCAATGAATTGAGGAAGGCTAATGAAGAGAAACTGAAAATTGCTGAACAGGAA |
| CTTGAGAAGCAGAATTTAGGATGGTTAGCAGCACAGCAAGAATTAAAGGAACTGG |
| CGCAACTTGCATCCAAGGACACAGATGATATCAAGGGTACTGTCACTGACTTTAAA |
| CGTGTGAGGTCCCTGCTGGATGCTGTACGGTCTGAACTAATCTCTTCAAAAGATA |
| ATTTCGCCTCCTCTCGCAGACAAATAGAAGAACAAACGGTGCAGTTGCAGAAGCA |
| AGTGCAAGAACTCAAGGACCAAAGGGTATTGCTGATGTCTTACACCCAGGATTTG |
| GAAGCTGCTCAACTGGAGATTCAAGGGAAGACAAAAGATCTCAATGCTGCACAGT |
| CTCGTTGCCATGAACTTGAATTGCAGTTACTTAAGGAAATGGAGAAGGTTGAGTCT |
| CTAGAAGCCGAGTTAACCAAAGAAAGAGAACTTGGAACAGAAAACTGAACAAG |
| TAGACTTTCTTCAGAAGGAGCTTGTTCAGAAGGAAAATGAGTGTGGTAATTCACAA |
| AAGCTTGTTAAAATAAAAGAGGCAGAGCTATTAGAAGCCAGACATGAAGTCCAAG |
| ATATGAAATCAAAGGTAGATTCTATCCAATTGGCTGTTCAAGAGAAGGATTCAGAG |
| CTTTCGGACACACAGAGCAGACTAACTGAAGTGAGCGGTGAAGTTGTTGAGCTTC |
| AGCAGTTGCTAAATAGCAAGGATGATCAACTTGTTCAGGTTAGAACTGAGTTACAT |
| GATAAAGAACAATATATAGAATCAATGCAGAGTGAATTAGAGAGCATAAGATTCAG |

| SEQUENCE LISTING |
|---|

```
ATGCTCGCAAGCTGAATCTGTGTTGCGAAGGATGGCTGAGCTCACTGGCGATCTT
GCTAGTTCCGTGAAAGCTGGAGAAATGGACATTTATGCATTACTGGATGATGAAAT
TTCAAGCACCAGTACAGTCCTTGAGTCCAATTTGCACAAGCATAATCAACTGGAGG
CTGACATAGAGATGTTAAGAGAATCCTTACGGCATAAGGACATGGACTTAAGAGC
TGCTCATGAAGCACTTGATGCCAAAGATCAAGAACTGAAGGCAGTAGTTGGAAAG
TGGGATTTCAAGGAGAAGGAACTGGATGAGGTGGAAGAGTTACAGAAAGATCCCA
TTGACATGAAGGAACTCCCTGTTCTTTCTAACGAGACAACAGGGGGCAGCATTAC
AGGAGAGATGGAGCTCAAGAAGCTTCAAATTGAAGCTGCCGAGGTGGAGGCACT
TGCTGCTACTACTGCACTAAAGAAGCTTGCGGATATGAGTAAGAAATACTTGAGAT
GCCGCAAAGCTGATTCTGGGATTGGTTTGGTTGCATCAGAAAGTGCAAACATTGG
TAAAGCGAATTCTAGGATGGAATTAAACAACAAGATGGATGTGATTTTTGAAGCTA
AACAAGAAATTGTTAGACTATTTTCATTGACAAAAGAGCTCATCACTGATGACGCA
ATAAATGATGCTGAGGAACGATAA
```

Z. mays CDS nucleic acid sequence (GRMZM2G104357_T01)

SEQ ID NO: 16

```
ATGCCCCTCTCCTCCACCACCTCGCCGTCGGCGGGGCGGCCGCCGCCGCCGC
AGTGCGCACCGCTTCGCCGCCTCGCCGCATCGCCACCCACGTTTTGTTCAGGCA
GAAGCTAGGCATTCCGGCGGGGTTCCAGGCTCAACATGTGAAATGTTTACCTCAT
TTGATCAGATCTATTGTAAGAGGTGCTAGATCAGATATCACTGACGGTGACAATGG
AACAACTGAGCCCGCGAGGGAACTATTGGAGCGTCTGTTTGCCAAGACAAAGAGT
CTAGATCCAAGCGCTTCTCAGGGTAGGGAACTGAGCATGAGCATTGAGGTCCTGA
AGACTGAGTTTGAGGCTGCCTTATCAATCCTAAGGAAGAAAGAGAAGGATCTTCG
TGATGCGGAGAAGAAAGTCTCCGTGGATAGGTCAAGGTTGAACCAGACGAAGCA
GGACCTCGATCAGAGGGAGGAGGACATCATCAAAGCATACTCGAGGCAACATGA
AATGGAGAAAGCACTGATGAAGGCGAGCAGGGATTTGACTCTACAAGTCCGACAG
ATCAATAACCTGAAGGTTATGATCGAGGAACAAGACAAAAAACTTGTTAGTTCACA
AGACGCACTTTCTAAGAAGGTTATTGAAGTGGATAAGCTTAAACAAGAGATGCTGA
AGAAGAATGATGAAGTAGCTTTGCTGCATTCAGAGATCGAGTCCAAGGAACAAGA
GCTTCTTGTAGCTAATCAGGCCATTGCACGTCAAGAAGCAACAATTAGGGAGCTT
CGAAGTGAAACTAAAGAAAGGAAACTGAGGTTGAGAGATTAAATGAATTGGCGA
AAGCTAATGAAGACAAACTGAAATTTGCAGAACAGGAACTTGAGAAGCAGAATTCA
GGATGGATTGCAGCACAGCAAGAGTTAAAGGAATTGGCACAAATGGCATTCAAGG
ATAAAGATGATATCAAGAATACAATCAATGACTTCAAACGGGTGAGGTATTTGCTG
GATGCTGTGCGTTCTGAACTAATAGCTTCAAAAGAGGCTTTAACCTTCTCACGCAA
GCAAGTAGAAGATCAAGCGGCACAGTTGAGTAACCAAGTGCAGGAACTCACAGAC
CAAAAGGCACTGATTATTTCTTATACCCGGAATCTGGAAGCTGCCCAGCTGGAGA
TTCAAGGAAAGTCAAATGAGCTCAGTACTGTACAATCTCGTTGTAGTGAACTTGAA
TCTCAGTTACTTGAGGAAACGGAGAAGGTTGAGTTCCTAGAGGCTATGTTAACCA
AAGAAAGGGAGATCTTGGAACAGAAAACTAAGGAAGTGGCGTTCCTTCAAGAGGA
GGTAGTTCAGAAGGAGAAGGATTACTTCAATTCACAAAAGCTTGTTGAAACAAAAG
AGACTGAGCTGTTAGAGGCGAGGCATGAAGTCGAAGATATGAATTGAAGGTGGA
TTCCATACAATTTGCTGTTCGAGAGAAGGATTTGGAGCTTCTGGAGGCACAAAGA
AAACTTGATGAAGTTAACAGCGAAGTTGTTGAACTTCAGCAGCTGATAAATAGCAA
GGAGGATCAACTGGTCCAAGTTAGAACTGAATTACAGGATAAAGAGCAATGCATA
CAATTGATGCAGGATGAATTGGATAAGATGAGATTAGGACGCTCGCAAGCTGAAT
CTGTGGTTCAAAAGATAGTCGAGCTTACTAGCAATCTCATAGGTTCTGTCAAAGGC
GAAGAATTCAACATTTATAACTTGCTGGATGATGAAATTTTAAGCACGAGCACAGC
CCTTGAGTACAGTTTGCATAAGCATAACCAACTGGAGGCTGACATAGACATGTTAA
AAGAATCCCTGCGACAGAAGGACATGGATCTGACTGCTGCTTATAAAGCGCTTGA
CGCCAAAGATCGAGAGTTGAAGGCAGTAGTTGGAAGGTTAGATGTTAGGGACAAG
GAACTAGACAAGTTGGAAGAGCTATCCATAGACCCCTATGGCACCAGGAAACTGT
CTAGAGTTGCTGATGAGGCAACCGAAGACAACATTGCTGGTGAAGCGGAGCTCC
AAAAGCATGAGATGGAATCTGTGGAGATGGAGGCACTAGCTGCTAGCACTATGTT
GAAGAAGCTTGCGGATGTGACTAAGAAATTCTTGAGAAGTGGTAGAACTGATTCT
GGTACCAATTTAGATTCAAACGTTAGTGAAGGTGCTTCTGAATTGGAACCACAAAG
GAAACTTAATGTGATTCTCGAGGCTAAAAAGGAGATTGTCGGCTATTTCTTTGA
CAGAAGAGCTCGTCACTGGTGCTCAAACGAAGGACGATGATGAGGAACCATAG
```

Z. mays genomic nucleic acid sequence (GRMZM2G104357) (5' UTR and 3'UTR are italicised)

SEQ ID NO: 17

*GCTGCACTCCATACGCGGCCGGGAGCTCCCCCGGTTCCACCACCTCCTCACCTC*
*ATCCGTCTGAAGCCGCCGCTTTTGCCTCGACCTCGCCCGCAGTCCGCGATAGCG*
*CGGGTTGCCACCCGTCCGATCGCGCCCGGACGACCGCGACCCCCTCCCCTCAT*
*GTTCCGGGCC*ATGCCCCTCTCCTCCACCACCTCGCCGTCGGCGGGGCGGCC
GCCGCCGCCGCAGTGCGCACCGCTTCGCCGCCTCGCCGCATCGCCACCCACGT
GAGCATTCTTGTACCTTCACTGATTCTTATAAATTATCATGCTGTGTTGTCACGGTA
TCGGGTTGCTGAGCTCAGTGGCGATTGTGTTCTTGGATGCCTTCCGAATTGCGGT
CTCGTGTAGACGTCCAGTACCTTTTTTTAGTTGTGTTTAACTGAAGATAAAAGATGA
ATTTTCGGATTCCTAACCCGTACTCTTTTGGTACCTTTCTCTTCGCCGGAGTCGAT
TTTATGGTGGTAGGTTCGTGCGCAGTTCAGATTAATCAAATCCATTACCAAAATTC
GGTCGAGTGAAGATAGCTGTGTATTTTCTTTAGCCCGTCTGAACTCTTCTAATTA
AAGCACAATTCGTGTGCATTATCCTAATAGCGCCCCACGCGTTTTTTTCCTTGT
AAACTCCCAGGTTTGTTCAGGCAGAAGCTAGGCATTCCGGCGGGGTTCCAGGCT
CAACATGTGAAATGTTTACCTCATTTGATCAGATCTATTGTAAGAGGTGCTAGATC
AGATATCACTGACGGTGACAATGGAACAACTGAGCCCGCGAGGGAACTATTGGA

| SEQUENCE LISTING |
|---|
| GCGTCTGTTTGCCAAGACAAAGAGTCTAGATCCAAGCGCTTCTCAGGGTAGGGAA |
| CTGAGCATGAGCATTGAGGTCCTGAAGACTGAGTTTGAGGCTGCCTTATCAATCC |
| TAAGGAAGAAAGAGAAGGATCTTCGTGATGCGGAGAAGAAAGTCTCCGTGGATAG |
| GTCAAGGTTGAACCAGACGAAGCAGGACCTCGATCAGAGGGAGGAGGACATCAT |
| CAAAGCATACTCGAGGCAACATGAAATGGAGAAAGCACTGATGAAGGCGAGCAG |
| GGATTTGACTCTACAAGTCCGACAGATCAATAACCTGAAGGTTATGATCGAGGAA |
| CAAGACAAAAAACTTGTTAGTTCACAAGACGCACTTTCTAAGAAGGTTATTGAAGT |
| GGATAAGCTTAAACAAGAGATGCTGAAGAAGAATGATGAAGTAGCTTTGCTGCATT |
| CAGAGATCGAGTCCAAGGAACAAGAGCTTCTTGTAGCTAATCAGGCCATTGCACG |
| TCAAGAAGCAACAATTAGGGAGCTTCGAAGTGAAACTAAAAGAAAGGAAACTGAG |
| GTTGAGAGATTAAATGAATTGGCGAAAGCTAATGAAGACAAACTGAAATTTGCAGA |
| ACAGGAACTTGAGAAGCAGAATTCAGGATGGATTGCAGCACAGCAAGAGTTAAAG |
| GAATTGGCACAAATGGCATTCAAGGATAAAGATGATATCAAGAATACAATCAATGA |
| CTTCAAACGGGTGAGGTATTTGCTGGATGCTGTGCGTTCTGAACTAATAGCTTCAA |
| AAGAGGCTTTAACCTTCTCACGCAAGCAAGTAGAAGATCAAGCGGCACAGTTGAG |
| TAACCAAGTGCAGGAACTCACAGACCAAAAGGCACTGATTATTTCTTATACCCGGA |
| ATCTGGAAGCTGCCCAGCTGGAGATTCAAGGAAAGTCAAATGAGCTCAGTACTGT |
| ACAATCGTTGTAGTGAACTTGAATCTCAGTTACTTGAGGAAACGGAGAAGGTTG |
| AGTTCCTAGAGGCTATGTTAACCAAAGAAGGGAGATCTTGGAACAGAAAACTAA |
| GGAAGTGGCGTTCCTTCAAGAGGAGGTAGTTCAGAAGGAGAAGGATTACTTCAAT |
| TCACAAAAGCTTGTTGAAACAAAAGAGACTGAGCTGTTAGAGGCGAGGCATGAAG |
| TCGAAGATATGAAATTGAAGGTGGATTCCATACAATTTGCTGTTCGAGAGAAGGAT |
| TTGGAGCTTCTGGAGGCACAAAGAAAACTTGATGAAGTTAACAGCGAAGTTGTTG |
| AACTTCAGCAGCTGATAAATAGCAAGGAGGATCAACTGGTCCAAGTTAGAACTGA |
| ATTACAGGATAAAGAGCAATGCATACAATTGATGCAGGATGAATTGGATAAGATGA |
| GATTAGGACGCTCGCAAGCTGAATCTGTGGTTCAAAAGATAGTCGAGCTTACTAG |
| CAATCTCATAGGTTCTGTCAAAGGCGAAGAATTCAACATTTATAACTTGCTGGATG |
| ATGAAATTTTAAGCACGAACGCACAGCCCTTGAGTACAGTTTGCATAAGCATAACCAA |
| CTGGAGGCTGACATAGACATGTTAAAAGAATCCCTGCGACAGAAGGACATGGATC |
| TGACTGCTGCTTATAAAGCGCTTGACGCCAAAGATCGAGAGTTGAAGGCAGTAGT |
| TGGAAGGTTAGATGTTAGGGACAAGGAACTAGACAAGTTGGAAGAGCTATCCATA |
| GACCCCTATGGCACCAGGAAACTGTCTAGAGTTGCTGATGAGGCAACCGAAGACA |
| ACATTGCTGGTGAAGCGGAGCTCCAAAAGCATGAGATGGAATCTGTGGAGATGGA |
| GGCACTAGCTGCTAGCACTATGTTGAAGAAGCTTGCGGATGTGACTAAGAAATTC |
| TTGAGAAGTGGTAGAACTGATTCTGGTACCAATTTAGATTCAAACGTTAGTGAAGG |
| TGCTTCTGAATTGGAACCACAAAGGAAACTTAATGTGATTCTCGAGGCTAAAAAGG |
| AGATTGTCGGGCTATTTTCTTTGACAGAAGAGCTCGTCACTGGTGCTCAAACGAA |
| GGACGATGATGAGGAACCATAGCATCATAAGTTCATAACTGAACATATAACTGCAT |
| *CATGAATGTTATGCATGTCAACTGGAATGACGCAGCTGAAATTGTTACCATCGTTT* |
| *CCTTTCCTTTTGGGGCTCAGGATTTCTTTATGTTCTTTTGGTTCATGGATGGCATC* |
| *GCAAAATGAAAAAAAAGATTGTTTAGATTTTGGTTAAAAGGATGATGATTGTGC* |

Z. mays amino acid sequence (GRMZM2G104357_T01)  SEQ ID NO: 18

MPLSSTTSPSAGAAAAAAVRTASPPRRIATHVLFRQKLGIPAGFQAQHVKCLPHLIRSI
VRGARSDITDGDNGTTEPARELLERLFAKTKSLDPSASQGRELSMSIEVLKTEFEAAL
SILRKKEKDLRDAEKKVSVDRSRLNQTKQDLDQREEDIIKAYSRQHEMEKALMKASRD
LTLQVRQINNLKVMIEEQDKKLVSSQDALSKKVIEVDKLKQEMLKKNDEVALLHSEIES
KEQELLVANQAIARQEATIRELRSETKRKETEVERLNELAKANEDKLKFAEQELEKQN
SGWIAAQQELKELAQMAFKDKDDIKNTINDFKRVRYLLDAVRSELIASKEALTFSRKQV
EDQAAQLSNQVQELTDQKALIISYTRNLEAAQLEIQGKSNELSTVQSRCSELESQLLEE
TEKVEFLEAMLTKEREILEQKTKEVAFLQEEVVQKEKDYFNSQKLVETKETELLEARHE
VEDMKLKVDSIQFAVREKDLELLEAQRKLDEVNSEVVELQQLINSKEDQLVQVRTELQ
DKEQCIQLMQDELDKMRLGRSQAESVVQKIVELTSNLIGSVKGEEFNIYNLLDDEILST
STALEYSLHKHNQLEADIDMLKESLRQKDMDLTAAYKALDAKDRELKAVVGRLDVRD
KELDKLEELSIDPYGTRKLSRVADEATEDNIAGEAELQKHEMESVEMEALAASTMLKK
LADVTKKFLRSGRTDSGTNLDSNVSEGASELEPQRKLNVILEAKKEIVGLFSLTEELVT
GAQTKDDDEEP*

O. sativa amino acid sequence (LOC_Os02g09340.1)  SEQ ID NO: 19

MPPLSPSSSPPATAAAVLRCGSPSCRPVTHELFRQKLSFMVSFQAQHMRCAPHLIKS
VVKGIRANITDGENGATEPARELLERLFAKTQRLDTSASQDSELSMSIDVLKSEFEAAL
STLRKKERDLRDAENRVSVDQVRLNRAKKDLDQRERGINRAYARQQEMERSLGKAS
RDLVLQVRQIDNLKLLVDEQDKKIASSQDLLSQKVTEVEKLKQDMLKKNEEVTLMRSEI
KSKEQLLLEANQAAEQQEATIKELRSEIKRKEIDFSRSNELRKANEQKLKIAEQELERQ
NMGWLAAQKELKEVAQLACKDMDGIKDTVSDFKRVRSLLDAVRSELIASKEAFSSSR
KQIEDQAVQMQKQVQELSGQRLLLSSFNQNLEAARLEIQGKAKELNAAQSRCHELES
LLLQEKEKVESLEAVLTKERESLEEKTKEVELLQKALVQKENEHSNSLKLVEIKESELLE
ARNEVQDMKSKVESIQIAVQEKDSELSETQRRLAEVNSEVVELKQLLDSKEDQLVQV
RTELQDKEQHIQTLQNKLDSMKFSCSQAESVVQKIAELTGNLASSVEGEEMDIYALLD
DEISSTGTALKSNLHKHNQLEADIEMLKESLHQKDMDLRAAHEALDAKDQELKAVMR
RWDVKEEVDKLEGFLKDPSDIKRPSDFSVHMGLQNLQTEAAEVEALAATTTLKKLAD
MAKGFLRSGKTDSGINLVASPSVNSTRIVSKTKPNKEMDMILDAEKEIAGLFSLTEQLIT
EAGIDVAHQA*

SEQUENCE LISTING

O. sativa genomic nucleic acid sequence (LOC_Os02g09340) (5' UTR and 3'UTR are italicised)

SEQ ID NO: 20

*GCAGTCCACACGCGTCCGGTTCGGCCTCCACATCATCATCTCCTCTCCTCTCTCG*
*TCTCCGCGCGCCGTGAGCCGTCCGATCTCGCGCGGGCGGCCGTGATCCGCTCC*
*CTCCCCCCCACCCACGTGCTAGGCCGCC*ATGCCACCCCTCTCCCCTTCCTCCTC
GCCGCCGGCGACGGCGGCGGCGGTTCTCCGCTGCGGCTCCCCGTCGTGCCGCC
CCGTCACACATGTGAGCATCCCTTCCCATCTCCTCGTATCTCCTCTCTCGTTGCTC
GTTGTTCGTTGTTGGTGGTGTGTGTTCTCGTTCGGTTTCCGATTCCGAGCTCGTCT
ACTAGCGGTTTGAAGGGGACGGAGGATCGGATTTTTTTTGGTTTTCTAGTTCAAGT
TGTGCTGCCTGGTAGTGGTAGTTTTTTAATTAGGAGTTTTTTGGCTGAAATTGGTTT
GACGGTGGTCAATTCCGGTACATCTTTAAACTAATCTTGATAACGGAGAACCTAAC
GAGAACTATTAGCGATTGTAGTTTGTGTGTGGCGATAGATTTGGGATCAAAATTCA
TCCGCTGCGCTATGTCGCTTTGCTGAAGATTGAAACTATGTGTGAATAAATATAGT
TCTGAATTTTTAGTTCAGAGTTAACTTTGGCATACTATATCATTTCAGTCCTTTGGT
TCACCGGGAGAATTTTCATGTACAAATAAAATCCCCATTTTTGCAGATAGGTTCAC
TAGGAGGTGTCCTGTTGCAACTTTTTTCTAGCAGTCTACTGATGCACACTGTTTTC
TGCAATCCCGACAGGAGCTGTTCAGGCAGAAGTTGAGTTTCATGGTGTCATTTCA
AGCTCAACATATGAGATGTGCTCCTCATTTGATCAAATCAGTTGTTAAAGGTATTA
GAGCAAATATCACTGATGGCGAGAATGGAGCAACTGAACCAGCTAGGGAGCTATT
GGAGCGGCTGTTTGCGAAGACGCAAAGGTTGGATACCAGTGCTTCCCAGGATAG
TGAGCTGAGTATGAGCATTGATGTACTGAAGTCTGAATTTGAGGCCGCCTTGTCTA
CCTTGAGGAAGAAAGAGGGATCTCCGAGATGCGGAGAATCGGGTTTCAGTTG
ATCAGGTACGCCTGAACCGGGCGAAGAAGGATCTTGATCAGAGAGAGCGTGGGA
TCAATAGAGCATATGCAAGGCAACAGGAAATGGAGAGATCACTGGGTAAGGCAAG
TAGAGATCTGGTTTTACAAGTGAGGCAGATCGATAACCTGAAGCTTCTTGTTGATG
AGCAAGACAAGAAAATTGCCAGCTCACAAGATTTGCTTTCTCAGAAGGTAACTGAA
GTGGAAAAGCTTAAGCAAGATATGTTGAAGAAGAATGAAGAAGTAACCTTGATGC
GTTCAGAGATCAAGTCCAAGGAACAGCTGCTTCTTGAAGCTAATCAGGCTGCTGA
GCAGCAAGAAGCAACAATTAAGGAGCTCCGGAGTGAAATTAAAAGAAAAGAAATT
GATTTTTCCAGATCGAATGAATTGAGAAAGGCCAATGAACAGAAACTAAAAATCGC
CGAGCAAGAACTTGAGAGGCAGAATATGGGATGGTTAGCAGCACAGAAAGAGTTA
AAGGAAGTGGCGCAACTAGCATGCAAGGATATGGATGGTATCAAGGATACAGTCA
GTGACTTCAAACGTGTGAGGTCTCTGCTGGATGCTGTACGGTCTGAACTAATCGC
TTCAAAAGAGGCTTTCTCCTCCTCTCGAAAACAGATAGAAGATCAAGCAGTGCAGA
TGCAGAAACAAGTTCAAGAACTCTCTGGTCAAAGGCTATTGCTTTCATCTTTCAAC
CAGAACTTGGAAGCTGCTCGGTTGGAGATTCAAGGCAAGGCAAAGGAGCTCAAT
GCTGCACAGTCTCGCTGTCATGAACTTGAATCACTGTTACTTCAGGAAAAGGAGA
AGGTTGAGTCTCTGGAAGCAGTGTTAACAAAAGAAAGAGAGCTTAGAAGAGAA
AACCAAAGAAGTTGAGTTGCTTCAAAAGGCGCTCGTTCAGAAGGAAAATGAGCAC
AGCAATTCATTAAAGCTTGTTGAAATAAAAGAATCTGAGCTGTTAGAAGCCCGAAA
TGAAGTCCAAGATATGAAATCAAAGGTGGAATCTATCCAAATAGCTGTTCAGGAGA
AGGATTCAGAGCTTTCTGAAACACAACGCAGACTTGCTGAAGTGAACAGTGAAGT
TGTTGAACTAAAGCAGCTGCTAGATAGCAAGGAAGATCAACTTGTTCAGGTTAGAA
CCGAATTACAGGATAAAGAACAACACATACAGACACTACAGAATAAATTGGATAGC
ATGAAATTCAGTTGCTCACAAGCTGAATCTGTGGTGCAAAGATAGCTGAACTCAC
TGGCAATCTTGCTAGTTCAGTAGAAGGCGAAGAGATGGACATTTATGCATTGCTG
GATGATGAGATTTCGAGCACAGGTACAGCCCTCAAGTCCAATTTGCACAAGCATA
ATCAACTGGAGGCTGACATAGAGATGTTAAAAGAATCCTTGCATCAGAAGGACAT
GGATTTAAGAGCTGCCCATGAAGCACTTGACGCGAAAGATCAAGAGCTGAAGGC
GGTAATGAGAAGGTGGGATGTGAAGGAGGAGGTAGACAAGTTGGAAGGGTTCCT
GAAAGATCCTAGTGACATCAAGAGACCTTCTGATTTTTCCGTTCATATGGGGCTCC
AAAATCTTCAAACTGAAGCTGCGGAGGTGGAGGCACTTGCTGCTACTACACATT
GAAGAAACTTGCAGATATGGCTAAGGGATTCCTGAGAAGTGGCAAAACTGATTCT
GGCATCAATCTGGTTGCATCGCCAAGTGTAAACAGTACTAGAATTGTTTCCAAGAC
CAAACCAAACAAGGAAATGGATATGATTCTTGATGCTGAAAAGGAAATTGCCGGG
CTCTTTTCGTTGACAGAACAGCTCATTACCGAGGCTGGAATAGATGTTGCTCACCA
AGCATAGCTTCAGAACCCAGAAATGTATATCATATTGCAGTTTTGCAACATTTAGAT
*AGTTGCTGTGAAGATTCAGCTGAAATTGTTAGCGTTTTCATTTCTTTTGCTTTGGGT*
*CTCATCGCCCTGTTTGCTGTTGGATTGCTCTGCTCCAAGTGCGAAAGGGAGACAT*
*CGATGTTGATATGCCTCTTACTGTTTACATGATATATTGCATCTGCTGAAATCCTAG*
*AAAAAAAATGATAAATTTGTGATCCAAAACCCCTTCTCTAGTCAGCCAGTGGCGGA*
*TTTGCTGACAACCTAGGCAGCTGCCTGTAATTCATATTCTCCAAAACTCCTTCAGA*
*CCGGAGTTAATGAAGATATCCAAAGCCTGTAAAATTGTTGCTGATTTTGGAGAGGT*
*GAGAAATAGTGAAGGATTTTACTTTCTGGACGGATACCAGGTTGCCCTTGATTTTG*
*GTCAGCTTTCGACATGTAGATTTGCTGAATTATATCTGTTTTTCTCTTCTCTGTAGT*
*TTCCCATCGGAGAGCTGTTGATTCTCATCATGTTATCCATATGTTAACCTGGAAAA*
*ATTGTACAGAATTTGCTGCTCAGCTTTAGTG*

O. sativa CDS nucleic acid sequence (LOC_Os02g09340.1)

SEQ ID NO: 21

ATGCCACCCCTCTCCCCTTCCTCCTCGCCGCCGGCGACGGCGGCGGCGGTTCTC
CGCTGCGGCTCCCCGTCGTGCCGCCCCGTCACACATGAGCTGTTCAGGCAGAAG
TTGAGTTTCATGGTGTCATTTCAAGCTCAACATATGAGATGTGCTCCTCATTTGATC
AAATCAGTTGTTAAAGGTATTAGAGCAAATATCACTGATGGCGAGAATGGAGCAAC
TGAACCAGCTAGGGAGCTATTGGAGCGGCTGTTTGCGAAGACGCAAAGGTTGGA

SEQUENCE LISTING

```
TACCAGTGCTTCCCAGGATAGTGAGCTGAGTATGAGCATTGATGTACTGAAGTCT
GAATTTGAGGCCGCCTTGTCTACCTTGAGGAAGAAAGAGAGGGATCTCCGAGATG
CGGAGAATCGGGTTTCAGTTGATCAGGTACGCCTGAACCGGGCGAAGAAGGATC
TTGATCAGAGAGAGCGTGGGATCAATAGAGCATATGCAAGGCAACAGGAAATGGA
GAGATCACTGGGTAAGGCAAGTAGAGATCTGGTTTTACAAGTGAGGCAGATCGAT
AACCTGAAGCTTCTTGTTGATGAGCAAGACAAGAAAATTGCCAGCTCACAAGATTT
GCTTTCTCAGAAGGTAACTGAAGTGGAAAAGCTTAAGCAAGATATGTTGAAGAAGA
ATGAAGAAGTAACCTTGATGCGTTCAGAGATCAAGTCCAAGGAACAGCTGCTTCTT
GAAGCTAATCAGGCTGCTGAGCAGCAAGAAGCAACAATTAAGGAGCTCCGGAGT
GAAATTAAAGAAAAGAAATTGATTTTTCCAGATCGAATGAATTGAGAAAGGCCAA
TGAACAGAAACTAAAAATCGCCGAGCAAGAACTTGAGAGGCAGAATATGGGATGG
TTAGCAGCACAGAAAGAGTTAAAGGAAGTGGCGCAACTAGCATGCAAGGATATGG
ATGGTATCAAGGATACAGTCAGTGACTTCAAACGTGTGAGGTCTCTGCTGGATGC
TGTACGGTCTGAACTAATCGCTTCAAAAGAGGCTTTCTCCTCCTCTCGAAAACAGA
TAGAAGATCAAGCAGTGCAGATGCAGAAACAAGTTCAAGAACTCTCTGGTCAAAG
GCTATTGCTTTCATCTTTCAACCAGAACTTGGAAGCTGCTCGGTTGGAGATTCAAG
GCAAGGCAAAGGAGCTCAATGCTGCACAGTCTCGCTGTCATGAACTTGAATCACT
GTTACTTCAGGAAAAGGAGAAGGTTGAGTCTCTGGAAGCAGTGTTAACAAAAGAA
AGAGAGAGCTTAGAAGAGAAAACCAAAGAAGTTGAGTTGCTTCAAAAGGCGCTCG
TTCAGAAGGAAAATGAGCACAGCAATTCATTAAAGCTTGTTGAAATAAAAGAATCT
GAGCTGTTAGAAGCCCGAAATGAAGTCCAAGATATGAAATCAAAGGTGGAATCTA
TCCAAATAGCTGTTCAGGAGAAGGATTCAGAGCTTTCTGAAACACAACGCAGACTT
GCTGAAGTAACAGTGAAGTTGTTGAACTAAAGCAGCTGCTAGATAGCAAGGAAG
ATCAACTTGTTCAGGTTAGAACCGAATTACAGGATAAAGAACAACACATACAGACA
CTACAGAATAAAATTGGATAGCATGAAATTCAGTTGCTCACAAGCTGAATCTGTGGT
GCAAAAGATAGCTGAACTCACTGGCAATCTTGCTAGTTCAGTAGAAGGCGAAGAG
ATGGACATTTATGCATTGCTGGATGATGAGATTTCGAGCACAGGTACAGCCCTCA
AGTCCAATTTGCACAAGCATAATCAACTGGAGGCTGACATAGAGATGTTAAAAGAA
TCCTTGCATCAGAAGGACATGGATTTAAGAGCTGCCCATGAAGCACTTGACGCGA
AAGATCAAGAGCTGAAGGGGTAATGAGAAGGTGGGATGTGAAGGAGGAGGTAG
ACAAGTTGGAAGGGTTCCTGAAAGATCCTAGTGACATCAAGAGACCTTCTGATTTT
TCCGTTCATATGGGGCTCCAAAATCTTCAAACTGAAGCTGCGGAGGTGGAGGCAC
TTGCTGCTACTACTACATTGAAGAAACTTGCAGATATGCTAAGGGATTCCTGAGA
AGTGGCAAAACTGATTCTGGCATCAATCTGGTTGCATCGCCAAGTGTAAACAGTA
CTAGAATTGTTTCCAAGACCAAACCAAACAAGGAAATGGATATGATTCTTGATGCT
GAAAAGGAAATTGCCGGGCTCTTTTCGTTGACAGAACAGCTCATTACCGAGGCTG
GAATAGATGTTGCTCACCAAGCATAG
```

SEQ ID NO: 22: TaMRC 6A (cv. Kronos (4n)) promoter sequence

```
TTAACCTGAAAATCTAAAAAGTGGCCGCGCACTTTTTAGTCGAACCGAGCGGCCG
GCTCTCACAGCGTATGCATGTGGTAATTTATTTGTCTGCTAGTGCATGTAGGCGTG
ACATTAAATACGTTCACACTGCTCTTTTAGTTTAAGAAAGACAGATCCATCTGCATT
TATTTTGGGTTTTTAAAAATTCAAAAAGCTATATCTTTCAAACCGCGCGTCGGAATT
CAAATCCGTTTTCACCATTGAAATCCTCGCGACGAGATCTTTGAAACTAGATCCCG
CATGGGTATATTTTGACGAATTTTTTTCGATGCCAACTTTGGAGCTATATAGTGCAA
CTCTATTACTGCAATGTGCAACTTTTATTACTACATCGTGCAACTTTTTTCCAAAAC
TAATGTTTGGAGCTGCACCTTCGTATGAGGTTACAACCTAGCAACCACGACAACTT
TGATGTGCGACTAGTCTATTGCCTCGACGAAAGTCGATGTGCAACCTCCTCTTGTA
ATGTAGTCTAGTCGCATACACATTGATGTTTAGTTGGCTTGTAATGTAGTCTAGTT
GCACATACATTGATATTTAGTTGGCTTGTAATGTAGTCTAGTTGCACACACATTAAT
GTTTAGTTGGCAGGAAGACTAATTGCACACGCATATGATTAGTTGGCTTGTAATTT
AGTCTAGTTGCACACACACTGATGTTTAGTTGGCAGGACACTAGTTGCACACACAT
ATGCTCAGTTGGCGTGGCAATCTAGTCTAGTTGCACACACATTGATGTTTAGTTGG
CAGGACTTTTTTGGCACACACACATATGCTCAGTTGGCGCGCAATCTAGTCTAGTT
GCACACACATTGATATTTAGTTGGCAGAAAGACTAGTTCGTCGAAACATCCCCATG
CGGGATAGTTTTGAAGAGCACGTCGCGAGGATTCCAGCGGTGAAAACGGATCT
TAATTCCGACGCGCGGTTTGGAAGATATAGCTTTTTGAAAATTTAAAAACCGAAAC
AAATGCATATGTGATCTGTTTTTTCCAACTGATTGTGACCGGTGTGAATGTATTAAA
TGCTAAAAGATACATGCGCTAGCGGACAAAAATTACACACATGCATGTCTATACAG
AGCAGACGCTAGCGAATAAAAAATTTCTATTTTAGGCCGGCCGCTCGCGCATGGC
AGCGAGCAGCCGGCCGCTACGTAGACTCGTCTTTTTTTAAGGCAACCAAAGTGTA
CCTTAATTTTTCATGTGTTATAAACTCATACATTTGGAACAGAAAGAAAAAAGGTAG
TAAGACGAGTGAACGGAGAAGAAAAGCTGTAGAACAGTAGAAGGCAAACGAGTAA
ACGACACAGCTCTCTCACGCTTCTCGCGTGGTCGACGTTGCAGTCCACACGCG
GCTGGGCGCGCCGGTTCAACCACACCTCATCTCCCGCACTCCCTCTGCCTCGTAT
CTCCTCGCCTTCCTCCGCACCCCGCAGGCGCATTGCCAGCCGTC
```

TaMRC 6A (cv. Cadenza (6n)) promoter sequence

SEQ ID NO: 23

```
TTAACCTGAAAATCTAAAAAGTGGCCGCGCACTTTTTAGTCGAACCGAGCGGCCG
GCTCTCACAGCGTATGCATGTGGTAATTTATTTGTCTGCTAGTGCATGTAGGCGTG
ACATTAAATACGTTCACACTGCTCTTTTAGTTTAAGAAAGACAGATCCATCTGCATT
TATTTTGGGTTTTTAAAAATTCAAAAAGCTATATCTTTCAAACCGCGCGTCGGAATT
CAAATCCGTTTTCACCATTGAAATCCTCGCGACGAGATCTTTGAAACTAGATCCCG
CATGGGTATATTTTGACGAATTTTTTTCGATGCCAACTTTGGAGCTATATAGTGCAA
CTCTATTACTGCAATGTGCAACTTTTATTACTACATCGTGCAACTTTTTTCCAAAAC
TAATGTTTGGAGCTGCACCTTCGTATGAGGTTACAACCTAGCAACCACGACAACTT
```

SEQUENCE LISTING

```
TGATGTGCGACTAGTCTATTGCCTCGACGAAAGTCGATGTGCAACCTCCTCTTGTA
ATGTAGTCTAGTCGCATACACATTGATGTTTAGTTGGCTTGTAATGTAGTCTAGTT
GCACATACATTGATATTTAGTTGGCTTGTAATGTAGTCTAGTTGCACACACATTAAT
GTTTAGTTGGCAGGAAGACTAATTGCACACGCATATGATTAGTTGGCTTGTAATTT
AGTCTAGTTGCACACACACTGATGTTTAGTTGGCAGGACACTAGTTGCACACACAT
ATGCTCAGTTGGCGTGGCAATCTAGTCTAGTTGCACACACATTGATGTTTAGTTGG
CAGGACTTTTTTGGCACACACACATATGCTCAGTTGGCGCGCAATCTAGTCTAGTT
GCACACACATTGATGTTTAGTTGGCAGAAAGACTAGTTCGTCGAAACATCCCCATG
CGGGATATAGTTTTGAAGAGCACGTCGCGAGGATTCCAGCGGTGAAAACGGATCT
TAATTCCGACGCGCGGTTTGGAAGATATAGCTTTTTGAAAATTTAAAAACCGAAAC
AAATGCATATGTGATCTGTTTTTTCCAACTGATTGTGACCGGTGTGAATGTATTAAA
TGCTAAAAGATACATGCGCTAGCGGACAAAAATTACACACATGCATGTCTATACAG
AGCAGACGCTAGCGAATAAAAAATTTCTATTTTAGGCCGGCCGCTCGCGCATGGC
AGCGAGCAGCCGGCCGCTACGTAGACTCGTCTTTTTTTAAGGCAACCAAAGTGTA
CCTTAATTTTTCATGTGTTATAAACTCATACATTTGGAACAGAAAGAAAAAAGGTAG
TAAGACGAGTGAACGGAGAAGAAAAGCTGTAGAACAGTAGAAGGCAAACGAGTAA
ACGACACAGCTCTCTCCACGCTTCTCGCGTGGTCGACGTTGCAGTCCACACGCG
GCTGGGCGCGCCGGTTCAACCACACCTCATCTCCCGCACTCCCTCTGCCTCGTAT
CTCCTCGCCTTCCTCCGCACCCCGCAGGCGCATTGCCAGCCGTC
```

TaMRC 6D (cv. Cadenza (6n)) promoter sequence          SEQ ID NO: 24

```
CGCTGGTAATCACCAGCGCAGCTAACCACCCCATGAGCTTCTAGTTACTGGTTAG
AAAAGGGATCGCGACCAACTAGAGGTGACTGAGCCGGTCTTCTCCATTATTTCTTT
CTTTTTTTCTTTTCTTTCTATATTTTTTTTCAAATACTTGTTCAAATTTTTTCAAATACT
TGTTCAATTTTTTCAAATACTTGTTCAATATTTTTATATACATGATCAACATTTTTAC
AAATACTTGTTCAATATTTTTATATACATGATCAATATTTTTTAAATACTTATTCAAC
ATTTTTTTCAAATAGTTGTTCAATTTTTTTGCAAATGCTTGATTATCATTTTTATATA
CATGATCAACATTTTTTAAATACTTCTTCAACAGTTTTCAAATACCTATTCAACAGT
TTTCAAATATTTGTTCAACATCTTTCAAGTACTTGTTCAACATTTTTTCAAATGCTTG
ATTTTATATGCATGATCAACATTTTTTCAAATACTTCTTCAACATTTTTAAATACCTAT
TCAACAGATAAATGGGTGCATGCACCTGTCGGCCTAGAGGAAGCAGACTGGGTG
CCAATCGACCAGCAGTGGGCCGACTGGGGCCAATCGGCCAGCAGTGGGCCGAC
TGGATCCAATCGGCCGGCAGTGGGCCGACTGAGGCCAATCGGCCAGCAGTAGG
CCGATTGGATCCAATCGGCCAGCAGTAGGCCGACTGGATCCAATTGGTCAGCAG
TAGGCCGACTGGGTAATATTTTAAAAAAATATAATTATGGCGTAATATTTCTGAAAT
TTAATATAAAACATGTATTATTTAAAAAATTAGTCCGACTATGAGTAGCTCTGCTAG
TTTAAATTTATGTCACCTATGTTTGAACTATGTTTGAATTTGATGTTTGAGCTATGTT
GAGATCAAATATAGTTGGTCGTTTCAGAATTTTACATCTTCGTTTTGGACCATCTGT
TGGAGTTGCTCTTTTACATCACCATTTTGGACTATCTGGTGGAGTTGAGCCGTTTT
CAAAGATGTAAAAAGCAATTTTTGATGATGTAAATTTTTACATCACCGGTTTGGAGC
ACCAAAATATACATCATCTATTGGAGATGCTCTTACCCTAGTATTCCGTTCCGAGT
CAAAATAGTCCCTGATAATTTTCATGTGTTATAAACTCATTCTTTTTAAAGTCAAGA
CTGTCCCTAACAATTTTCATGTGTTATATAAACTCATTTTTTAAGGCAGCCAAGGTG
TACCTTAAATTCCATGTGTTATAAACTCATAAATTTGGAATAGAAAGAAAAAAAGGG
AAGACCAGTGAACGGAGGAGAAAAGCAGTAGAAGGCAAACGACACAGCTCTCTC
TCACGCTTCTCCCGTGGTCGACGTTGCAGTCCACACGCGGCTGGGCGCGGCGGT
TCCACCACCTCCCTCATCTCCCGTACTCCCTCTGCCTCGTATCTCGTCGCCTTCCT
CTGCACCCCGCAGGCGCATTGCCAGCCGTC
```

HvMRC promoter sequence          SEQ ID NO: 25

```
CACCTCATCCCATTCCCCAGCATGGACCTTCTCCTCAAAGTACTTGGTGTTGAAGT
AGAATCCTGACTCTTGTTCAAGCCTGCAGCATCATGCATTGTCAAAATCACATAAA
AATATTGCAATACTCCATTGCACTAAACATAATAGATGGACCAGAGCTCGAAGGGG
AAAAAGAAAAATGGTATGGCGCTCAGGAAGACCTCGGCAATTCAATTCTTGAGCT
CACAACATTGGCCCAGTACTGCCAACCCGAGTTGTCTACCTGAGGCGTCACGCAT
GACTGTACTGACGACAATACAGAAGCAAGTGAAAACAGAGTTTCAGACTAATCCA
TTTGTTTCGATGGATGTTGGATACCCAGTTGTGCGCTCAATGTCCAAATTTGACA
GTGGCTTCGAACAATACTGCAATCCAGGTAAATGCCATCTACACTTTTCCATTTAC
TGATGTTTTACTCGGAAAAGGCACCGCACAGGAGACAACAATGCCACCAATCACT
ACAATCTAGGTAAATTCAGTGTGGTAAACTTTAATAAGTATTTTAAGCTTCTTGTAA
CATCATATTTCTTCCATTCGAAAGTAAGTTCATGAATCCTTGTGATGATTTTGTGGG
TGTTCTCTGCCACACTGAATAGAAAATCTGCAAAAATAGAAAAGAACAAATTCTAA
GGTGTGTGTGTAACTGAAGAACCTCGTCGGATCACTTGTCCGGCGTTGCAGC
TGGAGCCGCCTCCTCGGCACGAGGCTTCTCTGCGTCGCCATGGCTTCCTGCCA
CAAGTGGTGAAACACGGTGACGACGATAGGAAGGGAATCAACATCGCCATAGCC
TCGAGCCCTCGACACACTCCCTTGGCTTGTGATTCCCATCGTGGTGGAGATCTTG
AATCCGGCGACGTCGCAGGAGAAGAGAGACGCGACGAGCGGGGGAGGGGTC
GCGGCGAGCGGGGGAGGGGTCGCGGCGAGCGGCGGGAGGAGGCGCGGCGA
GCGGGGGAGGGGTCGAGGCGCGGTGGCGGGAGGAGTTGCGGCGAGCGGGGG
GAGGAGGCGCGGCGAGCGAGGGAGGAGTCGCGACGAGCGGCGGGAAGGGGT
CGAGGCGAACGGGGGAGGGGTCGCGGCAAGCATGCCGACCAGGAGGAGGGG
GTCTATTCGTGAGACGTGGAGCGTGAGTATTGATTAGCGCTAACGAAACCGTTT
TCGTTAACGGAGTATTTAGACCCTTGATTAAGCGATTAGACGGTTAAATTATGATT
TGGATCTGTCCTTTCGTGTTTTTATTATTTGAAATATAAAGGAAAAAAGCAAGACTA
ATGAACGGAGAAGGAAAGCAGTAGAAGGCAAACGGCACAGCGCTCTCTCACGCT
```

```
TTTCCCGTGGTCGACGTTGCAGTCCACACGCGGCTGGGGTCGGCTGGTTCCACC
ACCTCATCTCCCTGACTCCCTCTGCCTCGTATCTCGTCGCCTTGCTCCACACCCC
ACAGGCGCATTGTCAGCCGTC
```

Brachypodium MRC promoter sequence

SEQ ID NO: 26

```
TCCCATAATTTTTGTCGTGATTTTAGTTCAAATTTGAATTAAAACCAGCACAATAATT
ATGGGACTGAAGGAGTACTACGAAGTAGTAAAAAATACTTCCTCCGATCTATATTA
CTTGTCGCTGATTTAGTACAAGGGAGTAGTATTTTTTATTAGAGTCATCATGATAGT
ATATATGTTTACCGTATGTGTAAATATTAATACAATTTAACATAAATTTAGTCAAAAT
TTAATAAGCTCGTTTATGACAAAACTAAAACGTTTGTCCTCGTCTGTGCGCACGTG
CGATATCGGATCTACTGTAAGTCATGGAATAACCCCCCGCCACCTTCTCATGTGAA
ACGCTATGTTCCCCCTTCCCAGTAGCCCGTTTCCCCAATTTCCATCACAATTGTCG
TTCCCAGCTCTGGCGCTGCCCCAGGCTATGGCGCCCGACCCTCCTGCTCAGGTG
TTAGTAGCCATGGATTTCTGTTGTTCCTGCCAGGGGAAGTGGAGCGCATCCGCGA
AGGCTCCCCTCCACACCCCCTCGAAGCACCGCCATGGTGGCACCTCGAGGCGAT
GCGCGCCACGACGCGCGGGTTCCGCTCTACCTTCACTAGCTACTCGATCATGCG
ACTGCTATTCGAATGATTCATGCGCTCACTTTAAACCCTCCAATCTTGACATTAGG
GGCGGGCATTCGGTCATGACTGAAAGTTCGGTCTTCTAATTTAAGTCTTTTTTCGA
TTCGGTCCTTAAAATATAATACCCGAACTTTACTGAGAAACGTCGATGACCGAACT
TTAGAAAGATGGGTGATAATTCCAAAACAAAACGTGATTTGGTACCAATTTTAGCA
ACATTTCACTTATACTTCTCACAAATTTTCTTATTAACATGGGCATTGGAGATTAGG
AAAGTGAAACAGTCGATTGCCTCTCTTGTGCCATGATTTTTGCATGCGGAATAGTT
GATGCCTAGATTGTATCGTGAAAATGAGTTGGTTTTTACAAAGCGGAAAAGTTTGG
TCCTATTTGGTCTTTCAGTCTTTTGTGGATTGATACCCGAATTAATAGAATAAATTT
CGGTCTATAAATTTTTCTATCCAAATATCTAATCGGTCTTTTCGATCTCGGTCTATT
CGGTTTCGGTCCTCGGTTTTTATGCCCGCCCCTACTTGACATATACTTTAGAATAC
TTTATGTATAAACAGTTTTGCTCGATGCTAAGTGGCAGTGTTCCGTGCTTTGTCGA
CCCCACCCAAGATCCTAGCTTGTGTCTAAACATTTGAGAGAGAGAGCAAGAGATT
TCCCTCGTTTTCTTTAAAAATAAAAGGAAAATAGATAATTAATTAATTATTTTTCTTA
AGGAAAATAACTAGTACACGATTATATTGTTTTTTAGGAAAACGACATAATTATAGG
AGAGAAAGCAAACAACACGGGTCTCACGCTTCTCTACAGTCGACTAGGCTCGGAG
TCCACACGCGGCTGCTCGGCCCGCTTCCACCCCTACATCCCC
```

Z. mays MRC promoter sequence

SEQ ID NO: 27

```
TATCTATGGCTCGTACTTTTCTATAGGAAAGGGTCAGCAAGGACATTATGCACATA
TTAAGGCATTGTTTAGGACAACTCTAACTACATGACATTTTGTAGAGTTGGAGAAG
TAGGTCATTGGATGCTTTAGAAAATCGTGGAGCTCTGTAAACATATACAAGACATT
TAGATAAGTCATTTGTTTATTATTTAGATTAAAAATATTTTTAAAACTATTTTAAATTG
ATATTATAAACTATAGCTCTACACTGGAGGTTTAACCTGGAGCCATCTCAAACCTG
CCCTAAATTATGTACATAGTTCTTTTACATGCAATGCACTTATTGAATCACGATAAT
CTATTTTAGACCTAACATTCTCTTACATGTCCCTTCGTGCACAGAATATGGTAATG
TGGTGAAGAGTTTTTTTTTTTGCAAAAAATCTGTCCACATGATTTAGTCGCTTTAGA
TTTGTTCTAAGTGAAACTATTTAAATTTTGACCAACAATATATATAGTTAAATTATGT
TATACTAAAATAATTATATATTATGATAGTTCAAGTCATGATGGATCTGGCGACTTT
ACTTTTATATTGTAAAATTTTATAAAACATTCGGTATAACCGATCAAAGTTAATAGT
GATTGACTTAGGACAAATCTAAAACAGCTAATTCATATGGACAGTGTGAGTACAAA
GCAATAAGGGAACTAGGGAAGGTGTGTGAGGATGTTGGATCTTAGATGAGTAACT
CTGTGCACCAAAGATCTATATGCACTTAGGGGGTGTTTGGTTTGTAGTGTCTAATT
TTTAGTTCCACCATTTTGTTTTATTTGTCCCTAAATTATCAAATATGAAAACTAAAAT
AGAGTTTTATTTTCAGTATTTGATAATTTATGGACTAAAATGAAATAAAATGAATTGA
CTAAAAATTAGTCCCTAGAAACCAAACATCTCCTTTGGTTTCTAGGGACTAATTTTT
AGTCACTATATATTTTTTATTTTAGTTTCTAAATTGTACTTTCCATATTTGACAATTTA
AAGATTAAAATAAAAAGACTAAAAATTAGTCTTTACAAAATTAAACATCTCTTTAAGG
CTTTATCTGAATACCCTCGTATTCACCCTAATCCACGTGTATTGAGGTGGATTGAA
ATGTAAATTAGTTTAATTTACGCTTCAATTTATCTTAATAAATGTGATTGAGATAAAT
ACGAGAGTAGTAAGCCATAATATGTTTTCATTAGATGTAGGATTGTTTTTTCGCGT
GGACGCTGCATGATGTTCGTCTGACTTGGTAAGCCAGGTATGGACGGACCACGG
ATTTAGCAAATTTACAAGAAAATTCCCTCTCCTAACAAATACGTAGGAAATCTCGGA
AATACGCAGAAAAGAGGACGTCAAAAGGCAATTTTCTTTTCTAAGATAGGGAAAAA
GTGTGAAAAAGACAATTTCTCATCAGAAAATGGAAAACACAAGTCTCCAGTGCTCC
TCGCGTGATCGCATCCACGCTTC
```

SEQ ID NO: 28: O. sativa MRC promoter sequence
```
CAGCCGCCGGCCTCCGCTCGCCGCGACTGCCGTCCTCCGCTTGCCGCGGCCGC
TCGTCGCGGCCGCCGGCCCCCGCGCGGCGCAACCCGCCGCCCCCGCTCGCCG
TGGCTGCTGGCCTCCGCGCGGCACAAGCTCGCCGCGCCCGCCGTCCTCCGCGC
AGCGCCGCCCGCTGCCTCCGCACGGCGCCCGCCTCCCGCCGCGCAGCCCGCC
GGTCCCCACGCAGCGCCGCCTCCCGCCGACGCTGCCTTCACCGCCGTCCCCTC
CCCGCTTGCTGCCGCCGCCTGCTTCTTGTCAACGCTAGAAAAGAAAAGAGGAAGA
GGGGAAGGAAGGGGAGAAAGAATAAGGGAGTGGCTCACATATGGGTCCCGGTGT
CATAGTCAAAATAGAGAGGGTAGAATAGAGAGGCTGTTGGAGTATACAGTTAATTT
GACTAGCTAAATCAGATGGAGAGTTGGCTATATGGGTGTTTTAGGAGTTCGATTTG
GAGAGGCTGTTAGAGATACTCTTATGTGCAAAATATGTGCAGTTACCATGCATGTT
GGTACTGAAGAGCCAGAGCCATTCCAAGAAAGGAAGGATCTTTTCACCACGTAGA
ACTCCATTTTTCTGACATTTTTTAAAAGAAAGAATGAAGGTGACTAAGGGACAATAT
```

| SEQUENCE LISTING |
|---|
| TTTAATATAGCAGGATGATATAGAGATTCTCGAGGGACAATAAGGTTTTACACTTTT
ACAAAGGATTCTCAAGATATACATATTTCATTCTTGCTAGGGTTAGTGTAGGATGG
TGCAGTGCACACCATGAGAATCGGAGAATCTGTATGTGGTGCGAAGAAAAACTAA
GAACACCAGAAACAGAAAAAAAATGAAGAACAGAAACAAATCCATGCAAACTTGT
CATTCAGAGAGCAAATTATGTCTCAGATATCTCTATTTACCTGCTACTCCTGAAGA
GACTGGACTTGTTACTTCCTTTGACAGAAATAGCAGAACAAAAATATGTCACCTTTT
TGCAACTTTCATAAGATTTTCTTTTCTTTTTGCAAAGAATTTATGCATGCTAAAAACA
AGGGGGTGAGTTAGGAACTCACTGAAAAGAGCACAGCCTAGATGAGTAGGTGCG
CTCCCGTTTTTGGGCCCAGATGAAGGACAAGGCCCACCTAGAACTCCTACGGTG
GACCGCGGGCGGTTTTGATCCAACGGCCAGGGTTCTTCATCACCCATCCAACGG
TGACAATCCCACTAAATCCTTCCAAATTTTCGGTTTCTTTAAACATCTTCGAATTC
AAATTTCTCTCATCACGTAGTACAGCCCAGCATTTCCTGTCCTCACGTACCCCCGA
ATAAAAACGAAACGGCACCAGAACCCAGAACAGCAAGCAACACAAACCCATCAAA
ACAAACAAAACAAAAGAAAAGAAAAAGAAAAAAAAAGAGCAAGCGACACGAGCG
TCACGTGTCACGCTTACTCGAGTCATCAATCATCTACTACACCCCACCCCACTCCA
CTGCACTGCACT

SEQ ID NO: 29: TaMRC 6B partial amino acid sequence (cv. Kronos (4n))
PVSNESRKTNEEKLKVAEQELEKQSLGWLAAQQELKELAQLAFKDTDDINGIITDFKR
VRSLLDAVRSELISSKDAFASSRRQIEDQAVQLQEQVQELEDQRVLLMSYTHDLEAAK
LEIQGKTQELSYAQSRCHELESQLLQEREKVESLEAELAKEKQSLEHRTEEVGFLQKE
LVQKENECTKSQELVKVKEFELLEARQEVQDMKLKVESIQLAVQEKDSELSDTQSRLT
EVSSEIAELQQLLNSKKDQLLQARTELHDKEQHIETLESELDSIRLRCSQAESMVQRM
ADLTGDLASSVKAGEMDIYALLDDEISSTGTALESNLHKHNQLEADIEMLRECLRHKD
MELRAAHEALDAKDQELKAVLRKWDVKEREVRELEELPDPSATNELAGFSSETTEDG
IVGEMELPELQIEAVEVEALAATTALRKLADMTKDFFKHGKADSGIDLVASESQKISKC
DPKMEVHKKTDVILEAEKEIVRLFSLTKQIVTDDIINDVEE TaMRC 6B partial amino acid sequence (cv. Cadenza (6n))
                                                                                                    SEQ ID NO: 30
PVSNESRKTNEEKLKVAEQELEKQSLGWLAAQQELKELAQLAFKDTDDINGIITDFKR
VRSLLDAVRSELISSKDAFASSRRQIEDQAVQLQEQVQELEDQRVLLMSYTHDLEAAK
LEIQGKTQELSYAQSRCHELESQLLQEREKVESLEAELAKEKQSLEHRTEEVGFLQKE
LVQKENECTKSQELVKVKEFELLEARQEVQDMKLKVESIQLAVQEKDSELSDTQSRLT
EVSSEIAELQQLLNSKKDQLLQARTELHDKEQHIETLESELDSIRLRCSQAESMVQRM
ADLTGDLASSVKAGEMDIYALLDDEISSTGTALESNLHKHNQLEADIEMLRECLRHKD
MELRAAHEALDAKDQELKAVLRKWDVKEREVRELEELPDPSATNELAGFSSETTEDG
IVGEMELPELQIEAVEVEALAATTALRKLADMTKDFFKHGKADSGIDLVASESQKISKC
DPKMEVHKKTNVILEAEKEIVRLFSLTKQIVTDDIINDVEE SEQ ID NO: 31: TaMRC 6B genomic nucleic acid sequence (cv. Kronos (4n)) (3' UTR is
italicised)
CCAGTATCAAATGAATCGAGGAAAACTAATGAAGAGAAACTGAAAGTTGCTGAACA
GGAACTTGAGAAGCAGAGTTTAGGATGGTTAGCAGCACAACAAGAGTTAAAGGAA
CTTGCACAACTGGCATTCAAAGATACAGATGATATCAATGGTATTATCACTGACTT
CAAACGTGTGAGGTCTCTGCTAGATGCTGTACGCTCTGAATTAATCTCTTCAAAAG
ATGCTTTCGCTTCCTCTCGCAGACAAATAGAAGATCAAGCGGTTCAGTTGCAGGA
ACAAGTACAGGAACTCGAGGACCAAAGGGTATTACTGATGTCTTACACCCATGATT
TGGAGGCTGCTAAACTGGAATTCAAGGGAAGACACAGGAGCTCAGTTACGCAC
AGTCTCGTTGCCATGAACTTGAATCACAGTTACTTCAGGAAAGGGAGAAGGTCGA
GTCTCTAGAAGCCGAATTAGCCAAAGAAAACAGAGCTTAGAACATAGAACTGAA
GAAGTAGGCTTTCTTCAGAAGGAGCTTGTTCAGAAAGAAAATGAGTGCACCAAAT
CACAAGAACTTGTTAAAGTAAAAGAGTTTGAGCTGTTAGAAGCCAGACAGGAAGT
CCAAGACATGAAGTTAAAGGTAGAGTCTATTCAATTGGCTGTTCAAGAAAAGGATT
CAGAGCTTTCTGATACACAGAGCAGACTAACTGAAGTCAGCAGTGAAATTGCTGA
GCTTCAGCAGTTGCTAAATAGCAAGAAGGATCAACTGCTTCAGGCTAGAACTGAA
TTACATGATAAAGAGCAACATATAGAAACACTGGAGAGTGAGTTGGATAGCATACG
GCTCAGATGCTCGCAAGCTGAATCCATGGTTCAAAGGATGGCTGATCTCACTGGC
GATCTTGCTAGTTCCGTAAAAGCCGGAGAAATGGACATCTATGCATTACTGGATGA
TGAAATTTCAAGCACAGGTACAGCCCTCGAGTCCAATTTGCATAAGCATAATCAAC
TGGAGGCTGACATAGAGATGTTAAGAGAATGCTTGCGGCATAAGGACATGGAGTT
GAGAGCTGCTCATGAAGCACTTGATGCCAAAGATCAAGAGCTGAAGGCAGTACTT
AGAAAGTGGGATGTGAAGGAGCGGGAAGTACGTGAGTTAGAAGAGTTACCGGAT
CCCAGTGCCACAAATGAACTTGCTGGTTTTTCCAGTGAGACAACAGAGGACGGCA
TTGTAGGAGAGATGGAGCTCCCAGAGCTTCAAATTGAAGCTGTGGAGGTCGAAGC
ACTTGCTGCTACGACTGCATTGAGGAAGCTTGCGGATATGACTAAGGATTTCTTCA
AACACGGCAAAGCTGATTCTGGTATTGACTTGGTTGCATCAGAGAGTCAGAAAAT
CAGTAAATGTGATCCTAAAATGGAAGTACACAAGAAGACGGATGTGATTCTTGAAG
CTGAAAAAGAAATAGTTAGGCTCTTCTCATTGACAAAACAGATTGTCACTGATGAC
ATAATAAACGATGTTGAGGAATGATA*GCTTCAAACTGAAGCATGTAGTCTTC*

TaMRC 6B genomic nucleic acid sequence (cv. Cadenza (6n) (3' UTR
is italicised)
                                                                                                    SEQ ID NO: 32
CCAGTATCAAATGAATCGAGGAAAACTAATGAAGAGAAACTGAAAGTTGCTGAACA
GGAACTTGAGAAGCAGAGTTTAGGATGGTTAGCAGCACAACAAGAGTTAAAGGAA
CTTGCACAACTGGCATTCAAAGATACAGATGATATCAATGGTATTATCACTGACTT |

CAAACGTGTGAGGTCTCTGCTAGATGCTGTACGCTCTGAATTAATCTCTTCAAAAG
ATGCTTTCGCTTCCTCTCGCAGACAAATAGAAGATCAAGCGGTTCAGTTGCAGGA
ACAAGTACAGGAACTCGAGGACCAAAGGGTATTACTGATGTCTTACACCCATGATT
TGGAGGCTGCTAAACTGGAGATTCAAGGGAAGACACAGGAGCTCAGTTACGCAC
AGTCTCGTTGTCATGAACTTGAATCACAGTTACTTCAGGAAAGGGAGAAGGTCGA
GTCTCTAGAAGCCGAATTAGCCAAAGAAAAACAGAGCTTAGAACATAGAACTGAA
GAAGTAGGCTTTCTTCAGAAGGAGCTTGTTCAGAAAGAAAATGAGTGCACCAAAT
CACAAGAACTTGTTAAAGTAAAAGAGTTTGAGCTGTTAGAAGCCAGACAGGAAGT
CCAAGACATGAAGTTAAAGGTAGAGTCTATTCAATTGGCTGTTCAAGAAAAGGATT
CAGAGCTTTCTGATACACAGAGCAGACTAACTGAAGTCAGCAGTGAAATTGCTGA
GCTTCAGCAGTTGCTAAATAGCAAGAAGGATCAACTGCTTCAGGCTAGAACTGAA
TTACATGATAAAGAGCAACATATAGAAACACTGGAGAGTGAGTTGGATAGCATACG
GCTCAGATGCTCGCAAGCTGAATCCATGGTTCAAAGGATGGCTGATCTCACTGGC
GATCTTGCTAGTTCCGTAAAAGCCGGAGAAATGGACATCTATGCATTACTGGATGA
TGAAATTTCAAGCACAGGTACAGCCCTCGAGTCCAATTTGCATAAGCATAATCAAC
TGGAGGCTGACATAGAGATGTTAAGAGAATGCTTGCGGCATAAGGACATGGAGTT
GAGAGCTGCTCATGAAGCACTTGATGCCAAAGATCAAGAGCTGAAGGCAGTACTT
AGAAAGTGGGATGTGAAGGAGCGGGAAGTACGTGAGTTAGAAGAGTTACCGGAT
CCCAGTGCCACAAATGAACTTGCTGGTTTTTCCAGTGAGACAACAGAGGACGGCA
TTGTAGGAGAGATGGAGCTCCCAGAGCTTCAAATTGAAGCTGTGGAGGTCGAAGC
ACTTGCTGCTACGACTGCATTGAGGAAGCTTGCGGATATGACTAAGGATTTCTTCA
AACACGGCAAAGCTGATTCTGGTATTGACTTGGTTGCATCAGAGAGTCAGAAAAT
CAGTAAATGTGATCCTAAAATGGAAGTACACAAGAAGACAAATGTGATTCTTGAAG
CTGAAAAAGAAATAGTTAGGCTCTTCTCATTGACAAAACAGATTGTCACTGATGAC
ATAATAAACGATGTTGAGGAATGA*TAGCTTCAAACTGAAGCATGTAGTCTTC*

SEQ ID NO: 33: TaMRC 6B CDS nucleic acid sequence (cv. Kronos (4n))
CCAGTATCAAATGAATCGAGGAAAACTAATGAAGAGAAACTGAAAGTTGCTGAACA
GGAACTTGAGAAGCAGAGTTTAGGATGGTTAGCAGCACAACAAGAGTTAAAGGAA
CTTGCACAACTGGCATTCAAAGATACAGATGATATCAATGGTATTATCACTGACTT
CAAACGTGTGAGGTCTCTGCTAGATGCTGTACGCTCTGAATTAATCTCTTCAAAAG
ATGCTTTCGCTTCCTCTCGCAGACAAATAGAAGATCAAGCGGTTCAGTTGCAGGA
ACAAGTACAGGAACTCGAGGACCAAAGGGTATTACTGATGTCTTACACCCATGATT
TGGAGGCTGCTAAACTGGAGATTCAAGGGAAGACACAGGAGCTCAGTTACGCAC
AGTCTCGTTGCCATGAACTTGAATCACAGTTACTTCAGGAAAGGGAGAAGGTCGA
GTCTCTAGAAGCCGAATTAGCCAAAGAAAAACAGAGCTTAGAACATAGAACTGAA
GAAGTAGGCTTTCTTCAGAAGGAGCTTGTTCAGAAAGAAAATGAGTGCACCAAAT
CACAAGAACTTGTTAAAGTAAAAGAGTTTGAGCTGTTAGAAGCCAGACAGGAAGT
CCAAGACATGAAGTTAAAGGTAGAGTCTATTCAATTGGCTGTTCAAGAAAAGGATT
CAGAGCTTTCTGATACACAGAGCAGACTAACTGAAGTCAGCAGTGAAATTGCTGA
GCTTCAGCAGTTGCTAAATAGCAAGAAGGATCAACTGCTTCAGGCTAGAACTGAA
TTACATGATAAAGAGCAACATATAGAAACACTGGAGAGTGAGTTGGATAGCATACG
GCTCAGATGCTCGCAAGCTGAATCCATGGTTCAAAGGATGGCTGATCTCACTGGC
GATCTTGCTAGTTCCGTAAAAGCCGGAGAAATGGACATCTATGCATTACTGGATGA
TGAAATTTCAAGCACAGGTACAGCCCTCGAGTCCAATTTGCATAAGCATAATCAAC
TGGAGGCTGACATAGAGATGTTAAGAGAATGCTTGCGGCATAAGGACATGGAGTT
GAGAGCTGCTCATGAAGCACTTGATGCCAAAGATCAAGAGCTGAAGGCAGTACTT
AGAAAGTGGGATGTGAAGGAGCGGGAAGTACGTGAGTTAGAAGAGTTACCGGAT
CCCAGTGCCACAAATGAACTTGCTGGTTTTTCCAGTGAGACAACAGAGGACGGCA
TTGTAGGAGAGATGGAGCTCCCAGAGCTTCAAATTGAAGCTGTGGAGGTCGAAGC
ACTTGCTGCTACGACTGCATTGAGGAAGCTTGCGGATATGACTAAGGATTTCTTCA
AACACGGCAAAGCTGATTCTGGTATTGACTTGGTTGCATCAGAGAGTCAGAAAAT
CAGTAAATGTGATCCTAAAATGGAAGTACACAAGAAGACGGATGTGATTCTTGAAG
CTGAAAAAGAAATAGTTAGGCTCTTCTCATTGACAAAACAGATTGTCACTGATGAC
ATAATAAACGATGTTGAGGAATGA TaMRC 6B CDS nucleic acid sequence (cv. Cadenza (6n))                                                                                SEQ ID NO: 34
CCAGTATCAAATGAATCGAGGAAAACTAATGAAGAGAAACTGAAAGTTGCTGAACA
GGAACTTGAGAAGCAGAGTTTAGGATGGTTAGCAGCACAACAAGAGTTAAAGGAA
CTTGCACAACTGGCATTCAAAGATACAGATGATATCAATGGTATTATCACTGACTT
CAAACGTGTGAGGTCTCTGCTAGATGCTGTACGCTCTGAATTAATCTCTTCAAAAG
ATGCTTTCGCTTCCTCTCGCAGACAAATAGAAGATCAAGCGGTTCAGTTGCAGGA
ACAAGTACAGGAACTCGAGGACCAAAGGGTATTACTGATGTCTTACACCCATGATT
TGGAGGCTGCTAAACTGGAGATTCAAGGGAAGACACAGGAGCTCAGTTACGCAC
AGTCTCGTTGTCATGAACTTGAATCACAGTTACTTCAGGAAAGGGAGAAGGTCGA
GTCTCTAGAAGCCGAATTAGCCAAAGAAAAACAGAGCTTAGAACATAGAACTGAA
GAAGTAGGCTTTCTTCAGAAGGAGCTTGTTCAGAAAGAAAATGAGTGCACCAAAT
CACAAGAACTTGTTAAAGTAAAAGAGTTTGAGCTGTTAGAAGCCAGACAGGAAGT
CCAAGACATGAAGTTAAAGGTAGAGTCTATTCAATTGGCTGTTCAAGAAAAGGATT
CAGAGCTTTCTGATACACAGAGCAGACTAACTGAAGTCAGCAGTGAAATTGCTGA
GCTTCAGCAGTTGCTAAATAGCAAGAAGGATCAACTGCTTCAGGCTAGAACTGAA
TTACATGATAAAGAGCAACATATAGAAACACTGGAGAGTGAGTTGGATAGCATACG
GCTCAGATGCTCGCAAGCTGAATCCATGGTTCAAAGGATGGCTGATCTCACTGGC
GATCTTGCTAGTTCCGTAAAAGCCGGAGAAATGGACATCTATGCATTACTGGATGA
TGAAATTTCAAGCACAGGTACAGCCCTCGAGTCCAATTTGCATAAGCATAATCAAC
TGGAGGCTGACATAGAGATGTTAAGAGAATGCTTGCGGCATAAGGACATGGAGTT

```
GAGAGCTGCTCATGAAGCACTTGATGCCAAAGATCAAGAGCTGAAGGCAGTACTT
AGAAAGTGGGATGTGAAGGAGCGGGAAGTACGTGAGTTAGAAGAGTTACCGGAT
CCCAGTGCCACAAATGAACTTGCTGGTTTTTCCAGTGAGACAACAGAGGACGGCA
TTGTAGGAGAGATGGAGCTCCCAGAGCTTCAAATTGAAGCTGTGGAGGTCGAAGC
ACTTGCTGCTACGACTGCATTGAGGAAGCTTGCGGATATGACTAAGGATTTCTTCA
AACACGGCAAAGCTGATTCTGGTATTGACTTGGTTGCATCAGAGAGTCAGAAAAT
CAGTAAATGTGATCCTAAAATGGAAGTACACAAGAAGACAAATGTGATTCTTGAAG
CTGAAAAAGAAATAGTTAGGCTCTTCTCATTGACAAAACAGATTGTCACTGATGAC
ATAATAAACGATGTTGAGGAATGA

SEQ ID NO: 35: TaMRC 6B upstream sequence (cv. Kronos (4n))
CTGAGGCGGCCGTTTCAGGGGCGCCGATTTCTGTTTGGCAACGATGATGGCGTC
AAGAGGAGCTTGGGTCGCGGCTCGGGCTTTGGTAGTCGGATCTTCCCGGCGTGC
CCGAGGTGCTCTTTAGGGCACGGTCGGCGCAAGTCCTGCATATTTCCCTTGTGAG
GCTCGTCGTCAAAGTCGAAGTTGTCGGTTGTTGGCGCGTGTGGCCATCTGTTGGC
ATGTGCCGTCTTTGCTCTGTGTAGCTGTTTGCGAGGGCGACTTGTTGGTGGAGCT
CTATGGTGAAGTCGGAGTCGCCCGTTCGGAGATAACCGGTGATGACGATGACGC
TTGCGACTCCCCGACGTTCTTCTTTGCAGCTCATGTTTCATGTCGGTGGACAGGTT
GGCCGGTGGTGCCCATGTTATATGGGTTGGGTTGTATTGGTTTTAGCCCGGTTTT
CCGTCAATTAACCGGGCAATTCTTATTTCTTCTTAATCAATGAAAATGGCAAGTCTT
TTGCCTCGTTTCAAAAAAAATAAAAATAGGAGTAACTGAGCTGCAGTTATCGTCGC
CCGCGAGTGGTACACATCAATTGACATAAAGAGCTACGTCAACGGAGAATTACTC
CAAAATCTCCAGCCCAATCGACAGAGACGATTCGTTACCTTGTCACCGCCCCTTG
GCGTTGCCCGACGAGTCCTCTCCTGCCCACCCTGTCTCTTCGTCGCAGGAACG
ATTCATCCTGACCGCAAACGTCCGTCCGCCGGCAAGGTCAACAACATCAAGCACC
TCGCACAGATCGCGTCGACCAACCCGCGCCTCCTTCGTTCCCATGTGTGCGGTC
CATGATTTTTTTTCTCGTTTGATGATGGACACGAAAGCGATTACTACAGACCGAA
GGCCCAATAGGCCCAATTAACAGCAGATGGTGGATTTTGTTACGGGAGCAGCGG
CCAAATCCATGTGCGCGACCTGCATAGCGAAGGAAGCCCAGGCAGGATTAGAGG
AGGATCCAATGGCCAGAAACACCCACTACTTGAGATCCGACGGCTAAAAACGGTA
ATGGCCTGAGAGAGCTAGAAGAGTGCACGGTTATATAATGTATTTAAATTTGGAAC
AGAAAGAAAAAAGGTAGTAAGACGAGTGAACGGGGAAGAAAAAGCAGTAGAAGGC
AAACGACGCAGCTCTCTCTCACGCTTCTCCCGTGGTCGACGTTGCAGTCCACACG
CGGGCGGGCACGCGGCTGGGCGCGCCGGTTCCACCACCTCATCTCCCGCACTC
CCTCTGCCTCGTATCTCGTCGCCTTCCTCCACACCCCGCAGGAGCATTGCCAGCC
GTCCGATCGCGC TaMRC 6B promoter sequence (cv. Cadenza (6n))                                                SEQ ID NO: 36

CTGGATCTGGTCGGGCGTGGCTGGATCCGGGCGTTCTTCGGGGGTTTTCTGCTG
CAGCCTGTTCGTTGTCTCCGCGTGGTGCGGTTCCTGCGGCGTGGCGGCGGTGAC
CTCCTGCCCCAAGGCCTGGTGAGGGCGACGGCGTGAGGTCGGCCCGATGGCGG
TGACGGTGGTGTGCGTCCAGGGCCCGGCATCTGGTCGGGGGGCGCGCGGGAC
GGCCTTGGCAGGGCGGGCACTGACGGGAGGCTCCCCTCGGTGCTCTGCGGTG
CTGGTTTGGTGGAGGTTTTAGGGAGGCTTGATGGAGGTCTGTGGTTGGCCGGTA
CGGGCTGGTGGTGGTCGAGCATCTCAGGGAGAAATCCTTCTTCCGGCCTTTGCC
GGAGCTGGCGACGGCGGCGCCTGTGGGCGTCGCGCTCTTTCCTGGAAGCGTCG
TCGATGTATGGTGCTCCACCCCTCACCCCGCGGCCTTGGCTCCGGAGGGAAACC
TCTGATCTGCGGGATCGGGCGATGAAGGCGTCTTCACGTCTTCTTCCTCCTTGGG
GGCATCGTCTTGGAGCCGGCTACAACCTGAGACCGGTGGATGGCGGCATCTTCG
CCGCATGGAAGGGCGACATCTTCGTCGCGTGGGATGGCGGCATCTTCGCCGCGT
GGAAGGGCGACATCTTCGCTGCGTGGTTTGCTGAGGCGGCCGTTTCAGGGGCGC
CGATTTCTGTTTGGCAACGATAATGGCGTCAAGAGGAGCTTGGGTCGCGGCTCG
GGCTTTGGTAGTCGGATCTTCCCGGCGTGCCCGAGGTGCTCTTTAGGGCACGGT
CGGCGCAAGTCCTGCATATTTCCCTTGTGAGGCTCGTCGTCAAAGTCGAAGTTGT
CGGTTGTTGGCGCGTGTGGCCATCTGTTGGCATGTGCCGTCTTTGCTCTGTGTAG
TTGTTTGCGAGGGCGACTTGTTGGTGGAGCTCTATGGTGAAGTCGGAGTCGCCC
GTTCGGAGATAACCGGTGATGACGATGACGCTTGCGACTCCCCGGCGTTCTTCTT
TGCAGCTCATGTTTCATGTCGGTGGACAGGTTGGCCGGTGGTGCCCATGTTATAT
GGGTTGGGTTGTATTGGTTTTAGCCCGGTTTTCCGTCAATTAACCGGGCAATTCTT
ATTTCTTCTTAATCAATGAAAATGGCAAGTCTTTTGCCTCGTTTCAAAAAAAAAAAT
AGGAGTAACTGAGCTGCAGTTATCGTCGCCCGCGAGTGGTACACATCAATTGACA
TAAAGAGCTACGTCAACGGAGAATTACTCCAAAATCTCCAGCCCAATCGACAGAG
ACGATTCGTTACCTTGTCACCGCCCCTTGGCGTTGCCCGACGAGTCCTCTCCTGC
CCACCCTGTCTCTTGGTTCGCAGGAACGATTCATCCTGACCGCAAACGTCCGTCC
GCCGGCAAGGTCAACAACATCAAGCACCTCGCACAGATCGCGTCGACCAACCCG
CGCCTCCTTCGTTCCCATGTGTGCGGTCCATGATTTTTTTTCTCGTTTGATGATG
GACACGAAAGCGATTACTACAGACCGAAGGCCCAATAGGCCCAATTAACAGCAGA
TGGTGGATTTTGTTACGGGAGCAGCGGCCAAATCCATGTGCGCGACCTGCATAG
CGAAGGAAGCCCAGGCAGGATTAGAGGAGGATCCAATGGCCAGAAACACCCACT
ACTTGAGATCCGACGGCTAAAAACGGTAATGGCCTGAGAGAGCTAGAAGAGTGCA
CGGTTATATAATGTATTTAAATTTGGAACAGAAAGAAAAAAGGTAGTAAGACGAGT
GAACGGGGAAGAAAAGCAGTAGAAGGCAAACGGCGCAGCTCTCTCTCACGCTTC
TCCCGTGGTCGACGTTGCAGTCCACACGCGGGCGGGCACGCGGCTGGGCGCGC
CGGTTCCACCACCTCATCTCCCGCACTCCCTCTGCCTCGTATCTCGTCGCCTTCC
TCCACACCCCGCAGGAGCATTGCCAGCCGTCCGATCGCGC
```

SEQUENCE LISTING

SEQ ID NO: 38: *Arabidopsis thaliana* AtMRC
MGFSQAIRLNLASFSSPSPCDYCLTRVVNHKQKSLVAFPSITRRKRHLLLSVQSVLHN
TRPNINDNGSAESANVLFDKLFARTHRLERQTNQHSVYPDDDDLPYSNLGVLESDLE
AALVALLKREEDLHDAERKLLSDKNKLNRAKEELEKREKTISEASLKHESLQEELKRAN
VELASQAREIEELKHKLRERDEERAALQSSLTLKEEELEKMRQEIANRSKEVSMAISEF
ESKSQLLSKANEVVKRQEGEIYALQRALEEKEEELEISKATKKLEQEKLRETEANLKKQ
TEEWLIAQDEVNKLKEETVKRLGEANETMEDFMKVKKLLTDVRFELISSREALVFSRE
QMEEKELLLEKQLEELEEQRKSVLSYMQSLRDAHTEVESERVKLRVVEAKNFALEREI
SVQKELLEDLREELQKEKPLLELAMHDISVIQDELYKKANAFQVSQNLLQEKESSLVEA
KLEIQHLKSEQASLELLLQEKDEELAEARNKLGEVNQEVTELKALMISREDQLMEATE
MLKEKDVHLHRIEGELGSSKLKVTEAEMVVERIAELTNRLLMSTTNGQNQNAMRINNE
ISIDSMQQPLEKPHDDYGMENKRLVMELSFTRENLRMKEMEVLAVQRALTFKDEEINV
VMGRLEAKEQELKKLKEETINDSEDLKVLYALAQERVGEKTMGDLAIEMLQLEAANLE
VEAATSALQKLAKMSTELLTQADMSIEADTTHTVMPERGYSEGSNECLGEVKTEVVR
LWSLTEKLLENAGIVAGTSTCMEGVIL*

CRISPR constructs
SEQ ID NO: 39: TaMRC target sequence 1
GCGGCCATGCGCCTCTCCATCGG SEQ ID NO: 40: TaMRC target sequence 2
CAGGCAGAAGCTGAGTTTCATGG SEQ ID NO: 41: TaMRC target sequence 3
ATTAGATCAAATATAACTGATGG SEQ ID NO: 42: TaMRC target sequence 4
AATATAACTGATGGTGATAATGG SEQ ID NO: 43: TaMRC protospacer sequence 1
GCGGCCATGCGCCTCTCCAT SEQ ID NO: 44: TaMRC protospacer sequence 2
CAGGCAGAAGCTGAGTTTCA SEQ ID NO: 45: TaMRC protospacer sequence 3
ATTAGATCAAATATAACTGA SEQ ID NO: 46: TaMRC protospacer sequence 4
AATATAACTGATGGTGATAA SEQ ID NO: 47: tracrRNA sequence
GUUUUAGAGCUAGAAAUAGCAAGUUAAAAUAAGGCUAGUCCGUUAUCAACUUGA
AAAAGUGGCACCGAGUCGGUGCUUUUUUU SEQ ID NO: 48: TaMRC complete sgRNA-encoding nucleic acid sequence 1
GCGGCCATGCGCCTCTCCATGTTTTAGAGCTAGAAATAGCAAGTTAAAATAAGGC
TAGTCCGTTATCAACTTGAAAAAGTGGCACCGAGTCGGTGCTTTTTTT SEQ ID NO: 49: TaMRC complete sgRNA-encoding nucleic acid sequence 2
CAGGCAGAAGCTGAGTTTCAGTTTTAGAGCTAGAAATAGCAAGTTAAAATAAGGCT
AGTCCGTTATCAACTTGAAAAAGTGGCACCGAGTCGGTGCTTTTTTT SEQ ID NO: 50: TaMRC complete sgRNA-encoding nucleic acid sequence 3
ATTAGATCAAATATAACTGAGTTTTAGAGCTAGAAATAGCAAGTTAAAATAAGGCTA
GTCCGTTATCAACTTGAAAAAGTGGCACCGAGTCGGTGCTTTTTTT SEQ ID NO: 51: TaMRC complete sgRNA-encoding nucleic acid sequence 4
AATATAACTGATGGTGATAAGTTTTAGAGCTAGAAATAGCAAGTTAAAATAAGGCT
AGTCCGTTATCAACTTGAAAAAGTGGCACCGAGTCGGTGCTTTTTTT SEQ ID NO: 52: TaMRC complete sgRNA RNA sequence 1
GCGGCCAUGCGCCUCUCCAUGUUUUAGAGCUAGAAAUAGCAAGUUAAAAUAAG
GCUAGUCCGUUAUCAACUUGAAAAAGUGGCACCGAGUCGGUGCUUUUUUU SEQ ID NO: 53: TaMRC complete sgRNA RNA sequence 2
CAGGCAGAAGCUGAGUUUCAGUUUUAGAGCUAGAAAUAGCAAGUUAAAAUAAGG
CUAGUCCGUUAUCAACUUGAAAAAGUGGCACCGAGUCGGUGCUUUUUUU SEQ ID NO: 54: TaMRC complete sgRNA RNA sequence 3
AUUAGAUCAAAUAUAACUGAGUUUUAGAGCUAGAAAUAGCAAGUUAAAAUAAGG
CUAGUCCGUUAUCAACUUGAAAAAGUGGCACCGAGUCGGUGCUUUUUUU SEQ ID NO: 55: TaMRC complete sgRNA RNA sequence 4
AAUAUAACUGAUGGUGAUAAGUUUUAGAGCUAGAAAUAGCAAGUUAAAAUAAGG
CUAGUCCGUUAUCAACUUGAAAAAGUGGCACCGAGUCGGUGCUUUUUUU

SEQUENCE LISTING

SEQ ID NO: 56: Cas9 sequence
```
atggctcctaagaagaagcggaaggttggtattcacggggtgcctgcggctgacaagaagtactccatcggcctcgac
atcggcaccaacagcgtcggctgggcggtgatcaccgacgagtacaaggtcccgtccaagaagttcaaggtcctggg
caacaccgaccgccactccatcaagaagaacctcatcggcgccctcctcttcgactccggcgagacggcggaggcga
cccgcctcaagcgcaccgcccgccgccgctacacccgccgcaagaaccgcatctgctacctccaggagatcttctcca
acgagatggcgaaggtcgacgactccttcttccaccgcctcgaggagtccttcctcgtggaggaggacaagaagcacg
agcgccacccatcttcggcaacatcgtcgacgaggtcgcctaccacgagaagtacccactatctaccacccttcgtaa
gaagcttgttgactctactgataaggctgatcttcgtctcatctaccttgctctcgctcacatgatcaagttccgtggtcacttcct
tatcgagggtgaccttaaccctgataactccgacgtggacaagctcttcatccagctcgtccagacctacaaccagctctt
cgaggagaaccctatcaacgcttccggtgtcgacgctaaggcgatcctttccgctaggctctccaagtccaggcgtctcg
agaacctcatcgcccagctccctggtgagaagaagaacggtctttcggtaacctcatcgctctctccctcggtctgacccc
taacttcaagtccaacttcgacctcgctgaggacgctaagcttcagctctccaaggatacctacgacgatgatctcgacaa
cctcctcgctcagattggagatcagtacgctgatctcttccttgctgctaagaacctctccgatgctatcctccttcggatatc
cttagggttaacactgagatcactaaggctcctctttctgcttccatgatcaagcgctacgacgagcaccaccaggacctc
acccttcctcaaggctcttgttcgtcagcagctccccgagaagtacaaggagatcttcttcgaccagtccaagaacggcta
cgccggttacattgacggtggagctagccaggaggagttctacaagttcatcaagcgccaatccttggaagatggatggta
ctgaggagcttctcgttaagcttaaccgtgaggacctccttaggaagcagaggacttttcgataacggctctatccctcacc
agatccaccttggtgagcttcacgccatccttcgtaggcaggaggacttctacccttcctcaaggacaaccgtgagaag
atcgagaagatcccttactttccgtattccttactacgttggtcctcttgctcgtggtaactcccgtttcgcttggatgactaggaa
gtccgaggagactatcacccctggaacttcgaggaggttgttgacaaagggtgcttccgcccagtccttcatcgagcgcat
gaccaacttcgacaagaacctccccaacgagaaggtcctccccaagcactccctcctctacgagtacttcacggtctac
aacgagctcaccaaggtcaagtacgtcaccgagggtatgcgcaagctgccttcctctccggcgagcagaagaaggc
tatcgttgacctcctcttcaagaccaaccgcaaggtcaccgtcaagcagctcaaggaggactacttcaagaagatcgag
tgcttcgactccgtcgagatcagcggcgtggaccgtttcaacgcttctctcgctacctaccacgatctcctcaagatcat
caaggacaaggacttcctcgacaacgaggagaacgaggacatcctcgaggacatcgtcctcactcttactctcttcgag
gatagggagatgatcgaggagaggctcaagacttacgctcatctcttcgatgacaaggttatgaagcagctcaagcgtc
gccgttacaccggttggggtaggctctcccgcaagctcatcaacggtatcagggataagcagagcggcaagactatcct
cgacttcctcaagtctgatggtttcgctaacaggaacttcatgcagctcatccacgatgactctcttaccttcaaggaggata
ttcagaaggctcaggtgtccggtcagggcgactctctccacgagcacattgctaaccttgctggttccctgctatcaagaa
gggcatccttcagactgttaaggttgtcgatgagcttgtcaaggttatgggtcgtcacaagctgagaacatcgtcatcgag
atggctcgtgagaaccagactacccagaagggtcagaagaactcgagggagcgcatgaagaggattgaggagggt
atcaaggagcttggttctcagatccttaaggagcaccctgtcgagaacaaccagctccagaacgagaagctctacctct
actacctccagaacggtagggatatgtacgttgaccaggagctcgacatcaacaggctttctgactacgacgtcgacca
cattgttcctcagtctttccttaaggatgactccatcgacaacaaggtcctcacgaggtccgacaagaacagggtaagtc
ggacaacgtcccttccgaggaggttgtcaagaagatgaagaactactggaggcagcttctcaacgctaagctcattacc
cagaggaagttcgacaacctcacgaaggctgagagggtggccttccgagcttgacaaggctggtttcatcaagagg
cagcttgttgagacgaggcagattaccaagcagttgctcagatcctcgattctaggatgaacaccaagtacgacgaga
acgacaagctcatccgcgaggtcaaggtgatcaccctcaagtccaagctcgtctccgacttccgcaaggacttccagttc
tacaaggtccgcgagatcaacaactaccaccacgctcacgatgcttaccttaacgctgtcgttggtaccgctcttatcaag
aagtaccctaagcttgagtccgagttcgtctacggtgactacaaggtctacgacgttcgtaagatgatcgccaagtccgag
caggagatcggcaaggccaccgccaagtacttcttctactccaacatcatgaacttcttcaagaccgagatcaccctcgc
caacggcgagatccgcaagcgccctcttatcgagacgaacggtgagactggtgagatcgttgggacaagggtcgcg
acttcgctactgttcgcaaggtccttttctatgcctcaggttaacatcgtcaagaagaccgaggtccagaccggtggcttctcc
aaggagtctatccttccaaagagaaactcggacaagctcatcgctaggaagaaggattgggaccctaagaagtacggt
ggtttcgactcccctactgtcgcctactccgtcctcgtggtgccaaggtggagaagaagctcaagtc
cgtcaaggagctcctcggcatcaccatcatggagcgctcctccttcgagaagaacccgatcgacttcctcgaggccaag
ggctacaaggaggtcaagaaggacctcatcatcaagctccccaagtactctcttttcgagctcgagaacggtcgtaaga
ggatgctggcttccgctggtgagctccagaagggtaacgagcttgctcttccttccaagtacgtgaacttcctctacctcgcc
tcccactacgagaagctcaagggttcccctgaggataacgagcagaagcgcttcgtggagcagcacaagcacta
cctcgacgagatcatcgagcagatctccgagttctctccaagcgcgtcatcctcgctgacgctaacctcgacaaggtcctctc
cgcctacaacaagcaccgcgacaagcccatccgcgagcaggccgagaacatcatccacctcttcacgctcacgaac
ctcggcgcccctgctgctttcaagtacttcgacaccaccatcgacaggaagcgttacacgtccaccaaggaggttctcga
cgctactctcatccaccagtccatcaccggtctttacgagactcgtatcgacctttcccagcttggtggtgataagcgtcctg
ctgccaccaaaaaggccggacaggctaagaaaaagaagtag
```

Cys 4 endoribonuclease nucleic acid sequence

SEQ ID NO: 57
```
ATGGACCACTACCTCGACATCAGGCTCAGGCCAGACCCAGAGTTCCCACCAGCC
CAGCTCATGTCCGTCCTCTTCGGCAAGCTCCACCAGGCCCTCGTGGCCCAGGGC
GGCGACAGGATCGGCGTGTCCTTCCCAGACCTCGACGAGTCCAGGTCCAGGCTC
GGCGAGAGGCTCCGCATCCACGCCTCCGCCGACGACCTCAGGGCCCTCCTCGC
CAGGCCGTGGCTGGAGGGCCTCAGGGACCACCTCCAGTTCGGCGAGCCAGCCG
TGGTGCCACACCCAACCCCATACAGGCAAGTGTCCAGGGTGCAAGCCAAGTCCA
ACCCAGAGAGGCTCAGGAGGAGGCTCATGAGGAGGCACGACCTCTCCGAGGAA
GAGGCCAGGAAGCGCATCCCAGACACCGTGGCCAGGGCCCTCGACCTCCCATTC
GTGACCCTCAGGTCCCAGTCCACCGGCCAGCACTTCCGCCTCTTCATCAGGCAC
GGCCCACTCCAGGTGACCGCCGAGGAGGGCGGCTTTACCTGCTACGGCCTCTCC
AAGGGCGGCTTCGTGCCGTGGTTC
```

SEQ ID NO: 58: Wheat U6 promoter
```
GACCAAGCCCGTTATTCTGACAGTTCTGGTGCTCAACACATTTATATTTATCAAGG
AGCACATTGTTACTCACTGCTAGGAGGGAATCGAACTAGGAATATTGATCAGAGG
AACTACGAGAGAGCTGAAGATAACTGCCCTCTAGCTCTCACTGATCTGGGTCGCA
TAGTGAGATGCAGCCCACGTGAGTTCAGCAACGGTCTAGCGCTGGGCTTTTAGG
CCCGCATGATCGGGCTTTTGTCGGGTGGTCGACGTGTTCACGATTGGGGAGAGC
AACGCAGCAGTTCCTCTTAGTTTAGTCCCACCTCGCCTGTCCAGCAGAGTTCTGA
CCGGTTTATAAACTCGCTTGCTGCATCAGACTTG
```

SEQUENCE LISTING

SEQ ID NO: 59: Maize Ubiquitin1 promoter
TGCAGTGCAGCGTGACCCGGTCGTGCCCCTCTCTAGAGATAATGAGCATTGCATG
TCTAAGTTATAAAAAATTACCACATATTTTTTTTGTCACACTTGTTTGAAGTGCAGTT
TATCTATCTTTATACATATATTTAAACTTTACTCTACGAATAATATAATCTATAGTACT
ACAATAATATCAGTGTTTTAGAGAATCATATAAATGAACAGTTAGACATGGTCTAAA
GGACAATTGAGTATTTTGACAACAGGACTCTACAGTTTTATCTTTTTAGTGTGCATG
TGTTCTCCTTTTTTTTGCAAATAGCTTCACCTATATAATACTTCATCCATTTTATTA
GTACATCCATTTAGGGTTTAGGGTTAATGGTTTTTATAGACTAATTTTTTTAGTACA
TCTATTTTATTCTATTTTAGCCTCTAAATTAAGAAAACTAAAACTCTATTTTAGTTTTT
TTATTTAATAATTTAGATATAAAATAGAATAAAATAAAGTGACTAAAAATTAAACAAA
TACCCTTTAAGAAATTAAAAAAACTAAGGAAACATTTTTCTTGTTTCGAGTAGATAA
TGCCAGCCTGTTAAACGCCGTCGACGAGTCTAACGGACACCAACCAGCGAACCA
GCAGCGTCGCGTCGGGCCAAGCGAAGCAGACGGCACGGCATCTCTGTCGCTGC
CTCTGGACCCCTCTCGAGAGTTCCGCTCCACCGTTGGACTTGCTCCGCTGTCGG
CATCCAGAAATTGCGTGGCGGAGCGGCAGACGTGAGCCGGCACGGCAGGCGGC
CTCCTCCTCCTCTCACGGCACCGGCAGCTACGGGGGATTCCTTTCCCACCGCTC
CTTCGCTTTCCCTTCCTCGCCCGCCGTAATAAATAGACACCCCCTCCACACCCTCT
TTCCCCAACCTCGTGTTGTTCGGAGCGCACACACACACAACCAGATCTCCCCCAA
ATCCACCCGTCGGCACCTCCGCTTCAAG > StMRC (PGSC0003DMT400010993) amino acid sequence

SEQ ID NO: 60

MALPALPRATLSFSSLCQPTEFCFMRLEWKKRLVLMTAHHGRGPSSRIVRSVLDNRK
SNITGDEATEPARVLLERLFAQTQKLEQQIGRNIYFPQVAELGLNLGKLESDLQDALAA
LKKKEEDIQDTERKVLMEYNELNRAKIELEQRVEEMAAANSRQEKLENELRQANLILV
SQAAEIEDLKFRFNEIDQEISAAQTALVSKEDEINKMMIELKNKSDEVANTESQLRTKG
ELLDTANEVVQRQEVELQNLQREIQEKEKELQVFLTMQKTEEEKLKVSKSNLEKQAM
DWLIAKQEMKKLEVETSNYGGEANRSLEDFRRVKKLLADVRSELVSSQRALTSSRKK
MEEEQENLLEDRLEELEEQRRSVMSYMTSLKEAQNEVENEKVQLTVAEARNKELERDL
SIEKELVEELQTENNIKKSSLHVAINEKSALQEELDCKSAEFGETQNLLQVKESELVDA
RLEIQHLKSQCASLQLMLEEKDKELLDSRKTVDELNQEIAELRVNMNSQEQQLIQATS
MLKEKEESMQIMQLELNDTKMKYSEAETVVEHMVDLTNKLVISVKDDVLSPLSHTDEM
WSSQLVEKPTDAFRWHKNQLENELELTRESLRSREMDSLAAQRALKLKEQELKIVRQ
KLNDREEEINKMKNMTRDADGPRQSYVLAQERTGEKSTGDLAVEKLQFEGAQLEVE
AATTALQKLAELSRDLLNKASLTIEADYDSSLLLVDIPETAANVSSSFECLAEVYSEMA
QLSALSEKLVKEAGILCPQ

> StMRC (PGSC0003DMG400004306) genomic nucleic acid sequence

SEQ ID NO: 61

ATGGCGTTGCCAGCCTTACCGCGCGCCACTTTATCGTTTTCCTCTCTTTGCCAGC
CAACGGAGGTGAAAGTCTCTTCTTCTTTTTTGTTGTTGTTTTCTCCTTATTTATTCT
GTTCACAGAGTATTTTTTTTTACATTTTCCTACATTTCAATTTCTTCAATGGGATCTT
TTGCTTTTTCTGCAAAATAAATAAATAAATTGTTAATGTTGGAAAAGATTAGGTATA
TAGATGTCTTTACAACCTTCCTTTATAGAGTAAATTGCACAGGTTTGCTAATGGTTT
AGGTAACAATTCAAAGAAGGAACTTACGAGTTCTGCCGCTAGCACTGATTTACAAC
TCTAAATTGTTTCCGATTGCTCTTTTATTTCATATTACTATTAGTAGTGATAAGAGAT
GGATGTCGTTTATAACTAGATACATGATCATACGTAATATAGGTGGTTATTTTGTTT
CATTCAATCAAATATTAACCAGATTGGAATTGTTGTGAAAATCTGTAAAGTAAAATA
AGGAATTAAGGATTGGAACAATTAATGTTTAATGTTTGAGTTGAGAAGAGTAAAATT
TTAGTACTAATATCTGAATTTAGAGAGAGATTGCATAGTAGACAAATTTGGTCATG
GAGATACATAATAGTGCTTCAACATCCATAATTGTGTCCAAGCACTTTTGTTCTTCT
CAGCATTTGTCATGTTGGCAAAAATATTTTTGCTTCTTAAAATGGTTTCGGAGTGATG
TTAACTCCAAAGAACAGATCTCAGTTCTCGGACATCTCTCTAATTAGGATGTAGCT
GATATGGTCATCAACTGTGTAGATAGGATTCTATTTGGTTATTACAACTTTATAATT
TTCTTTGGAGGTTGAAATAAGGTTCACCTTTTTGGAATGTGAAAGTATACAATTGCA
TTTATGTTGATGGATCTTGCATGAAAGTTGTGATATAAATGTTCCATAATGATTTAT
TTCAGTGAGTTTGGATGAAATCGATCGATCAATCAATCAACCATACCTCAATCCCA
AACTAGTTGGTCAAATATATGAATTTTCTATATCCATTCTACTTTATCCGTGACCATT
TGTTGTATGAGTGAACGTTAAAATATAGTCTGAACAAGGAAGTAACAAATTGTTAT
GACCATGGGATGTGAGAAACCATAACAAGAGTATACAAGACATCTCTTATTCTTAT
TTCTTCACCAAGAGTTGTGGGGATGGATGGGGAGGTGAAAAATGAAATATATCAA
CGGTTTCCCCTGTTGATTTATTTCACCTTGTCTTACAAAAGGAAAAATAAGGGAAG
CTAAAGAAGAAAAATTAAGAGATTAACTATGAGCCGCTTTCTTGCATATATACTGG
AGAAAATACACTGTACTGACTACTGTGGAGTAAAACTAATTCAGTTATCTTGCCCG
TACTACCAAATTGAACTTGTGCATAGGAATTCTTCTCCAATTGTGCCTTTGTCTTAT
ACATCTTCACTTGCTTATCACTGGTCTGTTAATACTACTGTATGAATTGTGCTGGGA
GTCCCATGGAATAGATGACAGGTTTGTCTTTCATAAAAGTAGGAAGCTCTACACGT
GATAATATTGTGGTGTAATTACTGACATCTCTTTGTGTACAGTTCTGTTTTATGAGG
CTCGAATGGAAGAAGAGATTAGTGCTTATGACAGCTCATCATGGGGGGGTCCTT
CCTCAAGAATTGTCAGGTCTGTCTTGGATAACAGGAAATCAAATATCACCGGCGAT
GAAGCAACTGAGCCGGCTAGGGTTCTTCTTGAGAGGTTGTTTGCCCAGACCCAGA
AACTAGAACAACAGATTGGCAGAAATATTTATTTTCCTCAGGTTGCTGAGCTGGGA
CTAAATCTTGGCAAGCTAGAGTCGGATTTGCAGGATGCTCTTGCAGCCTTGAAGA
AAAAGGAAGAAGATATTCAAGATACAGAGAGAAAGTATTGATGGAGTACAATGAA
TTAAACCGTGCAAAGATAGAATTGGAGCAACGTGTGGAGGAGATGGCAGCTGCTA
ATTCTAGGCAGGAAAAACTGGAAAATGAGCTAAGGCAGGCTAATCTGATCTTAGTA

SEQUENCE LISTING

```
TCTCAAGCTGCAGAAATTGAAGATCTAAAGTTTCGTTTCAACGAGATAGATCAGGA
GATATCTGCTGCGCAAACAGCCCTAGTTTCAAAAGAAGATGAAATAAATAAAATGA
TGATTGAGTTGAAGAATAAAAGTGATGAAGTGGCTAATACTGAATCACAACTCAGA
ACCAAGGGTGAACTACTCGATACAGCAAATGAAGTAGTTCAAAGACAGGAGGTTG
AACTACAAAATCTCCAAAGAGAAATTCAAGAGAAAGAGAAAGAGCTACAAGTCTTC
TTGACGATGCAGAAAACCGAAGAAGAGAAACTTAAAGTTTCCAAATCCAATTTGGA
GAAGCAGGCAATGGATTGGCTCATAGCAAAGCAAGAAATGAAGAAATTGGAAGTG
GAAACATCTAACTATGGTGGAGAAGCAAATCGGTCCCTTGAGGATTTCAGAAGAG
TCAAGAAGCTACTTGCCGATGTAAGGTCTGAGTTAGTCTCATCTCAGAGAGCTTTG
ACATCCTCTAGAAAGAAATGGAAGAGCAGGAAAATCTATTAGAAGATCGTCTCGA
AGAACTTGAAGAGCAGAGAAGAAGTGTTATGTCTTACATGACAAGTTTGAAAGAAG
CTCAAAATGAGGTAGAGAATGAGAAAGTGCAACTTACGGTTGCTGAAGCTCGAAA
CAAAGAACTTGAGAGGGATTTATCCATAGAAAGGAGCTCGTTGAGGAGTTGCAG
ACTGAGAATAATATTAAGAAATCTTCTCTGCATGTAGCTATCAATGAAAAATCTGCT
CTCCAGGAGGAGCTTGACTGTAAGAGTGCAGAGTTTGGAGAAACACAGAATCTTC
TTCAGGTTAAAGAGTCAGAGCTAGTAGATGCTAGATTAGAGATTCAGCACTTGAAG
TCTCAGTGCGCTTCTCTTCAGCTGATGTTGGAAGAAAAGATAAGGAACTTCTGGA
TTCAAGAAAGACAGTAGATGAACTAAATCAGGAAATAGCTGAGCTGAGGGTGAAC
ATGAACAGTCAAGAACAGCAACTTATTCAGGCAACAAGTATGTTGAAAGAAAAGA
GGAATCCATGCAGATAATGCAACTTGAGTTAAATGATACAAAAATGAAATATTCAG
AAGCTGAGACCGTTGTGGAACATATGGTAGACCTGACTAACAAATTGGTTATTTCT
GTTAAGGATGACGTGTTGAGCCCACTCAGTCACACAGATGAAATGTGGTCATCTC
AGCTGGTGGAGAAACCAACTGATGCTTTTAGGTGGCACAAAAACCAGCTTGAAAA
TGAACTTGAGTTAACCAGAGAAAGCCTGAGGAGTAGAGAAATGGATTCTCTTGCA
GCACAAAGGGCTCTTAAACTCAAAGAGCAGGAGCTCAAAATAGTTCGTCAAAAATT
AAATGATAGGGAGGAAGAAATAAATAAAATGAAGAATATGACCCGGGACGCAGAT
GGCCCAAGGCAATCTTATGTTTTGGCACAGGAAAGAACAGGTGAAAAGAGCACTG
GAGATCTGGCAGTTGAAAAGCTCCAATTCGAGGGAGCTCAATTGGAAGTTGAAGC
TGCAACCACTGCTCTCCAGAACTCGCTGAACTCAGCCGTGACCTTTTGAATAAAG
CTAGTTTGACCATTGAGGCTGACTATGATAGCAGCCTTTTGTTGGTTGACATCCCA
GAAACTGCAGCAAATGTCTCTAGCAGTTTTGAGTGTCTTGCTGAAGTTTATTCAGA
GATGGCACAACTTTCAGCTTTGAGTGAGAAGCTAGTGAAAGAAGCTGGTATTTTAT
GCCCCCAGTAG
```

> StMRC (PGSC0003DMT400010993) CDS nucleic acid sequence  SEQ ID NO: 62

```
ATGGCGTTGCCAGCCTTACCGCGCGCCACTTTATCGTTTTCCTCTCTTTGCCAGC
CAACGGAGTTCTGTTTTATGAGGCTCGAATGGAAGAGATTAGTGCTTATGACA
GCTCATCATGGGGGGGTCCTTCCTCAAGAATTGTCAGGTCTGTCTTGGATAACA
GGAAATCAAATATCACCGGCGATGAAGCAACTGAGCCGGCTAGGGTTCTTCTTGA
GAGGTTGTTTGCCCAGACCCAGAAACTAGAACAACAGATTGGCAGAAATATTTATT
TTCCTCAGGTTGCTGAGCTGGGACTAAATCTTGGCAAGCTAGAGTCGGATTTGCA
GGATGCTCTTGCAGCCTTGAAGAAAAGGAAGAAGATATTCAAGATACAGAGAGA
AAAGTATTGATGGAGTACAATGAATTAAACCGTGCAAAGATAGAATTGGAGCAACG
TGTGGAGGAGATGGCAGCTGCTAATTCTAGGCAGGAAAAACTGGAAAATGAGCTA
AGGCAGGCTAATCTGATCTTAGTATCTCAAGCTGCAGAAATTGAAGATCTAAAGTT
TCGTTTCAACGAGATAGATCAGGAGATATCTGCTGCGCAAACAGCCCTAGTTTCAA
AAGAAGATGAAATAAATAAAATGATGATTGAGTTGAAGAATAAAAGTGATGAAGTG
GCTAATACTGAATCACAACTCAGAACCAAGGGTGAACTACTCGATACAGCAAATGA
AGTAGTTCAAAGACAGGAGGTTGAACTACAAAATCTCCAAAGAGAAATTCAAGAGA
AAGAGAAAGAGCTACAAGTCTTCTTGACGATGCAGAAAACCGAAGAAGAGAAACT
TAAAGTTTCCAAATCCAATTTGGAGAAGCAGGCAATGGATTGGCTCATAGCAAAGC
AAGAAATGAAGAAATTGGAAGTGGAAACATCTAACTATGGTGGAGAAGCAAATCG
GTCCCTTGAGGATTTCAGAAGAGTCAAGAAGCTACTTGCCGATGTAAGGTCTGAG
TTAGTCTCATCTCAGAGAGCTTTGACATCCTCTAGAAAGAAATGGAAGAGCAGGA
AAATCTATTAGAAGATCGTCTCGAAGAACTTGAAGAGCAGAGAAGAAGTGTTATGT
CTTACATGACAAGTTTGAAAGAAGCTCAAAATGAGGTAGAGAATGAGAAAGTGCAA
CTTACGGTTGCTGAAGCTCGAAACAAAGAACTTGAGAGGGATTTATCCATAGAAAA
GGAGCTCGTTGAGGAGTTGCAGACTGAGAATAATATTAAGAAATCTTCTCTGCATG
TAGCTATCAATGAAAAATCTGCTCTCCAGGAGGAGCTTGACTGTAAGAGTGCAGA
GTTTGGAGAAACACAGAATCTTCTTCAGGTTAAAGAGTCAGAGCTAGTAGATGCTA
GATTAGAGATTCAGCACTTGAAGTCTCAGTGCGCTTCTCTTCAGCTGATGTTGGAA
GAAAAGATAAGGAACTTCTGGATTCAAGAAAGACAGTAGATGAACTAAATCAGGA
AATAGCTGAGCTGAGGGTGAACATGAACAGTCAAGAACAGCAACTTATTCAGGCA
ACAAGTATGTTGAAAGAAAAGAGGAATCCATGCAGATAATGCAACTTGAGTTAAA
TGATACAAAAATGAAATATTCAGAAGCTGAGACCGTTGTGGAACATATGGTAGACC
TGACTAACAAATTGGTTATTTCTGTTAAGGATGACGTGTTGAGCCCACTCAGTCAC
ACAGATGAAATGTGGTCATCTCAGCTGGTGGAGAAACCAACTGATGCTTTTAGGT
GGCACAAAAACCAGCTTGAAAATGAACTTGAGTTAACCAGAGAAAGCCTGAGGAG
TAGAGAAATGGATTCTCTTGCAGCACAAAGGGCTCTTAAACTCAAAGAGCAGGAG
CTCAAAATAGTTCGTCAAAAATTAAATGATAGGGAGGAAGAAATAAATAAAATGAA
GAATATGACCCGGGACGCAGATGGCCCAAGGCAATCTTATGTTTTGGCACAGGAA
AGAACAGGTGAAAAGAGCACTGGAGATCTGGCAGTTGAAAAGCTCCAATTCGAGG
GAGCTCAATTGGAAGTTGAAGCTGCAACCACTGCTCTCCAGAACTCGCTGAACT
CAGCCGTGACCTTTTGAATAAAGCTAGTTTGACCATTGAGGCTGACTATGATAGCA
GCCTTTTGTTGGTTGACATCCCAGAAACTGCAGCAAATGTCTCTAGCAGTTTTGAG
TGTCTTGCTGAAGTTTATTCAGAGATGGCACAACTTTCAGCTTTGAGTGAGAAGCT
```

| SEQUENCE LISTING |
|---|

AGTGAAAGAAGCTGGTATTTTATGCCCCCAGTAG

Selaginella

SEQ ID NO: 63

QVSAVLDTPSERTNSSDPSEPARVALERLFEELKRKEEELKTAETVAREDHHQLENSK
FALVKRGDVLEDARQGQGKKRDEIGNLYKELAEQAKEAENAQKVVDEQQRQLEALQ
KTLSKKQELIARSKAQIFAKDEALAQCRRELKVRDSRLKHANEVIAQQAVELKELRSSL
ELKEAGLRTLEENVKFKQEQIQKTEADLSTRVIAYLSVERELKSLEADLSKSKALNVEA
GKELKGVKDLLTEVQEELRFSQMRLQQYKKTVEEQSIQIKSQQEEIALQKSLVESFEF
SLAEAKERTKREEEQVRLAKGSYKKLEEQSTNERLEAEKLQLELRNEKSALQEATTEI
NSLKRELQQKETALSDTQLALRLKEAELTASQVELQELKSDFTSMKLELDQKDSELRH
AQTVVNALQQDVKRLKALLSAKEEKHVEVVAALKDKEEELVSMRKKLDANNVKMSQV
NFAVEQISALSEALVDSIADDKPSLLSRESV

Brassica Rapa. FASTA ref: >Brara.A00570.1

SEQ ID NO: 64

TVKSVLNNTRPSFNDNGADEPSKILLDKLFARMALLKREEDLQDAERKVLSEKKKLSK
AKEGLEKRERVILQASLKHESLQEELKRANVELASQAREIEELKHKLRERDEELVAMQ
ASLTFKERELDRMRVEISIKTKEASVASFEFENKSQLLIQANEIVKKQEDEIEALQRALK
EKEEELEVSTEAKKLEQEKLRETEASLRKQTEEWLVAQEEVSKLQEETVKRLGEANE
TMEDFRRVRKLLTDVRFELVSSREVLLSSREQMGEKEVLLEKQLEELEEQRRSVLSY
MQSLRDARGEVESERVKLRVAEAKNFALEREISIQKELLEELREELKKEKSLLEQAMH
DVSTIQDELDKKTNEFQVSQTLLQEKESSLVEAKLEIQHLKSEQASLELLLQEKDEELT
EARNQLEVVNREVTELKMLMRTREDQLTQATELLKEKDVHLNRIEDELGSSKIQASEA
EMVVERIAELTSRLVQDQMQQQPLEKQPYGD

Amborella

SEQ ID NO: 65

LIRSVVDKPTSNIGSNGPSESARVLLERLFAQAALKKKEEDLQYAEKMVLMDRAKLTD
VKQDLDHREEEIIAAHAKQAKLEEDLKKAQEDFASQEKQIEELKHLVKEKDREMQNAR
SALSLKEAGLDILRNELVEKTEEVERINLDLKSRDQILEQTNKVIRKQEAEVQDLKEAIM
SKEEELADTIQQRKNDEEKLKNAKANLEQRAVEWLSSQEELKKIAEEEASKYKAEAKGT
AQELKRVRVLLADVKTELIASQKSLASSGRRLDDQGVELKKQLEDLNEEKSLLTSYMT
NLKEAQLEVESERKKLRYAEARNQELEQKISKEQAMIEKLQNELNREKLSLEKTTKDV
GSLTALLEQKISDLDNTLKLLKVKESELVSARSEIQLLKSDHESIQLLLKEKDVELSLANK
NLEDLDKEVRDLKKLMREKEEQLIQATLGLQEKDQLVEMMRLEIDDTKLKYLEAAAVV
GRIMQLTNILVNTAREETWNLESHGSL

Gossypium

SEQ ID NO: 66

IVESVLNNSKSSINDNGAAESAKVLLERLFAQTALKQKEDDLQDAEKMVVLEQSELSR
AKDELEQREKEIAAASSKHEKLEEKLTQANLAFASQASQIEDLKLQLKEQDHKVAAAQ
STLSAKEDEMDKMRHELVKKTEEAEKIRSELTSKSQLLNEANEVMKKQEIELQELREAI
WEREEELETSLTQRKLEEEKLKVAEAKLQQQTMEWLLAQEELKKLAEQASRHMGEA
NEAFKDPTRVKQLLSDVRSELVSSQKSLASSRQQMEQQEQLLKMQLEELEEQRKSV
ASYMESLKNAQIEVESERVKLRVVEARNKDLERDLSVERELIKELQEELKKEKYSLQLA
IQDASFLRKQLGKKHTEFVEMNNVLQNKEVDLVEAKLEIQHLKSERASLQLILEEKDQE
LSDAKKNLEQLNQEIAELKMLSSKENQLIQATALLKEKDEYALKVQDELNDTKMKFS
EAETVIERIAELTNRLVISVKDEDNNVLRPVDD

Vitis vinefera

SEQ ID NO: 67

IVKSVLNNRKSSINDNGSTEPARVLLERLFAQVALKKKEEDLQDAAGMVLMEHTELNR
AKEELKRHAEEIAVACSKHEKLEEELKQANLNLASRARQIEDLKLQLKDRDQEIFAARS
ALSSKQDEMDKMRNELMKKTEEAAKKESELQSMAKLLDEANEVVKKQEIELQELQKSI
QEKEEELEESMMLRKLEEKKLKVAEANLEKKTMDWLLAKEELKKLAEDAAKHMGESN
KTMKEFRRAKRLLHDVRSELVSSQKSLASSRQKMQEQEKLLEKQLAELEEQKTSINH
YMTSLKDAQIEVESERVKLRVAESRNKELEWDLSVKKELMEELQEELRKEKSSLQQVI
QETSFLQKELDQKTTEFGELHNLLQVKESELVEARLEIQHLKSEQVSLQLILKERDLEL
FNAQKKLEEVNQEVSELKMLMNNREDQLMQATTLLKEKEEHLLIMQHELNDTKLKFS
EAESVVERIVDLTNKLVICTKDEECTATSPFDD

Manihot

SEQ ID NO: 68

IVKSVLNCSKSSINDNGATEPARILLERLFAQDALRKKEEDLQHAEKQVLSEHNDLNFA
KQELQQREKEIAVAHSKHEKLEGELREANLNLASQARQIEDIKLQLKEREEEVAAGQS
ALLIKQHEIEKKISELTKKSEEVAKMDSELQYKAQLLDEANEVVKKQEIEIQRLKKGLQE
KEKELEVSVALRKVEEEKLKVVQTNLEKQAMEWLIAQEGLKRLANETSKRMVETNET
MKDFKRVKKLLVDVRSELVSSQKSLAFSRKRMEEQDLLLKKQLLELEEERESVMSYM
TSLKDAQMEVESEKGKLRAAEARNKELEQKLSLEKEIMEEIREELNKEKSSLEQMVQE
MSYLQQELAAKNTEFGEMHDILQFKESELVEAKLEIQHLKSVQCSLQLLSEEKDLQLL
DAKKKLEELDQEVAELKMLLSSKEDQLIQATNMLMEKEERVQMMQDELNDARLKISE
AETVVERIVDLTNKLVITVKDEDYNAVRPSGS

Medicago

SEQ ID NO: 69

TVKSVLNDNRPSFNNYGAPESAR-

SEQUENCE LISTING

```
LLERLFEQMELKEKEDHLQEVERTVLLENGKLKDAKEELERQEGEIKAAREKYERLED
EMKEAMASLVSQAGQVEELKLRLRDRDSETDGLRDALSLKEEEMEKMKIGLAKKSEE
AAYVDSELRQKVQLLSEANEVVKKQEIELQELRSVVQQREEELRLSVAARDVEGEKLK
VAEASLEKQAMEWLLTQEELKRLEEEASKHAQERSETLEDFRRVKKLLSDVRSELVS
SQQSLASSRYKMQVQEGLLEQQLAELADQRESVMLYMENLKDAQIEVENERTKLSVA
EALNKELEQDLSVEKELMKKLQEELKKEKASLEQAVQEMALLQEELDIKSAEFKEKSA
LLDVKESELVDAKLQIQELKTEKASLQALLEEKDLELSSARKMLVELNQEISDLKMLMN
DKETQLIEATNMLREKDEHVKVIQNKLNNTSLKAFEAETVVGRVLDLTNKLVASIKNEDI
NSSRPLNE
```

Citrus, C. sinensis_orange

SEQ ID NO: 70

```
LVRAVLDGKKSSVNGYGLGEPARILLERLFAQAALKKKEEDLEDAERRVCLEHSELNR
AKEELLRREREIDVACSRHEKLEEELGQSNLKLVSQARHIEDKLRLKERDQEIAAMQ
SALSLKELELEKMRSELLKKSEEAAKIDSELKSKAQMLNEANEVVKKQETEIQSLRKVI
QEKEEELEASVALRKVEEEKLKVVEANLEKRTMEWLLSQDALKKLAEEASRRMEETN
DTLEDFRRVKKLLSDVRSELVSSQKSLASSRKQMEEQEHLLGKQLVELEEQKKSLTS
YMTSLKDAQVEVESERVKLRVTEARNKELERDLSMEKELVEELQNELNKEKYSLQQAI
DEVSSLQEELGRKNTEFGETENLLRVKESDLVEAKLEIQNLKSKQASLQLILEEKDFEL
SNARQMLEELNNEVRELKMIMSSREEQLVQAMDTLQEKDEHVLILQNELDGTKLKVS
EAETVVEQIVDLTHKLVISNKNDESSTSMPTDD
```

Solanum (tub.)

SEQ ID NO: 71

```
IVRSVLDNRKSNITGDEATEPARVLLERLFAQAALKKKEEDIQDTERKVLMEYNELNRA
KIELEQRVEEMAAANSRQEKLENELRQANLILVSQAAEIEDLKFRFNEIDQEISAAQTAL
VSKEDEINKMMIELKNKSDEVANTESQLRTKGELLDTANEVVQRQEVELQNLQREIQE
KEKELQVFLTMQKTEEEKLKVSKSNLEKQAMDWLIAKQEMKKLEVETSNYGGEANRS
LEDFRRVKKLLADVRSELVSSQRALTSSRKKMEEQENLLEDRLEELEEQRRSVMSYM
TSLKEAQNEVENEKVQLTVAEARNKELERDLSIEKELVEELQTENNIKKSSLHVAINEK
SALQEELDCKSAEFGETQNLLQVKESELVDARLEIQHLKSQCASLQLMLEEKDKELLD
SRKTVDELNQEIAELRVNMNSQEQQLIQATSMLKEKEESMQIMQLELNDTKMKYSEA
ETVVEHMVDLTNKLVISVKDDVLSPLSHTDE
```

Solanum (lyc.)

SEQ ID NO: 72

```
IVRSVLDNRKSNITGEEETEPARVLLERLFAQAALKKKEDDIQDTERKVLMEYNELNRA
KIELEQRVEEMEAANSRQEKLENELRQANLVLVSQAAEIEDLKFRFNEIDQEISAAQIAL
VSKEDEINKMMIELKNKCDEAAKTESQLRTKGELLDTANEVVQRQEVELQNLRREIQE
KEKELQVFLTMQKTEDEKLKVSKSNLEKQAMDWLIAKQEMKKLEEETSKYGGGANRS
LEDFRRVKKLLADVRSELVSSQRALTSSRKKMEEQENLLENRLEELEEQRKSVMSYM
TSLKEAQNEVENEKMQLTVAEARNKELERDLSMEKELVEELQTENNIKKSSLYVAINE
KSALQEELDRKSAEFGETQNLLQVTESELVDARLEIQHLKSQCASLQLMLEEKNKELL
DSRKTLDELNQEIAELRVLMNSQEQQLIQATSMLKEKEEFMQIMQLELNDTKKKYLEA
ETVVEQMVDLTNKLVISVKDDVLSSLSHTDE
```

KASP Markers 5' → 3'
TaMRC 6A. Kronos3272 Wildtype

SEQ ID NO: 73 agcaacagttagggagctgc

TaMRC 6A. Kronos3272 Mutant

SEQ ID NO: 74 agcaacagttagggagctgt

TaMRC 6A. Kronos3272 Common

SEQ ID NO: 75 cctcgattcatttgatctggcg

TaMRC 6A. Kronos4681 Wildtype

SEQ ID NO: 76 catacggctcagatgctcgc

TaMRC 6A. Kronos4681Mutant

SEQ ID NO: 77 catacggctcagatgctcgt

TaMRC 6A. Kronos4681Common

SEQ ID NO: 78 gcaagatcgccagtgagc

TaMRC 6A. Kronos775 Wildtype

SEQ ID NO: 79 attcaagggaagacacaggagC

TaMRC 6A. Kronos775 Mutant

SEQ ID NO: 80

SEQUENCE LISTING

| | |
|---|---|
| attcaagggaagacacaggagT | |
| TaMRC 6A. Kronos775 Common | SEQ ID NO: 81 |
| tcatgacaacgagactgtgcA | |
| TaMRC 6A. Kronos2485 Wildtype | SEQ ID NO: 82 |
| cttgatctttggcatcaagtgC | |
| TaMRC 6A. Kronos2485 Mutant | SEQ ID NO: 83 |
| cttgatctttggcatcaagtgT | |
| TaMRC 6A. Kronos2485 Common | SEQ ID NO: 84 |
| acagccctcgagtccaatttA | |
| TaMRC 6A. Kronos2096 Wildtype | SEQ ID NO: 85 |
| tgtaggagagatggagctGC | |
| TaMRC 6A. Kronos2096 Mutant | SEQ ID NO: 86 |
| tgtaggagagatggagctGT | |
| TaMRC 6A. Kronos2096 Common | SEQ ID NO: 87 |
| gcttcgacctccGcagcA | |
| TaMRC 6A. Kronos3078 Wildtype | SEQ ID NO: 88 |
| ctcgttgtcatgaacttgaatcac | |
| TaMRC 6B. Kronos3078 Mutant | SEQ ID NO: 89 |
| ctcgttgtcatgaacttgaatcat | |
| TaMRC 6B. Kronos3078 Common | SEQ ID NO: 90 |
| tcgaccttctccctttcctg | |
| TaMRC 6B. Kronos4305 Wildtype | SEQ ID NO: 91 |
| ttgagaagcagagtttaggatgg | |
| TaMRC 6B. Kronos4305 Mutant | SEQ ID NO: 92 |
| ttgagaagcagagtttaggatga | |
| TaMRC 6B. Kronos4305 Common | SEQ ID NO: 93 |
| acgtttgaagtcagtgataatacca | |
| TaMRC 6A. Cadenza0199 Wildtype | SEQ ID NO: 94 |
| acttggttgcatcagagagtc | |
| TaMRC 6A. Cadenza0199 Mutant | SEQ ID NO: 95 |
| acttggttgcatcagagagtt | |
| TaMRC 6A. Cadenza0199 Common | SEQ ID NO: 96 |
| acttccattttaggatcgcatttaa | |
| TaMRC 6A. Cadenza0377 Wildtype | SEQ ID NO: 97 |
| cgagttcctgtacttgttcctg | |
| TaMRC 6A. Cadenza0377 Mutant | SEQ ID NO: 98 |
| Cgagttcctgtacttgttccta | |
| TaMRC 6A. Cadenza0377 Common | SEQ ID NO: 99 |
| gatgctgtacgctctgaattg | |

SEQUENCE LISTING

| | |
|---|---|
| TaMRC 6B. Cadenza1715 Wildtype<br>tggctgttcaagaaaaggattcag | SEQ ID NO: 100 |
| TaMRC 6B. Cadenza1715 Mutant<br>Tggctgttcaagaaaaggattcaa | SEQ ID NO: 101 |
| TaMRC 6B. Cadenza1715 Common<br>Tgaagctcagcaatttcactgc | SEQ ID NO: 102 |
| TaMRC 6D. Cadenza1012 Wildtype<br>Agcaacagttagggagctgc | SEQ ID NO: 103 |
| TaMRC 6D. Cadenza1012 Mutant<br>Agcaacagttagggagctgt | SEQ ID NO: 104 |
| TaMRC 6D. Cadenza1012 Common<br>Attcatttgatctggcgatatcg | SEQ ID NO: 105 |
| TaMRC 6D. Cadenza1092 Wildtype<br>Cctttcttgaacagccaattg | SEQ ID NO: 106 |
| TaMRC 6D. Cadenza1092 Mutant<br>Cctttcttgaacagccaatta | SEQ ID NO: 107 |
| TaMRC 6D. Cadenza1092 Common<br>cttcagaaggagcttgttcg | SEQ ID NO: 108 |

SEQUENCE LISTING

<160> NUMBER OF SEQ ID NOS: 62

<210> SEQ ID NO 1
<211> LENGTH: 773
<212> TYPE: PRT
<213> ORGANISM: Artificial Sequence
<220> FEATURE:
<223> OTHER INFORMATION: TaMRC 6A (cv. Kronos (4n))

<400> SEQUENCE: 1

```
Met Arg Leu Ser Ile Gly Ser Pro Ser Pro Ser Pro Pro Ala Val
1               5                   10                  15

Ala Ala Ala Leu Arg Ser Thr Pro Pro Ser Arg Arg Thr Ala Ser His
            20                  25                  30

Val Met Phe Arg Gln Lys Leu Ser Phe Met Glu Ala Phe Gln Thr Gln
        35                  40                  45

His Leu Lys Tyr Ala Pro Arg Leu Ile Lys Ser Val Val Lys Gly Ile
    50                  55                  60

Arg Ser Asn Ile Thr Asp Gly Asp Asn Gly Thr Thr Glu Pro Ala Arg
65                  70                  75                  80

Glu Leu Leu Glu Arg Leu Phe Ala Arg Thr Gln Ser Leu Asp Thr Gly
                85                  90                  95

Ala Ser His Asp Ser Glu Leu Ser Val Ser Ile Glu Val Leu Lys Ser
            100                 105                 110

Glu Phe Glu Gly Ala Leu Ser Ile Leu Arg Asn Lys Glu Arg Asp Leu
        115                 120                 125
```

```
Arg Ser Ala Glu Lys Arg Val Ser Asp Asp Arg Ile Arg Leu Ser Lys
            130                 135                 140

Thr Lys Gln Asp Leu Asp Gln Arg Glu Glu Ala Ile Arg Lys Ala Tyr
145                 150                 155                 160

Val Arg Gln Gln Gly Ile Glu Lys Ala Leu Lys Lys Ala Ser Arg Asp
                165                 170                 175

Leu Ala Leu Arg Val Lys Gln Ile Ser Asp Leu Lys Leu Leu Val Glu
            180                 185                 190

Gly Gln Asp Arg Thr Ile Ala Arg Ser Gln Ala Leu Leu Ser Gln Lys
            195                 200                 205

Val Thr Glu Val Glu Asn Leu Lys Arg Asp Met Phe Lys Lys Asn Glu
210                 215                 220

Glu Ala Asp Leu Met Arg Ser Glu Ile Arg Ser Lys Glu Lys Leu Leu
225                 230                 235                 240

Leu Thr Ala Asn Gln Ala Ile Ala Gln Gln Glu Ala Thr Val Arg Glu
            245                 250                 255

Leu Gln Ser Glu Ile Lys Arg Lys Thr Met Asp Ile Ala Arg Ser Asn
            260                 265                 270

Glu Ser Arg Lys Thr Asn Glu Glu Lys Leu Lys Val Ala Glu Gln Glu
            275                 280                 285

Leu Glu Lys Gln Ser Leu Gly Trp Leu Ala Ala Gln Gln Glu Leu Lys
            290                 295                 300

Glu Leu Ala Gln Leu Ala Phe Lys Asp Thr Asp Asp Ile Lys Gly Ile
305                 310                 315                 320

Ile Thr Asp Phe Lys Arg Val Arg Ser Leu Leu Asp Ala Val Arg Ser
                325                 330                 335

Glu Leu Ile Ser Ser Lys Asp Ala Phe Ala Ser Ser Arg Arg Gln Ile
            340                 345                 350

Glu Asp Gln Ala Val Gln Leu Gln Glu Gln Val Gln Glu Leu Glu Asp
            355                 360                 365

Gln Arg Val Leu Leu Met Ser Tyr Thr His Asp Leu Glu Ala Ala Gln
            370                 375                 380

Leu Glu Ile Gln Gly Lys Thr Gln Glu Leu Asn Tyr Ala Gln Ser Arg
385                 390                 395                 400

Cys His Glu Leu Glu Ser Gln Leu Leu Lys Glu Met Glu Lys Val Glu
                405                 410                 415

Ser Leu Glu Ala Glu Leu Thr Lys Glu Lys Gln Ser Leu Glu His Arg
            420                 425                 430

Thr Glu Glu Val Gly Phe Leu Gln Lys Glu Leu Val Gln Lys Glu Asn
            435                 440                 445

Glu Cys Thr Lys Ser Gln Glu Leu Val Lys Val Lys Glu Phe Glu Leu
450                 455                 460

Leu Glu Ala Arg Gln Glu Val Gln Asp Met Lys Leu Lys Val Glu Ser
465                 470                 475                 480

Ile Gln Leu Ala Val Gln Glu Lys Asp Ser Glu Leu Ser Asp Thr Gln
                485                 490                 495

Ser Arg Leu Thr Glu Val Ser Ser Glu Ile Val Glu Leu Gln Gln Leu
            500                 505                 510

Leu Asn Ser Lys Lys Asp Gln Leu Val Gln Ala Arg Thr Glu Leu His
            515                 520                 525

Asp Lys Glu Gln His Ile Glu Thr Leu Glu Ser Glu Leu Asp Ser Ile
530                 535                 540
```

```
Arg Leu Arg Cys Ser Gln Ala Glu Ser Met Val Gln Arg Met Ala Glu
545                 550                 555                 560

Leu Thr Gly Asp Leu Ala Ser Ser Val Lys Ala Gly Glu Met Asp Ile
            565                 570                 575

Tyr Thr Leu Leu Asp Asp Glu Ile Ser Ser Thr Ser Thr Ala Leu Glu
            580                 585                 590

Ser Asn Leu His Lys His Asn Gln Leu Glu Ala Asp Ile Glu Met Leu
            595                 600                 605

Arg Glu Cys Leu Arg His Lys Asp Met Glu Leu Arg Ala Ala His Glu
    610                 615                 620

Ala Leu Asp Ala Lys Asp Gln Glu Leu Lys Ala Val Leu Lys Lys Trp
625                 630                 635                 640

Asp Val Lys Glu Arg Glu Leu Arg Glu Leu Glu Glu Leu Pro Asp Pro
                645                 650                 655

Ser Ala Thr Asn Glu Leu Ala Gly Phe Ser Ser Glu Thr Thr Glu Gly
            660                 665                 670

Gly Ile Val Gly Glu Met Glu Leu Pro Glu Leu Gln Ile Asp Ala Ala
            675                 680                 685

Glu Val Glu Ala Leu Ala Ala Thr Thr Ala Leu Arg Lys Leu Ala Asp
            690                 695                 700

Met Thr Lys Asp Phe Phe Lys His Val Lys Ala Asp Ser Gly Ile Asn
705                 710                 715                 720

Leu Val Ala Ser Glu Ser Gln Lys Ile Ile Lys Cys Asp Pro Lys Met
                725                 730                 735

Glu Val His Lys Lys Thr Asp Val Ile Leu Glu Ala Glu Lys Glu Ile
            740                 745                 750

Val Arg Leu Phe Ser Leu Thr Lys Gln Ile Val Thr Asp Asp Ile Ile
                755                 760                 765

Asn Asp Val Glu Glu
            770

<210> SEQ ID NO 2
<211> LENGTH: 773
<212> TYPE: PRT
<213> ORGANISM: Artificial Sequence
<220> FEATURE:
<223> OTHER INFORMATION: TaMRC 6A (cv. Cadenza (6n))

<400> SEQUENCE: 2

Met Arg Leu Ser Ile Gly Ser Pro Ser Pro Ser Pro Pro Ala Val
1               5                   10                  15

Ala Ala Ala Leu Arg Ser Thr Pro Pro Ser Arg Arg Thr Ala Ser His
                20                  25                  30

Val Met Phe Arg Gln Lys Leu Ser Phe Met Glu Ala Phe Gln Thr Gln
            35                  40                  45

His Leu Lys Tyr Ala Pro Arg Leu Ile Lys Ser Val Val Lys Gly Ile
    50                  55                  60

Arg Ser Asn Ile Thr Asp Gly Asp Asn Gly Thr Glu Pro Ala Arg
65                  70                  75                  80

Glu Leu Leu Glu Arg Leu Phe Ala Arg Thr Gln Ser Leu Asp Thr Gly
                85                  90                  95

Ala Ser His Asp Ser Glu Leu Ser Val Ser Ile Glu Val Leu Lys Ser
            100                 105                 110

Glu Phe Glu Gly Ala Leu Ser Ile Leu Arg Asn Lys Glu Arg Asp Leu
            115                 120                 125
```

-continued

```
Arg Ser Ala Glu Lys Arg Val Ser Asp Asp Arg Ile Arg Leu Ser Lys
    130                 135                 140
Thr Lys Gln Asp Leu Asp Gln Arg Glu Ala Ile Arg Lys Ala Tyr
145                 150                 155                 160
Val Arg Gln Gln Gly Ile Glu Lys Ala Leu Lys Lys Ala Ser Arg Asp
                165                 170                 175
Leu Ala Leu Arg Val Lys Gln Ile Ser Asp Leu Lys Leu Leu Val Glu
            180                 185                 190
Gly Gln Asp Arg Thr Ile Ala Arg Ser Gln Ala Leu Leu Ser Gln Lys
        195                 200                 205
Val Thr Glu Val Glu Asn Leu Lys Arg Asp Met Phe Lys Lys Asn Glu
    210                 215                 220
Glu Ala Asp Leu Met Arg Ser Glu Ile Arg Ser Lys Glu Lys Leu Leu
225                 230                 235                 240
Leu Thr Ala Asn Gln Ala Ile Ala Gln Gln Glu Ala Thr Val Arg Glu
                245                 250                 255
Leu Gln Ser Glu Ile Lys Arg Lys Thr Met Asp Ile Ala Arg Ser Asn
            260                 265                 270
Glu Ser Arg Lys Thr Asn Glu Glu Lys Leu Lys Val Ala Glu Gln Glu
        275                 280                 285
Leu Glu Lys Gln Ser Leu Gly Trp Leu Ala Ala Gln Gln Glu Leu Lys
    290                 295                 300
Glu Leu Ala Gln Leu Ala Phe Lys Asp Thr Asp Asp Ile Lys Gly Ile
305                 310                 315                 320
Ile Thr Asp Phe Lys Arg Val Arg Ser Leu Leu Asp Ala Val Arg Ser
                325                 330                 335
Glu Leu Ile Ser Ser Lys Asp Ala Phe Ala Ser Ser Arg Arg Gln Ile
            340                 345                 350
Glu Asp Gln Ala Val Gln Leu Gln Glu Gln Val Gln Glu Leu Glu Asp
        355                 360                 365
Gln Arg Val Leu Leu Met Ser Tyr Thr His Asp Leu Glu Ala Ala Gln
    370                 375                 380
Leu Glu Ile Gln Gly Lys Thr Gln Glu Leu Asn Tyr Ala Gln Ser Arg
385                 390                 395                 400
Cys His Glu Leu Glu Ser Gln Leu Leu Lys Glu Met Glu Lys Val Glu
                405                 410                 415
Ser Leu Glu Ala Glu Leu Thr Lys Glu Lys Gln Ser Leu Glu His Arg
            420                 425                 430
Thr Glu Glu Val Gly Phe Leu Gln Lys Glu Leu Val Gln Lys Glu Asn
        435                 440                 445
Glu Cys Thr Lys Ser Gln Glu Leu Val Lys Val Lys Glu Phe Glu Leu
    450                 455                 460
Leu Glu Ala Arg Gln Glu Val Gln Asp Met Lys Leu Lys Val Glu Ser
465                 470                 475                 480
Ile Gln Leu Ala Val Gln Glu Lys Asp Ser Glu Leu Ser Asp Thr Gln
                485                 490                 495
Ser Arg Leu Thr Glu Val Ser Ser Glu Ile Val Glu Leu Gln Gln Leu
            500                 505                 510
Leu Asn Ser Lys Lys Asp Gln Leu Val Gln Ala Arg Thr Glu Leu His
        515                 520                 525
Asp Lys Glu Gln His Ile Glu Thr Leu Glu Ser Glu Leu Asp Ser Ile
    530                 535                 540
Arg Leu Arg Cys Ser Gln Ala Glu Ser Met Val Gln Arg Met Ala Glu
```

```
                 545                 550                 555                 560

Leu Thr Gly Asp Leu Ala Ser Ser Val Lys Ala Gly Glu Met Asp Ile
                565                 570                 575

Tyr Thr Leu Leu Asp Asp Glu Ile Ser Ser Thr Ser Thr Ala Leu Glu
                580                 585                 590

Ser Asn Leu His Lys His Asn Gln Leu Glu Ala Asp Ile Glu Met Leu
                595                 600                 605

Arg Glu Cys Leu Arg His Lys Asp Met Glu Leu Arg Ala Ala His Glu
            610                 615                 620

Ala Leu Asp Ala Lys Asp Gln Glu Leu Lys Ala Val Leu Lys Lys Trp
625                 630                 635                 640

Asp Val Lys Glu Arg Glu Leu Arg Glu Leu Glu Leu Pro Asp Pro
                645                 650                 655

Ser Ala Thr Asn Glu Leu Ala Gly Phe Ser Ser Glu Thr Thr Glu Gly
            660                 665                 670

Gly Ile Val Gly Glu Met Glu Leu Pro Glu Leu Gln Ile Asp Ala Ala
            675                 680                 685

Glu Val Glu Ala Leu Ala Ala Thr Thr Ala Leu Arg Lys Leu Ala Asp
            690                 695                 700

Met Thr Lys Asp Phe Phe Lys His Val Lys Ala Asp Ser Gly Ile Asn
705                 710                 715                 720

Leu Val Ala Ser Glu Ser Gln Lys Ile Ile Lys Cys Asp Pro Lys Met
                725                 730                 735

Glu Val His Lys Lys Thr Asp Val Ile Leu Glu Ala Glu Lys Glu Ile
                740                 745                 750

Val Arg Leu Phe Ser Leu Thr Lys Gln Ile Val Thr Asp Asp Ile Ile
                755                 760                 765

Asn Asp Val Glu Glu
            770

<210> SEQ ID NO 3
<211> LENGTH: 773
<212> TYPE: PRT
<213> ORGANISM: Artificial Sequence
<220> FEATURE:
<223> OTHER INFORMATION: TaMRC 6D (cv. Cadenza (6n))

<400> SEQUENCE: 3

Met Arg Leu Ser Ile Gly Ser Pro Ser Pro Ser Pro Pro Pro Ala Val
1               5                   10                  15

Ala Ala Ala Leu Arg Ser Thr Ser Pro Ser Cys Arg Thr Ala Ser His
                20                  25                  30

Val Met Phe Arg Gln Lys Leu Ser Phe Met Val Ala Ser Gln Thr Gln
            35                  40                  45

His Leu Lys Tyr Ala Pro Arg Leu Ile Lys Ser Val Ile Lys Gly Ile
        50                  55                  60

Arg Ser Asn Ile Thr Asp Gly Asp Asn Gly Thr Thr Glu Pro Ala Arg
65                  70                  75                  80

Glu Leu Leu Glu Arg Leu Phe Ala Lys Thr Gln Ser Leu Asp Thr Gly
                85                  90                  95

Ala Ser His Asp Ser Glu Leu Ser Val Ser Ile Glu Val Leu Lys Ser
            100                 105                 110

Glu Phe Glu Gly Ala Leu Ser Ile Leu Arg Asn Lys Glu Arg Asp Leu
        115                 120                 125

Arg Ser Ala Glu Lys Arg Val Ser Asp Asp Arg Ile Arg Leu Ser Lys
```

```
              130                 135                 140
Thr Lys Gln Asp Leu Asp Gln Arg Glu Glu Ala Ile Arg Lys Ala Tyr
145                 150                 155                 160

Val Arg Gln Gln Gly Ile Glu Lys Ala Leu Lys Lys Ala Ser Arg Asp
                    165                 170                 175

Leu Ala Leu Arg Val Lys Gln Ile Ser Asn Leu Lys Leu Gln Val Glu
                180                 185                 190

Gly Gln Asp Arg Thr Ile Ala Ser Ser Gln Ala Leu Leu Ser Gln Lys
                    195                 200                 205

Val Ile Glu Val Glu Asn Leu Lys Arg Asp Met Phe Lys Lys Asn Glu
    210                 215                 220

Glu Ala Asp Leu Val Arg Ser Glu Ile Arg Ser Lys Glu Gln Gln Leu
225                 230                 235                 240

Leu Thr Ala Asn Lys Ala Ile Ala Gln Gln Glu Ala Thr Val Arg Glu
                    245                 250                 255

Leu Gln Ser Glu Ile Lys Arg Lys Thr Ile Asp Ile Ala Arg Ser Asn
                260                 265                 270

Glu Ser Arg Lys Thr Asn Glu Glu Lys Leu Lys Val Ala Glu Gln Glu
            275                 280                 285

Leu Glu Lys Gln Ser Leu Gly Trp Leu Ala Ala Gln Gln Glu Leu Lys
        290                 295                 300

Glu Leu Ala Gln Leu Ala Phe Lys Asp Thr Asp Ile Lys Gly Ile
305                 310                 315                 320

Ile Thr Asp Phe Lys Arg Val Arg Ser Leu Leu Asp Ala Val Arg Cys
                    325                 330                 335

Glu Leu Ile Ser Ser Lys Asp Ala Phe Ala Ser Ser Arg Arg Gln Ile
                340                 345                 350

Glu Asp Gln Ala Val Gln Leu Gln Lys Gln Ala Leu Glu Leu Glu Asp
            355                 360                 365

Gln Gln Val Leu Leu Met Ser Tyr Thr His Asp Leu Glu Ala Ala Gln
        370                 375                 380

Leu Glu Ile Gln Gly Lys Thr Gln Glu Leu Lys Tyr Ala Gln Ser Arg
385                 390                 395                 400

Cys His Glu Leu Glu Ser Gln Leu Leu Gln Glu Met Glu Lys Val Glu
                    405                 410                 415

Ser Leu Glu Thr Glu Leu Thr Lys Glu Arg Gln Ser Leu Asp His Arg
                420                 425                 430

Thr Glu Glu Val Gly Phe Leu Gln Lys Glu Leu Val Arg Lys Glu Asn
            435                 440                 445

Glu Cys Thr Lys Ser Gln Glu Leu Val Lys Val Lys Glu Phe Glu Leu
        450                 455                 460

Leu Glu Ala Arg Gln Glu Val Gln Asp Met Lys Leu Lys Val Glu Ser
465                 470                 475                 480

Ile Gln Leu Ala Val Gln Glu Lys Asp Ser Glu Leu Ser Asp Thr Gln
                    485                 490                 495

Ser Arg Leu Thr Glu Val Ser Ser Glu Ile Val Glu Leu Gln Gln Leu
                500                 505                 510

Leu Asn Ser Lys Lys Asp Gln Leu Val Gln Ala Arg Thr Glu Leu His
            515                 520                 525

Asp Lys Glu Gln His Ile Glu Thr Leu Glu Ser Glu Leu Asp Ser Ile
        530                 535                 540

Arg Phe Arg Cys Ser Gln Ala Glu Ser Met Val Gln Arg Met Ala Glu
545                 550                 555                 560
```

Leu Thr Gly Asp Leu Ala Ser Ser Val Lys Ala Gly Glu Met Asp Ile
                565                 570                 575

Tyr Thr Leu Leu Asp Asp Glu Ile Ser Ser Thr Gly Thr Ala Leu Glu
            580                 585                 590

Ser Asn Leu His Lys His Asn Gln Leu Glu Ala Asp Ile Glu Met Leu
        595                 600                 605

Arg Glu Cys Leu Arg His Lys Asp Met Asp Leu Arg Ala Ala His Glu
    610                 615                 620

Ala Leu Asp Ala Lys Asp Gln Glu Leu Lys Ala Val Leu Lys Lys Trp
625                 630                 635                 640

Asp Val Lys Glu Arg Glu Leu Arg Glu Leu Glu Leu Pro Asp Pro
                645                 650                 655

Ser Ala Thr Asn Glu Leu Ala Val Phe Ser Ser Glu Thr Thr Glu Asp
                660                 665                 670

Gly Ile Val Gly Glu Met Glu Leu Pro Glu Leu Gln Ile Glu Ala Ala
                675                 680                 685

Gly Val Glu Ala Leu Ala Ala Thr Ala Leu Arg Lys Leu Ala Asp
690                 695                 700

Met Thr Lys Asp Phe Phe Lys His Gly Lys Ala Asp Ser Gly Ile Asp
705                 710                 715                 720

Leu Val Ala Ser Glu Ser Gln Lys Ile Ser Lys Cys Asp Pro Lys Met
                725                 730                 735

Glu Val His Lys Lys Thr Asp Val Ile Leu Glu Ala Glu Lys Glu Ile
                740                 745                 750

Val Arg Leu Phe Ser Leu Thr Lys Gln Ile Val Thr Asp Asp Thr Ile
                755                 760                 765

Asn Asn Leu Glu Glu
    770

<210> SEQ ID NO 4
<211> LENGTH: 3073
<212> TYPE: DNA
<213> ORGANISM: Artificial Sequence
<220> FEATURE:
<223> OTHER INFORMATION: 4 TaMRC 6A (cv. Kronos (4n))

<400> SEQUENCE: 4

```
cgatcgcgcc cgggccgcgg tggttccctc tccccatgtt ccgcggccat gcgcctctcc      60
atcggctccc catccccgtc gccgccgccg gcggtggccg ccgctctccg cagcacaccc     120
ccgtcgcgcc gtaccgccag tcatgtgagc gcccgctgat cttttcttcc ttttctcata     180
tcgctgtttc gtggtaccac gctgctcact gttacatgga ctgcttgcgt cgtgttttc      240
ccgattccgt gcccgtccac atgtgtttga agtagaagga taccagattc ggtgtcctaa     300
ttcatgttct gctagtacta gtactttttt taaaactttt tctggaattg gttcaattgt     360
gataaattca gtaaactgcg atcaaatttc atcagttatg atacttcacc ttatgtagca     420
gtgagtttct gaagttcagt gtactgtcct tcagttcttc catttacaaa acaaattttt     480
acgtgcttag tttgaggaaa ggatattcct cagattgctt cactaggttg tgaccatttc     540
cttatcctaa tatcctactt atgcattgtt tcctgcaact ctctcaggtt atgttcaggc     600
agaagctgag tttcatggag gcatttcaga ctcagcatct gaaatatgct cctcgtttga     660
tcaaatcagt cgtaaaaggt attagatcaa atataactga tggtgataat gaacgactg      720
agccagctag agagttgctg gagcggctat ttgcgaggac acaaagttta gacactggtg     780
```

```
cttctcatga tagtgaactg agcgtgagca ttgaggtcct gaagtctgaa ttcgagggtg    840
ccttgtctat cctcagaaac aaagagaggg atcttcgcag cgcagagaag agggtttccg    900
atgatcggat aaggttgagc aagacaaagc aggaccttga tcagagagag gaagcgatcc    960
gcaaagctta tgtaaggcaa caaggaatag agaaagcact gaaaaaggca agtgagatc    1020 tggcgttgcg agtgaagcag atcagtgatc tgaagcttct ggttgagggg caagacagga   1080
ctattgccag gtcacaagct ttgctttctc agaaggtaac tgaagtggaa aatctcaaac   1140
gagatatgtt caagaagaac gaggaagcag acctgatgcg ttcagagatc aggtccaaag   1200
aaaagctgct tcttacagct aatcaagcta ttgcgcagca agaagcaaca gttagggagc   1260
tgcagagtga attaaaaga aagacaatgg atatcgccag atcaaatgaa tcgaggaaaa   1320
ctaatgaaga gaaactgaaa gttgctgaac aggaacttga gaagcagagt ttaggatggt   1380
tagcagcaca acaagagtta aaggaacttg cacaactggc attcaaagat acagatgata   1440
tcaagggtat tatcactgac ttcaaacgtg tgaggtctct gctagatgct gtacgctctg   1500
aattgatctc ttcaaaagat gctttcgctt cctctcgcag acaaatagaa gatcaagcgg   1560
ttcagttgca ggaacaagta caggaactcg aggaccaaag ggtattactg atgtcttaca   1620
cccatgattt ggaggctgct caactggaga ttcaagggaa gacacaggag ctcaattatg   1680
cacagtctcg ttgtcatgaa cttgaatcac agttacttaa ggaaatggag aaggtcgagt   1740
ctctagaagc cgaattaacg aaagaaaaac agagcttaga acatagaact gaagaagtag   1800
gctttcttca gaaggagctt gttcagaaag aaaatgagtg caccaaatca caagaacttg   1860
ttaaagtaaa agagtttgag ctgttagaag ccagacagga agtccaagat atgaagttaa   1920
aggtagagtc tattcaattg gctgttcaag aaaaggattc agagctttct gatacacaga   1980
gcagactaac tgaagtcagc agtgaaattg ttgagcttca gcagttgcta aatagcaaga   2040
aggatcaact ggttcaggct agaactgaat tacatgataa agaacaacat atagaaacac   2100
tggagagtga gttggatagc atacggctca gatgctcgca agctgaatcc atggttcaaa   2160
ggatggctga gctcactggc gatcttgcta gttccgtaaa agccggagaa atggacatct   2220
atacattact ggatgatgaa atttcaagca caagtacagc cctcgagtcc aatttacata   2280
agcataatca actggaggct gacatagaga tgttaagaga atgcttgcgg cataaggaca   2340
tggagttgag agctgctcat gaagcacttg atgccaaaga tcaagagctg aaggcagtac   2400
ttaaaaaatg ggatgtgaag gagagggaac tacgtgagtt ggaagagtta ccggatccca   2460
gtgccacaaa tgaacttgct ggtttttcca gtgagacaac agagggcggt attgtaggag   2520
agatggagct gccagagctt caaattgatg ctgcggaggt cgaagcactt gctgctacga   2580
ctgcattgag gaagcttgcg gatatgacta aggatttctt caaacacgtc aaagctgatt   2640
ctggtattaa cttggttgca tcagagagtc aaaaaatcat taaatgcgat cctaaaatgg   2700
aagtacacaa gaagacggat gtgattcttg aagctgaaaa agaaatagtt aggctcttct   2760
cattgacaaa acagattgtc actgatgaca taataaacga tgttgaggaa tgatagcttc   2820
aaactaaagc atgtagtctt ccaattctat caaggtagat cttccaagat agcttcagag   2880
tagagatata ccagatagat cgttcgaaca tttatggaca gcgatgtcgc ccagaaggat   2940
gagatcttct ctggttgatt tcacaaactg ccattttgaa aaagggtaac atgttgagca   3000
gaagctggtc atctgatcct ttgtgctctt tttgtaatgt gcctcaaact attcctcaga   3060
tctttgttca atg                                                     3073
```

<210> SEQ ID NO 5
<211> LENGTH: 3073
<212> TYPE: DNA
<213> ORGANISM: Artificial Sequence
<220> FEATURE:
<223> OTHER INFORMATION: TaMRC 6A (cv. Cadenza (6n))

<400> SEQUENCE: 5

```
cgatcgcgcc cgggccgcgg tggttccctc tccccatgtt ccgcggccat gcgcctctcc      60
atcggctccc catcccgtc gccgccgccg gcggtggccg ccgctctccg cagcacaccc      120
ccgtcgcgcc gtaccgccag tcatgtgagc gcccgctgat cttttcttcc ttttctcata     180
tcgctgtttc gtggtaccac gctgctcact gttacatgga ctgcttgcgt tcgtgttttc     240
ccgattccgt gcccgtccac atgtgtttga agtagaagga taccagattc ggtgtcctaa     300
ttcatgttct gctagtacta gtactttttt taaaaacttt tctggaattg gttcaattgt     360
gataaattca gtaaactgcg atcaaatttc atcagttatg atacttcacc ttatgtagca     420
gtgagtttct gaagttcagt gtactgtcct tcagttcttc catttacaaa acaaattttt     480
acgtgcttag tttgaggaaa ggatattcct cagattgctt cactaggttg tgaccatttc     540
cttatcctaa tatcctactt atgcattgtt tcctgcaact ctctcaggtt atgttcaggc     600
agaagctgag tttcatggag gcatttcaga ctcagcatct gaaatatgct cctcgtttga     660
tcaaatcagt cgtaaaaggt attagatcaa atataactga tggtgataat ggaacgactg     720
agccagctag agagttgctg gagcggctat ttgcgaggac acaaagttta gacactggtg     780
cttctcatga tagtgaactg agcgtgagca ttgaggtcct gaagtctgaa ttcgagggtg     840
ccttgtctat cctcagaaac aaagagaggg atcttcgcag cgcagagaag agggtttccg     900
atgatcggat aaggttgagc aagacaaagc aggaccttga tcagagagag aagcgatcc      960
gcaaagctta tgtaaggcaa caaggaatag agaaagcact gaaaaaggca agtagagatc     1020
tggcgttgcg agtgaagcag atcagtgatc tgaagcttct ggttgagggg caagacagga     1080
ctattgccag gtcacaagct ttgctttctc agaaggtaac tgaagtggaa atctcaaac      1140
gagatatgtt caagaagaac gaggaagcag acctgatgcg ttcagagatc aggtccaaag     1200
aaaagctgct tcttacagct aatcaagcta ttgcgcagca agaagcaaca gttagggagc     1260
tgcagagtga aattaaaaga agacaatgg atatcgccag atcaaatgaa tcgaggaaaa     1320
ctaatgaaga gaaactgaaa gttgctgaac aggaacttga gaagcagagt ttaggatggt     1380
tagcagcaca acaagagtta aaggaacttg cacaactggc attcaaagat acagatgata     1440
tcaagggtat tatcactgac ttcaaacgtg tgaggtctct gctagatgct gtacgctctg     1500
aattgatctc ttcaaaagat gctttcgctt cctctcgcag acaaatagaa gatcaagcgg     1560
ttcagttgca ggaacaagta caggaactcg aggaccaaag ggtattactg atgtcttaca     1620
cccatgattt ggaggctgct caactggaga ttcaagggaa gacacaggag ctcaattatg     1680
cacagtctcg ttgtcatgaa cttgaatcac agttacttaa ggaatggag aaggtcgagt      1740
ctctagaagc cgaattaacg aaagaaaaac agagcttaga acatagaact gaagaagtag     1800
gctttcttca gaaggagctt gttcagaaag aaaatgagtg caccaaatca caagaacttg     1860
ttaaagtaaa agagtttgag ctgttagaag ccagacagga agtccaagat atgaagttaa     1920
aggtagagtc tattcaattg gctgttcaag aaaaggactc agagctttct gatacacaga     1980
gcagactaac tgaagtcagc agtgaaattg ttgagcttca gcagttgcta aatagcaaga     2040
aggatcaact ggttcaggct agaactgaat tacatgataa agaacaacat atagaaacac     2100
```

-continued

```
tggagagtga gttggatagc atacggctca gatgctcgca agctgaatcc atggttcaaa    2160
ggatggctga gctcactggc gatcttgcta gttccgtaaa agccggagaa atggacatct    2220
atacattact ggatgatgaa atttcaagca caagtacagc cctcgagtcc aatttacata    2280
agcataatca actggaggct gacatagaga tgttaagaga atgcttgcgg cataaggaca    2340
tggagttgag agctgctcat gaagcacttg atgccaaaga tcaagagctg aaggcagtac    2400
ttaaaaaatg ggatgtgaag gagagggaac tacgtgagtt ggaagagtta ccggatccca    2460
gtgccacaaa tgaacttgct ggttttttcca gtgagacaac agagggcggt attgtaggag    2520
agatggagct gccagagctt caaattgatg ctgcggaggt cgaagcactt gctgctacga    2580
ctgcattgag gaagcttgcg gatatgacta aggatttctt caaacacgtc aaagctgatt    2640
ctggtattaa cttggttgca tcagagagtc aaaaaatcat taaatgcgat cctaaaatgg    2700
aagtacacaa gaagacggat gtgattcttg aagctgaaaa agaaatagtt aggctcttct    2760
cattgacaaa acagattgtc actgatgaca taataaacga tgttgaggaa tgatagcttc    2820
aaactaaagc atgtagtctt ccaattctat caaggtagat cttccaagat agcttcagag    2880
tagagatata ccagatagat cgttcgaaca tttatggaca gcgatgtcgc ccagaaggat    2940
gagatcttct ctggttgatt tcacaaactg ccatttttgaa aaagggtaac atgttgagca    3000
gaagctggtc atctgatcct ttgtgctctt tttgtaatgt gcctcaaact attcctcaga    3060
tctttgttca atg                                                        3073
```

<210> SEQ ID NO 6
<211> LENGTH: 3162
<212> TYPE: DNA
<213> ORGANISM: Artificial Sequence
<220> FEATURE:
<223> OTHER INFORMATION: TaMRC 6D (cv. Cadenza (6n))

<400> SEQUENCE: 6

```
cgatcgcgcc cgggcggcgg tggttccctc tccccatgtt ccgcggccat gcgcctctcc      60
atcggctccc catccccgtc gccgccgccg gcggtggccg ccgctctccg cagcacatcc     120
ccgtcgtgcc gtaccgccag tcatgtgagc gcccgctgat cttttcttcc ttttctcata     180
tcgctgtttc gtggtaccac gctgctcact gttacatggg ctgcttgcgt tcgtgttttc     240
ccgattccgt gcccgtccac atgtgtttga agtagaagga tgccagattt ggtgtcctaa     300
ttcatgttct gctagtacta gtaccttttt taaaaacttttt ctggaattgg ttcgattgtg    360
ataaattcag taaactgcac ctggctgaac aaatcttgat tggagaacgg cctatgaact     420
caaaaaaaat tactgaacag atgaaatgtt tatgcagagg taggcttgag atcaaatttc     480
atcggttatg atacttcacc ttatatagca gtgaatttct gaagttcagt gtactgtctt     540
tcagttcttc gatttacaaa acaaattttt acgtgcttag tttgaggaaa ggatattcct     600
cagattgctt cactaggttg tgaccatttc cttatcctac tatcctactt atgcattgtt     660
tcctgcaact ctctcaggtt atgttcaggc agaagctgag tttcatggtg gcatctcaga     720
ctcagcatct gaaatatgct cctcgtttga tcaaatcagt cataaaaggt attagatcaa     780
atataactga tggtgataat ggaacgactg agccagctag agagttgctg gagcggctat     840
ttgcaaagac acaaagttta gacactggtg cttctcatga tagtgaactg agcgtgagca     900
ttgaggtcct gaagtctgaa ttcgaggggtg ccttgtctat cctcagaaac aaagagaggg    960
atcttcgcag cgcagagaag aggggtttccg atgatcggat aaggttgagc aagacaaagc   1020
aggaccttga tcagagagag gaagcgatcc gcaaagctta tgtaaggcaa caaggaatag   1080
```

```
agaaagcact gaaaaaggca agtagagatc tggcgttgcg agtgaagcag atcagtaatc    1140
tgaagcttca ggttgagggg caagacagga ctattgccag ttcacaagct ttgctttctc    1200
agaaggtaat tgaggtggaa aatctcaaac gagatatgtt caagaagaac gaggaagccg    1260
acctggtgcg ttcagagatc aggtccaaag agcagcagct tcttacagct aataaagcta    1320
ttgcgcagca agaagcaaca gttagggagc tgcagagtga aattaaaaga aagacaatcg    1380
atatcgccag atcaaatgaa tcgaggaaaa ctaatgaaga gaaactgaaa gttgctgaac    1440
aggaacttga gaagcagagt ttaggatggt tagcagcaca acaagagtta aaggaacttg    1500
cacaactggc attcaaagat acagatgata tcaagggtat tatcactgac ttcaaacgtg    1560
tgaggtctct cctagatgct gtacgctgtg aattaatctc ttcgaaagat gctttcgctt    1620
cctctcgcag acaaatagaa gatcaagcgg tgcagttgca gaaacaagca ctggaactcg    1680
aggaccaaca ggtattactg atgtcttaca cccatgattt ggaagctgct caactggaga    1740
ttcaagggaa gacacaggag ctcaagtacg cacagtctcg ttgtcatgaa cttgaatcac    1800
agttacttca ggaaatggag aaggtcgagt ctcttgaaac cgaattaacc aaagaaagac    1860
agagcttaga tcatagaact gaagaagtag gctttcttca gaaggagctt gttcggaaag    1920
aaaatgagtg caccaaatca caagaacttg ttaaagtaaa agagtttgag ctgttagaag    1980
ccagacagga agtccaagat atgaagttaa aggtagagtc tattcaattg gctgttcaag    2040
aaaaggattc agagctttct gatacacaga gcagactaac tgaagtcagc agtgaaattg    2100
ttgagcttca gcagttgcta aatagcaaga aggatcaact ggttcaggct agaactgaat    2160
tacatgataa agaacaacat atagaaacac tggagagtga gttggatagc atacggttca    2220
gatgctcgca agctgaatcc atggttcaaa ggatggctga gctcactggc gatcttgcta    2280
gttccgtaaa agctggagaa atggacatct atacattact ggatgatgaa atttcaagca    2340
caggtacagc cctcgagtcc aatttgcata agcataatca actggaggct gacatagaga    2400
tgttaagaga atgcttgcgg cataaggaca tggacttgag agctgctcat gaagcacttg    2460
atgccaaaga tcaagagctg aaggcagtac ttaaaaagtg ggatgtgaag gagagggaac    2520
tacgtgagtt ggaagagtta ccggatccca gtgccacaaa tgaacttgct gttttttcca    2580
gtgagacaac agaggacggc attgtaggag agatggagct ccctgagctt caaattgaag    2640 ctgcggggt cgaagcactt gctgctacga ctgcattgag gaagcttgcg gatatgacta    2700
aggatttctt caaacacggc aaagctgatt ctggtattga cttggttgca tcagagagtc    2760
aaaaaatcag taaatgtgat cctaaaatgg aagtacacaa gaagacggat gtgattcttg    2820
aagctgaaaa agaaatagtt aggctcttct cattgacaaa acagattgtc actgatgaca    2880
caataaacaa tcttgaggaa tgatagcttc aaactaaagc atgtagtctt ccaattctat    2940
caaggtagat cttccaagat agcttcagag tagagatata ccagatagat ctttcaaaca    3000
ttgatggaca gcgacgtcgc ccagaaggat gagatcttct ctggttgata tcacaactgc    3060
cattttgaaa aagggtaaca tgttgagcag aagctggtca tctgatcttt tgtgctcctt    3120
ttgtattgta cctcaagcta ttcctcagat ctttgttcaa tg                       3162
```

<210> SEQ ID NO 7
<211> LENGTH: 2322
<212> TYPE: DNA
<213> ORGANISM: Artificial Sequence
<220> FEATURE:
<223> OTHER INFORMATION: TaMRC 6A (cv. Kronos (4n)) CDS

<400> SEQUENCE: 7

```
atgcgcctct ccatcggctc cccatccccg tcgccgccgc cggcggtggc cgccgctctc      60
cgcagcacac ccccgtcgcg ccgtaccgcc agtcatgtta tgttcaggca gaagctgagt     120
ttcatggagg catttcagac tcagcatctg aaatatgctc ctcgtttgat caaatcagtc     180
gtaaaaggta ttagatcaaa tataactgat ggtgataatg aacgactga gccagctaga     240
gagttgctgg agcggctatt tgcgaggaca caaagtttag acactggtgc ttctcatgat     300
agtgaactga gcgtgagcat tgaggtcctg aagtctgaat tcgagggtgc cttgtctatc     360
ctcagaaaca aagagaggga tcttcgcagc gcagagaaga gggtttccga tgatcggata     420
aggttgagca agacaaagca ggaccttgat cagagagagg aagcgatccg caaagcttat     480
gtaaggcaac aaggaataga gaaagcactg aaaaaggcaa gtagagatct ggcgttgcga     540
gtgaagcaga tcagtgatct gaagcttctg gttgagggc aagacaggac tattgccagg     600
tcacaagctt tgcttttctca gaaggtaact gaagtggaaa atctcaaacg agatatgttc     660
aagaagaacg aggaagcaga cctgatgcgt tcagagatca ggtccaaaga aaagctgctt     720
cttacagcta atcaagctat tgcgcagcaa gaagcaacag ttagggagct gcagagtgaa     780
attaaaagaa agacaatgga tatcgccaga tcaaatgaat cgaggaaaac taatgaagag     840
aaactgaaag ttgctgaaca ggaacttgag aagcagagtt taggatggtt agcagcacaa     900
caagagttaa aggaacttgc acaactggca ttcaaagata cagatgatat caagggtatt     960
atcactgact caaacgtgt gaggtctctg ctagatgctg tacgctctga attgatctct    1020
tcaaaagatg ctttcgcttc ctctcgcaga caaatagaag atcaagcggt tcagttgcag    1080
gaacaagtac aggaactcga ggaccaaagg gtattactga tgtcttacac ccatgatttg    1140
gaggctgctc aactggagat tcaagggaag acacaggagc tcaattatgc acagtctcgt    1200
tgtcatgaac ttgaatcaca gttacttaag gaaatggaga aggtcgagtc tctagaagcc    1260
gaattaacga aagaaaaaca gagccttagaa catagaactg aagaagtagg ctttcttcag    1320
aaggagcttg ttcagaaaga aaatgagtgc accaaatcac aagaacttgt taaagtaaaa    1380
gagtttgagc tgttagaagc cagacaggaa gtccaagata tgaagttaaa ggtagagtct    1440
attcaattgg ctgttcaaga aaaggattca gagctttctg atacacagag cagactaact    1500
gaagtcagca gtgaaattgt tgagcttcag cagttgctaa atagcaagaa ggatcaactg    1560
gttcaggcta gaactgaatt acatgataaa gaacaacata tagaaacact ggagagtgag    1620
ttggatagca tacggctcag atgctcgcaa gctgaatcca tggttcaaag gatggctgag    1680
ctcactggcg atcttgctag ttccgtaaaa gccggagaaa tggacatcta tacattactg    1740
gatgatgaaa tttcaagcac aagtacagcc ctcgagtcca atttacataa gcataatcaa    1800
ctggaggctg acatagagat gttaagagaa tgcttgcggc ataaggacat ggagttgaga    1860
gctgctcatg aagcacttga tgccaaagat caagagctga aggcagtact taaaaaatgg    1920
gatgtgaagg agagggaact acgtgagttg aagagttac cggatcccag tgccacaaat    1980
gaacttgctg gttttttccag tgagacaaca gagggcggta ttgtaggaga gatggagctg    2040
ccagagcttc aaattgatgc tgcggaggtc gaagcacttg ctgctacgac tgcattgagg    2100
aagcttgcgg atatgactaa ggatttcttc aaacacgtca aagctgattc tggtattaac    2160
ttggttgcat cagagagtca aaaaatcatt aaatgcgatc ctaaaatgga agtcacaaag    2220
aagacggatg tgattcttga agctgaaaaa gaaatagtta ggctcttctc attgacaaaa    2280
cagattgtca ctgatgacat aataaacgat gttgaggaat ga                       2322
```

<210> SEQ ID NO 8
<211> LENGTH: 2322
<212> TYPE: DNA
<213> ORGANISM: Artificial Sequence
<220> FEATURE:
<223> OTHER INFORMATION: TaMRC 6A (cv. Cadenza (6n)) CDS

<400> SEQUENCE: 8

| | | | | | |
|---|---|---|---|---|---|
| atgcgcctct | ccatcggctc | cccatccccg | tcgccgccgc | cggcggtggc | cgccgctctc | 60 |
| cgcagcacac | ccccgtcgcg | ccgtaccgcc | agtcatgtta | tgttcaggca | gaagctgagt | 120 |
| ttcatggagg | catttcagac | tcagcatctg | aaatatgctc | ctcgtttgat | caaatcagtc | 180 |
| gtaaaaggta | ttagatcaaa | tataactgat | ggtgataatg | aacgactga | gccagctaga | 240 |
| gagttgctgg | agcggctatt | tgcgaggaca | caaagtttag | acactggtgc | ttctcatgat | 300 |
| agtgaactga | gcgtgagcat | tgaggtcctg | aagtctgaat | tcgagggtgc | cttgtctatc | 360 |
| ctcagaaaca | aagagaggga | tcttcgcagc | gcagagaaga | gggtttccga | tgatcggata | 420 |
| aggttgagca | agacaaagca | ggaccttgat | cagagagagg | aagcgatccg | caaagcttat | 480 |
| gtaaggcaac | aaggaataga | gaaagcactg | aaaaaggcaa | gtagagatct | ggcgttgcga | 540 |
| gtgaagcaga | tcagtgatct | gaagcttctg | gttgaggggc | aagacaggac | tattgccagg | 600 |
| tcacaagctt | tgcttctctca | gaaggtaact | gaagtggaaa | atctcaaacg | agatatgttc | 660 |
| aagaagaacg | aggaagcaga | cctgatgcgt | tcagagatca | ggtccaaaga | aaagctgctt | 720 |
| cttacagcta | atcaagctat | tgcgcagcaa | gaagcaacag | ttagggagct | gcagagtgaa | 780 |
| attaaaagaa | agacaatgga | tatcgccaga | tcaaatgaat | cgaggaaaac | taatgaagag | 840 |
| aaactgaaag | ttgctgaaca | ggaacttgag | aagcagagtt | taggatggtt | agcagcacaa | 900 |
| caagagttaa | aggaacttgc | acaactggca | ttcaaagata | cagatgatat | caagggtatt | 960 |
| atcactgact | tcaaacgtgt | gaggtctctg | ctagatgctg | tacgctctga | attgatctct | 1020 |
| tcaaaagatg | ctttcgcttc | ctctcgcaga | caaatagaag | atcaagcggt | tcagttgcag | 1080 |
| gaacaagtac | aggaactcga | ggaccaaagg | gtattactga | tgtcttacac | ccatgatttg | 1140 |
| gaggctgctc | aactggagat | tcaagggaag | acacaggagc | tcaattatgc | acagtctcgt | 1200 |
| tgtcatgaac | ttgaatcaca | gttacttaag | gaaatggaga | aggtcgagtc | tctagaagcc | 1260 |
| gaattaacga | agaaaaaaca | gagcttagaa | catagaactg | aagaagtagg | ctttcttcag | 1320 |
| aaggagcttg | ttcagaaaga | aaatgagtgc | accaaatcac | aagaacttgt | taaagtaaaa | 1380 |
| gagtttgagc | tgttagaagc | cagacaggaa | gtccaagata | tgaagttaaa | ggtagagtct | 1440 |
| attcaattgg | ctgttcaaga | aaaggactca | gagcttctg | atacacagag | cagactaact | 1500 |
| gaagtcagca | gtgaaattgt | tgagcttcag | cagttgctaa | atagcaagaa | ggatcaactg | 1560 |
| gttcaggcta | gaactgaatt | acatgataaa | gaacaacata | gaaacact | ggagagtgag | 1620 |
| ttggatagca | tacggctcag | atgctcgcaa | gctgaatcca | tggttcaaag | gatggctgag | 1680 |
| ctcactggcg | atcttgctag | ttccgtaaaa | gccggagaaa | tggacatcta | cattactg | 1740 |
| gatgatgaaa | tttcaagcac | aagtacagcc | ctcgagtcca | atttacataa | gcataatcaa | 1800 |
| ctggaggctg | acatagagat | gttaagagaa | tgcttgcggc | ataaggacat | ggagttgaga | 1860 |
| gctgctcatg | aagcacttga | tgccaaagat | caagagctga | aggcagtact | taaaaaatgg | 1920 |
| gatgtgaagg | agagggaact | acgtgagttg | aagagttac | cggatcccag | tgccacaaat | 1980 |
| gaacttgctg | gttttccag | tgagacaaca | gagggcggta | ttgtaggaga | gatggagctg | 2040 |

```
ccagagcttc aaattgatgc tgcggaggtc gaagcacttg ctgctacgac tgcattgagg   2100
aagcttgcgg atatgactaa ggatttcttc aaacacgtca aagctgattc tggtattaac   2160
ttggttgcat cagagagtca aaaaatcatt aaatgcgatc ctaaaatgga agtacacaag   2220
aagacggatg tgattcttga agctgaaaaa gaaatagtta ggctcttctc attgacaaaa   2280
cagattgtca ctgatgacat aataaacgat gttgaggaat ga                      2322

<210> SEQ ID NO 9
<211> LENGTH: 2322
<212> TYPE: DNA
<213> ORGANISM: Artificial Sequence
<220> FEATURE:
<223> OTHER INFORMATION: TaMRC 6D (cv. Cadenza (6n)) CDS

<400> SEQUENCE: 9
atgcgcctct ccatcggctc cccatccccg tcgccgccgc cggcggtggc cgccgctctc     60
cgcagcacat ccccgtcgtg ccgtaccgcc agtcatgtta tgttcaggca gaagctgagt    120
ttcatggtgg catctcagac tcagcatctg aaatatgctc ctcgtttgat caaatcagtc    180
ataaaaggta ttagatcaaa tataactgat ggtgataatg aacgactga gccagctaga     240 gagttgctgg agcggctatt tgcaaagaca caaagtttag acactggtgc ttctcatgat    300
agtgaactga gcgtgagcat tgaggtcctg aagtctgaat tcgagggtgc cttgtctatc    360
ctcagaaaca aagagaggga tcttcgcagc gcagagaaga gggtttccga tgatcggata    420
aggttgagca agacaaagca ggaccttgat cagagagagg aagcgatccg caaagcttat    480
gtaaggcaac aaggaataga gaaagcactg aaaaaggcaa gtagagatct ggcgttgcga    540
gtgaagcaga tcagtaatct gaagcttcag gttgaggggc aagacaggac tattgccagt    600
tcacaagctt tgctttctca aaggtaattg aggtgaaaa atctcaaacg agatatgttc     660
aagaagaacg aggaagccga cctggtgcgt tcagagatca ggtccaaaga gcagcagctt    720
cttacagcta ataagctat tgcgcagcaa gaagcaacag ttagggagct gcagagtgaa     780
attaaaagaa agacaatcga tatcgccaga tcaaatgaat cgaggaaaac taatgaagag    840
aaactgaaag ttgctgaaca ggaacttgag aagcagagtt taggatggtt agcagcacaa    900
caagagttaa aggaacttgc acaactggca ttcaaagata cagatgatat caagggtatt    960
atcactgact caaacgtgt gaggtctctc tagatgctg tacgctgtga attaatctct     1020
tcgaaagatg ctttcgcttc ctctcgcaga caaatagaag atcaagcggt gcagttgcag    1080
aaacaagcac tggaactcga ggaccaacag gtattactga tgtcttacac ccatgatttg    1140
gaagctgctc aactggagat tcaagggaag acacaggagc tcaagtacgc acagtctcgt    1200
tgtcatgaac ttgaatcaca gttacttcag gaaatggaga aggtcgagtc tcttgaaacc    1260
gaattaacca agaaagaca gagcttagat catagaactg aagaagtagg cttttcttcag   1320 aaggagcttg ttcggaaaga aaatgagtgc accaaatcac aagaacttgt taaagtaaaa    1380
gagtttgagc tgttagaagc cagacaggaa gtccaagata tgaagttaaa ggtagagtct    1440
attcaattgg ctgttcaaga aaaggattca gagcttttctg atacacagag cagactaact    1500
gaagtcagca gtgaaattgt tgagcttcag cagttgctaa atagcaagaa ggatcaactg    1560
gttcaggcta gaactgaatt acatgataaa gaacaacata tagaaacact ggagagtgag    1620
ttggatagca tacggttcag atgctcgcaa gctgaatcca tggttcaaag gatggctgag    1680
ctcactggcg atcttgctag ttccgtaaaa gctggagaaa tggacatcta tacattactg    1740
gatgatgaaa tttcaagcac aggtacagcc ctcgagtcca atttgcataa gcataatcaa    1800
```

-continued

```
ctggaggctg acatagagat gttaagagaa tgcttgcggc ataaggacat ggacttgaga    1860
gctgctcatg aagcacttga tgccaaagat caagagctga aggcagtact taaaaagtgg    1920
gatgtgaagg agagggaact acgtgagttg aagagttac cggatcccag tgccacaaat     1980
gaacttgctg ttttttccag tgagacaaca gaggacggca ttgtaggaga gatggagctc    2040
cctgagcttc aaattgaagc tgcggggtc gaagcacttg ctgctacgac tgcattgagg     2100
aagcttgcgg atatgactaa ggatttcttc aaacacggca agctgattc tggtattgac     2160 ttggttgcat cagagagtca aaaatcagt aaatgtgatc ctaaaatgga agtacacaag     2220
aagacggatg tgattcttga agctgaaaaa gaaatagtta ggctcttctc attgacaaaa    2280
cagattgtca ctgatgacac aataaacaat cttgaggaat ga                       2322
```

<210> SEQ ID NO 10
<211> LENGTH: 774
<212> TYPE: PRT
<213> ORGANISM: Artificial Sequence
<220> FEATURE:
<223> OTHER INFORMATION: HvMRC (HORVU6Hr1G036020.1)

<400> SEQUENCE: 10

```
Met Arg Leu Ser Thr Gly Cys Pro Ser Pro Ser Ala Ala Ala Leu
1               5                   10                  15

Ala Ala Ala His Arg Ser Thr Ser Pro Ser Cys Arg Thr Ala Thr His
            20                  25                  30

Val Met Phe Arg His Lys Leu Ser Phe Met Val Ala Phe Gln Thr Gln
        35                  40                  45

His Leu Lys Tyr Ala Pro Cys Leu Ile Lys Ser Val Lys Ser Ile
    50                  55                  60

Arg Ser Asn Ile Thr Asp Gly Asp Asn Gly Thr Thr Glu Pro Ala Arg
65                  70                  75                  80

Glu Leu Leu Glu Arg Leu Phe Ala Lys Thr Gln Ser Leu Asp Thr Gly
                85                  90                  95

Ala Ser Asn Asp Ser Glu Leu Gly Val Ser Ile Glu Val Leu Lys Ser
            100                 105                 110

Glu Phe Glu Gly Ala Leu Ser Ile Leu Arg Lys Lys Glu Arg Asp Leu
        115                 120                 125

Arg Asn Ala Glu Lys Arg Val Ser Asp Asp Arg Thr Arg Leu Ser Lys
    130                 135                 140

Thr Lys Gln Asp Leu Asp Gln Arg Glu Glu Thr Ile Arg Lys Val Tyr
145                 150                 155                 160

Val Arg Gln Gln Asp Ile Glu Lys Ala Leu Lys Arg Ala Ser Arg Asp
                165                 170                 175

Leu Ala Leu Arg Val Lys Gln Ile Ser Asn Leu Lys Leu Leu Val Glu
            180                 185                 190

Gly Gln Asp Arg Thr Ile Ala Ser Ser Gln Ala Leu Leu Ser Gln Lys
        195                 200                 205

Val Ile Glu Val Glu Asn Leu Lys Gln Asp Met Phe Thr Lys Asn Glu
    210                 215                 220

Glu Ala Asp Leu Met Arg Ser Glu Ile Lys Ser Lys Glu Gln Leu Leu
225                 230                 235                 240

Leu Thr Ala Asn Gln Ala Val Val Gln Glu Ala Thr Val Arg Glu
                245                 250                 255

Leu Gln Ser Glu Ile Lys Arg Lys Ile Ile Asp Ile Ala Arg Ser Asp
            260                 265                 270
```

```
Glu Leu Arg Lys Thr Asn Glu Asp Lys Leu Lys Val Ala Glu Gln Glu
            275                 280                 285

Leu Glu Lys Gln Asn Leu Gly Trp Leu Ala Ala Gln Gln Glu Leu Lys
        290                 295                 300

Glu Leu Ala Gln Leu Ala Ser Asp Thr Asp Ile Lys Gly Ile
305                 310                 315                 320

Ile Thr Asp Phe Lys Arg Val Arg Ser Leu Leu Asp Val Val Arg Ser
                325                 330                 335

Glu Leu Ile Ser Ser Lys Asp Ala Phe Ala Ser Ser Arg Arg Gln Ile
                340                 345                 350

Glu Asp Gln Ala Val Gln Leu Arg Glu Gln Val Gln Glu Leu Glu Asp
            355                 360                 365

Gln Arg Val Leu Leu Met Ser His Thr His Asp Leu Glu Ala Ala Arg
        370                 375                 380

Leu Glu Ile Gln Gly Lys Thr Gln Glu Leu Asn Tyr Ala Gln Ser Arg
385                 390                 395                 400

Cys His Glu Leu Glu Ser His Leu Leu Gln Met Glu Lys Val Glu
                    405                 410                 415

Ser Leu Glu Ala Glu Leu Thr Lys Glu Arg Gln Ser Leu Glu His Arg
                420                 425                 430

Thr Glu Glu Val Asp Phe Leu Gln Lys Glu Leu Val Gln Lys Glu Asn
            435                 440                 445

Glu Cys Thr Lys Ser Gln Glu Leu Val Lys Val Lys Glu Phe Glu Leu
        450                 455                 460

Leu Glu Ala Arg Tyr Glu Val Gln Asp Met Lys Leu Lys Val Glu Ser
465                 470                 475                 480

Ile Gln Leu Ala Val Gln Glu Lys Asp Ser Glu Leu Ser Ala Thr Gln
                485                 490                 495

Ser Arg Leu Thr Glu Val Ser Ser Glu Val Val Lys Leu Gln Gln Leu
                500                 505                 510

Leu Asn Ser Lys Glu Asp Gln Leu Val Gln Ala Arg Thr Glu Leu His
            515                 520                 525

Asp Lys Glu Gln His Ile Glu Thr Leu Glu Ser Glu Leu Asp Ser Ile
        530                 535                 540

Arg Leu Arg Cys Ser Gln Ala Glu Ser Val Val Gln Arg Met Ala Glu
545                 550                 555                 560

Leu Thr Gly Asp Leu Ala Ser Ser Val Lys Thr Gly Glu Thr Asp Ile
                565                 570                 575

Tyr Thr Leu Leu Asp Asp Glu Ile Ala Ser Ala Gly Thr Thr Leu Glu
                580                 585                 590

Ser Asn Leu His Lys His Asn Gln Leu Glu Ala Asp Ile Glu Met Leu
            595                 600                 605

Arg Glu Cys Leu Arg His Lys Asp Met Asp Leu Arg Ala Ala His Glu
        610                 615                 620

Ala Leu Asp Ala Lys Asp Gln Glu Leu Lys Ala Val Leu Lys Lys Trp
625                 630                 635                 640

Asp Val Lys Glu Arg Glu Leu His Glu Leu Glu Glu Leu Leu Asp Pro
                645                 650                 655

Ser Ala Thr Asn Glu Leu Ala Cys Phe Ser Asn Glu Thr Thr Glu Gly
                660                 665                 670

Gly Val Val Gly Glu Met Glu Leu Gln Glu Leu Gln Ile Gly Ala Ala
            675                 680                 685
```

```
Glu Val Glu Ala Leu Ala Ala Thr Thr Ala Leu Arg Lys Leu Ala Asp
    690                 695                 700
Met Thr Lys Asp Leu Phe Lys His Asp Lys Gly Asp Ser Gly Ile Asp
705                 710                 715                 720
Leu Ala Ala Ser Gly Ser Gln Lys Leu Arg Asn Cys Asp Ser Lys Met
                725                 730                 735
Glu Val His Lys Lys Thr Asp Val Ile Leu Glu Ala Glu Lys Glu Ile
            740                 745                 750
Thr Arg Leu Phe Ser Leu Thr Lys Gln Ile Val Thr Asp Ile Ile
        755                 760                 765
Asn Asp Val Asp Glu Arg
    770

<210> SEQ ID NO 11
<211> LENGTH: 3217
<212> TYPE: DNA
<213> ORGANISM: Artificial Sequence
<220> FEATURE:
<223> OTHER INFORMATION: HvMRC (HORVU6Hr1G036020 cv. Morex)

<400> SEQUENCE: 11
cgatcgcgcc cgggcggcgg tggttccctc tccccatgtt ccgcggccat gcgcctctcc      60
accggctgcc catcccctc gccggcggcg gcgctggccg ccgctcaccg cagcacatcc      120
ccgtcgtgcc gtaccgccac tcatgtgagc accgctgat cttttcttcc ttctcccata     180
tcactgtttc ctggtaccac gctgctcact gttacatggg ctgcttgtgt tcacatgtgt    240
ttgaagtaga gatttggcgt cgctaattca tgttctgcca gtatcggtac tttttttact    300
tttctggaat tggttctatt gtgataaatt ctgtaaactg tacctggctg aacaaatctt    360
gattggagaa ctgcctataa actcaaaaat tgtaccgagc agatgaaata tgtatgcagg    420
ggcaggtttg aggtcaaatt tcatcagtta tgatacctca ccttatatta atagcagtga    480
atttgtctga agagttgtac ctgatttttt cttctggag ttcagtgccc tgcccttcta    540
gttcttcgat ttacaaaaca atttttacgt ccttagtttg aggaaagaat attcctcgga    600
taatagcttc actattgttc tcgaaaaaag ataatagctt cactagcttg tgccctgctt    660
cacttatcct aatatgctac ttatgcattg tttcctgcaa ctctctcagg ttatgttcag    720
acataagctg agtttcatgg tggcatttca gactcagcat ctgaaatatg ctccttgctt    780
gatcaaatca gtcgtaaaaa gtattagatc aaatataact gatggtgata atggaacgac    840
tgagccagct agagaattgc tggagcggct atttgcgaag acacaaagtt tagacactgg    900
tgcttcaaat gacagtgaac tgggcgtgag cattgaggtc ctgaaatctg aattcgaggg    960
tgccttgtct atcctcagaa agaaagagag ggatcttcgc aacgcagaga gagggtttc   1020 cgatgatcgg acaaggttga gcaagacgaa gcaggacctt gatcagagag aggagacgat   1080
ccgcaaagtt tatgtaaggc aacaagatat agagaaagca ctgaaaaggg caagtagaga   1140
tctggcgttg cgagtgaagc agatcagtaa tctgaagctt ctggttgagg ggcaagatag   1200
gactattgcc agttcacaag ctttgctttc tcagaaggta attgaagtgg aaaatctcaa   1260
acaagacatg ttcacaaaga acgaggaagc tgacctgatg cgttcagaga tcaagtccaa   1320
agaacagctg cttcttacag ctaatcaagc tgttgtgcag caagaagcaa cagttaggga   1380
gctgcagagt gaaattaaaa gaaagataat cgatatcgcc agatcagatg aattgaggaa   1440
aactaatgaa gataaactga agttgctga acaggaactt gagaagcaga atttaggatg   1500
gttagcagca cagcaagagt taaggaact tgcccaactg gcatccgatg atacagatga   1560
```

| | |
|---|---|
| tatcaagggt attatcactg acttcaaacg tgtgaggtct ctgctagatg ttgtacgctc | 1620 |
| tgaattgatc tcttcaaaag atgctttcgc ttcctctcgc agacaaatag aagatcaagc | 1680 |
| ggtgcagctg cgggaacaag tacaggaact tgaggaccaa agggtattgc tgatgtctca | 1740 |
| cacccatgat ttggaggctg ctcgactgga gattcagggg aagacacagg agctcaatta | 1800 |
| cgcacagtct cgttgtcatg aacttgagtc acatttactt caggaaatgg agaaggtcga | 1860 |
| gtctctagaa gccgaattaa ccaaagaaag acagagctta gaacatagaa ctgaagaagt | 1920 |
| agactttctt cagaaggagc ttgtacagaa agaaaatgag tgcaccaaat cacaagaact | 1980 |
| tgttaaagta aaagagtttg agctgttaga agccagatat gaagtccaag atatgaagtt | 2040 |
| aaaggtagag tctattcaat tggctgttca agaaaaggat tcagagcttt ctgctacaca | 2100 |
| gagcagacta actgaagtca gcagtgaagt tgttaaactt cagcagttgc taaatagcaa | 2160 |
| ggaggatcaa ctggttcagg ctagaactga attgcatgat aaagaacaac atatagaaac | 2220 |
| actggagagt gaattggata gcatacgact cagatgctcg caagctgaat ccgtggttca | 2280 |
| aaggatggct gagctcactg gcgatcttgc tagttccgta aaaactggag aaacggacat | 2340 |
| ctatacatta ctggatgatg aaattgcaag cgcaggtaca acccctcgagt ccaatttgca | 2400 |
| taagcataat caactggagg ctgacataga gatgttaaga gaatgcttgc ggcataagga | 2460 |
| catggacttg agagctgctc atgaagcact tgatgccaaa gatcaagagc tgaaggcagt | 2520 |
| acttaaaaag tgggatgtga aggagaggga actacatgag ttggaagagt tactggatcc | 2580 |
| cagtgccaca aatgaacttg cttgtttctc caatgagaca accgagggcg gagttgtagg | 2640 |
| agagatggag ctccaagagc ttcaaattgg agctgcggag gtggaagcac ttgctgctac | 2700 |
| gactgcattg aggaagcttg cagacatgac taaggatctc ttcaaacacg acaaaggtga | 2760 |
| ttctggtatt gatttggctg catcagggag tcaaaaactc agaaattgtg attctaaaat | 2820 |
| ggaagtacac aagaagacgg atgtgattct tgaagctgaa aaagaaataa ctaggctctt | 2880 |
| ctcattgaca aaacagattg ttactgatga cataataaac gatgttgatg aacgatagct | 2940 |
| tcaaactaaa gcatgtagtc ttccaattct atcgaaggta gatcttccaa gatagcttca | 3000 |
| gagtagtaat ataccagata gatctttcca acattatgga cagtgacgtt gcccagaaag | 3060 |
| ataagatctt ctctagttga tttgacaact gccattttga aaaagggtaa cttatttagc | 3120 |
| agaagctggt catttgatcc tttgtcccct ttttgtaatg tacccaaact attccttgta | 3180 |
| tctttgttca attatgttcc ctctaaatat acgtggg | 3217 |

<210> SEQ ID NO 12
<211> LENGTH: 2325
<212> TYPE: DNA
<213> ORGANISM: Artificial Sequence
<220> FEATURE:
<223> OTHER INFORMATION: HvMRC CDS (HORVU6Hr1G036020.1 cv. Morex)

<400> SEQUENCE: 12

| | |
|---|---|
| atgcgcctct ccaccggctg cccatccccc tcgccggcgg cggcgctggc cgccgctcac | 60 |
| cgcagcacat ccccgtcgtg ccgtaccgcc actcatgtta tgttcagaca taagctgagt | 120 |
| ttcatggtgg catttcagac tcagcatctg aaatatgctc cttgcttgat caaatcagtc | 180 |
| gtaaaaagta ttagatcaaa tataactgat ggtgataatg aacgactga gccagctaga | 240 |
| gaattgctgg agcggctatt tgcgaagaca caaagtttag acactggtgc ttcaaatgac | 300 |
| agtgaactgg gcgtgagcat tgaggtcctg aaatctgaat tcgagggtgc cttgtctatc | 360 |

| | | |
|---|---|---|
| ctcagaaaga aagagaggga tcttcgcaac gcagagaaga gggtttccga tgatcggaca | 420 | |
| aggttgagca agacgaagca ggaccttgat cagagagagg agacgatccg caaagtttat | 480 | |
| gtaaggcaac aagatataga gaaagcactg aaaagggcaa gtagagatct ggcgttgcga | 540 | |
| gtgaagcaga tcagtaatct gaagcttctg gttgaggggc aagataggac tattgccagt | 600 | |
| tcacaagctt tgctttctca gaaggtaatt gaagtggaaa atctcaaaca agacatgttc | 660 | |
| acaaagaacg aggaagctga cctgatgcgt tcagagatca agtccaaaga acagctgctt | 720 | |
| cttacagcta atcaagctgt tgtgcagcaa gaagcaacag ttagggagct gcagagtgaa | 780 | |
| attaaaagaa agataatcga tatcgccaga tcagatgaat tgaggaaaac taatgaagat | 840 | |
| aaactgaaag ttgctgaaca ggaacttgag aagcagaatt taggatggtt agcagcacag | 900 | |
| caagagttaa aggaacttgc ccaactggca tccgatgata cagatgatat caagggtatt | 960 | |
| atcactgact tcaaacgtgt gaggtctctg ctagatgttg tacgctctga attgatctct | 1020 | |
| tcaaaagatg ctttcgcttc ctctcgcaga caaatagaag atcaagcggt gcagctgcgg | 1080 | |
| gaacaagtac aggaacttga ggaccaaagg gtattgctga tgtctcacac ccatgatttg | 1140 | |
| gaggctgctc gactggagat tcaagggaag acacaggagc tcaattacgc acagtctcgt | 1200 | |
| tgtcatgaac ttgagtcaca tttacttcag gaaatggaga aggtcgagtc tctagaagcc | 1260 | |
| gaattaacca agaaagaca gagcttagaa catagaactg aagaagtaga ctttcttcag | 1320 | |
| aaggagcttg tacagaaaga aaatgagtgc accaaatcac aagaacttgt taaagtaaaa | 1380 | |
| gagtttgagc tgttagaagc cagatatgaa gtccaagata tgaagttaaa ggtagagtct | 1440 | |
| attcaattgg ctgttcaaga aaaggattca gagctttctg ctacacagag cagactaact | 1500 | |
| gaagtcagca gtgaagttgt taaacttcag cagttgctaa atagcaagga ggatcaactg | 1560 | |
| gttcaggcta gaactgaatt gcatgataaa gaacaacata tagaaacact ggagagtgaa | 1620 | |
| ttggatagca tacgactcag atgctcgcaa gctgaatccg tggttcaaag gatggctgag | 1680 | |
| ctcactggcg atcttgctag ttccgtaaaa actggagaaa cggacatcta tacattactg | 1740 | |
| gatgatgaaa ttgcaagcgc aggtacaacc ctcgagtcca atttgcataa gcataatcaa | 1800 | |
| ctggaggctg acatagagat gttaagagaa tgcttgcggc ataaggacat ggacttgaga | 1860 | |
| gctgctcatg aagcacttga tgccaaagat caagagctga aggcagtact taaaaagtgg | 1920 | |
| gatgtgaagg agagggaact acatgagttg gaagagttac tggatcccag tgccacaaat | 1980 | |
| gaacttgctt gtttctccaa tgagacaacc gagggcggag ttgtaggaga gatggagctc | 2040 | |
| caagagcttc aaattggagc tgcggaggtg gaagcacttg ctgctacgac tgcattgagg | 2100 | |
| aagcttgcag acatgactaa ggatctcttc aaacacgaca aaggtgattc tggtattgat | 2160 | |
| ttggctgcat cagggagtca aaaactcaga aattgtgatt ctaaaatgga agtcacacaag | 2220 | |
| aagacggatg tgattcttga agctgaaaaa gaaataacta ggctcttctc attgacaaaa | 2280 | |
| cagattgtta ctgatgacat aataaacgat gttgatgaac gatag | 2325 | |

<210> SEQ ID NO 13
<211> LENGTH: 780
<212> TYPE: PRT
<213> ORGANISM: Artificial Sequence
<220> FEATURE:
<223> OTHER INFORMATION: Brachypodium (Bradi3g06260)

<400> SEQUENCE: 13

Met Phe Arg Gly His Ala Pro Leu His Arg Leu Pro Ser Pro Pro Pro
1               5                   10                  15

```
Pro Pro Ala Ala Ala Gly Ala Leu Pro Ser Ala Ser Pro Ser Cys
            20              25              30

Arg Thr Ser Thr His Val Pro Phe Arg Pro Lys Leu Ser Phe Met Val
        35              40              45

Ala Phe Gln Ala Gln His Val Lys Tyr Ala Pro Asn Leu Ile Lys Ser
    50              55              60

Val Val Lys Ser Leu Arg Ser Asn Ile Thr Asp Gly Asp Asn Gly Met
65              70              75              80

Thr Glu Pro Ala Arg Glu Leu Leu Glu Arg Leu Phe Ala Lys Thr Gln
            85              90              95

Ser Leu Asp Thr Ser Ala Ser His Asp Ser Glu Leu Ser Met Ser Ile
            100             105             110

Glu Val Leu Lys Ser Glu Phe Glu Arg Ala Leu Ser Ile Leu Arg Lys
        115             120             125

Lys Glu Arg Tyr Leu Arg Asn Ala Glu Lys Arg Val Ser Asp Asp Gln
        130             135             140

Leu Arg Leu Asn Gln Thr Lys Gln Asp Leu Asp Gln Arg Glu Gln Glu
145             150             155             160

Ile Ser Lys Ala His Ala Lys Gln Gln Met Glu Lys Ala Leu Lys
                165             170             175

Lys Ala Ser Arg Asp Leu Ser Leu Arg Val Lys Gln Ile Asn Asn Leu
        180             185             190

Lys Leu Leu Val Glu Arg Gln Asp Arg Lys Ile Ala Ser Ser Glu Ala
        195             200             205

Leu Leu Ser Gln Lys Val Ile Glu Val Glu Asn Leu Lys Gln Asp Met
210             215             220

Phe Asn Lys Asn Lys Glu Ala Asp Leu Ile Arg Ser Glu Ile Lys Leu
225             230             235             240

Lys Glu Gln Leu Leu Leu Glu Ala Asn Gln Asp Val Val Gln Gln Glu
            245             250             255

Ala Thr Val Arg Glu Leu Arg Ser Glu Thr Lys Lys Ala Ile Asp
            260             265             270

Ile Ala Ile Ser Asn Glu Leu Arg Lys Ala Asn Glu Glu Lys Leu Lys
        275             280             285

Ile Ala Glu Gln Glu Leu Glu Lys Gln Asn Leu Gly Trp Leu Ala Ala
        290             295             300

Gln Gln Glu Leu Lys Glu Leu Ala Gln Leu Ala Ser Lys Asp Thr Asp
305             310             315             320

Asp Ile Lys Gly Thr Val Thr Asp Phe Lys Arg Val Arg Ser Leu Leu
            325             330             335

Asp Ala Val Arg Ser Glu Leu Ile Ser Ser Lys Asp Asn Phe Ala Ser
            340             345             350

Ser Arg Arg Gln Ile Glu Glu Thr Val Gln Leu Gln Lys Gln Val
        355             360             365

Gln Glu Leu Lys Asp Gln Arg Val Leu Leu Met Ser Tyr Thr Gln Asp
        370             375             380

Leu Glu Ala Ala Gln Leu Glu Ile Gln Gly Lys Thr Lys Asp Leu Asn
385             390             395             400

Ala Ala Gln Ser Arg Cys His Glu Leu Glu Gln Leu Leu Lys Glu
            405             410             415

Met Glu Lys Val Glu Ser Leu Glu Ala Glu Leu Thr Lys Glu Arg Glu
            420             425             430

Asn Leu Glu Gln Lys Thr Glu Gln Val Asp Phe Leu Gln Lys Glu Leu
```

```
                435                 440                 445
Val Gln Lys Glu Asn Glu Cys Gly Asn Ser Gln Lys Leu Val Lys Ile
450                 455                 460

Lys Glu Ala Glu Leu Leu Glu Ala Arg His Glu Val Gln Asp Met Lys
465                 470                 475                 480

Ser Lys Val Asp Ser Ile Gln Leu Ala Val Gln Glu Lys Asp Ser Glu
                485                 490                 495

Leu Ser Asp Thr Gln Ser Arg Leu Thr Glu Val Ser Gly Glu Val Val
                500                 505                 510

Glu Leu Gln Gln Leu Leu Asn Ser Lys Asp Asp Gln Leu Val Gln Val
515                 520                 525

Arg Thr Glu Leu His Asp Lys Glu Gln Tyr Ile Glu Ser Met Gln Ser
530                 535                 540

Glu Leu Glu Ser Ile Arg Phe Arg Cys Ser Gln Ala Glu Ser Val Leu
545                 550                 555                 560

Arg Arg Met Ala Glu Leu Thr Gly Asp Leu Ala Ser Ser Val Lys Ala
                565                 570                 575

Gly Glu Met Asp Ile Tyr Ala Leu Leu Asp Asp Glu Ile Ser Ser Thr
                580                 585                 590

Ser Thr Val Leu Glu Ser Asn Leu His Lys His Asn Gln Leu Glu Ala
                595                 600                 605

Asp Ile Glu Met Leu Arg Glu Ser Leu Arg His Lys Asp Met Asp Leu
610                 615                 620

Arg Ala Ala His Glu Ala Leu Asp Ala Lys Asp Gln Glu Leu Lys Ala
625                 630                 635                 640

Val Val Gly Lys Trp Asp Phe Lys Glu Lys Glu Leu Asp Glu Val Glu
                645                 650                 655

Glu Leu Gln Lys Asp Pro Ile Asp Met Lys Glu Leu Pro Val Leu Ser
                660                 665                 670

Asn Glu Thr Thr Gly Gly Ser Ile Thr Gly Glu Met Glu Leu Lys Lys
                675                 680                 685

Leu Gln Ile Glu Ala Ala Glu Val Glu Ala Leu Ala Ala Thr Thr Ala
690                 695                 700

Leu Lys Lys Leu Ala Asp Met Ser Lys Lys Tyr Leu Arg Cys Arg Lys
705                 710                 715                 720

Ala Asp Ser Gly Ile Gly Leu Val Ala Ser Glu Ser Ala Asn Ile Gly
                725                 730                 735

Lys Ala Asn Ser Arg Met Glu Leu Asn Asn Lys Met Asp Val Ile Phe
                740                 745                 750

Glu Ala Lys Gln Glu Ile Val Arg Leu Phe Ser Leu Thr Lys Glu Leu
755                 760                 765

Ile Thr Asp Asp Ala Ile Asn Asp Ala Glu Glu Arg
770                 775                 780

<210> SEQ ID NO 14
<211> LENGTH: 3615
<212> TYPE: DNA
<213> ORGANISM: Artificial Sequence
<220> FEATURE:
<223> OTHER INFORMATION: Brachypodium (Bradi3g06260)

<400> SEQUENCE: 14
ctcgtgccgt ctcggcgtct tcctccacag tccacaaacc cgcacgcgca tcgccagccg      60
tccgatcgcg ctcgggcggc cctggtccgc ttcctcaaat gttccgcggc catgcccctc     120
```

```
tccaccggct cccctcgccg ccgccgccac cggcggcggc cgccggcgca ctccccagcg      180 cgtcccgtc gtgccgcacc tccactcatg tgagcaattg ctgttttttc tgtatcttcc        240
tcatatgtct gtttctgatt tggctctacc acgctgcctg cgctattgga atccttcttc      300
gttcccccga ttccgagccc cgcctgcgtg cgtttgaagt ggaaggggac cggattttgc      360
gtttgctaat tcatggtctg ttagtagttc cttagttttc tggagttagt tcgattttga     420
taaatccaat ataatagctt ctggtagaac aaatcctgat tacagaaagg cctaatgggc    480
tatcaactaa aaatggtata gataacaaaa gttgagcttc cctagcctgt gcttatttcc    540
ttatcccaat agtctaagca ttgttttctg caacccctatc aggttcccctt caggccgaag  600 ttgagcttca tggtggcatt tcaggctcaa catgtgaaat atgctcctaa cctgatcaaa    660
tcagtagtaa aaagtcttag atcaaacatc actgatggtg acaatggaat gaccgagcca    720
gctagggaat tgttggaacg gctgtttgcg aagacacaga gtctagacac aagtgcttct    780
catgatagtg aactgagcat gagcatcgag gtcctcaagt ctgaattcga gcgcgccttg    840
tcgattctca gaaagaaaga gaggtacctt cggaatgcag agaagagggt ttctgatgat    900
cagttaaggt tgaaccagac gaagcaggac ctggatcaga gagagcaaga gatcagcaaa    960
gcacatgcaa agcagcaaca aatggagaaa gcactgaaaa aggcaagtag agatctgtcg  1020
ttgcgagtga agcagatcaa taatctgaag cttctggttg agaggcaaga caggaaaatt  1080
gccagttcag aagctttgct ttctcaaaag gtaattgaag tggaaaatct caaacaagat  1140
atgttcaaca agaataagga agcagacttg ataagatcag agattaagtt gaaagaacaa  1200
ctgcttcttg aagctaatca ggacgtcgtg cagcaagagg caacagttag ggagctgcgg  1260
agtgaaactg aaaaaaaggc tattgatatt gccatatcca atgaattgag gaaggctaat  1320
gaagagaaac tgaaaattgc tgaacaggaa cttgagaagc agaatttagg atggttagca  1380
gcacagcaag aattaaagga actggcgcaa cttgcatcca aggacacaga tgatatcaag  1440
ggtactgtca ctgactttaa acgtgtgagg tccctgctgg atgctgtacg gtctgaacta  1500
atctcttcaa aagataattt cgcctcctct cgcagacaaa tagaagaaca aacggtgcag  1560
ttgcagaagc aagtgcaaga actcaaggac caaagggtat tgctgatgtc ttacacccag  1620
gatttggaag ctgctcaact ggagattcaa gggaagacaa aagatctcaa tgctgcacag  1680
tctcgttgcc atgaacttga attgcagtta cttaaggaaa tggagaaggt tgagtctcta  1740
gaagccgagt taaccaaaga aagagagaac ttggaacaga aaactgaaca agtagacttt  1800
cttcagaagc agcttgttca gaaggaaaat gagtgtggta attcacaaaa gcttgttaaa  1860
ataaaagagg cagagctatt agaagccaga catgaagtcc aagatatgaa atcaaaggta  1920
gattctatcc aattggctgt tcaagagaag gattcagagc tttcggacac acagagcaga  1980
ctaactgaag tgagcggtga agttgttgag cttcagcagt tgctaaatag caaggatgat  2040
caacttgttc aggttagaac tgagttacat gataaagaac aatatataga atcaatgcag  2100
agtgaattag agagcataag attcagatgc tcgcaagctg aatctgtgtt gcgaaggatg  2160
gctgagctca ctggcgatct tgctagttcc gtgaaagctg agaaatggga catttatgca  2220
ttactggatg atgaaatttc aagcaccagt acagtccttg agtccaattt gcacaagcat  2280
aatcaactgg aggctgacat agagatgtta agagaatcct tacggcataa ggacatggac  2340
ttaagagctg ctcatgaagc acttgatgcc aaagatcaag aactgaaggc agtagttgga  2400
aagtgggatt tcaaggagaa ggaactggat gaggtggaag agttacagaa agatcccatt  2460
gacatgaagg aactccctgt tcttttctaac gagacaacag ggggcagcat tacaggagag  2520
```

-continued

```
atggagctca agaagcttca aattgaagct gccgaggtgg aggcacttgc tgctactact      2580
gcactaaaga agcttgcgga tatgagtaag aaatacttga gatgccgcaa agctgattct      2640
gggattggtt tggttgcatc agaaagtgca acattggta aagcgaattc taggatggaa       2700
ttaaacaaca agatggatgt gatttttgaa gctaaacaag aaattgttag actattttca      2760
ttgacaaaag agctcatcac tgatgacgca ataaatgatg ctgaggaacg ataactttag      2820
agctaaaata ttcagccagc caattctacc aagatagctt cagaatagag gtatggcaga      2880
tagatctcag acatttatga gcagctgggt cgcatagcaa gaccaaaatc tgtcgctggt      2940
tgattcggca atggcgttc taacaaagga taaagaaac tgtccatgtg tgtattttcg        3000
gagacgaacc tcaaactctt cctaataatg ttttccgatg tgttgctgta aatatatgtg      3060
gggagttact ggtatggcat ttggtgctgg ttgtccccac acactgtaca ttggacgatg      3120
ctccaggttt tgttgttggt taactgaaat gatgttcagt gtttgctatt gttgttgcac      3180
cacaaagtgg atgatgttcc aaattagagc aacaaggaaa gaaagggaga tgactgtcaa      3240
gaaaaaggga agaaaggag atagctatag ttcatctaaa aaggggagat ggaaattttg       3300
agctggaagt caccaatctt caaggcgcaa ccttttaaat tttgcacaga agtattcag       3360 tatttcaggg tttaactgtt aggattctgt tatttgtaga gtctttaaga ttctattcca      3420
agtgcaatgc ccctcaatgt cacttcgagg cagagacaaa ctctatctct atgctttctc      3480
agtttctctt aactccaggt caccaaaatt cttatgtggc aataccctta caggtagttg      3540
atgtaagcct atgcatacat tgcatagtca gttctttctc tgattgagag gcactaactt      3600
tcttcatcag ataaa                                                      3615
```

<210> SEQ ID NO 15
<211> LENGTH: 2343
<212> TYPE: DNA
<213> ORGANISM: Artificial Sequence
<220> FEATURE:
<223> OTHER INFORMATION: Brachypodium CDS (Bradi3g06260)

<400> SEQUENCE: 15

```
atgttccgcg ccatgcccc tctccaccgg ctccctcgc cgccgccgcc accggcggcg        60
gccgccggcg cactccccag cgcgtccccg tcgtgccgca cctccactca tgttcccttc     120
aggccgaagt tgagcttcat ggtggcattt caggctcaac atgtgaaata tgctcctaac     180
ctgatcaaat cagtagtaaa aagtcttaga tcaaacatca ctgatggtga caatggaatg     240
accgagccag ctagggaatt gttggaacgg ctgtttgcga agacacagag tctagacaca     300
agtgcttctc atgatagtga actgagcatg agcatcgagg tcctcaagtc tgaattcgag     360
cgcgccttgt cgattctcag aaagaaagag aggtaccttc ggaatgcaga aagagggtt     420 tctgatgatc agttaaggtt gaaccagacg aagcaggacc tggatcagag agagcaagag     480
atcagcaaag cacatgcaaa gcagcaacaa atggagaaag cactgaaaaa ggcaagtaga     540
gatctgtcgt tgcgagtgaa gcagatcaat aatctgaagc ttctggttga gaggcaagac     600
aggaaaattg ccagttcaga agctttgctt tctcaaaagg taattgaagt ggaaaatctc     660
aaacaagata tgttcaacaa gaataaggaa gcagacttga agatcaga gattaagttg       720 aagaacaac tgcttcttga agctaatcag gacgtcgtgc agcaagaggc aacagttagg      780
gagctgcgga gtgaaactga aaaaaggct attgatattg ccatatccaa tgaattgagg     840
aaggctaatg aagagaaact gaaaattgct gaacaggaac ttgagaagca gaatttagga    900
```

```
tggttagcag cacagcaaga attaaaggaa ctggcgcaac ttgcatccaa ggacacagat    960
gatatcaagg gtactgtcac tgactttaaa cgtgtgaggt ccctgctgga tgctgtacgg   1020
tctgaactaa tctcttcaaa agataatttc gcctcctctc gcagacaaat agaagaacaa   1080
acggtgcagt tgcagaagca agtgcaagaa ctcaaggacc aaagggtatt gctgatgtct   1140
tacacccagg atttggaagc tgctcaactg gagattcaag ggaagacaaa agatctcaat   1200
gctgcacagt ctcgttgcca tgaacttgaa ttgcagttac ttaaggaaat ggagaaggtt   1260
gagtctctag aagccgagtt aaccaaagaa agagagaact tggaacagaa aactgaacaa   1320
gtagactttc ttcagaagga gcttgttcag aaggaaaatg agtgtggtaa ttcacaaaag   1380
cttgttaaaa taaagagggc agagctatta gaagccagac atgaagtcca agatatgaaa   1440
tcaaaggtag attctatcca attggctgtt caagagaagg attcagagct ttcggacaca   1500
cagagcagac taactgaagt gagcggtgaa gttgttgagc ttcagcagtt gctaaatagc   1560
aaggatgatc aacttgttca ggttagaact gagttacatg ataaagaaca atatatagaa   1620
tcaatgcaga gtgaattaga gagcataaga ttcagatgct cgcaagctga atctgtgttg   1680
cgaaggatgg ctgagctcac tggcgatctt gctagttccg tgaaagctgg agaaatggac   1740
atttatgcat tactggatga tgaaatttca agcaccagta cagtccttga gtccaatttg   1800
cacaagcata atcaactgga ggctgacata gagatgttaa gagaatcctt acggcataag   1860
gacatggact aagagctgc tcatgaagca cttgatgcca aagatcaaga actgaaggca   1920
gtagttggaa agtgggattt caaggagaag gaactggatg aggtggaaga gttacagaaa   1980
gatcccattg acatgaagga actccctgtt ctttctaacg agacaacagg gggcagcatt   2040
acaggagaga tggagctcaa gaagcttcaa attgaagctg ccgaggtgga ggcacttgct   2100
gctactactg cactaaagaa gcttgcggat atgagtaaga aatacttgag atgccgcaaa   2160
gctgattctg ggattggttt ggttgcatca gaaagtgcaa acattggtaa agcgaattct   2220
aggatggaat aaacaacaa gatggatgtg atttttgaag ctaaacaaga aattgttaga   2280
ctattttcat tgacaaaaga gctcatcact gatgacgcaa taaatgatgc tgaggaacga   2340
taa                                                                 2343
```

<210> SEQ ID NO 16
<211> LENGTH: 2316
<212> TYPE: DNA
<213> ORGANISM: Artificial Sequence
<220> FEATURE:
<223> OTHER INFORMATION: Z.mays CDS (GRMZM2G104357_T01)

<400> SEQUENCE: 16

```
atgcccctct cctccaccac ctcgccgtcg gcggggcgg ccgccgccgc cgcagtgcgc     60
accgcttcgc cgcctcgccg catcgccacc cacgttttgt tcaggcagaa gctaggcatt    120 ccggcgggt tccaggctca acatgtgaaa tgtttacctc atttgatcag atctattgta    180
agaggtgcta gatcagatat cactgacggt gacaatggaa caactgagcc cgcgagggaa    240
ctattggagc gtctgtttgc caagacaaag agtctagatc caagcgcttc tcagggtagg    300
gaactgagca tgagcattga ggtcctgaag actgagtttg aggctgcctt atcaatccta    360
aggaagaaag agaaggatct tcgtgatgcg gagaagaaag tctccgtgga taggtcaagg    420
ttgaaccaga cgaagcagga cctcgatcag agggaggagg acatcatcaa agcatactcg    480
aggcaacatg aaatggagaa agcactgatg aaggcgagca gggatttgac tctacaagtc    540
cgacagatca ataacctgaa ggttatgatc gaggaacaag acaaaaaaact tgttagttca    600
```

-continued

```
caagacgcac tttctaagaa ggttattgaa gtggataagc ttaaacaaga gatgctgaag      660
aagaatgatg aagtagcttt gctgcattca gagatcgagt ccaaggaaca agagcttctt      720
gtagctaatc aggccattgc acgtcaagaa gcaacaatta gggagcttcg aagtgaaact      780
aaaagaaagg aaactgaggt tgagagatta aatgaattgg cgaaagctaa tgaagacaaa      840
ctgaaatttg cagaacagga acttgagaag cagaattcag gatggattgc agcacagcaa      900
gagttaaagg aattggcaca aatggcattc aaggataaag atgatatcaa gaatacaatc      960
aatgacttca acgggtgag gtatttgctg gatgctgtgc gttctgaact aatagcttca     1020
aaagaggctt taaccttctc acgcaagcaa gtagaagatc aagcggcaca gttgagtaac     1080
caagtgcagg aactcacaga ccaaaaggca ctgattattt cttataccccg gaatctggaa    1140 gctgcccagc tggagattca aggaaagtca atgagctca gtactgtaca atctcgttgt     1200
agtgaacttg aatctcagtt acttgaggaa acggagaagg ttgagttcct agaggctatg     1260
ttaaccaaag aaagggagat cttggaacag aaaactaagg aagtggcgtt ccttcaagag     1320
gaggtagttc agaaggagaa ggattacttc aattcacaaa agcttgttga aacaaaagag     1380
actgagctgt tagaggcgag gcatgaagtc gaagatatga aattgaaggt ggattccata     1440
caatttgctg ttcgagagaa ggatttggag cttctggagg cacaaagaaa acttgatgaa     1500
gttaacagcg aagttgttga acttcagcag ctgataaata gcaaggagga tcaactggtc     1560
caagttagaa ctgaattaca ggataaagag caatgcatac aattgatgca ggatgaattg     1620
gataagatga gattaggacg ctcgcaagct gaatctgtgg ttcaaaagat agtcgagctt     1680
actagcaatc tcataggttc tgtcaaaggc gaagaattca acatttataa cttgctggat     1740
gatgaaattt taagcacgag cacagcccctt gagtacagtt tgcataagca taaccaactg    1800
gaggctgaca tagacatgtt aaaagaatcc ctgcgacaga aggacatgga tctgactgct     1860
gcttataaag cgcttgacgc caaagatcga gagttgaagg cagtagttgg aaggttagat     1920
gttagggaca aggaactaga caagttggaa gagctatcca tagaccccta tggcaccagg     1980
aaactgtcta gagttgctga tgaggcaacc gaagacaaca ttgctggtga agcggagctc     2040
caaaagcatg agatggaatc tgtggagatg gaggcactag ctgctagcac tatgttgaag     2100
aagcttgcgg atgtgactaa gaaattcttg agaagtggta gaactgattc tggtaccaat     2160
ttagattcaa acgttagtga aggtgcttct gaattggaac cacaaaggaa acttaatgtg     2220
attctcgagg ctaaaaagga gattgtcggg ctattttctt tgacagaaga gctcgtcact     2280
ggtgctcaaa cgaaggacga tgatgaggaa ccatag                               2316
```

<210> SEQ ID NO 17
<211> LENGTH: 3094
<212> TYPE: DNA
<213> ORGANISM: Artificial Sequence
<220> FEATURE:
<223> OTHER INFORMATION: Z.mays (GRMZM2G104357)

<400> SEQUENCE: 17

```
gctgcactcc atacgcggcc gggagctccc ccggttccac cacctcctca cctcatccgt       60
ctgaagccgc cgcttttgcc tcgacctcgc ccgcagtccg cgatacgcg ggttgccacc       120 cgtccgatcg cgcccggacg accgcgaccc cctcccctca tgttccgcgg ccatgcccct      180
ctcctccacc acctcgccgt cggcggggge ggccgccgcc gccgcagtgc cgccgcttc       240 gccgcctcgc cgcatcgcca cccacgtgag cattcttgta ccttcactga ttcttataaa     300
```

```
ttatcatgct gtgttgtcac ggtatcgggt tgctgagctc agtggcgatt gtgttcttgg    360
atgccttccg aattgcggtc tcgtgtagac gtccagtacc ttttttttagt tgtgtttaac   420
tgaagataaa agatgaattt tcggattcct aacccgtact cttttggtac ctttctcttc   480
gccggagtcg attttatggt ggtaggttcg tgcgcagttc agattaatca aatccattac   540
caaaattcgg tcgagtgaag atagctgtgt attttctttt agcccgtctg aactcttcta   600
attaaagcac aattcgtgtg cattatccta atagcgcccc cacgcgtttt ttttccttgt   660
aaactcccag gttttgttca ggcagaagct aggcattccg gcggggttcc aggctcaaca   720
tgtgaaatgt ttacctcatt tgatcagatc tattgtaaga ggtgctagat cagatatcac   780
tgacggtgac aatggaacaa ctgagcccgc gagggaacta ttggagcgtc tgtttgccaa   840
gacaaagagt ctagatccaa gcgcttctca gggtagggaa ctgagcatga gcattgaggt   900
cctgaagact gagtttgagg ctgccttatc aatcctaagg aagaaagaga aggatcttcg   960
tgatgcggag aagaaagtct ccgtggatag gtcaaggttg aaccagacga agcaggacct  1020
cgatcagagg gaggaggaca tcatcaaagc atactcgagg caacatgaaa tggagaaagc  1080
actgatgaag gcgagcaggg atttgactct acaagtccga cagatcaata acctgaaggt  1140
tatgatcgag gaacaagaca aaaaacttgt tagttcacaa gacgcacttt ctaagaaggt  1200
tattgaagtg gataagctta acaagagagt gctgaagaag aatgatgaag tagctttgct  1260
gcattcagag atcgagtcca aggaacaaga gcttcttgta gctaatcagg ccattgcacg  1320
tcaagaagca acaattaggg agcttcgaag tgaaactaaa agaaaggaaa ctgaggttga  1380
gagattaaat gaattggcga aagctaatga agacaaactg aaatttgcag aacaggaact  1440
tgagaagcag aattcaggat ggattgcagc acagcaagag ttaaaggaat tggcacaaat  1500
ggcattcaag gataaagatg atatcaagaa tacaatcaat gacttcaaac gggtgaggta  1560
tttgctggat gctgtgcgtt ctgaactaat agcttcaaaa gaggctttaa ccttctcacg  1620
caagcaagta aagatcaagc ggcacagtt gagtaaccaa gtgcaggaac tcacagacca  1680
aaaggcactg attatttctt ataccccggaa tctggaagct gcccagctgg agattcaagg  1740
aaagtcaaat gagctcagta ctgtacaatc tcgttgtagt gaacttgaat ctcagttact  1800
tgaggaaacg gagaaggttg agttcctaga ggctatgtta accaaagaaa gggagatctt  1860
ggaacagaaa actaaggaag tggcgttcct tcaagaggag gtagttcaga aggagaagga  1920
ttacttcaat tcacaaaagc ttgttgaaac aaaaagagact gagctgttag aggcgaggca  1980
tgaagtcgaa gatatgaaat tgaaggtgga ttccatacaa tttgctgttc gagagaagga  2040
tttggagctt ctggaggcac aaagaaaact tgatgaagtt aacagcgaag ttgttgaact  2100
tcagcagctg ataaatagca aggaggatca actggtccaa gttagaactg aattacagga  2160
taaagagcaa tgcatacaat tgatgcagga tgaattggat aagatgagat taggacgctc  2220
gcaagctgaa tctgtggttc aaaagatagt cgagcttact agcaatctca taggttctgt  2280
caaaggcgaa gaattcaaca tttataactt gctggatgat gaaattttaa gcacgagcac  2340
agcccttgag tacagtttgc ataagcataa ccaactggag gctgacatag acatgttaaa  2400
agaatccctg cgacagaagg acatggatct gactgctgct tataaagcgc ttgacgccaa  2460
agatcgagag ttgaaggcag tagttggaag gttagatgtt agggacaagg aactagacaa  2520
gttggaagag ctatccatag acccctatgg caccaggaaa ctgtctagag ttgctgatga  2580
ggcaaccgaa gacaacattg ctggtgaagc ggagctccaa aagcatgaga tggaatctgt  2640
ggagatggag gcactagctg ctagcactat gttgaagaag cttgcggatg tgactaagaa  2700
```

```
attcttgaga agtggtagaa ctgattctgg taccaattta gattcaaacg ttagtgaagg    2760
tgcttctgaa ttggaaccac aaaggaaact taatgtgatt ctcgaggcta aaaaggagat    2820
tgtcgggcta ttttctttga cagaagagct cgtcactggt gctcaaacga aggacgatga    2880
tgaggaacca tagcatcata agttcataac tgaacatata actgcatcat gaatgttatg    2940
catgtcaact ggaatgacgc agctgaaatt gttaccatcg tttcctttcc ttttggggct    3000
caggatttct ttatgttctt ttggttcatg gatggcatcg caaatgaaa aaaaagatt     3060 gtttagattt tggttaaaag gatgatgatt gtgc                                3094
```

\<210\> SEQ ID NO 18
\<211\> LENGTH: 771
\<212\> TYPE: PRT
\<213\> ORGANISM: Artificial Sequence
\<220\> FEATURE:
\<223\> OTHER INFORMATION: Z.mays (GRMZM2G104357_T01)

\<400\> SEQUENCE: 18

```
Met Pro Leu Ser Ser Thr Thr Ser Pro Ser Ala Gly Ala Ala Ala Ala
1               5                   10                  15

Ala Ala Val Arg Thr Ala Ser Pro Pro Arg Arg Ile Ala Thr His Val
            20                  25                  30

Leu Phe Arg Gln Lys Leu Gly Ile Pro Ala Gly Phe Gln Ala Gln His
        35                  40                  45

Val Lys Cys Leu Pro His Leu Ile Arg Ser Ile Val Arg Gly Ala Arg
    50                  55                  60

Ser Asp Ile Thr Asp Gly Asp Asn Gly Thr Thr Glu Pro Ala Arg Glu
65                  70                  75                  80

Leu Leu Glu Arg Leu Phe Ala Lys Thr Lys Ser Leu Asp Pro Ser Ala
                85                  90                  95

Ser Gln Gly Arg Glu Leu Ser Met Ser Ile Glu Val Leu Lys Thr Glu
            100                 105                 110

Phe Glu Ala Ala Leu Ser Ile Leu Arg Lys Lys Glu Lys Asp Leu Arg
        115                 120                 125

Asp Ala Glu Lys Lys Val Ser Val Asp Arg Ser Arg Leu Asn Gln Thr
    130                 135                 140

Lys Gln Asp Leu Asp Gln Arg Glu Glu Asp Ile Ile Lys Ala Tyr Ser
145                 150                 155                 160

Arg Gln His Glu Met Glu Lys Ala Leu Met Lys Ala Ser Arg Asp Leu
                165                 170                 175

Thr Leu Gln Val Arg Gln Ile Asn Asn Leu Lys Val Met Ile Glu Glu
            180                 185                 190

Gln Asp Lys Lys Leu Val Ser Ser Gln Asp Ala Leu Ser Lys Lys Val
        195                 200                 205

Ile Glu Val Asp Lys Leu Lys Gln Glu Met Leu Lys Lys Asn Asp Glu
    210                 215                 220

Val Ala Leu Leu His Ser Glu Ile Glu Ser Lys Glu Gln Glu Leu Leu
225                 230                 235                 240

Val Ala Asn Gln Ala Ile Ala Arg Gln Glu Ala Thr Ile Arg Glu Leu
                245                 250                 255

Arg Ser Glu Thr Lys Arg Lys Glu Thr Glu Val Glu Arg Leu Asn Glu
            260                 265                 270

Leu Ala Lys Ala Asn Glu Asp Lys Leu Lys Phe Ala Glu Gln Glu Leu
        275                 280                 285
```

-continued

```
Glu Lys Gln Asn Ser Gly Trp Ile Ala Ala Gln Gln Glu Leu Lys Glu
    290                 295                 300
Leu Ala Gln Met Ala Phe Lys Asp Lys Asp Ile Lys Asn Thr Ile
305                 310                 315                 320
Asn Asp Phe Lys Arg Val Arg Tyr Leu Leu Asp Ala Val Arg Ser Glu
                    325                 330                 335
Leu Ile Ala Ser Lys Glu Ala Leu Thr Phe Ser Arg Lys Gln Val Glu
                340                 345                 350
Asp Gln Ala Ala Gln Leu Ser Asn Gln Val Gln Glu Leu Thr Asp Gln
                355                 360                 365
Lys Ala Leu Ile Ile Ser Tyr Thr Arg Asn Leu Glu Ala Ala Gln Leu
370                 375                 380
Glu Ile Gln Gly Lys Ser Asn Glu Leu Ser Thr Val Gln Ser Arg Cys
385                 390                 395                 400
Ser Glu Leu Glu Ser Gln Leu Leu Glu Thr Glu Lys Val Glu Phe
                    405                 410                 415
Leu Glu Ala Met Leu Thr Lys Glu Arg Glu Ile Leu Glu Gln Lys Thr
                420                 425                 430
Lys Glu Val Ala Phe Leu Gln Glu Val Val Gln Lys Glu Lys Asp
                    435                 440                 445
Tyr Phe Asn Ser Gln Lys Leu Val Glu Thr Lys Glu Thr Glu Leu Leu
450                 455                 460
Glu Ala Arg His Glu Val Glu Asp Met Lys Leu Lys Val Asp Ser Ile
465                 470                 475                 480
Gln Phe Ala Val Arg Glu Lys Asp Leu Glu Leu Leu Glu Ala Gln Arg
                    485                 490                 495
Lys Leu Asp Glu Val Asn Ser Glu Val Val Glu Leu Gln Gln Leu Ile
                    500                 505                 510
Asn Ser Lys Glu Asp Gln Leu Val Gln Val Arg Thr Glu Leu Gln Asp
            515                 520                 525
Lys Glu Gln Cys Ile Gln Leu Met Gln Asp Glu Leu Asp Lys Met Arg
530                 535                 540
Leu Gly Arg Ser Gln Ala Glu Ser Val Val Gln Lys Ile Val Glu Leu
545                 550                 555                 560
Thr Ser Asn Leu Ile Gly Ser Val Lys Gly Glu Glu Phe Asn Ile Tyr
                565                 570                 575
Asn Leu Leu Asp Asp Glu Ile Leu Ser Thr Ser Thr Ala Leu Glu Tyr
                580                 585                 590
Ser Leu His Lys His Asn Gln Leu Glu Ala Asp Ile Asp Met Leu Lys
            595                 600                 605
Glu Ser Leu Arg Gln Lys Asp Met Asp Leu Thr Ala Ala Tyr Lys Ala
            610                 615                 620
Leu Asp Ala Lys Asp Arg Glu Leu Lys Ala Val Val Gly Arg Leu Asp
625                 630                 635                 640
Val Arg Asp Lys Glu Leu Asp Lys Leu Glu Glu Leu Ser Ile Asp Pro
                    645                 650                 655
Tyr Gly Thr Arg Lys Leu Ser Arg Val Ala Asp Glu Ala Thr Glu Asp
                660                 665                 670
Asn Ile Ala Gly Glu Ala Glu Leu Gln Lys His Glu Met Glu Ser Val
            675                 680                 685
Glu Met Glu Ala Leu Ala Ala Ser Thr Met Leu Lys Lys Leu Ala Asp
690                 695                 700
Val Thr Lys Lys Phe Leu Arg Ser Gly Arg Thr Asp Ser Gly Thr Asn
```

```
                705                 710                 715                 720
Leu Asp Ser Asn Val Ser Glu Gly Ala Ser Glu Leu Glu Pro Gln Arg
                    725                 730                 735

Lys Leu Asn Val Ile Leu Glu Ala Lys Lys Glu Ile Val Gly Leu Phe
                740                 745                 750

Ser Leu Thr Glu Glu Leu Val Thr Gly Ala Gln Thr Lys Asp Asp Asp
                755                 760                 765

Glu Glu Pro
        770

<210> SEQ ID NO 19
<211> LENGTH: 763
<212> TYPE: PRT
<213> ORGANISM: Artificial Sequence
<220> FEATURE:
<223> OTHER INFORMATION: O. sativa (LOC_Os02g09340.1)

<400> SEQUENCE: 19

Met Pro Pro Leu Ser Pro Ser Ser Pro Ala Thr Ala Ala Ala
1               5                   10                  15

Val Leu Arg Cys Gly Ser Pro Ser Cys Arg Pro Val Thr His Glu Leu
            20                  25                  30

Phe Arg Gln Lys Leu Ser Phe Met Val Ser Phe Gln Ala Gln His Met
        35                  40                  45

Arg Cys Ala Pro His Leu Ile Lys Ser Val Val Lys Gly Ile Arg Ala
    50                  55                  60

Asn Ile Thr Asp Gly Glu Asn Gly Ala Thr Glu Pro Ala Arg Glu Leu
65                  70                  75                  80

Leu Glu Arg Leu Phe Ala Lys Thr Gln Arg Leu Asp Thr Ser Ala Ser
                85                  90                  95

Gln Asp Ser Glu Leu Ser Met Ser Ile Asp Val Leu Lys Ser Glu Phe
            100                 105                 110

Glu Ala Ala Leu Ser Thr Leu Arg Lys Lys Glu Arg Asp Leu Arg Asp
        115                 120                 125

Ala Glu Asn Arg Val Ser Val Asp Gln Val Arg Leu Asn Arg Ala Lys
    130                 135                 140

Lys Asp Leu Asp Gln Arg Glu Arg Gly Ile Asn Arg Ala Tyr Ala Arg
145                 150                 155                 160

Gln Gln Glu Met Glu Arg Ser Leu Gly Lys Ala Ser Arg Asp Leu Val
                165                 170                 175

Leu Gln Val Arg Gln Ile Asp Asn Leu Lys Leu Leu Val Asp Glu Gln
            180                 185                 190

Asp Lys Lys Ile Ala Ser Ser Gln Asp Leu Leu Ser Gln Lys Val Thr
        195                 200                 205

Glu Val Glu Lys Leu Lys Gln Asp Met Leu Lys Lys Asn Glu Glu Val
    210                 215                 220

Thr Leu Met Arg Ser Glu Ile Lys Ser Lys Glu Gln Leu Leu Leu Glu
225                 230                 235                 240

Ala Asn Gln Ala Ala Glu Gln Gln Glu Ala Thr Ile Lys Glu Leu Arg
                245                 250                 255

Ser Glu Ile Lys Arg Lys Glu Ile Asp Phe Ser Arg Ser Asn Glu Leu
            260                 265                 270

Arg Lys Ala Asn Glu Gln Lys Leu Lys Ile Ala Glu Gln Glu Leu Glu
        275                 280                 285

Arg Gln Asn Met Gly Trp Leu Ala Ala Gln Lys Glu Leu Lys Glu Val
```

```
            290                 295                 300
Ala Gln Leu Ala Cys Lys Asp Met Asp Gly Ile Lys Asp Thr Val Ser
305                 310                 315                 320

Asp Phe Lys Arg Val Arg Ser Leu Leu Asp Ala Val Arg Ser Glu Leu
                    325                 330                 335

Ile Ala Ser Lys Glu Ala Phe Ser Ser Arg Lys Gln Ile Glu Asp
                340                 345                 350

Gln Ala Val Gln Met Gln Lys Gln Val Gln Glu Leu Ser Gly Gln Arg
                355                 360                 365

Leu Leu Leu Ser Ser Phe Asn Gln Asn Leu Glu Ala Ala Arg Leu Glu
            370                 375                 380

Ile Gln Gly Lys Ala Lys Glu Leu Asn Ala Ala Gln Ser Arg Cys His
385                 390                 395                 400

Glu Leu Glu Ser Leu Leu Gln Glu Lys Val Glu Ser Leu
                    405                 410                 415

Glu Ala Val Leu Thr Lys Glu Arg Glu Ser Leu Glu Glu Lys Thr Lys
                420                 425                 430

Glu Val Glu Leu Leu Gln Lys Ala Leu Val Gln Lys Glu Asn Glu His
            435                 440                 445

Ser Asn Ser Leu Lys Leu Val Glu Ile Lys Glu Ser Glu Leu Leu Glu
450                 455                 460

Ala Arg Asn Glu Val Gln Asp Met Lys Ser Lys Val Glu Ser Ile Gln
465                 470                 475                 480

Ile Ala Val Gln Glu Lys Asp Ser Glu Leu Ser Glu Thr Gln Arg Arg
                485                 490                 495

Leu Ala Glu Val Asn Ser Glu Val Val Glu Leu Lys Gln Leu Leu Asp
                500                 505                 510

Ser Lys Glu Asp Gln Leu Val Gln Val Arg Thr Glu Leu Gln Asp Lys
                515                 520                 525

Glu Gln His Ile Gln Thr Leu Gln Asn Lys Leu Asp Ser Met Lys Phe
530                 535                 540

Ser Cys Ser Gln Ala Glu Ser Val Val Gln Lys Ile Ala Glu Leu Thr
545                 550                 555                 560

Gly Asn Leu Ala Ser Ser Val Glu Gly Glu Met Asp Ile Tyr Ala
                565                 570                 575

Leu Leu Asp Asp Glu Ile Ser Ser Thr Gly Thr Ala Leu Lys Ser Asn
                580                 585                 590

Leu His Lys His Asn Gln Leu Glu Ala Asp Ile Glu Met Leu Lys Glu
        595                 600                 605

Ser Leu His Gln Lys Asp Met Asp Leu Arg Ala Ala His Glu Ala Leu
    610                 615                 620

Asp Ala Lys Asp Gln Glu Leu Lys Ala Val Met Arg Arg Trp Asp Val
625                 630                 635                 640

Lys Glu Glu Val Asp Lys Leu Glu Gly Phe Leu Lys Asp Pro Ser Asp
                645                 650                 655

Ile Lys Arg Pro Ser Asp Phe Ser Val His Met Gly Leu Gln Asn Leu
                660                 665                 670

Gln Thr Glu Ala Ala Glu Val Glu Ala Leu Ala Ala Thr Thr Thr Leu
            675                 680                 685

Lys Lys Leu Ala Asp Met Ala Lys Gly Phe Leu Arg Ser Gly Lys Thr
        690                 695                 700

Asp Ser Gly Ile Asn Leu Val Ala Ser Pro Ser Val Asn Ser Thr Arg
705                 710                 715                 720
```

Ile Val Ser Lys Thr Lys Pro Asn Lys Glu Met Asp Met Ile Leu Asp
            725                 730                 735

Ala Glu Lys Glu Ile Ala Gly Leu Phe Ser Leu Thr Glu Gln Leu Ile
        740                 745                 750

Thr Glu Ala Gly Ile Asp Val Ala His Gln Ala
        755                 760

<210> SEQ ID NO 20
<211> LENGTH: 3580
<212> TYPE: DNA
<213> ORGANISM: Artificial Sequence
<220> FEATURE:
<223> OTHER INFORMATION: O. sativa (LOC_Os02g09340)

<400> SEQUENCE: 20

| | | | | | |
|---|---|---|---|---|---|
| gcagtccaca | cgcgtccggt | tcggcctcca | catcatcatc | tcctctcctc | tctcgtctcc | 60 |
| gcgcgccgtg | agccgtccga | tctcgcgcgg | gcggccgtga | tccgctccct | ccccccacc | 120 |
| cacgtgctag | gccgccatgc | cacccctctc | cccttcctcc | tcgccgccgg | cgacggcggc | 180 |
| ggcggttctc | cgctgcggct | ccccgtcgtg | ccgccccgtc | acacatgtga | gcatcccttc | 240 |
| ccatctcctc | gtatctcctc | tctcgttgct | cgttgttcgt | tgttggtggt | gtgtgttctc | 300 |
| gttcggtttc | cgattccgag | ctcgtctact | agcggtttga | aggggacgga | ggatcggatt | 360 |
| ttttttggtt | ttctagttca | agttgtgctg | cctggtagtg | gtagtttttt | aattaggagt | 420 |
| tttttggctg | aaattggttt | gacggtggtc | aattccggta | catctttaaa | ctaatcttga | 480 |
| taacggagaa | cctaacgaga | actattagcg | attgtagttt | gtgtgtggcg | atagatttgg | 540 |
| gatcaaaatt | catccgctgc | gctatgtcgc | tttgctgaag | attgaaacta | tgtgtgaata | 600 |
| aatatagttc | tgaattttta | gttcagagtt | aactttggca | tactatatca | tttcagtcct | 660 |
| ttggttcacc | gggagaattt | tcatgtacaa | ataaaatccc | catttttgca | gataggttca | 720 |
| ctaggaggtg | tcctgttgca | acttttttct | agcagtctac | tgatgcacac | tgttttctgc | 780 |
| aatcccgaca | ggagctgttc | aggcagaagt | tgagtttcat | ggtgtcattt | caagctcaac | 840 |
| atatgagatg | tgctcctcat | ttgatcaaat | cagttgttaa | aggtattaga | gcaaatatca | 900 |
| ctgatggcga | gaatggagca | actgaaccag | ctagggagct | attggagcgg | ctgtttgcga | 960 |
| agacgcaaag | gttggatacc | agtgcttccc | aggatagtga | gctgagtatg | agcattgatg | 1020 |
| tactgaagtc | tgaatttgag | gccgccttgt | ctaccttgag | gaagaaagag | agggatctcc | 1080 |
| gagatgcgga | gaatcgggtt | tcagttgatc | aggtacgcct | gaaccgggcg | aagaaggatc | 1140 |
| ttgatcagag | agagcgtggg | atcaatagag | catatgcaag | gcaacaggaa | atggagagat | 1200 |
| cactgggtaa | ggcaagtaga | gatctggttt | tacaagtgag | gcagatcgat | aacctgaagc | 1260 |
| ttcttgttga | tgagcaagac | aagaaaattg | ccagctcaca | agatttgctt | tctcagaagg | 1320 |
| taactgaagt | ggaaaagctt | aagcaagata | tgttgaagaa | gaatgaagaa | gtaaccttga | 1380 |
| tgcgttcaga | gatcaagtcc | aaggaacagc | tgcttcttga | agctaatcag | gctgctgagc | 1440 |
| agcaagaagc | aacaattaag | gagctccgga | gtgaaattaa | agaaaagaa | attgattttt | 1500 |
| ccagatcgaa | tgaattgaga | aaggccaatg | aacagaaact | aaaaatcgcc | gagcaagaac | 1560 |
| ttgagaggca | gaatatggga | tggttagcag | cacagaaaga | gttaaaggaa | gtggcgcaac | 1620 |
| tagcatgcaa | ggatatggat | ggtatcaagg | atacagtcag | tgacttcaaa | cgtgtgaggt | 1680 |
| ctctgctgga | tgctgtacgg | tctgaactaa | tcgcttcaaa | agaggctttc | tcctcctctc | 1740 |
| gaaaacagat | agaagatcaa | gcagtgcaga | tgcagaaaca | agttcaagaa | ctctctggtc | 1800 |

```
aaaggctatt gctttcatct ttcaaccaga acttggaagc tgctcggttg gagattcaag    1860
gcaaggcaaa ggagctcaat gctgcacagt ctcgctgtca tgaacttgaa tcactgttac    1920
ttcaggaaaa ggagaaggtt gagtctctgg aagcagtgtt aacaaaagaa agagagagct    1980
tagaagagaa aaccaaagaa gttgagttgc ttcaaaaggc gctcgttcag aaggaaaatg    2040
agcacagcaa ttcattaaag cttgttgaaa taaaagaatc tgagctgtta gaagcccgaa    2100
atgaagtcca agatatgaaa tcaaaggtgg aatctatcca aatagctgtt caggagaagg    2160
attcagagct ttctgaaaca caacgcagac ttgctgaagt gaacagtgaa gttgttgaac    2220
taaagcagct gctagatagc aaggaagatc aacttgttca ggttagaacc gaattacagg    2280
ataaagaaca acacatacag acactacaga ataaattgga tagcatgaaa ttcagttgct    2340
cacaagctga atctgtggtg caaaagatag ctgaactcac tggcaatctt gctagttcag    2400
tagaaggcga agagatggac atttatgcat tgctggatga tgagatttcg agcacaggta    2460
cagccctcaa gtccaatttg cacaagcata atcaactgga ggctgacata gagatgttaa    2520
aagaatcctt gcatcagaag gacatggatt taagagctgc ccatgaagca cttgacgcga    2580
aagatcaaga gctgaaggcg gtaatgagaa ggtgggatgt gaaggaggag gtagacaagt    2640
tggaagggtt cctgaaagat cctagtgaca tcaagagacc ttctgatttt tccgttcata    2700
tggggctcca aaatcttcaa actgaagctg cggaggtgga ggcacttgct gctactacta    2760
cattgaagaa acttgcagat atggctaagg gattcctgag aagtggcaaa actgattctg    2820
gcatcaatct ggttgcatcg ccaagtgtaa acagtactag aattgtttcc aagaccaaac    2880
caaacaagga aatggatatg attcttgatg ctgaaaagga aattgccggg ctcttttcgt    2940
tgacagaaca gctcattacc gaggctggaa tagatgttgc tcaccaagca tagcttcaga    3000
acccagaaat gtatatcata ttgcagtttt gcaacattta gatagttgct gtgaagattc    3060
agctgaaatt gttagcgttt tcatttcttt tgctttgggt ctcatcgccc tgtttgctgt    3120
tggattgctc tgctccaagt gcgaaaggga gacatcgatg ttgatatgcc tcttactgtt    3180
tacatgatat attgcatctg ctgaaatcct agaaaaaaaa tgataaattt gtgatccaaa    3240
accccttctc tagtcagcca gtggcggatt tgctgacaac ctaggcagct gcctgtaatt    3300
catattctcc aaaactcctt cagaccggag ttaatgaaga tatccaaagc ctgtaaaatt    3360
gttgctgatt tggagaggt gagaaatagt gaaggatttt actttctgga cggataccag    3420
gttgcccttg atttttggtca gctttcgaca tgtagatttg ctgaattata tctgtttttc    3480
tcttctctgt agtttcccat cggagagctg ttgattctca tcatgttatc catatgttaa    3540
cctggaaaaa ttgtacagaa tttgctgctc agctttagtg                          3580
```

<210> SEQ ID NO 21
<211> LENGTH: 2292
<212> TYPE: DNA
<213> ORGANISM: Artificial Sequence
<220> FEATURE:
<223> OTHER INFORMATION: O. sativa CDS (LOC_Os02g09340.1)

<400> SEQUENCE: 21

```
atgccacccc tctcccttc ctcctcgccg ccggcgacgg cggcggcggt tctccgctgc     60
ggctccccgt cgtgccgccc cgtcacacat gagctgttca ggcagaagtt gagtttcatg    120
gtgtcatttc aagctcaaca tatgagatgt gctcctcatt tgatcaaatc agttgttaaa    180
ggtattagag caaatatcac tgatggcgag aatggagcaa ctgaaccagc tagggagcta    240
```

```
ttggagcggc tgtttgcgaa gacgcaaagg ttggatacca gtgcttccca ggatagtgag    300
ctgagtatga gcattgatgt actgaagtct gaatttgagg ccgccttgtc taccttgagg    360
aagaaagaga gggatctccg agatgcggag aatcgggttt cagttgatca ggtacgcctg    420
aaccgggcga agaaggatct tgatcagaga gagcgtggga tcaatagagc atatgcaagg    480
caacaggaaa tggagagatc actgggtaag gcaagtagag atctggtttt acaagtgagg    540
cagatcgata acctgaagct tcttgttgat gagcaagaca agaaaattgc cagctcacaa    600
gatttgcttt ctcagaaggt aactgaagtg gaaaagctta agcaagatat gttgaagaag    660
aatgaagaag taaccttgat gcgttcagag atcaagtcca aggaacagct gcttcttgaa    720
gctaatcagg ctgctgagca gcaagaagca acaattaagg agctccggag tgaaattaaa    780
agaaaagaaa ttgattttt cagatcgaat gaattgagaa aggccaatga acagaaacta    840
aaaatcgccg agcaagaact tgagaggcag aatatgggat ggttagcagc acagaaagag    900
ttaaaggaag tggcgcaact agcatgcaag gatatggatg gtatcaagga tacagtcagt    960
gacttcaaac gtgtgaggtc tctgctggat gctgtacggt ctgaactaat cgcttcaaaa   1020
gaggctttct cctcctctcg aaaacagata gaagatcaag cagtgcagat gcagaaacaa   1080
gttcaagaac tctctggtca aaggctattg ctttcatctt tcaaccagaa cttggaagct   1140
gctcggttgg agattcaagg caaggcaaag gagctcaatg ctgcacagtc tcgctgtcat   1200
gaacttgaat cactgttact tcaggaaaag gagaaggttg agtctctgga gcagtgtta   1260
acaaaagaaa gagagagctt agaagagaaa accaagaag ttgagttgct tcaaaaggcg   1320
ctcgttcaga aggaaaatga gcacagcaat tcattaaagc ttgttgaaat aaaagaatct   1380
gagctgttag aagcccgaaa tgaagtccaa gatatgaaat caaggtgga atctatccaa   1440
atagctgttc aggagaagga ttcagagctt tctgaaacac aacgcagact tgctgaagtg   1500
aacagtgaag ttgttgaact aaagcagctg ctagatagca aggaagatca acttgttcag   1560
gttagaaccg aattacagga taagaacaa cacatacaga cactacgaa taaattggat   1620
agcatgaaat tcagttgctc acaagctgaa tctgtggtgc aaaagatagc tgaactcact   1680
ggcaatcttg ctagttcagt agaaggcgaa gagatgggaca tttatgcatt gctggatgat   1740
gagatttcga gcacaggtac agccctcaag tccaatttgc acaagcataa tcaactggag   1800
gctgacatag atgttaaa agaatccttg catcagaagg acatggattt aagagctgcc   1860
catgaagcac ttgacgcgaa agatcaagag ctgaaggcgg taatgagaag gtgggatgtg   1920
aaggaggagg tagacaagtt ggaagggttc ctgaaagatc ctagtgacat caagagacct   1980
tctgatttttt ccgttcatat ggggctccaa aatcttcaaa ctgaagctgc ggaggtggag   2040
gcacttgctg ctactactac attgaagaaa cttgcagata tggctaaggg attcctgaga   2100
agtggcaaaa ctgattctgg catcaatctg gttgcatcgc caagtgtaaa cagtactaga   2160
attgttccca agaccaaacc aaacaaggaa atggatatga ttcttgatgc tgaaaaggaa   2220
attgccgggc tctttccgtt gacagaacag ctcattaccg aggctggaat agatgttgct   2280
caccaagcat ag                                                        2292
```

<210> SEQ ID NO 22
<211> LENGTH: 1500
<212> TYPE: DNA
<213> ORGANISM: Artificial Sequence
<220> FEATURE:
<223> OTHER INFORMATION: TaMRC 6A (cv. Kronos (4n)) promoter sequence

<400> SEQUENCE: 22

```
ttaacctgaa aatctaaaaa gtggccgcgc acttttagt cgaaccgagc ggccggctct      60
cacagcgtat gcatgtggta atttatttgt ctgctagtgc atgtaggcgt gacattaaat    120
acgttcacac tgctctttta gtttaagaaa gacagatcca tctgcattta ttttgggttt    180
ttaaaaattc aaaaagctat atctttcaaa ccgcgcgtcg gaattcaaat ccgttttcac    240
cattgaaatc ctcgcgacga gatctttgaa actagatccc gcatgggtat attttgacga    300 attttttcg atgccaactt tggagctata tagtgcaact ctattactgc aatgtgcaac     360
ttttattact acatcgtgca acttttttcc aaaactaatg tttggagctg caccttcgta    420
tgaggttaca acctagcaac cacgacaact ttgatgtgcg actagtctat tgcctcgacg    480
aaagtcgatg tgcaacctcc tcttgtaatg tagtctagtc gcatacacat tgatgtttag    540
ttggcttgta atgtagtcta gttgcacata cattgatatt tagttggctt gtaatgtagt    600
ctagttgcac acacattaat gtttagttgg caggaagact aattgcacac gcatatgatt    660
agttggcttg taatttagtc tagttgcaca cacactgatg tttagttggc aggacactag    720
ttgcacacac atatgctcag ttggcgtggc aatctagtct agttgcacac acattgatgt    780
ttagttggca ggactttttt ggcacacaca catatgctca gttggcgcgc aatctagtct    840
agttgcacac acattgatat ttagttggca gaaagactag ttcgtcgaaa catccccatg    900
cgggatatag ttttgaagag cacgtcgcga ggattccagc ggtgaaaacg gatcttaatt    960
ccgacgcgcg gtttggaaga tatagctttt tgaaaattta aaaaccgaaa caaatgcata   1020
tgtgatctgt tttttccaac tgattgtgac cggtgtgaat gtattaaatg ctaaaagata   1080
catgcgctag cggacaaaaa ttacacacat gcatgtctat acagagcaga cgctagcgaa   1140
taaaaatttt ctattttagg ccggccgctc gcgcatggca gcgagcagcc ggccgctacg   1200
tagactcgtc ttttttaag gcaaccaaag tgtaccttaa ttttcatgt gttataaact    1260 catacatttg gaacgaaaag aaaaaaggta gtaagacgag tgaacggaga agaaaagctg   1320
tagaacagta gaaggcaaac gagtaaacga cacagctctc tctcacgctt ctcgcgtggt   1380
cgacgttgca gtccacacgc ggctgggcgc gccggttcaa ccacacctca tctcccgcac   1440
tccctctgcc tcgtatctcc tcgccttcct ccgcaccccg caggcgcatt gccagccgtc   1500
```

<210> SEQ ID NO 23
<211> LENGTH: 1500
<212> TYPE: DNA
<213> ORGANISM: Artificial Sequence
<220> FEATURE:
<223> OTHER INFORMATION: TaMRC 6A (cv. Cadenza (6n)) promoter sequence

<400> SEQUENCE: 23

```
ttaacctgaa aatctaaaaa gtggccgcgc acttttagt cgaaccgagc ggccggctct      60
cacagcgtat gcatgtggta atttatttgt ctgctagtgc atgtaggcgt gacattaaat    120
acgttcacac tgctctttta gtttaagaaa gacagatcca tctgcattta ttttgggttt    180
ttaaaaattc aaaaagctat atctttcaaa ccgcgcgtcg gaattcaaat ccgttttcac    240
cattgaaatc ctcgcgacga gatctttgaa actagatccc gcatgggtat attttgacga    300 attttttcg atgccaactt tggagctata tagtgcaact ctattactgc aatgtgcaac     360
ttttattact acatcgtgca acttttttcc aaaactaatg tttggagctg caccttcgta    420
tgaggttaca acctagcaac cacgacaact ttgatgtgcg actagtctat tgcctcgacg    480
aaagtcgatg tgcaacctcc tcttgtaatg tagtctagtc gcatacacat tgatgtttag    540
```

```
ttggcttgta atgtagtcta gttgcacata cattgatatt tagttggctt gtaatgtagt    600
ctagttgcac acacattaat gtttagttgg caggaagact aattgcacac gcatatgatt    660
agttggcttg taatttagtc tagttgcaca cacactgatg tttagttggc aggacactag    720
ttgcacacac atatgctcag ttggcgtggc aatctagtct agttgcacac acattgatgt    780
ttagttggca ggactttttt ggcacacaca catatgctca gttggcgcgc aatctagtct    840
agttgcacac acattgatgt ttagttggca gaaagactag ttcgtcgaaa catccccatg    900
cgggatatag ttttgaagag cacgtcgcga ggattccagc ggtgaaaacg gatcttaatt    960
ccgacgcgcg gtttggaaga tatagctttt tgaaaattta aaaccgaaa caaatgcata   1020 tgtgatctgt tttttccaac tgattgtgac cggtgtgaat gtattaaatg ctaaaagata   1080
catgcgctag cggacaaaaa ttacacacat gcatgtctat acagagcaga cgctagcgaa   1140
taaaaatttt ctattttagg ccggccgctc gcgcatggca gcgagcagcc ggccgctacg   1200
tagactcgtc ttttttaag gcaaccaaag tgtaccttaa ttttcatgt gttataaact    1260 catacatttg gaacagaaag aaaaaaggta gtaagacgag tgaacggaga agaaaagctg   1320
tagaacagta gaaggcaaac gagtaaacga cacagctctc tctcacgctt ctcgcgtggt   1380
cgacgttgca gtccacacgc ggctgggcgc gccggttcaa ccacacctca tctcccgcac   1440
tccctctgcc tcgtatctcc tcgccttcct ccgcaccccg caggcgcatt gccagccgtc   1500
```

<210> SEQ ID NO 24
<211> LENGTH: 1500
<212> TYPE: DNA
<213> ORGANISM: Artificial Sequence
<220> FEATURE:
<223> OTHER INFORMATION: TaMRC 6D (cv. Cadenza (6n)) promoter sequence

<400> SEQUENCE: 24

```
cgctggtaat caccagcgca gctaaccacc ccatgagctt ctagttactg gttagaaaag     60
ggatcgcgac caactagagg tgactgagcc ggtcttctcc attatttctt tcttttttc    120 ttttctttct atatttttt tcaaatactt gttcaaattt tttcaaatac ttgttcaaat    180
tttttcaaat acttgttcaa tattttttata tacatgatca acatttttac aaatacttgt    240
tcaatatttt tatatacatg atcaatattt ttttaaatac ttattcaaca tttttttcaa    300
atagttgttc aatttttttt gcaaatgctt gattatcatt tttatataca tgatcaacat    360
tttttaaaat acttcttcaa cagttttcaa ataccttattc aacagttttc aaatatttgt    420
tcaacatctt tcaagtactt gttcaacatt ttttcaaatg cttgatttta tatgcatgat    480
caacattttt tcaaatactt cttcaacatt tttaaatacc tattcaacag ataaatgggt    540
gcatgcacct gtcggcctag aggaagcaga ctgggtgcca atcgaccagc agtgggccga    600
ctggggccaa tcggccagca gtgggccgac tggatccaat cggccggcag tgggccgact    660
gaggccaatc ggccagcagt aggccgattg gatccaatcg gccagcagta ggccgactgg    720
atccaattgg tcagcagtag gccgactggg taatatttta aaaaaatata attatggcgt    780
aatatttctg aaatttaata taaaacatgt attatttaaa aaattagtcc gactatgagt    840
agctctgcta gttaaatttt atgtcaccta tgtttgaact atgttgaat ttgatgtttg    900 agctatgttg agatcaaata tagttggtcg tttcagaatt ttacatcttc gttttggacc    960
atctgttgga gttgctcttt tacatccacca ttttggacta tctggtggag ttgagccgtt   1020
ttcaaagatg taaaaagcaa tttttgatga tgtaaatttt tacatcaccg gtttggagca   1080
ccaaaatata catcatctat tggagatgct cttaccctag tattccgttc cgagtcaaaa   1140
```

```
tagtccctga taattttcat gtgttataaa ctcattcttt ttaaagtcaa gactgtccct    1200
aacaattttc atgtgttata taaactcatt ttttaaggca gccaaggtgt accttaaatt    1260
ccatgtgtta taaactcata aatttggaat agaaagaaaa aaagggaaga ccagtgaacg    1320
gaggagaaaa gcagtagaag gcaaacgaca cagctctctc tcacgcttct cccgtggtcg    1380
acgttgcagt ccacacgcgg ctgggcgcgg cggttccacc acctccctca tctcccgtac    1440
tccctctgcc tcgtatctcg tcgccttcct ctgcaccccg caggcgcatt gccagccgtc    1500
```

<210> SEQ ID NO 25
<211> LENGTH: 1500
<212> TYPE: DNA
<213> ORGANISM: Artificial Sequence
<220> FEATURE:
<223> OTHER INFORMATION: HvMRC promoter sequence

<400> SEQUENCE: 25

```
cacctcatcc cattcccag catggacctt ctcctcaaag tacttggtgt tgaagtagaa      60
tcctgactct tgttcaagcc tgcagcatca tgcattgtca aaatcacata aaaatattgc     120
aatactccat tgcactaaac ataatagatg gaccagagct cgaagggaa aaagaaaaat     180 ggtatggcgc tcaggaagac ctcggcaatt caattcttga gctcacaaca ttggcccagt    240
actgccaacc cgagttgtct acctgaggcg tcacgcatga ctgtactgac gacaatacag    300
aagacaagtg aaaacagagt ttcagactaa tccatttgtt tcgatggatg gttggatacc    360
cagttgtgcg ctcaatgtcc aaatttgaca gtggcttcga acaatactgc aatccaggta    420
aatgccatct acacttttcc atttactgat gttttactcg gaaaaggcac cgcacaggag    480
acaacaatgc caccaatcac tacaatctag gtaaattcag tgtggtaaac tttaataagt    540
attttaagct tcttgtaaca tcatatttct tccattcgaa agtaagttca tgaatccttg    600
tgatgatttt gtgggtgttc tctgccacac tgaatagaaa atctgcaaaa atagaaaaga    660
acaaattcta aggtgtgtgt gtgtaactga agaacctcgt cgggatcact tgtccggcgt    720
tgcagctgga gccgcctcct cggcacgagg cttctctgcg tccgccatgg cttcctgcca    780
caagtggtga aacacggtga cgacgatagg aagggaatca acatcgccat agcctcgagc    840
cctcgacaca ctcccttggc ttgtgattcc catcgtggtg gagatcttga atccggcgac    900
gtcgcaggag aagagagacg cgacgagcgg ggggagggggt cgcggcgagc ggggggaggg    960
gtcgcggcga gcggcgggag gaggcgcggc gagcgggga gggtcgagg cgcggtggcg    1020 ggaggagttg cggcgagcgg ggggaggagg cgcggcgagc gagggaggag tcgcgacgag    1080
cggcggggaa ggggtcgagg cgaacggggg gagggtcgc ggcaagcatg ccgaccagga    1140 ggaggggtc tattcgtgag acgtggagcg tgagtattga ttagcgctaa cgaaaaccgt    1200
tttcgttaac ggagtattta gacccttgat taagcgatta gacggttaaa attatgattt    1260
ggatctgtcc tttcgtgttt ttattatttg aaatataaag gaaaaaagca agactaatga    1320
acggagaagg aaagcagtag aaggcaaacg gcacagcgct ctctcacgct tttcccgtgg    1380
tcgacgttgc agtccacacg cggctgggt cggctggttc caccacctca tctccctgac    1440
tccctctgcc tcgtatctcg tcgccttgct ccacacccca caggcgcatt gtcagccgtc    1500
```

<210> SEQ ID NO 26
<211> LENGTH: 1500
<212> TYPE: DNA
<213> ORGANISM: Artificial Sequence
<220> FEATURE:

<223> OTHER INFORMATION: Brachypodium MRC promoter sequence

<400> SEQUENCE: 26

```
tcccataatt tttgtcgtga ttttagttca aatttgaatt aaaaccagca caataattat    60
gggactgaag gagtactacg aagtagtaaa aaatacttcc tccgatctat attacttgtc   120
gctgatttag tacaagggag tagtattttt tattagagtc atcatgatag tatatatgtt   180
taccgtatgt gtaaatatta atacaattta acataaattt agtcaaaatt taataagctc   240
gtttatgaca aaactaaaac gtttgtcctc gtctgtgcgc acgtgcgata tcggatctac   300
tgtaagtcat ggaataaccc cccgccacct tctcatgtga aacgctatgt tccccttcc   360
cagtagcccg tttccccaat tccatcaca attgtcgttc ccagctctgg cgctgcccca   420
ggctatggcg cccgaccctc ctgctcaggt gttagtagcc atggatttct gttgttcctg   480
ccagggggaag tggagcgcat ccgcgaaggc tcccctccac accccctcga agcaccgcca   540
tggtggcacc tcgaggcgat gcgcgccacg acgcgcgggt tccgctctac cttcactagc   600
tactcgatca tgcgactgct attcgaatga ttcatgcgct cactttaaac cctccaatct   660
tgacattagg ggcgggcatt cggtcatgac tgaaagttcg gtcttctaat ttaagtcttt   720
tttcgattcg gtccttaaaa tataatacc gaacttact gagaaacgtc gatgaccgaa    780
ctttagaaag atgggtgata attccaaaac aaaacgtgat ttggtaccaa ttttagcaac   840
atttcactta tacttctcac aaattttctt attaacatgg gcattggaga ttaggaaagt   900
gaaacagtcg attgcctctc ttgtgccatg attttttgcat gcggaatagt tgatgcctag   960
attgtatcgt gaaatgagt tggttttac aaagcggaaa agtttggtcc tatttggtct    1020
ttcagtcttt tgtggattga tacccgaatt aatagaataa atttcggtct ataaattttt   1080
ctatccaaat atctaatcgg tctttttcgat ctcggtctat tcggtttcgg tcctcggttt  1140
ttatgcccgc ccctacttga catatacttt agaatacttt atgtataaac agttttgctc   1200
gatgctaagt ggcagtgttc cgtgctttgt cgacccacc caagatccta gcttgtgtct    1260
aaacatttga gagagagagc aagagatttc cctcgtttc tttaaaaata aaggaaaat    1320
agataattaa ttaattattt ttcttaagga aaataactag tacacgatta tattgtttt    1380
taggaaaacg acataattat aggagagaaa gcaaacaaca cgggtctcac gcttctctac   1440
agtcgactag gctcggagtc cacacgcggc tgctcggccc gcttccaccc ctacatcccc   1500
```

<210> SEQ ID NO 27
<211> LENGTH: 1500
<212> TYPE: DNA
<213> ORGANISM: Artificial Sequence
<220> FEATURE:
<223> OTHER INFORMATION: Z.mays MRC promoter sequence

<400> SEQUENCE: 27

```
tatctatggc tcgtactttt ctataggaaa gggtcagcaa ggacattatg cacatattaa    60
ggcattgttt aggacaactc taactacatg acattttgta gagttggaga agtaggtcat   120
tggatgcttt agaaaatcgt ggagctctgt aaacatatac aagacattta gataagtcat   180
tttgtttatt atttagatta aaaatatttt taaaactatt taaattgata ttataaacta   240
tagctctaca ctggaggttt aacctggagc catctcaaac ctgccctaaa ttatgtacat   300
agttctttta catgcaatgc acttattgaa tcacgataat ctattttaga cctaacattc   360
tcttacatgt cccttcgtgc acagaatatg gtgaatgtgg tgaagagttt ttttttttgc   420
aaaaaatctg tccacatgat ttagtcgctt tagatttgtt ctaagtgaaa ctatttaaat   480
```

```
tttgaccaac aatatatata gttaaattat gttatactaa aataattata tattatgata    540
gttcaagtca tgatggatct ggcgacttta cttttatatt gtaaaatttt ataaaacatt    600
cggtataacc gatcaaaagt taatagtgat tgacttagga caaatctaaa acagctaatt    660
catatggaca gtgtgagtac aaagcaataa gggaactagg gaaggtgtgt gaggatgttg    720
gatcttagat gagtaactct gtgcaccaaa gatctatatg cacttagggg gtgtttggtt    780
tgtagtgtct aattttagt tccaccattt tgttttattt gtccctaaat tatcaaaatat    840 gaaaactaaa atagagtttt attttcagta tttgataatt tatggactaa aatgaaataa    900
aatgaattga ctaaaaatta gtccctagaa accaaacatc tcctttggtt tctagggact    960
aatttttagt cactatatat tttttatttt agtttctaaa ttgtactttc catatttgac    1020
aatttaaaga ttaaaataaa aagactaaaa attagtcttt acaaaattaa acatctcttt    1080
aaggctttat ctgaatacccc tcgtattcac cctaatccac gtgtattgag gtggattgaa    1140
atgtaaatta gttaattta cgcttcaatt tatcttaata aatgtgattg agataaatac     1200
gagagtagta agccataata tgttttcatt agatgtagga ttgttttttc gcgtggacgc    1260
tgcatgatgt tcgtctgact tggtaagcca ggtatggacg gaccacggat ttagcaaatt    1320
tacaagaaaa ttccctctcc taacaaatac gtaggaaatc tcggaaatac gcagaaaaga    1380
ggacgtcaaa aggcaatttt cttttctaag ataggggaaa agtgtgaaaa agacaatttc    1440
tcatcagaaa atggaaaaca caagtctcca gtgctcctcg cgtgatcgca tccacgcttc    1500

<210> SEQ ID NO 28
<211> LENGTH: 1500
<212> TYPE: DNA
<213> ORGANISM: Artificial Sequence
<220> FEATURE:
<223> OTHER INFORMATION: O.sativa MRC promoter sequence

<400> SEQUENCE: 28
cagccgccgg cctccgctcg ccgcgactgc cgtcctccgc ttgccgcggc cgctcgtcgc      60
ggccgccggc ccccgcgcgg cgcaacccgc cgccccccgct cgccgtggct gctggcctcc    120
gcgcggcaca agctcgccgc gcccgccgtc ctccgcgcag cgccgccgc tgcctccgca     180 cggcgcccgc ctcccgccgc gcagcccgcc ggtccccacg cagcgccgcc tcccgccgac    240
gctgccttca ccgccgtccc ctcccccgctt gctgccgccg cctgcttctt gtcaacgcta    300
gaaaagaaaa gaggaagagg ggaaggaagg ggagaaagaa taagggagtg gctcacatat    360
gggtcccggt gtcatagtca aaatagagag ggtagaatag agaggctgtt ggagtataca    420
gttaatttga ctagctaaat cagatggaga gttggctata tgggtgtttt aggagttcga    480
tttggagagg ctgttagaga tactcttatg tgcaaaatat gtgcagttac catgcatgtt    540
ggtactgaag agccagagcc attccaagaa aggaaggatc ttttcaccac gtagaactcc    600 attttctga catttttaa aagaaagaat gaaggtgact aagggacaat attttaatat     660
agcaggatga tatagagatt ctcgagggac aataaggttt tacacttttta caaaggattc    720 tcaagatata catatttcat tcttgctagg gttagtgtag gatggtgcag tgcacaccat    780
gagaatcgga gaatctgtat gtggtgcgaa gaaaactaa gaacaccaga aacagaaaaa    840
aaatgaagaa cagaaacaaa tccatgcaaa acttgtcatt cagagagcaa attatgtctc    900
agatatctct atttacctgc tactcctgaa gagactggac ttgttacttc ctttgacaga    960
aatagcagaa caaaaatatg tcacctttt gcaactttca taagatttc ttttcttttt      1020
```

-continued

```
gcaaagaatt tatgcatgct aaaaacaagg gggtgagtta ggaactcact gaaaagagca      1080
cagcctagat gagtaggtgc gctcccgttt ttgggcccag atgaaggaca aggcccacct      1140
agaactccta cggtggaccg cgggcggttt tgatccaacg gccagggttc ttcatcaccc      1200
atccaacggt gacaatccca ctaaaatcct tccaaatttt cggtttcttt aaacatcttc      1260
gaattcaaat ttctctcatc acgtagtaca gcccagcatt tcctgtcctc acgtaccccc      1320
gaataaaaac gaaacggcac cagaacccag aacagcaagc aacacaaacc catcaaaaca      1380
aacaaaacaa aagaaaaga aaaagaaaaa aaaagagcaa gcgacacgag cgtcacgtgt      1440
cacgcttact cgagtcatca atcatctact acaccccacc ccactccact gcactgcact      1500
```

<210> SEQ ID NO 29
<211> LENGTH: 505
<212> TYPE: PRT
<213> ORGANISM: Artificial Sequence
<220> FEATURE:
<223> OTHER INFORMATION: TaMRC 6B partial (cv. Kronos (4n))

<400> SEQUENCE: 29

```
Pro Val Ser Asn Glu Ser Arg Lys Thr Asn Glu Glu Lys Leu Lys Val
1               5                   10                  15

Ala Glu Gln Glu Leu Glu Lys Gln Ser Leu Gly Trp Leu Ala Ala Gln
                20                  25                  30

Gln Glu Leu Lys Glu Leu Ala Gln Leu Ala Phe Lys Asp Thr Asp Asp
            35                  40                  45

Ile Asn Gly Ile Ile Thr Asp Phe Lys Arg Val Arg Ser Leu Leu Asp
        50                  55                  60

Ala Val Arg Ser Glu Leu Ile Ser Ser Lys Asp Ala Phe Ala Ser Ser
65                  70                  75                  80

Arg Arg Gln Ile Glu Asp Gln Ala Val Gln Leu Gln Glu Gln Val Gln
                85                  90                  95

Glu Leu Glu Asp Gln Arg Val Leu Leu Met Ser Tyr Thr His Asp Leu
            100                 105                 110

Glu Ala Ala Lys Leu Glu Ile Gln Gly Lys Thr Gln Glu Leu Ser Tyr
        115                 120                 125

Ala Gln Ser Arg Cys His Glu Leu Ser Gln Leu Leu Gln Glu Arg
    130                 135                 140

Glu Lys Val Glu Ser Leu Glu Ala Glu Leu Ala Lys Glu Lys Gln Ser
145                 150                 155                 160

Leu Glu His Arg Thr Glu Glu Val Gly Phe Leu Gln Lys Glu Leu Val
                165                 170                 175

Gln Lys Glu Asn Glu Cys Thr Lys Ser Gln Glu Leu Val Lys Val Lys
            180                 185                 190

Glu Phe Glu Leu Leu Glu Ala Arg Gln Glu Val Gln Asp Met Lys Leu
        195                 200                 205

Lys Val Glu Ser Ile Gln Leu Ala Val Gln Lys Asp Ser Glu Leu
    210                 215                 220

Ser Asp Thr Gln Ser Arg Leu Thr Glu Val Ser Ser Glu Ile Ala Glu
225                 230                 235                 240

Leu Gln Gln Leu Leu Asn Ser Lys Lys Asp Gln Leu Leu Gln Ala Arg
                245                 250                 255

Thr Glu Leu His Asp Lys Glu Gln His Ile Glu Thr Leu Glu Ser Glu
            260                 265                 270

Leu Asp Ser Ile Arg Leu Arg Cys Ser Gln Ala Glu Ser Met Val Gln
        275                 280                 285
```

```
Arg Met Ala Asp Leu Thr Gly Asp Leu Ala Ser Ser Val Lys Ala Gly
    290                 295                 300

Glu Met Asp Ile Tyr Ala Leu Leu Asp Asp Glu Ile Ser Ser Thr Gly
305                 310                 315                 320

Thr Ala Leu Glu Ser Asn Leu His Lys His Asn Gln Leu Glu Ala Asp
                325                 330                 335

Ile Glu Met Leu Arg Glu Cys Leu Arg His Lys Asp Met Glu Leu Arg
                340                 345                 350

Ala Ala His Glu Ala Leu Asp Ala Lys Asp Gln Glu Leu Lys Ala Val
            355                 360                 365

Leu Arg Lys Trp Asp Val Lys Glu Arg Glu Val Arg Glu Leu Glu Glu
        370                 375                 380

Leu Pro Asp Pro Ser Ala Thr Asn Glu Leu Ala Gly Phe Ser Ser Glu
385                 390                 395                 400

Thr Thr Glu Asp Gly Ile Val Gly Glu Met Glu Leu Pro Glu Leu Gln
                405                 410                 415

Ile Glu Ala Val Glu Val Glu Ala Leu Ala Ala Thr Thr Ala Leu Arg
                420                 425                 430

Lys Leu Ala Asp Met Thr Lys Asp Phe Phe Lys His Gly Lys Ala Asp
            435                 440                 445

Ser Gly Ile Asp Leu Val Ala Ser Glu Ser Gln Lys Ile Ser Lys Cys
    450                 455                 460

Asp Pro Lys Met Glu Val His Lys Lys Thr Asp Val Ile Leu Glu Ala
465                 470                 475                 480

Glu Lys Glu Ile Val Arg Leu Phe Ser Leu Thr Lys Gln Ile Val Thr
                485                 490                 495

Asp Asp Ile Ile Asn Asp Val Glu Glu
            500                 505

<210> SEQ ID NO 30
<211> LENGTH: 505
<212> TYPE: PRT
<213> ORGANISM: Artificial Sequence
<220> FEATURE:
<223> OTHER INFORMATION: TaMRC 6B partial (cv. Cadenza (6n))

<400> SEQUENCE: 30

Pro Val Ser Asn Glu Ser Arg Lys Thr Asn Glu Glu Lys Leu Lys Val
1               5                   10                  15

Ala Glu Gln Glu Leu Glu Lys Gln Ser Leu Gly Trp Leu Ala Ala Gln
            20                  25                  30

Gln Glu Leu Lys Glu Leu Ala Gln Leu Ala Phe Lys Asp Thr Asp Asp
        35                  40                  45

Ile Asn Gly Ile Ile Thr Asp Phe Lys Arg Val Arg Ser Leu Leu Asp
    50                  55                  60

Ala Val Arg Ser Glu Leu Ile Ser Ser Lys Asp Ala Phe Ala Ser Ser
65                  70                  75                  80

Arg Arg Gln Ile Glu Asp Gln Ala Val Gln Leu Gln Glu Gln Val Gln
                85                  90                  95

Glu Leu Glu Asp Gln Arg Val Leu Leu Met Ser Tyr Thr His Asp Leu
            100                 105                 110

Glu Ala Ala Lys Leu Glu Ile Gln Gly Lys Thr Gln Glu Leu Ser Tyr
        115                 120                 125

Ala Gln Ser Arg Cys His Glu Leu Glu Ser Gln Leu Leu Gln Glu Arg
    130                 135                 140
```

Glu Lys Val Glu Ser Leu Glu Ala Glu Leu Ala Lys Glu Lys Gln Ser
145                 150                 155                 160

Leu Glu His Arg Thr Glu Val Gly Phe Leu Gln Lys Glu Leu Val
            165                 170                 175

Gln Lys Glu Asn Glu Cys Thr Lys Ser Gln Glu Leu Val Lys Val Lys
            180                 185                 190

Glu Phe Glu Leu Leu Glu Ala Arg Gln Glu Val Gln Asp Met Lys Leu
        195                 200                 205

Lys Val Glu Ser Ile Gln Leu Ala Val Gln Glu Lys Asp Ser Glu Leu
        210                 215                 220

Ser Asp Thr Gln Ser Arg Leu Thr Glu Val Ser Ser Glu Ile Ala Glu
225                 230                 235                 240

Leu Gln Gln Leu Leu Asn Ser Lys Lys Asp Gln Leu Leu Gln Ala Arg
                245                 250                 255

Thr Glu Leu His Asp Lys Glu Gln His Ile Glu Thr Leu Glu Ser Glu
            260                 265                 270

Leu Asp Ser Ile Arg Leu Arg Cys Ser Gln Ala Glu Ser Met Val Gln
        275                 280                 285

Arg Met Ala Asp Leu Thr Gly Asp Leu Ala Ser Ser Val Lys Ala Gly
290                 295                 300

Glu Met Asp Ile Tyr Ala Leu Leu Asp Asp Glu Ile Ser Ser Thr Gly
305                 310                 315                 320

Thr Ala Leu Glu Ser Asn Leu His Lys His Asn Gln Leu Glu Ala Asp
                325                 330                 335

Ile Glu Met Leu Arg Glu Cys Leu Arg His Lys Asp Met Glu Leu Arg
            340                 345                 350

Ala Ala His Glu Ala Leu Asp Ala Lys Asp Gln Glu Leu Lys Ala Val
        355                 360                 365

Leu Arg Lys Trp Asp Val Lys Glu Arg Glu Val Arg Glu Leu Glu Glu
        370                 375                 380

Leu Pro Asp Pro Ser Ala Thr Asn Glu Leu Ala Gly Phe Ser Ser Glu
385                 390                 395                 400

Thr Thr Glu Asp Gly Ile Val Gly Glu Met Leu Pro Glu Leu Gln
                405                 410                 415

Ile Glu Ala Val Glu Val Glu Ala Leu Ala Ala Thr Thr Ala Leu Arg
            420                 425                 430

Lys Leu Ala Asp Met Thr Lys Asp Phe Phe Lys His Gly Lys Ala Asp
        435                 440                 445

Ser Gly Ile Asp Leu Val Ala Ser Glu Ser Gln Lys Ile Ser Lys Cys
        450                 455                 460

Asp Pro Lys Met Glu Val His Lys Lys Thr Asn Val Ile Leu Glu Ala
465                 470                 475                 480

Glu Lys Glu Ile Val Arg Leu Phe Ser Leu Thr Lys Gln Ile Val Thr
                485                 490                 495

Asp Asp Ile Ile Asn Asp Val Glu Glu
            500                 505

<210> SEQ ID NO 31
<211> LENGTH: 1546
<212> TYPE: DNA
<213> ORGANISM: Artificial Sequence
<220> FEATURE:
<223> OTHER INFORMATION: TaMRC 6B (cv. Kronos (4n))

<400> SEQUENCE: 31

```
ccagtatcaa atgaatcgag gaaaactaat gaagagaaac tgaaagttgc tgaacaggaa      60
cttgagaagc agagtttagg atggttagca gcacaacaag agttaaagga acttgcacaa     120
ctggcattca aagatacaga tgatatcaat ggtattatca ctgacttcaa acgtgtgagg     180
tctctgctag atgctgtacg ctctgaatta atctcttcaa aagatgcttt cgcttcctct     240
cgcagacaaa tagaagatca agcggttcag ttgcaggaac aagtacagga actcgaggac     300
caaagggtat tactgatgtc ttacacccat gatttggagg ctgctaaact ggagattcaa     360
gggaagacac aggagctcag ttacgcacag tctcgttgcc atgaacttga atcacagtta     420
cttcaggaaa gggagaaggt cgagtctcta gaagccgaat tagccaaaga aaacagagc     480 ttagaacata gaactgaaga agtaggcttt cttcagaagg agcttgttca gaaagaaaat     540
gagtgcacca aatcacaaga acttgttaaa gtaaaagagt ttgagctgtt agaagccaga     600
caggaagtcc aagacatgaa gttaaaggta gagtctattc aattggctgt tcaagaaaag     660
gattcagagc tttctgatac acagagcaga ctaactgaag tcagcagtga aattgctgag     720
cttcagcagt tgctaaatag caagaaggat caactgcttc aggctagaac tgaattacat     780
gataaagagc aacatataga aacactggag agtgagttgg atagcatacg gctcagatgc     840
tcgcaagctg aatccatggt tcaaaggatg gctgatctca ctggcgatct tgctagttcc     900
gtaaaagccg gagaaatgga catctatgca ttactggatg atgaaatttc aagcacaggt     960
acagccctcg agtccaattt gcataagcat aatcaactgg aggctgacat agagatgtta    1020
agagaatgct tgcggcataa ggacatggag ttgagagctg tcatgaagc acttgatgcc    1080 aaagatcaag agctgaaggc agtacttaga aagtgggatg tgaaggagcg ggaagtacgt    1140
gagttagaag agttaccgga tcccagtgcc acaaatgaac ttgctggttt ttccagtgag    1200
acaacagagg acggcattgt aggagagatg gagctcccag agcttcaaat tgaagctgtg    1260
gaggtcgaag cacttgctgc tacgactgca ttgaggaagc ttgcggatat gactaaggat    1320
ttcttcaaac acggcaaagc tgattctggt attgacttgg ttgcatcaga gagtcagaaa    1380
atcagtaaat gtgatcctaa aatggaagta cacaagaaga cggatgtgat tcttgaagct    1440 gaaaagaaa tagttaggct cttctcattg acaaaacaga ttgtcactga tgacataata    1500
aacgatgttg aggaatgata gcttcaaact gaagcatgta gtcttc                   1546
```

<210> SEQ ID NO 32
<211> LENGTH: 1546
<212> TYPE: DNA
<213> ORGANISM: Artificial Sequence
<220> FEATURE:
<223> OTHER INFORMATION: TaMRC 6B (cv. Cadenza (6n)

<400> SEQUENCE: 32

```
ccagtatcaa atgaatcgag gaaaactaat gaagagaaac tgaaagttgc tgaacaggaa      60
cttgagaagc agagtttagg atggttagca gcacaacaag agttaaagga acttgcacaa     120
ctggcattca aagatacaga tgatatcaat ggtattatca ctgacttcaa acgtgtgagg     180
tctctgctag atgctgtacg ctctgaatta atctcttcaa aagatgcttt cgcttcctct     240
cgcagacaaa tagaagatca agcggttcag ttgcaggaac aagtacagga actcgaggac     300
caaagggtat tactgatgtc ttacacccat gatttggagg ctgctaaact ggagattcaa     360
gggaagacac aggagctcag ttacgcacag tctcgttgtc atgaacttga atcacagtta     420
cttcaggaaa gggagaaggt cgagtctcta gaagccgaat tagccaaaga aaacagagc     480
```

```
ttagaacata gaactgaaga agtaggcttt cttcagaagg agcttgttca gaaagaaaat    540
gagtgcacca atcacaaga acttgttaaa gtaaaagagt ttgagctgtt agaagccaga    600
caggaagtcc aagacatgaa gttaaaggta gagtctattc aattggctgt tcaagaaaag    660
gattcagagc tttctgatac acagagcaga ctaactgaag tcagcagtga aattgctgag    720
cttcagcagt tgctaaatag caagaaggat caactgcttc aggctagaac tgaattacat    780
gataaagagc aacatataga aacactggag agtgagttgg atagcatacg gctcagatgc    840
tcgcaagctg aatccatggt tcaaaggatg gctgatctca ctggcgatct tgctagttcc    900
gtaaaagccg gagaaatgga catctatgca ttactggatg atgaaatttc aagcacaggt    960
acagccctcg agtccaattt gcataagcat aatcaactgg aggctgacat agagatgtta   1020
agagaatgct tgcggcataa ggacatggag ttgagagctg ctcatgaagc acttgatgcc   1080
aaagatcaag agctgaaggc agtacttaga agtgggatg tgaaggagcg ggaagtacgt    1140
gagttagaag agttaccgga tcccagtgcc acaaatgaac ttgctggttt ttccagtgag   1200
acaacagagg acggcattgt aggagagatg gagctcccag agcttcaaat tgaagctgtg   1260
gaggtcgaag cacttgctgc tacgactgca ttgaggaagc ttgcggatat gactaaggat   1320
ttcttcaaac acggcaaagc tgattctggt attgacttgg ttgcatcaga gagtcagaaa   1380
atcagtaaat gtgatcctaa aatggaagta cacaagaaga caaatgtgat tcttgaagct   1440
gaaaaagaaa tagttaggct cttctcattg acaaaacaga ttgtcactga tgacataata   1500
aacgatgttg aggaatgata gcttcaaact gaagcatgta gtcttc              1546
```

<210> SEQ ID NO 33
<211> LENGTH: 1518
<212> TYPE: DNA
<213> ORGANISM: Artificial Sequence
<220> FEATURE:
<223> OTHER INFORMATION: TaMRC 6B CDS (cv. Kronos (4n))

<400> SEQUENCE: 33

```
ccagtatcaa atgaatcgag gaaaactaat gaagagaaac tgaaagttgc tgaacaggaa     60
cttgagaagc agagtttagg atggttagca gcacaacaag agttaaagga acttgcacaa    120
ctggcattca aagatacaga tgatatcaat ggtattatca ctgacttcaa acgtgtgagg    180
tctctgctag atgctgtacg ctctgaatta atctcttcaa aagatgcttt cgcttcctct    240
cgcagacaaa tagaagatca agcggttcag ttgcaggaac aagtacagga actcgaggac    300
caaagggtat tactgatgtc ttacacccat gatttggagg ctgctaaact ggagattcaa    360
gggaagacac aggagctcag ttacgcacag tctcgttgcc atgaacttga atcacagtta    420
cttcaggaaa gggagaaggt cgagtctcta gaagccgaat tagccaaaga aaacagagc    480 ttagaacata gaactgaaga agtaggcttt cttcagaagg agcttgttca gaaagaaaat    540
gagtgcacca atcacaaga acttgttaaa gtaaaagagt ttgagctgtt agaagccaga    600
caggaagtcc aagacatgaa gttaaaggta gagtctattc aattggctgt tcaagaaaag    660
gattcagagc tttctgatac acagagcaga ctaactgaag tcagcagtga aattgctgag    720
cttcagcagt tgctaaatag caagaaggat caactgcttc aggctagaac tgaattacat    780
gataaagagc aacatataga aacactggag agtgagttgg atagcatacg gctcagatgc    840
tcgcaagctg aatccatggt tcaaaggatg gctgatctca ctggcgatct tgctagttcc    900
gtaaaagccg gagaaatgga catctatgca ttactggatg atgaaatttc aagcacaggt    960
acagccctcg agtccaattt gcataagcat aatcaactgg aggctgacat agagatgtta   1020
```

```
agagaatgct tgcggcataa ggacatggag ttgagagctg ctcatgaagc acttgatgcc    1080
aaagatcaag agctgaaggc agtacttaga aagtgggatg tgaaggagcg ggaagtacgt    1140
gagttagaag agttaccgga tcccagtgcc acaaatgaac ttgctggttt ttccagtgag    1200
acaacagagg acggcattgt aggagagatg gagctcccag agcttcaaat tgaagctgtg    1260
gaggtcgaag cacttgctgc tacgactgca ttgaggaagc ttgcggatat gactaaggat    1320
ttcttcaaac acggcaaagc tgattctggt attgacttgg ttgcatcaga gagtcagaaa    1380
atcagtaaat gtgatcctaa aatggaagta cacaagaaga cggatgtgat tcttgaagct    1440 gaaaagaaa tagttaggct cttctcattg acaaaacaga ttgtcactga tgacataata    1500
aacgatgttg aggaatga                                                  1518
```

<210> SEQ ID NO 34
<211> LENGTH: 1518
<212> TYPE: DNA
<213> ORGANISM: Artificial Sequence
<220> FEATURE:
<223> OTHER INFORMATION: TaMRC 6B CDS (cv. Cadenza (6n))

<400> SEQUENCE: 34

```
ccagtatcaa atgaatcgag gaaaactaat gaagagaaac tgaaagttgc tgaacaggaa     60
cttgagaagc agagtttagg atggttagca gcacaacaag agttaaagga acttgcacaa    120
ctggcattca aagatacaga tgatatcaat ggtattatca ctgacttcaa acgtgtgagg    180
tctctgctag atgctgtacg ctctgaatta atctcttcaa aagatgcttt cgcttcctct    240
cgcagacaaa tagaagatca agcggttcag ttgcaggaac aagtacagga actcgaggac    300
caaagggtat tactgatgtc ttacacccat gatttggagg ctgctaaact ggagattcaa    360
gggaagacac aggagctcag ttacgcacag tctcgttgtc atgaacttga atcacagtta    420
cttcaggaaa gggagaaggt cgagtctcta aagccgaat tagccaaaga aaacagagc    480 ttagaacata gaactgaaga agtaggcttt cttcagaagg agcttgttca gaaagaaaat    540
gagtgcacca atcacaaga acttgttaaa gtaaaagagt ttgagctgtt agaagccaga    600
caggaagtcc aagacatgaa gttaaaggta gagtctattc aattggctgt tcaagaaaag    660
gattcagagc tttctgatac acagagcaga ctaactgaag tcagcagtga aattgctgag    720
cttcagcagt tgctaaatag caagaaggat caactgcttc aggctagaac tgaattacat    780
gataaagagc aacatataga aacactggag agtgagttgg atagcatacg gctcagatgc    840
tcgcaagctg aatccatggt tcaaggatg gctgatctca ctggcgatct tgctagttcc    900
gtaaaagccg gagaaatgga catctatgca ttactggatg atgaaatttc aagcacaggt    960
acagccctcg agtccaattt gcataagcat aatcaactgg aggctgacat agagatgtta    1020
agagaatgct tgcggcataa ggacatggag ttgagagctg ctcatgaagc acttgatgcc    1080
aaagatcaag agctgaaggc agtacttaga aagtgggatg tgaaggagcg ggaagtacgt    1140
gagttagaag agttaccgga tcccagtgcc acaaatgaac ttgctggttt ttccagtgag    1200
acaacagagg acggcattgt aggagagatg gagctcccag agcttcaaat tgaagctgtg    1260
gaggtcgaag cacttgctgc tacgactgca ttgaggaagc ttgcggatat gactaaggat    1320
ttcttcaaac acggcaaagc tgattctggt attgacttgg ttgcatcaga gagtcagaaa    1380
atcagtaaat gtgatcctaa aatggaagta cacaagaaga caatgtgat tcttgaagct    1440 gaaaagaaa tagttaggct cttctcattg acaaaacaga ttgtcactga tgacataata    1500
```

```
aacgatgttg aggaatga                                               1518

<210> SEQ ID NO 35
<211> LENGTH: 1328
<212> TYPE: DNA
<213> ORGANISM: Artificial Sequence
<220> FEATURE:
<223> OTHER INFORMATION: TaMRC 6B upstream sequence (cv. Kronos (4n))

<400> SEQUENCE: 35
ctgaggcggc cgtttcaggg gcgccgattt ctgtttggca acgatgatgg cgtcaagagg     60
agcttgggtc gcggctcggg ctttggtagt cggatcttcc cggcgtgccc gaggtgctct    120
ttagggcacg gtcggcgcaa gtcctgcata tttcccttgt gaggctcgtc gtcaaagtcg    180
aagttgtcgg ttgttggcgc gtgtggccat ctgttggcat gtgccgtctt tgctctgtgt    240
agctgtttgc gagggcgact tgttggtgga gctctatggt gaagtcggag tcgcccgttc    300
ggagataacc ggtgatgacg atgacgcttg cgactcccg acgttcttct ttgcagctca     360
tgtttcatgt cggtggacag gttggccggt ggtgcccatg ttatatgggt tgggttgtat    420
tggttttagc ccggttttcc gtcaattaac cgggcaattc ttatttcttc ttaatcaatg    480
aaaatggcaa gtcttttgcc tcgtttcaaa aaaaataaaa ataggagtaa ctgagctgca    540
gttatcgtcg cccgcgagtg gtacacatca attgacataa agagctacgt caacggagaa    600
ttactccaaa atctccagcc caatcgacag agacgattcg ttaccttgtc accgcccctt    660
ggcgttgccc gacgagtcct ctcctgccca ccctgtctct tggttcgcag gaacgattca    720
tcctgaccgc aaacgtccgt ccgccggcaa ggtcaacaac atcaagcacc tcgcacagat    780
cgcgtcgacc aacccgcgcc tccttcgttc ccatgtgtgc ggtccatgat tttttttct     840 cgtttgatga tggacacgaa agcgattact acagaccgaa ggcccaatag gcccaattaa    900
cagcagatgg tggattttgt tacgggagca gcggccaaat ccatgtgcgc gacctgcata    960
gcgaaggaag cccaggcagg attagaggag gatccaatgg ccagaaacac ccactacttg   1020
agatccgacg gctaaaaacg gtaatggcct gagagagcta aagagtgca cggttatata    1080 atgtatttaa atttggaaca gaaagaaaaa aggtagtaag acgagtgaac ggggaagaaa   1140
agcagtagaa ggcaaacgac gcagctctct ctcacgcttc tcccgtggtc gacgttgcag   1200
tccacacgcg ggcgggcacg cggctgggcg cgccggttcc accacctcat ctcccgcact   1260
ccctctgcct cgtatctcgt cgccttcctc cacaccccgc aggagcattg ccagccgtcc   1320
gatcgcgc                                                          1328

<210> SEQ ID NO 36
<211> LENGTH: 2000
<212> TYPE: DNA
<213> ORGANISM: Artificial Sequence
<220> FEATURE:
<223> OTHER INFORMATION: TaMRC 6B promoter sequence (cv. Cadenza (6n))

<400> SEQUENCE: 36
ctggatctgg tcgggcgtgg ctggatccgg gcgttcttcg ggggttttct gctgcagcct     60
gttcgttgtc tccgcgtggt gcggttcctg cggcgtggcg gcggtgacct cctgccccaa    120
ggcctggtga gggcgacggc gtgaggtcgg cccgatggcg gtgacggtgg tgtgcgtcca    180
gggcccggca tctggtcggg cgggcgcgcg ggacggcctt ggcaggggcg ggcactgacg    240
ggaggctccc ctcggtgctc tgcggtgctg gtttggtgga ggttttaggg aggcttgatg    300
gaggtctgtg gctggccggt acgggctggt ggtggtcgag catctcaggg agaaatcctt    360
```

-continued

| | |
|---|---|
| cttccggcct tgccggagc tggcgacggc ggcgcctgtg ggcgtcgcgc tctttcctgg | 420 |
| aagcgtcgtc gatgtatggt gctccacccc tcaccccgcg gccttggctc cggagggaaa | 480 |
| cctctgatct gcgggatcgg gcgatgaagg cgtcttcacg tcttcttcct ccttgggggc | 540 |
| atcgtcttgg agccggctac aacctgagac cggtggatgg cggcatcttc gccgcatgga | 600 |
| agggcgacat cttcgtcgcg tgggatggcg gcatcttcgc cgcgtggaag ggcgacatct | 660 |
| tcgctgcgtg gtttgctgag gcggccgttt caggggcgcc gatttctgtt tggcaacgat | 720 |
| aatggcgtca agaggagctt gggtcgcggc tcgggctttg gtagtcggat cttcccggcg | 780 |
| tgcccgaggt gctctttagg gcacggtcgg cgcaagtcct gcatatttcc cttgtgaggc | 840 |
| tcgtcgtcaa agtcgaagtt gtcggttgtt ggcgcgtgtg gccatctgtt ggcatgtgcc | 900 |
| gtctttgctc tgtgtagttg tttgcgaggg cgacttgttg gtggagctct atggtgaagt | 960 |
| cggagtcgcc cgttcggaga taaccggtga tgacgatgac gcttgcgact ccccggcgtt | 1020 |
| cttctttgca gctcatgttt catgtcggtg gacaggttgg ccggtggtgc ccatgttata | 1080 |
| tgggttgggt tgtattggtt ttagcccggt tttccgtcaa ttaaccgggc aattcttatt | 1140 |
| tcttcttaat caatgaaaat ggcaagtctt ttgcctcgtt tcaaaaaaaa aaataggagt | 1200 |
| aactgagctg cagttatcgt cgcccgcgag tggtacacat caattgacat aaagagctac | 1260 |
| gtcaacggag aattactcca aaatctccag cccaatcgac agagacgatt cgttaccttg | 1320 |
| tcaccgcccc ttggcgttgc ccgacgagtc ctctcctgcc caccctgtct cttggttcgc | 1380 |
| aggaacgatt catcctgacc gcaaacgtcc gtccgccggc aaggtcaaca acatcaagca | 1440 |
| cctcgcacag atcgcgtcga ccaacccgcg cctccttcgt tcccatgtgt gcggtccatg | 1500 |
| attttttttt ctcgtttgat gatggacacg aaagcgatta ctacagaccg aaggcccaat | 1560 |
| aggcccaatt aacagcagat ggtggatttt gttacggag cagcggccaa atccatgtgc | 1620 |
| gcgacctgca tagcgaagga agcccaggca ggattagagg aggatccaat ggccagaaac | 1680 |
| acccactact tgagatccga cggctaaaaa cggtaatggc ctgagagagc tagaagagtg | 1740 |
| cacggttata taatgtattt aaatttggaa cagaaagaaa aaaggtagta agacgagtga | 1800 |
| acggggaaga aaagcagtag aaggcaaacg gcgcagctct ctctcacgct tctcccgtgg | 1860 |
| tcgacgttgc agtccacacg cgggcgggca cgcggctggg cgcgccggtt ccaccacctc | 1920 |
| atctcccgca ctccctctgc ctcgtatctc gtcgccttcc tccacacccc gcaggagcat | 1980 |
| tgccagccgt ccgatcgcgc | 2000 |

<210> SEQ ID NO 37
<211> LENGTH: 6
<212> TYPE: PRT
<213> ORGANISM: Artificial Sequence
<220> FEATURE:
<223> OTHER INFORMATION: Conserved domain of the MRC nucleic acid
     (coding)
<220> FEATURE:
<221> NAME/KEY: X1
<222> LOCATION: (2)..(2)
<223> OTHER INFORMATION: Either L or F
<220> FEATURE:
<221> NAME/KEY: X2
<222> LOCATION: (3)..(3)
<223> OTHER INFORMATION: Either D or E
<220> FEATURE:
<221> NAME/KEY: X3
<222> LOCATION: (4)..(4)
<223> OTHER INFORMATION: Either K or R

<400> SEQUENCE: 37

```
Leu Xaa Xaa Xaa Leu Phe
1               5

<210> SEQ ID NO 38
<211> LENGTH: 783
<212> TYPE: PRT
<213> ORGANISM: Artificial Sequence
<220> FEATURE:
<223> OTHER INFORMATION: Arabidopsis thaliana AtMRC

<400> SEQUENCE: 38

Met Gly Phe Ser Gln Ala Ile Arg Leu Asn Leu Ala Ser Phe Ser Ser
1               5                   10                  15

Pro Ser Pro Cys Asp Tyr Cys Leu Thr Arg Val Val Asn His Lys Gln
                20                  25                  30

Lys Ser Leu Val Ala Phe Pro Ser Ile Thr Arg Arg Lys Arg His Leu
            35                  40                  45

Leu Leu Ser Val Gln Ser Val Leu His Asn Thr Arg Pro Asn Ile Asn
        50                  55                  60

Asp Asn Gly Ser Ala Glu Ser Ala Asn Val Leu Phe Asp Lys Leu Phe
65                  70                  75                  80

Ala Arg Thr His Arg Leu Glu Arg Gln Thr Asn Gln His Ser Val Tyr
                85                  90                  95

Pro Asp Asp Asp Leu Pro Tyr Ser Asn Leu Gly Val Leu Glu Ser
                100                 105                 110

Asp Leu Glu Ala Ala Leu Val Ala Leu Leu Lys Arg Glu Glu Asp Leu
            115                 120                 125

His Asp Ala Glu Arg Lys Leu Leu Ser Asp Lys Asn Lys Leu Asn Arg
        130                 135                 140

Ala Lys Glu Glu Leu Glu Lys Arg Glu Lys Thr Ile Ser Glu Ala Ser
145                 150                 155                 160

Leu Lys His Glu Ser Leu Gln Glu Glu Leu Lys Arg Ala Asn Val Glu
                165                 170                 175

Leu Ala Ser Gln Ala Arg Glu Ile Glu Glu Leu Lys His Lys Leu Arg
            180                 185                 190

Glu Arg Asp Glu Glu Arg Ala Ala Leu Gln Ser Ser Leu Thr Leu Lys
        195                 200                 205

Glu Glu Glu Leu Glu Lys Met Arg Gln Glu Ile Ala Asn Arg Ser Lys
210                 215                 220

Glu Val Ser Met Ala Ile Ser Glu Phe Glu Ser Lys Ser Gln Leu Leu
225                 230                 235                 240

Ser Lys Ala Asn Glu Val Val Lys Arg Gln Glu Gly Glu Ile Tyr Ala
                245                 250                 255

Leu Gln Arg Ala Leu Glu Glu Lys Glu Glu Leu Glu Ile Ser Lys
            260                 265                 270

Ala Thr Lys Lys Leu Glu Gln Glu Lys Leu Arg Glu Thr Glu Ala Asn
        275                 280                 285

Leu Lys Lys Gln Thr Glu Glu Trp Leu Ile Ala Gln Asp Glu Val Asn
290                 295                 300

Lys Leu Lys Glu Glu Thr Val Lys Arg Leu Gly Glu Ala Asn Glu Thr
305                 310                 315                 320

Met Glu Asp Phe Met Lys Val Lys Lys Leu Leu Thr Asp Val Arg Phe
                325                 330                 335

Glu Leu Ile Ser Ser Arg Glu Ala Leu Val Phe Ser Arg Glu Gln Met
            340                 345                 350
```

```
Glu Glu Lys Glu Leu Leu Glu Lys Gln Leu Glu Glu Leu Glu Glu
            355                 360                 365

Gln Arg Lys Ser Val Leu Ser Tyr Met Gln Ser Leu Arg Asp Ala His
    370                 375                 380

Thr Glu Val Glu Ser Glu Arg Val Lys Leu Arg Val Val Glu Ala Lys
385                 390                 395                 400

Asn Phe Ala Leu Glu Arg Glu Ile Ser Val Gln Lys Glu Leu Leu Glu
                405                 410                 415

Asp Leu Arg Glu Glu Leu Gln Lys Glu Lys Pro Leu Leu Glu Leu Ala
            420                 425                 430

Met His Asp Ile Ser Val Ile Gln Asp Glu Leu Tyr Lys Lys Ala Asn
            435                 440                 445

Ala Phe Gln Val Ser Gln Asn Leu Leu Gln Glu Lys Glu Ser Ser Leu
            450                 455                 460

Val Glu Ala Lys Leu Glu Ile Gln His Leu Lys Ser Glu Gln Ala Ser
465                 470                 475                 480

Leu Glu Leu Leu Leu Gln Glu Lys Asp Glu Glu Leu Ala Glu Ala Arg
                485                 490                 495

Asn Lys Leu Gly Glu Val Asn Gln Glu Val Thr Glu Leu Lys Ala Leu
            500                 505                 510

Met Ile Ser Arg Glu Asp Gln Leu Met Glu Ala Thr Glu Met Leu Lys
            515                 520                 525

Glu Lys Asp Val His Leu His Arg Ile Glu Gly Glu Leu Gly Ser Ser
            530                 535                 540

Lys Leu Lys Val Thr Glu Ala Glu Met Val Val Glu Arg Ile Ala Glu
545                 550                 555                 560

Leu Thr Asn Arg Leu Leu Met Ser Thr Thr Asn Gly Gln Asn Gln Asn
                565                 570                 575

Ala Met Arg Ile Asn Asn Glu Ile Ser Ile Asp Ser Met Gln Gln Pro
            580                 585                 590

Leu Glu Lys Pro His Asp Asp Tyr Gly Met Glu Asn Lys Arg Leu Val
            595                 600                 605

Met Glu Leu Ser Phe Thr Arg Glu Asn Leu Arg Met Lys Glu Met Glu
            610                 615                 620

Val Leu Ala Val Gln Arg Ala Leu Thr Phe Lys Asp Glu Glu Ile Asn
625                 630                 635                 640

Val Val Met Gly Arg Leu Glu Ala Lys Glu Gln Glu Leu Lys Lys Leu
                645                 650                 655

Lys Glu Glu Thr Ile Asn Asp Ser Glu Asp Leu Lys Val Leu Tyr Ala
            660                 665                 670

Leu Ala Gln Glu Arg Val Gly Glu Lys Thr Met Gly Asp Leu Ala Ile
            675                 680                 685

Glu Met Leu Gln Leu Glu Ala Ala Asn Leu Glu Val Glu Ala Ala Thr
            690                 695                 700

Ser Ala Leu Gln Lys Leu Ala Lys Met Ser Thr Glu Leu Leu Thr Gln
705                 710                 715                 720

Ala Asp Met Ser Ile Glu Ala Asp Thr Thr His Thr Val Met Pro Glu
                725                 730                 735

Arg Gly Tyr Ser Glu Gly Ser Asn Glu Cys Leu Gly Glu Val Lys Thr
            740                 745                 750

Glu Val Val Arg Leu Trp Ser Leu Thr Glu Lys Leu Leu Glu Asn Ala
            755                 760                 765
```

Gly Ile Val Ala Gly Thr Ser Thr Cys Met Glu Gly Val Ile Leu
            770                 775                 780

<210> SEQ ID NO 39
<211> LENGTH: 23
<212> TYPE: DNA
<213> ORGANISM: Artificial Sequence
<220> FEATURE:
<223> OTHER INFORMATION: TaMRC target sequence 1

<400> SEQUENCE: 39
gcggccatgc gcctctccat cgg                                            23

<210> SEQ ID NO 40
<211> LENGTH: 23
<212> TYPE: DNA
<213> ORGANISM: Artificial Sequence
<220> FEATURE:
<223> OTHER INFORMATION: SEQ ID NO: 40: TaMRC target sequence 2

<400> SEQUENCE: 40
caggcagaag ctgagtttca tgg                                            23

<210> SEQ ID NO 41
<211> LENGTH: 23
<212> TYPE: DNA
<213> ORGANISM: Artificial Sequence
<220> FEATURE:
<223> OTHER INFORMATION: SEQ ID NO: 41: TaMRC target sequence 3

<400> SEQUENCE: 41
attagatcaa atataactga tgg                                            23

<210> SEQ ID NO 42
<211> LENGTH: 23
<212> TYPE: DNA
<213> ORGANISM: Artificial Sequence
<220> FEATURE:
<223> OTHER INFORMATION: TaMRC target sequence 4

<400> SEQUENCE: 42
aatataactg atggtgataa tgg                                            23

<210> SEQ ID NO 43
<211> LENGTH: 20
<212> TYPE: DNA
<213> ORGANISM: Artificial Sequence
<220> FEATURE:
<223> OTHER INFORMATION: TaMRC protospacer sequence 1

<400> SEQUENCE: 43
gcggccatgc gcctctccat                                                20

<210> SEQ ID NO 44
<211> LENGTH: 20
<212> TYPE: DNA
<213> ORGANISM: Artificial Sequence
<220> FEATURE:
<223> OTHER INFORMATION: TaMRC protospacer sequence 2

<400> SEQUENCE: 44
caggcagaag ctgagtttca                                                20

<210> SEQ ID NO 45
<211> LENGTH: 20
<212> TYPE: DNA

```
<213> ORGANISM: Artificial Sequence
<220> FEATURE:
<223> OTHER INFORMATION: TaMRC protospacer sequence 3

<400> SEQUENCE: 45
attagatcaa atataactga                                                   20

<210> SEQ ID NO 46
<211> LENGTH: 20
<212> TYPE: DNA
<213> ORGANISM: Artificial Sequence
<220> FEATURE:
<223> OTHER INFORMATION: TaMRC protospacer sequence 4

<400> SEQUENCE: 46
aatataactg atggtgataa                                                   20

<210> SEQ ID NO 47
<211> LENGTH: 83
<212> TYPE: RNA
<213> ORGANISM: Artificial Sequence
<220> FEATURE:
<223> OTHER INFORMATION: tracrRNA sequence

<400> SEQUENCE: 47
guuuuagagc uagaaauagc aaguuaaaau aaggcuaguc cguuaucaac uugaaaaagu       60
ggcaccgagu cggugcuuuu uuu                                               83

<210> SEQ ID NO 48
<211> LENGTH: 103
<212> TYPE: DNA
<213> ORGANISM: Artificial Sequence
<220> FEATURE:
<223> OTHER INFORMATION: TaMRC complete sgRNA-encoding nucleic acid
      sequence 1

<400> SEQUENCE: 48
gcggccatgc gcctctccat gttttagagc tagaaatagc aagttaaaat aaggctagtc       60
cgttatcaac ttgaaaaagt ggcaccgagt cggtgctttt ttt                        103

<210> SEQ ID NO 49
<211> LENGTH: 103
<212> TYPE: DNA
<213> ORGANISM: Artificial Sequence
<220> FEATURE:
<223> OTHER INFORMATION: TaMRC complete sgRNA-encoding nucleic acid
      sequence 2

<400> SEQUENCE: 49
caggcagaag ctgagtttca gttttagagc tagaaatagc aagttaaaat aaggctagtc       60
cgttatcaac ttgaaaaagt ggcaccgagt cggtgcttt ttt                         103

<210> SEQ ID NO 50
<211> LENGTH: 103
<212> TYPE: DNA
<213> ORGANISM: Artificial Sequence
<220> FEATURE:
<223> OTHER INFORMATION: TaMRC complete sgRNA-encoding nucleic acid
      sequence 3

<400> SEQUENCE: 50
attagatcaa atataactga gttttagagc tagaaatagc aagttaaaat aaggctagtc       60
cgttatcaac ttgaaaaagt ggcaccgagt cggtgctttt ttt                        103
```

```
<210> SEQ ID NO 51
<211> LENGTH: 103
<212> TYPE: DNA
<213> ORGANISM: Artificial Sequence
<220> FEATURE:
<223> OTHER INFORMATION: TaMRC complete sgRNA-encoding nucleic acid
      sequence 4

<400> SEQUENCE: 51
aatataactg atggtgataa gttttagagc tagaaatagc aagttaaaat aaggctagtc    60
cgttatcaac ttgaaaaagt ggcaccgagt cggtgctttt ttt                     103

<210> SEQ ID NO 52
<211> LENGTH: 103
<212> TYPE: RNA
<213> ORGANISM: Artificial Sequence
<220> FEATURE:
<223> OTHER INFORMATION: TaMRC complete sgRNA RNA sequence 1

<400> SEQUENCE: 52
gcggccaugc gccucuccau guuuuagagc uagaaauagc aaguuaaaau aaggcuaguc    60
cguuaucaac uugaaaaagu ggcaccgagu cggugcuuuu uuu                     103

<210> SEQ ID NO 53
<211> LENGTH: 103
<212> TYPE: RNA
<213> ORGANISM: Artificial Sequence
<220> FEATURE:
<223> OTHER INFORMATION: TaMRC complete sgRNA RNA sequence 2

<400> SEQUENCE: 53
caggcagaag cugaguuuca guuuuagagc uagaaauagc aaguuaaaau aaggcuaguc    60
cguuaucaac uugaaaaagu ggcaccgagu cggugcuuuu uuu                     103

<210> SEQ ID NO 54
<211> LENGTH: 103
<212> TYPE: RNA
<213> ORGANISM: Artificial Sequence
<220> FEATURE:
<223> OTHER INFORMATION: TaMRC complete sgRNA RNA sequence 3

<400> SEQUENCE: 54
auuagaucaa auauaacuga guuuuagagc uagaaauagc aaguuaaaau aaggcuaguc    60
cguuaucaac uugaaaaagu ggcaccgagu cggugcuuuu uuu                     103

<210> SEQ ID NO 55
<211> LENGTH: 103
<212> TYPE: RNA
<213> ORGANISM: Artificial Sequence
<220> FEATURE:
<223> OTHER INFORMATION: TaMRC complete sgRNA RNA sequence 4

<400> SEQUENCE: 55
aauauaacug auggugauaa guuuuagagc uagaaauagc aaguuaaaau aaggcuaguc    60
cguuaucaac uugaaaaagu ggcaccgagu cggugcuuuu uuu                     103

<210> SEQ ID NO 56
<211> LENGTH: 4203
<212> TYPE: DNA
<213> ORGANISM: Artificial Sequence
<220> FEATURE:
<223> OTHER INFORMATION: Cas9 sequence
```

<400> SEQUENCE: 56

```
atggctccta agaagaagcg gaaggttggt attcacgggg tgcctgcggc tgacaagaag      60
tactccatcg gcctcgacat cggcaccaac agcgtcggct gggcggtgat caccgacgag     120
tacaaggtcc cgtccaagaa gttcaaggtc ctgggcaaca ccgaccgcca ctccatcaag     180
aagaacctca tcggcgccct cctcttcgac tccggcgaga cggcggaggc gacccgcctc     240
aagcgcaccg cccgccgccg ctacacccgc gcaagaacc gcatctgcta cctccaggag     300
atcttctcca acgagatggc gaaggtcgac gactccttct ccaccgcct cgaggagtcc     360
ttcctcgtgg aggaggacaa gaagcacgag cgccaccca tcttcggcaa catcgtcgac     420
gaggtcgcct accacgagaa gtaccccact atctaccacc ttcgtaagaa gcttgttgac     480
tctactgata aggctgatct tcgtctcatc taccttgctc tcgctcacat gatcaagttc     540
cgtggtcact tccttatcga gggtgacctt aaccctgata actccgacgt ggacaagctc     600
ttcatccagc tcgtccagac ctacaaccag ctcttcgagg agaaccctat caacgcttcc     660
ggtgtcgacg ctaaggcgat cctttccgct aggctctcca gtccaggcg tctcgagaac     720
ctcatcgccc agctccctgg tgagaagaag aacggtcttt cggtaaccct catcgctctc     780
tccctcggtc tgacccctaa cttcaagtcc aacttcgacc tcgctgagga cgctaagctt     840
cagctctcca aggataccta cgacgatgat ctcgacaacc tcctcgctca gattggagat     900
cagtacgctg atctcttcct tgctgctaag aacctctccg atgctatcct cctttcggat     960
atccttaggg ttaacactga gatcactaag gctcctcttt ctgcttccat gatcaagcgc    1020
tacgacgagc accaccagga cctcacccctc ctcaaggctc ttgttcgtca gcagctcccc    1080
gagaagtaca aggagatctt cttcgaccag tccaagaacg gctacgccgg ttacattgac    1140
ggtggagcta gccaggagga gttctacaag ttcatcaagc caatccttga gaagatggat    1200
ggtactgagg agcttctcgt taagcttaac cgtgaggacc tccttaggaa gcagaggact    1260
ttcgataacg gctctatccc tcaccagatc caccttggtg agcttcacgc catccttcgt    1320
aggcaggagg acttctaccc tttcctcaag gacaaccgtg agaagatcga aagatccttg    1380
actttccgta ttccttacta cgttggtcct cttgctcgtg gtaactcccg tttcgcttgg    1440
atgactagga agtccgagga gactatcacc ccttggaact tcgaggaggt tgttgacaag    1500
ggtgcttccg cccagtcctt catcgagcgc atgaccaact tcgacaagaa cctccccaac    1560
gagaaggtcc tccccaagca ctccctcctc tacgagtact tcacggtcta caacgagctc    1620
accaaggtca agtacgtcac cgagggtatg cgcaagcctg ccttcctctc cggcgagcag    1680
aagaaggcta tcgttgacct cctcttcaag accaaccgca aggtcaccgt caagcagctc    1740
aaggaggact acttcaagaa gatcgagtgc ttcgactccg tcgagatcag cggcgttgag    1800
gaccgttttca acgcttctct cggtacctac cacgatctcc tcaagatcat caaggacaag    1860
gacttcctcg acaacgagga gaacgaggac atcctcgagg acatcgtcct cactcttact    1920
ctcttcgagg atagggagat gatcgaggag aggctcaaga cttacgctca tctcttcgat    1980
gacaaggtta tgaagcagct caagcgtcgc cgttacaccg gttgggggtag gctctcccgc    2040
aagctcatca acggtatcag ggataagcag agcggcaaga ctatcctcga cttcctcaag    2100
tctgatggtt tcgctaacag gaacttcatg cagctcatcc acgatgactc tcttaccttc    2160
aaggaggata ttcagaaggc tcaggtgtcc ggtcagggcg actctctcca cgagcacatt    2220
gctaaccttg ctggttcccc tgctatcaag aagggcatcc ttcagactgt taaggttgtc    2280
gatgagcttg tcaaggttat gggtcgtcac aagcctgaga acatcgtcat cgagatggct    2340
```

```
cgtgagaacc agactaccca gaagggtcag aagaactcga gggagcgcat gaagaggatt   2400
gaggagggta tcaaggagct tggttctcag atccttaagg agcaccctgt cgagaacacc   2460
cagctccaga acgagaagct ctacctctac tacctccaga acggtaggga tatgtacgtt   2520
gaccaggagc tcgacatcaa caggcttcct gactacgacg tcgaccacat tgttcctcag   2580
tctttcctta aggatgactc catcgacaac aaggtcctca cgaggtccga caagaacagg   2640
ggtaagtcgg acaacgtccc ttccgaggag gttgtcaaga agatgaagaa ctactggagg   2700
cagcttctca acgctaagct cattacccag aggaagttcg acaacctcac gaaggctgag   2760
aggggtggcc tttccgagct tgacaaggct ggtttcatca agaggcagct tgttgagacg   2820
aggcagatta ccaagcacgt tgctcagatc ctcgattcta ggatgaacac caagtacgac   2880
gagaacgaca agctcatccg cgaggtcaag gtgatcaccc tcaagtccaa gctcgtctcc   2940
gacttccgca aggacttcca gttctacaag gtccgcgaga tcaacaacta ccaccacgct   3000
cacgatgctt accttaacgc tgtcgttggt accgctctta tcaagaagta ccctaagctt   3060
gagtccgagt tcgtctacgg tgactacaag gtctacgacg ttcgtaagat gatcgccaag   3120
tccgagcagg agatcggcaa ggccaccgcc aagtacttct tctactccaa catcatgaac   3180
ttcttcaaga ccgagatcac cctcgccaac ggcgagatcc gcaagcgccc tcttatcgag   3240
acgaacggtg agactggtga gatcgtttgg gacaagggtc gcgacttcgc tactgttcgc   3300
aaggtccttt ctatgcctca ggttaacatc gtcaagaaga ccgaggtcca gaccggtggc   3360
ttctccaagg agtctatcct tccaaagaga aactcggaca agctcatcgc taggaagaag   3420
gattgggacc ctaagaagta cggtggtttc gactccccta ctgtcgccta ctccgtcctc   3480
gtggtcgcca aggtggagaa gggtaagtcg aagaagctca gtccgtcaa ggagctcctc   3540
ggcatcacca tcatggagcg ctcctccttc gagaagaacc cgatcgactt cctcgaggcc   3600
aagggctaca aggaggtcaa gaaggacctc atcatcaagc tccccaagta ctctcttttc   3660
gagctcgaga acggtcgtaa gaggatgctg gcttccgctg gtgagctcca gaagggtaac   3720
gagcttgctc ttccttccaa gtacgtgaac ttcctctacc tcgcctccca ctacgagaag   3780
ctcaagggtt cccctgagga taacgagcag aagcagctct tcgtggagca gcacaagcac   3840
tacctcgacg agatcatcga gcagatctcc gagttctcca gcgcgtcat cctcgctgac   3900
gctaacctcg acaaggtcct ctccgcctac aacaagcacc gcgacaagcc catccgcgag   3960
caggccgaga acatcatcca cctcttcacg ctcacgaacc tcggcgcccc tgctgctttc   4020
aagtacttcg acaccaccat cgacaggaag cgttacacgt ccaccaagga ggttctcgac   4080
gctactctca tccaccagtc catcaccggt ctttacgaga ctcgtatcga cctttcccag   4140
cttggtggtg ataagcgtcc tgctgccacc aaaaaggccg acaggctaa gaaaaagaag   4200
tag                                                                4203
```

<210> SEQ ID NO 57  
<211> LENGTH: 561  
<212> TYPE: DNA  
<213> ORGANISM: Artificial Sequence  
<220> FEATURE:  
<223> OTHER INFORMATION: Cys 4 endoribonuclease nucleic acid sequence

<400> SEQUENCE: 57

```
atggaccact acctcgacat caggctcagg ccagacccag agttcccacc agcccagctc     60
atgtccgtcc tcttcggcaa gctccaccag gccctcgtgg cccagggcgg cgacaggatc    120
```

```
ggcgtgtcct tcccagacct cgacgagtcc aggtccaggc tcggcgagag gctccgcatc     180
cacgcctccg ccgacgacct cagggccctc ctcgccaggc cgtggctgga gggcctcagg     240
gaccacctcc agttcggcga gccagccgtg gtgccacacc caaccccata caggcaagtg     300
tccagggtgc aagccaagtc caacccagag aggctcagga ggaggctcat gaggaggcac     360
gacctctccg aggaagaggc caggaagcgc atcccagaca ccgtggccag ggccctcgac     420
ctcccattcg tgaccctcag gtcccagtcc accggccagc acttccgcct cttcatcagg     480
cacggcccac tccaggtgac cgccgaggag ggcggcttta cctgctacgg cctctccaag     540
ggcggcttcg tgccgtggtt c                                              561

<210> SEQ ID NO 58
<211> LENGTH: 363
<212> TYPE: DNA
<213> ORGANISM: Artificial Sequence
<220> FEATURE:
<223> OTHER INFORMATION: Wheat U6 promoter

<400> SEQUENCE: 58
gaccaagccc gttattctga cagttctggt gctcaacaca tttatattta tcaaggagca     60
cattgttact cactgctagg agggaatcga actaggaata ttgatcagag gaactacgag    120
agagctgaag ataactgccc tctagctctc actgatctgg gtcgcatagt gagatgcagc    180
ccacgtgagt tcagcaacgg tctagcgctg ggcttttagg cccgcatgat cgggcttttg    240
tcgggtggtc gacgtgttca cgattgggga gagcaacgca gcagttcctc ttagtttagt    300
cccacctcgc ctgtccagca gagttctgac cggtttataa actcgcttgc tgcatcagac    360
ttg                                                                  363

<210> SEQ ID NO 59
<211> LENGTH: 982
<212> TYPE: DNA
<213> ORGANISM: Artificial Sequence
<220> FEATURE:
<223> OTHER INFORMATION: Maize Ubiquitin1 promoter

<400> SEQUENCE: 59
tgcagtgcag cgtgacccgg tcgtgcccct ctctagagat aatgagcatt gcatgtctaa     60
gttataaaaa attaccacat attttttttg tcacacttgt ttgaagtgca gtttatctat    120
ctttatacat atatttaaac tttactctac gaataatata atctatagta ctacaataat    180
atcagtgttt tagagaatca tataaatgaa cagttagaca tggtctaaag gacaattgag    240
tattttgaca acaggactct acagttttat cttttagtg tgcatgtgtt ctccttttt     300 tttgcaaata gcttcaccta tataatactt catccatttt attagtacat ccatttaggg    360
tttagggtta atggttttta tagactaatt tttttagtac atctattta ttctatttta    420 gcctctaaat taagaaaact aaaactctat tttagttttt ttatttaata atttagatat    480
aaaatagaat aaaataaagt gactaaaaat taaacaaata ccctttaaga aattaaaaaa    540
actaaggaaa cattttttctt gtttcgagta gataatgcca gcctgttaaa cgccgtcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
ctccttcgct ttcccttcct cgcccgccgt aataaataga cacccctcc acaccctctt    900
```
tccccaacct cgtgttgttc ggagcgcaca cacacacaac cagatctccc ccaaatccac    960
ccgtcggcac ctccgcttca ag                                              982

<210> SEQ ID NO 60
<211> LENGTH: 770
<212> TYPE: PRT
<213> ORGANISM: Artificial Sequence
<220> FEATURE:
<223> OTHER INFORMATION: Solanum MRC StMRC (PGSC0003DMT400010993)

<400> SEQUENCE: 60

Met Ala Leu Pro Ala Leu Pro Arg Ala Thr Leu Ser Phe Ser Ser Leu
1               5                   10                  15

Cys Gln Pro Thr Glu Phe Cys Phe Met Arg Leu Glu Trp Lys Lys Arg
            20                  25                  30

Leu Val Leu Met Thr Ala His His Gly Arg Gly Pro Ser Ser Arg Ile
        35                  40                  45

Val Arg Ser Val Leu Asp Asn Arg Lys Ser Asn Ile Thr Gly Asp Glu
    50                  55                  60

Ala Thr Glu Pro Ala Arg Val Leu Leu Glu Arg Leu Phe Ala Gln Thr
65                  70                  75                  80

Gln Lys Leu Glu Gln Gln Ile Gly Arg Asn Ile Tyr Phe Pro Gln Val
                85                  90                  95

Ala Glu Leu Gly Leu Asn Leu Gly Lys Leu Glu Ser Asp Leu Gln Asp
            100                 105                 110

Ala Leu Ala Ala Leu Lys Lys Lys Glu Glu Asp Ile Gln Asp Thr Glu
        115                 120                 125

Arg Lys Val Leu Met Glu Tyr Asn Glu Leu Asn Arg Ala Lys Ile Glu
    130                 135                 140

Leu Glu Gln Arg Val Glu Glu Met Ala Ala Ala Asn Ser Arg Gln Glu
145                 150                 155                 160

Lys Leu Glu Asn Glu Leu Arg Gln Ala Asn Leu Ile Leu Val Ser Gln
                165                 170                 175

Ala Ala Glu Ile Glu Asp Leu Lys Phe Arg Phe Asn Glu Ile Asp Gln
            180                 185                 190

Glu Ile Ser Ala Ala Gln Thr Ala Leu Val Ser Lys Glu Asp Glu Ile
        195                 200                 205

Asn Lys Met Met Ile Glu Leu Lys Asn Lys Ser Asp Glu Val Ala Asn
    210                 215                 220

Thr Glu Ser Gln Leu Arg Thr Lys Gly Glu Leu Leu Asp Thr Ala Asn
225                 230                 235                 240

Glu Val Val Gln Arg Gln Glu Val Glu Leu Gln Asn Leu Gln Arg Glu
                245                 250                 255

Ile Gln Glu Lys Glu Lys Glu Leu Gln Val Phe Leu Thr Met Gln Lys
            260                 265                 270

Thr Glu Glu Glu Lys Leu Lys Val Ser Lys Ser Asn Leu Glu Lys Gln
        275                 280                 285

Ala Met Asp Trp Leu Ile Ala Lys Gln Glu Met Lys Lys Leu Glu Val
    290                 295                 300

Glu Thr Ser Asn Tyr Gly Gly Glu Ala Asn Arg Ser Leu Glu Asp Phe
305                 310                 315                 320

Arg Arg Val Lys Lys Leu Leu Ala Asp Val Arg Ser Glu Leu Val Ser
                325                 330                 335

Ser Gln Arg Ala Leu Thr Ser Ser Arg Lys Lys Met Glu Glu Gln Glu

```
                    340                 345                 350
Asn Leu Leu Glu Asp Arg Leu Glu Glu Leu Glu Glu Gln Arg Arg Ser
                355                 360                 365

Val Met Ser Tyr Met Thr Ser Leu Lys Glu Ala Gln Asn Glu Val Glu
            370                 375                 380

Asn Glu Lys Val Gln Leu Thr Val Ala Glu Ala Arg Asn Lys Glu Leu
385                 390                 395                 400

Glu Arg Asp Leu Ser Ile Glu Lys Glu Leu Val Glu Glu Leu Gln Thr
                405                 410                 415

Glu Asn Asn Ile Lys Lys Ser Ser Leu His Val Ala Ile Asn Glu Lys
            420                 425                 430

Ser Ala Leu Gln Glu Glu Leu Asp Cys Lys Ser Ala Glu Phe Gly Glu
        435                 440                 445

Thr Gln Asn Leu Leu Gln Val Lys Glu Ser Glu Leu Val Asp Ala Arg
        450                 455                 460

Leu Glu Ile Gln His Leu Lys Ser Gln Cys Ala Ser Leu Gln Leu Met
465                 470                 475                 480

Leu Glu Glu Lys Asp Lys Glu Leu Leu Asp Ser Arg Lys Thr Val Asp
                485                 490                 495

Glu Leu Asn Gln Glu Ile Ala Glu Leu Arg Val Asn Met Asn Ser Gln
            500                 505                 510

Glu Gln Gln Leu Ile Gln Ala Thr Ser Met Leu Lys Glu Lys Glu Glu
        515                 520                 525

Ser Met Gln Ile Met Gln Leu Glu Leu Asn Asp Thr Lys Met Lys Tyr
        530                 535                 540

Ser Glu Ala Glu Thr Val Val Glu His Met Val Asp Leu Thr Asn Lys
545                 550                 555                 560

Leu Val Ile Ser Val Lys Asp Asp Val Leu Ser Pro Leu Ser His Thr
                565                 570                 575

Asp Glu Met Trp Ser Ser Gln Leu Val Glu Lys Pro Thr Asp Ala Phe
            580                 585                 590

Arg Trp His Lys Asn Gln Leu Glu Asn Glu Leu Glu Leu Thr Arg Glu
        595                 600                 605

Ser Leu Arg Ser Arg Glu Met Asp Ser Leu Ala Ala Gln Arg Ala Leu
        610                 615                 620

Lys Leu Lys Glu Gln Glu Leu Lys Ile Val Arg Gln Lys Leu Asn Asp
625                 630                 635                 640

Arg Glu Glu Glu Ile Asn Lys Met Lys Asn Met Thr Arg Asp Ala Asp
                645                 650                 655

Gly Pro Arg Gln Ser Tyr Val Leu Ala Gln Glu Arg Thr Gly Glu Lys
            660                 665                 670

Ser Thr Gly Asp Leu Ala Val Glu Lys Leu Gln Phe Glu Gly Ala Gln
        675                 680                 685

Leu Glu Val Glu Ala Ala Thr Thr Ala Leu Gln Lys Leu Ala Glu Leu
        690                 695                 700

Ser Arg Asp Leu Leu Asn Lys Ala Ser Leu Thr Ile Glu Ala Asp Tyr
705                 710                 715                 720

Asp Ser Ser Leu Leu Val Asp Ile Pro Glu Thr Ala Ala Asn Val
                725                 730                 735

Ser Ser Ser Phe Glu Cys Leu Ala Glu Val Tyr Ser Glu Met Ala Gln
            740                 745                 750

Leu Ser Ala Leu Ser Glu Lys Leu Val Lys Glu Ala Gly Ile Leu Cys
        755                 760                 765
```

Pro Gln
    770

<210> SEQ ID NO 61
<211> LENGTH: 3877
<212> TYPE: DNA
<213> ORGANISM: Artificial Sequence
<220> FEATURE:
<223> OTHER INFORMATION: Solanum StMRC (PGSC0003DMG400004306) genomic

<400> SEQUENCE: 61

```
atggcgttgc cagccttacc gcgcgccact ttatcgtttt cctctctttg ccagccaacg      60
gaggtgaaag tctcttcttc ttttttgttg ttgttttctc cttatttatt ctgttcacag     120
agtatttttt tttacatttt cctacatttc aatttcttca atgggatctt ttgctttttc     180
tgcaaaaata aataaataaa ttgttaatgt tggaaaagat taggtatata gatgtcttta     240
caaccttcct ttatagagta aattgcacag gtttgctaat ggtttaggta acaattcaaa     300
gaaggaactt acgagttctg ccgctagcac tgatttacaa ctctaaattg tttccgattg     360
ctctttattt tcatattact attagtagtg ataagagatg gatgtcgttt ataactagat     420
acatgatcat acgtaatata ggtggttatt tgtttcatt caatcaaata ttaaccagat      480
tggaattgtt gtgaaaatct gtaaagtaaa ataaggaatt aaggattgga acaattaatg     540
tttaatgttt gagttgagaa gagtaaaatt ttagtactaa tatctgaatt tagagagaga     600
ttgcatagta gacaaatttg gtcatggaga tacataatag tgcttcaaca tccataattg     660
tgtccaagca cttttgttct tctcagcatt tgtcatgttg gcaaaaatat ttttgcttct     720
taaaatggtt cggagtgatg ttaactccaa agaacagatc tcagttctcg gacatctctc     780
taattaggat gtagctgata tggtcatcaa ctgtgtagat aggattctat ttggttatta     840
caactttata attttctttg gaggttgaaa taaggttcac cttttttggaa tgtgaaagta     900
tacaattgca tttatgttga tggatcttgc atgaaagttg tgatataaat gttccataat     960
gatttatttc agtgagtttg gatgaaatcg atcgatcaat caatcaacca tacctcaatc    1020
ccaaactagt tggtcaaata tatgaatttt ctatatccat tctactttat ccgtgaccat    1080
tgttgtatg agtgaacgtt aaaatatagt ctgaacaagg aagtaacaaa ttgttatgac    1140
catgggatgt gagaaaccat aacaagagta tacaagacat ctcttattct tatttcttca    1200
ccaagagttg tggggatgga tggggaggtg aaaaatgaaa tatatcaacg gtttcccctg    1260
ttgatttatt tcaccttgtc ttacaaaagg aaaaataagg gaagctaaag aagaaaaatt    1320
aagagattaa ctatgagccg ctttcttgca tatatactgg agaaaataca ctgtactgac    1380
tactgtggag taaaactaat tcagttatct tgcccgtact accaaattga acttgtgcat    1440
aggaattctt ctccaattgt gcctttgtct tatacatctt cacttgctta tcactggtct    1500
gttaatacta ctgtatgaat tgtgctggga gtcccatgga atagatgaca ggtttgtctt    1560
tcataaaagt aggaagctct acacgtgata atattgtggt gtaattactg acatctcttt    1620
gtgtacagtt ctgtttttatg aggctcgaat ggaagaagag attagtgctt atgacagctc    1680
atcatgggcg gggtccttcc tcaagaattg tcaggtctgt cttggataac aggaaatcaa    1740
atatcaccgg cgatgaagca actgagccgg ctagggttct tcttgagagg ttgtttgccc    1800
agacccagaa actagaacaa cagattggca gaaatattta ttttcctcag gttgctgagc    1860
tgggactaaa tcttggcaag ctagagtcgg atttgcagga tgctcttgca gccttgaaga    1920
aaaggaaga agatattcaa gatacagaga gaaaagtatt gatggagtac aatgaattaa    1980
```

| | |
|---|---|
| accgtgcaaa gatagaattg gagcaacgtg tggaggagat ggcagctgct aattctaggc | 2040 |
| aggaaaaact ggaaaatgag ctaaggcagg ctaatctgat cttagtatct caagctgcag | 2100 |
| aaattgaaga tctaaagttt cgtttcaacg agatagatca ggagatatct gctgcgcaaa | 2160 |
| cagccctagt ttcaaaagaa gatgaaataa ataaaatgat gattgagttg aagaataaaa | 2220 |
| gtgatgaagt ggctaatact gaatcacaac tcagaaccaa gggtgaacta ctcgatacag | 2280 |
| caaatgaagt agttcaaaga caggaggttg aactacaaaa tctccaaaga gaaattcaag | 2340 |
| agaaagagaa agagctacaa gtcttcttga cgatgcagaa aaccgaagaa gagaaactta | 2400 |
| aagtttccaa atccaatttg gagaagcagg caatggattg gctcatagca aagcaagaaa | 2460 |
| tgaagaaatt ggaagtggaa acatctaact atggtggaga agcaaatcgg tcccttgagg | 2520 |
| atttcagaag agtcaagaag ctacttgccg atgtaaggtc tgagttagtc tcatctcaga | 2580 |
| gagctttgac atcctctaga aagaaaatgg aagagcagga aaatctatta gaagatcgtc | 2640 |
| tcgaagaact tgaagagcag agaagaagtg ttatgtctta catgacaagt ttgaaagaag | 2700 |
| ctcaaaatga ggtagagaat gagaaagtgc aacttacggt tgctgaagct cgaaacaaag | 2760 |
| aacttgagag ggatttatcc atagaaaagg agctcgttga ggagttgcag actgagaata | 2820 |
| atattaagaa atcttctctg catgtagcta tcaatgaaaa atctgctctc caggaggagc | 2880 |
| ttgactgtaa gagtgcagag tttggagaaa cacagaatct tcttcaggtt aaagagtcag | 2940 |
| agctagtaga tgctagatta gagattcagc acttgaagtc tcagtgcgct tctcttcagc | 3000 |
| tgatgttgga agaaaaagat aaggaacttc tggattcaag aaagacagta gatgaactaa | 3060 |
| atcaggaaat agctgagctg agggtgaaca tgaacagtca agaacagcaa cttattcagg | 3120 |
| caacaagtat gttgaaagaa aaagaggaat ccatgcagat aatgcaactt gagttaaatg | 3180 |
| atacaaaaat gaaatattca gaagctgaga ccgttgtgga acatatggta gacctgacta | 3240 |
| acaaattggt tatttctgtt aaggatgacg tgttgagccc actcagtcac acagatgaaa | 3300 |
| tgtggtcatc tcagctggtg gagaaaccaa ctgatgcttt taggtggcac aaaaaccagc | 3360 |
| ttgaaaatga acttgagtta accagagaaa gcctgaggag tagagaaatg gattctcttg | 3420 |
| cagcacaaag ggctcttaaa ctcaaagagc aggagctcaa aatagttcgt caaaaattaa | 3480 |
| atgataggga ggaagaaata aataaaatga gaatatgac ccgggacgca gatggcccaa | 3540 |
| ggcaatctta tgttttggca caggaaagaa caggtgaaaa gagcactgga gatctggcag | 3600 |
| ttgaaaagct ccaattcgag ggagctcaat tggaagttga agctgcaacc actgctctcc | 3660 |
| agaactcgct gaactcagcc gtgacctttt gaataaagct agtttgacca ttgaggctga | 3720 |
| ctatgatagc agccttttgt tggttgacat cccagaaact gcagcaaatg tctctagcag | 3780 |
| ttttgagtgt cttgctgaag tttattcaga gatggcacaa ctttcagctt tgagtgagaa | 3840 |
| gctagtgaaa gaagctggta ttttatgccc ccagtag | 3877 |

<210> SEQ ID NO 62
<211> LENGTH: 2313
<212> TYPE: DNA
<213> ORGANISM: Artificial Sequence
<220> FEATURE:
<223> OTHER INFORMATION: Solanum MRC CDS StMRC (PGSC0003DMT400010993)

<400> SEQUENCE: 62

| | |
|---|---|
| atggcgttgc cagccttacc gcgcgccact ttatcgtttt cctctctttg ccagccaacg | 60 |
| gagttctgtt ttatgaggct cgaatggaag aagagattag tgcttatgac agctcatcat | 120 |

```
gggcggggtc cttcctcaag aattgtcagg tctgtcttgg ataacaggaa atcaaatatc      180
accggcgatg aagcaactga gccggctagg gttcttcttg agaggttgtt tgcccagacc      240
cagaaactag aacaacagat tggcagaaat atttattttc ctcaggttgc tgagctggga      300
ctaaatcttg gcaagctaga gtcggatttg caggatgctc ttgcagcctt gaagaaaaag      360
gaagaagata ttcaagatac agagagaaaa gtattgatgg agtacaatga attaaaccgt      420
gcaaagatag aattggagca acgtgtggag gagatggcag ctgctaattc taggcaggaa      480
aaactggaaa atgagctaag gcaggctaat ctgatcttag tatctcaagc tgcagaaatt      540
gaagatctaa agtttcgttt caacgagata gatcaggaga tatctgctgc gcaaacagcc      600
ctagtttcaa aagaagatga aataaataaa atgatgattg agttgaagaa taaaagtgat      660
gaagtggcta atactgaatc acaactcaga accaagggtg aactactcga tacagcaaat      720
gaagtagttc aaagacagga ggttgaacta caaaatctcc aaagagaaat tcaagagaaa      780
gagaaagagc tacaagtctt cttgacgatg cagaaaaccg aagaagagaa acttaaagtt      840
tccaaatcca atttggagaa gcaggcaatg gattggctca tagcaaagca agaaatgaag      900
aaattggaag tggaaacatc taactatggt ggagaagcaa atcggtccct tgaggatttc      960
agaagagtca agaagctact tgccgatgta aggtctgagt tagtctcatc tcagagagct     1020
ttgacatcct ctagaaagaa aatggaagag caggaaaatc tattagaaga tcgtctcgaa     1080
gaacttgaag agcagagaag aagtgttatg tcttacatga caagtttgaa agaagctcaa     1140
aatgaggtag agaatgagaa agtgcaactt acggttgctg aagctcgaaa caaagaactt     1200
gagagggatt tatccataga aaaggagctc gttgaggagt tgcagactga gaataatatt     1260
aagaaatctt ctctgcatgt agctatcaat gaaaaatctg ctctccagga ggagcttgac     1320
tgtaagagtg cagagtttgg agaaacacag aatcttcttc aggttaaaga gtcagagcta     1380
gtagatgcta gattagagat tcagcacttg aagtctcagt gcgcttctct tcagctgatg     1440
ttggaagaaa aagataagga acttctggat tcaagaaaga cagtagatga actaaatcag     1500
gaaatagctg agctgagggt gaacatgaac agtcaagaac agcaacttat tcaggcaaca     1560
agtatgttga agaaaaaga ggaatccatg cagataatgc aacttgagtt aaatgataca     1620
aaaatgaaat attcagaagc tgagaccgtt gtggaacata tggtagacct gactaacaaa     1680
ttggttattt ctgttaagga tgacgtgttg agcccactca gtcacacaga tgaaatgtgg     1740
tcatctcagc tggtggagaa accaactgat gcttttaggt ggcacaaaaa ccagcttgaa     1800
aatgaacttg agttaaccag agaaagcctg aggagtagag aaatggattc tcttgcagca     1860
caaagggctc ttaaactcaa agagcaggag ctcaaaatag ttcgtcaaaa attaaatgat     1920
agggaggaag aaataaataa aatgaagaat atgacccggg acgcagatgg cccaaggcaa     1980
tcttatgttt tggcacagga agaacaggt gaaaagagca ctggagatct ggcagttgaa     2040
aagctccaat tcgagggagc tcaattggaa gttgaagctg caaccactgc tctccagaaa     2100
ctcgctgaac tcagccgtga ccttttgaat aaagctagtt tgaccattga ggctgactat     2160
gatagcagcc ttttgttggt tgacatccca gaaactgcag caaatgtctc tagcagtttt     2220
gagtgtcttg ctgaagtttt attcagagatg gcacaacttt cagctttgag tgagaagcta     2280
gtgaaagaag ctggtatttt atgcccccag tag                                  2313
```

The invention claimed is:

1. A method for altering starch granule size distribution in a plant grain or seed wherein
altering the granule size distribution comprises shifting the granule size distribution towards smaller granules compared to a control or wild-type grain or seed, wherein the method comprises decreasing the expression of at least one MRC (MYOSIN-RESEMBLING CHLOROPLAST PROTEIN) nucleic acid and/or decreasing the activity of a MRC polypeptide compared to the level of expression or activity in a control or wild-type grain or seed;
and wherein the at least one MRC nucleic acid sequence encodes an MRC polypeptide comprising an amino acid sequence with at least 90% overall sequence identity to SEQ ID NO: 1, 2, 3, 10, 29 or 30; and
wherein the method comprises introducing at least one mutation into the at least one nucleic acid sequence encoding the MRC polypeptide, wherein the mutation is a partial or complete loss of function mutation; and
wherein the plant is wheat or barley.

2. A method of altering a physiochemical property of starch within a plant grain or seed compared to a control or wild-type grain, or seed, the method comprising decreasing the expression of at least one MRC (MYOSIN-RESEMBLING CHLOROPLAST PROTEIN) nucleic acid and/or decreasing the activity of a MRC polypeptide, in a plant grain or seed, compared to a control or wild-type grain or seed, and wherein the physiochemical property is selected from gelatinization temperature, swelling power and viscosity,
and wherein the at least one MRC nucleic acid sequence encodes an MRC polypeptide comprising an amino acid sequence with at least 90% overall sequence identity to SEQ ID NO: 1, 2, 3, 10, 29 or 30; and
wherein the plant grain or seed comprises at least one mutation in the at least one nucleic acid encoding the MRC polypeptide, and wherein the mutation is a partial or complete loss of function mutation; and
wherein the plant is wheat or barley.

3. A genetically altered plant, part thereof or plant cell, wherein said plant, part thereof or plant cell is characterized by an altered starch granule size distribution within a grain or seed, wherein the altered granule size distribution is a shift in granule size distribution towards smaller granules compared to a control or wild-type grain or seed, and, wherein the plant grain or seed has reduced or abolished expression of at least one MYOSIN-RESEMBLING CHLOROPLAST PROTEIN (MRC) nucleic acid and/or reduced or abolished activity of a MRC polypeptide compared to a control or wild-type, wherein the plant grain or seed comprises at least one mutation in at least one nucleic acid encoding a MRC polypeptide, and wherein the mutation is a partial or complete loss of function mutation;
and wherein the nucleic acid sequence encodes an MRC polypeptide comprising an amino acid sequence with at least 90% overall sequence identity to SEQ ID NO: 1, 3, 10, 29 or 30; and
wherein the genetically altered plant, part thereof or plant cell is wheat or barley.

4. The plant part of claim 3, wherein said plant part is grain or a seed obtained or obtainable therefrom, and wherein the grain or seed is characterized by reduced or abolished expression of at least one nucleic acid and/or reduced or abolished activity of the MRC polypeptide compared to a control or wild-type grain or seed.

5. A food or feed composition prepared from the grain or seed of claim 4.

6. A method for selecting a wheat or barley plant that will have altered starch granule size distribution within a grain or a seed,
wherein the altered granule size distribution is a shift in granule size distribution towards smaller granules compared to a control or wild-type grain or seed,
wherein the method comprises detecting in the wheat or barley plant, or wheat or barley plant germplasm, at least one mutation in an MRC (MYOSIN-RESEMBLING CHLOROPLAST) gene,
wherein said MRC gene encodes an MRC polypeptide comprising an amino acid sequence with at least 90% overall sequence identity to SEQ ID NO: 1, 2, 3, 10, 29 or 30, and
selecting said wheat or barley plant germplasm comprising the at least one mutation,
wherein the at least one mutation is a partial or complete loss of function mutation.

7. The plant part of claim 3, wherein said plant part is starch and wherein the starch is characterized by an increase in at least one of starch viscosity, swelling power and gelatinization temperature, wherein the increase is compared to starch from a wild-type or control plant.

8. A food or feed composition prepared from the starch of claim 7.

* * * * *